United States Patent
Dumble

(10) Patent No.: US 12,419,880 B2
(45) Date of Patent: *Sep. 23, 2025

(54) COMPANION DIAGNOSTIC TOOL FOR MUTANT P53 REACTIVATING COMPOUNDS

(71) Applicant: PMV Pharmaceuticals, Inc., Cranbury, NJ (US)

(72) Inventor: Melissa Dumble, Watchung, NJ (US)

(73) Assignee: PMV PHARMACEUTICALS, INC., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/351,880

(22) Filed: Jun. 18, 2021

(65) Prior Publication Data

US 2023/0044826 A1 Feb. 9, 2023

Related U.S. Application Data

(60) Provisional application No. 63/162,812, filed on Mar. 18, 2021, provisional application No. 63/043,307, filed on Jun. 24, 2020.

(51) Int. Cl.

| | | |
|---|---|---|
| *A61K 31/454* | (2006.01) | |
| *A61K 31/404* | (2006.01) | |
| *A61K 31/4045* | (2006.01) | |
| *A61K 31/438* | (2006.01) | |
| *A61K 31/4439* | (2006.01) | |
| *A61K 31/4545* | (2006.01) | |
| *A61K 31/496* | (2006.01) | |
| *A61K 31/506* | (2006.01) | |
| *A61K 31/5377* | (2006.01) | |
| *A61K 31/538* | (2006.01) | |
| *A61P 35/00* | (2006.01) | |

(52) U.S. Cl.
CPC .......... *A61K 31/454* (2013.01); *A61K 31/404* (2013.01); *A61K 31/4045* (2013.01); *A61K 31/438* (2013.01); *A61K 31/4439* (2013.01); *A61K 31/4545* (2013.01); *A61K 31/496* (2013.01); *A61K 31/506* (2013.01); *A61K 31/5377* (2013.01); *A61K 31/538* (2013.01); *A61P 35/00* (2018.01)

(58) Field of Classification Search
CPC ............... A61K 31/454; A61K 31/404; A61K 31/4045; A61K 31/438; A61K 31/4439; A61K 31/4545; A61P 35/00
See application file for complete search history.

(56) References Cited

U.S. PATENT DOCUMENTS

| | | | |
|---|---|---|---|
| 9,447,103 B2 | 9/2016 | Lu et al. | |
| 10,138,219 B2 * | 11/2018 | Vu | C07D 491/107 |
| 11,339,141 B2 | 5/2022 | Vu et al. | |
| 11,807,644 B2 | 11/2023 | Vu et al. | |
| 11,814,373 B2 * | 11/2023 | Vu | C07D 498/06 |
| 11,963,953 B2 * | 4/2024 | Vu | A61K 31/454 |
| 2010/0130731 A1 | 5/2010 | Fersht et al. | |
| 2017/0095479 A1 * | 4/2017 | Marton | A61P 35/00 |
| 2017/0165240 A1 | 6/2017 | Ghanem et al. | |
| 2017/0240525 A1 * | 8/2017 | Vu | C07D 401/12 |
| 2019/0002460 A1 | 1/2019 | Whitehead et al. | |
| 2019/0314508 A1 | 10/2019 | Miyamoto et al. | |
| 2020/0299777 A1 | 9/2020 | Buckhaults et al. | |
| 2021/0002252 A1 | 1/2021 | Vu et al. | |
| 2022/0184087 A1 | 6/2022 | Dinavahi et al. | |
| 2022/0213062 A1 | 7/2022 | Vu et al. | |
| 2022/0315564 A1 | 10/2022 | Vu et al. | |
| 2023/0002403 A1 | 1/2023 | Vu et al. | |
| 2023/0024905 A1 | 1/2023 | Vu et al. | |
| 2023/0033324 A1 * | 2/2023 | Levine | A61K 31/5377 |
| 2023/0049952 A1 * | 2/2023 | Levine | A61P 35/00 |
| 2023/0312539 A1 * | 10/2023 | Vu | C07D 413/14 536/29.11 |
| 2024/0043436 A1 | 2/2024 | Vu et al. | |
| 2024/0269126 A1 | 8/2024 | Levine et al. | |

FOREIGN PATENT DOCUMENTS

| | | |
|---|---|---|
| CA | 3084777 A1 | 7/2019 |
| WO | WO-2012135149 A2 | 10/2012 |
| WO | WO-2017165299 A2 | 9/2017 |
| WO | WO-2018075937 A1 | 4/2018 |
| WO | WO-2018191587 A1 | 10/2018 |
| WO | WO-2021087096 A1 | 5/2021 |
| WO | WO-2022061001 A1 | 3/2022 |

OTHER PUBLICATIONS (Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*
J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*
International Search Report and Written Opinion issued in PCT/US2021/038013 issued Sep. 30, 2021.
U.S. Appl. No. 18/330,978, inventors Vu; Binh et al., filed Jun. 7, 2023.
U.S. Appl. No. 17/351,970 Non-Final Office Action issued Sep. 25, 2023.
Patani, G.A. et al., "Bioisosterism: A rational approach in drug design," Chemical Reviews, 1996;96:3147-3176.
Bauer, et al., Harnessing Fluorine-Sulfur Contacts and Multipolar Interactions for the Design of p53 Mutant Y220C Rescue Drugs, ACS Chem. Biol., 11:2265-2274, (2016).

(Continued)

*Primary Examiner* — Amanda L. Aguirre
*Assistant Examiner* — Chris E Simmons
(74) *Attorney, Agent, or Firm* — WILSON SONSINI GOODRICH & ROSATI

(57) ABSTRACT

Mutations in oncogenes and tumor suppressors contribute to the development and progression of cancer. The present disclosure describes compounds and methods that restore DNA binding affinity of p53 mutants. The compounds of the present disclosure can bind to mutant p53 and restore the ability of the p53 mutant to bind DNA and activate downstream effectors involved in tumor suppression. The disclosed compounds can be used to reduce the progression of cancers that contain a p53 mutation.

16 Claims, No Drawings

Specification includes a Sequence Listing.

(56) References Cited

OTHER PUBLICATIONS

Boeckler, et al., Targeted Rescue of a Destabilized Mutant of p53 by an In Silico Screened Drug, PNAS, 105:10360-10365, (2008).
Bohm, et al., Fluorine in Medicinal Chemistry. Chembiochem., 5:637-643, (2004).
EP20210829156.5 Extended European Search Report dated Jul. 3, 2024.
Gillis, et al., Applications of Fluorine in Medicinal Chemistry, J. Med. Chem., 58:8315-8359, (2015).
Joerger, et al., Crystal Structure of a Superstable Mutant of Human p53 Core Domain. Insights into the Mechanism of Rescuing Oncogenic Mutations, J. Biol. Chem., 279:1291-1296, (2004).
Joerger, et al., Structural Basis for Understanding Oncogenic p53 Mutations and Designing Rescue Drugs, PNAS, 103:15056-15061, (2006).
Nairoukh, et al., Understanding the Conformational Behavior of Fluorinated Piperidines: The Origin of the Axial-F Preference, Chem. Eur. J., 26:6141-6146, (2020).
Welsch, et al., Privileged Scaffolds for Library Design and Drug Discovery, Curr. Opin. Chem. Biol., 14:347-361, (2010).
Wilcken, et al., Halogen-Enriched Fragment Libraries as Leads for Drug Rescue of Mutant p53, J. Am. Chem. Soc., 134:6810-6818, (2012).
European Serial No. 21829156.5 Search Report dated Jul. 3, 2024.

* cited by examiner

SEQUENCE LISTING

```
<160> NUMBER OF SEQ ID NOS: 1

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ser Ser Val Pro Ser Gln Lys Thr Tyr Gln Gly Ser Tyr Gly Phe
 1               5                  10                  15

Arg Leu Gly Phe Leu His Ser Gly Thr Ala Lys Ser Val Thr Cys Thr
            20                  25                  30

Tyr Ser Pro Ala Leu Asn Lys Met Phe Cys Gln Leu Ala Lys Thr Cys
        35                  40                  45

Pro Val Gln Leu Trp Val Asp Ser Thr Pro Pro Gly Thr Arg Val
    50                  55                  60

Arg Ala Met Ala Ile Tyr Lys Gln Ser Gln His Met Thr Glu Val Val
65                  70                  75                  80

Arg Arg Cys Pro His His Glu Arg Cys Ser Asp Ser Asp Gly Leu Ala
                85                  90                  95

Pro Pro Gln His Leu Ile Arg Val Glu Gly Asn Leu Arg Val Glu Tyr
            100                 105                 110

Leu Asp Asp Arg Asn Thr Phe Arg His Ser Val Val Val Pro Cys Glu
        115                 120                 125

Pro Pro Glu Val Gly Ser Asp Cys Thr Thr Ile His Tyr Asn Tyr Met
    130                 135                 140

Cys Asn Ser Ser Cys Met Gly Gly Met Asn Arg Arg Pro Ile Leu Thr
145                 150                 155                 160

Ile Ile Thr Leu Glu Asp Ser Ser Gly Asn Leu Leu Gly Arg Asn Ser
                165                 170                 175

Phe Glu Val His Val Cys Ala Cys Pro Gly Arg Asp Arg Arg Thr Glu
            180                 185                 190

Glu Glu Asn Leu Arg Lys Lys Gly Glu Pro His His Glu Leu Pro Pro
        195                 200                 205

Gly Ser Thr Lys Arg Ala Leu Ser Asn Asn Thr
    210                 215
```

COMPANION DIAGNOSTIC TOOL FOR MUTANT P53 REACTIVATING COMPOUNDS

CROSS-REFERENCE

This application claims the benefit of U.S. Provisional Application No. 63/043,307, filed Jun. 24, 2020; and U.S. Provisional Application No. 63/162,812, filed Mar. 18, 2021, which are incorporated herein by reference.

The instant application contains a Sequence Listing, which has been submitted electronically in ASCII format and is hereby incorporated by reference in its entirety. The ASCII copy, created on Jul. 28, 2021, is named 44727-715.201_SL.txt and is 4,096 bytes in size.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild-type and mutant conformations of p53 are implicated in the progression of cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Provided herein is a method of treating a condition in a subject in need thereof, the method comprising administering to the subject a therapeutically-effective amount of a small molecule compound, wherein the subject has been previously determined to have a mutation in a TP53 gene that encodes a p53 mutant protein in the subject based on an assay performed on a biological sample of the subject, wherein the small molecule compound does not contain arsenic, antimony, or bismuth.

Also provided herein is a method of treating a condition in a subject in need thereof, the method comprising: a) based on a result of an assay performed on a biological sample of the subject, determining that the subject harbors a mutation in a TP53 gene that encodes a p53 mutant protein; b) based on the result of the assay, administering to the subject a therapeutically-effective amount of a small molecule compound, wherein the small molecule compound does not contain arsenic, antimony, or bismuth.

DETAILED DESCRIPTION

The present disclosure provides companion diagnostic methods for restoring wild-type function to mutant p53 using compounds disclosed herein. The compounds can bind to mutant p53 and restore the ability of the p53 mutant to bind DNA. The restoration of activity of the p53 mutant can allow for the activation of downstream effectors of p53 leading to inhibition of cancer progression. The disclosure further provides companion diagnostic methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo1, KILLER/DR5, Bax, Puma, Noxa, Bid, caspase-3, caspase-6, caspase-7, caspase-8, caspase-9, and p21 (WAF1). Additionally, p53 can indirectly repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids, and makes specific contact with various p53 response elements.

Due to the prevalence of p53 mutations in virtually every type of cancer, the reactivation of wild-type p53 function in a cancerous cell can be an effective therapy. Mutations in p53 located in the DNA-binding domain of the protein or periphery of the DNA-binding surface can result in aberrant protein folding required for DNA recognition and binding or reduction in DNA binding affinity. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273C, R273H, and R282H. p53 mutations can distort the structure of the DNA-binding site, thermodynamically destabilize the folded protein at body temperature, or weaken consensus DNA binding. Wild-type function of p53 mutants can be recovered by binding of the p53 mutant to a compound that can shift the folding-unfolding equilibrium towards the folded state, thereby reducing the rate of unfolding and destabilization; or by conjugating a small molecule to the DNA binding interface to restore consensus DNA binding.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Disclosure.

The compounds of the present disclosure can selectively bind to a p53 mutant and can recover wild-type activity of the p53 mutant including, for example, DNA binding function and activation of downstream targets involved in tumor suppression. In some embodiments, a compound of the disclosure selectively binds to the p53 Y220C mutant. The Y220C mutant is a temperature sensitive mutant, which binds to DNA at lower temperature and is denatured at body temperature. A compound of the disclosure can stabilize the Y220C mutant to reduce the likelihood of denaturation of the protein at body temperature.

In some embodiments, the compounds of the disclosure stabilize a mutant p53 and allows the mutant p53 to bind to DNA, thereby shifting the equilibrium of wild type and mutant p53 proteins to wild type p53. In some embodiments, the compounds of the disclosure reactivate the mutant p53 protein to provide wild type p53 activity. In some embodiments, the compounds of the disclosure reactivate the mutant p53 protein to provide pro-apoptotic p53 activity. In some embodiments, the compounds of the disclosure reactivate the mutant p53 protein to block angiogenesis. In some embodiments, the compounds of the disclosure reactivate the mutant p53 protein to induce cellular senescence. In some embodiments, the compounds of the disclosure reactivate the mutant p53 protein to induce cell cycle arrest.

Located in the periphery of the p53 β-sandwich connecting β-strands S7 and S8, the aromatic ring of Y220 is an integral part of the hydrophobic core of the β-sandwich. The Y220C mutation can be highly destabilizing, due to the formation of an internal surface cavity. A compound of the disclosure can bind to and occupy this surface crevice to stabilize the β-sandwich, thereby restoring wild-type p53 DNA-binding activity.

To determine the ability of a compound of the disclosure to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild-type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC-P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as β-galactosidase staining.

A p53 mutant that can be used to determine the effectiveness of a compound of the disclosure to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

(SEQ ID NO. 1)
SSSVPSQ KTYQGSYGFR LGFLHSGTAK SVTCTYSPAL

NKMFCQLAKT CPVQLWVDST PPPGTRVRAM AIYKQSQHMT

EVVRRCPHHE RCSDSDGLAP PQHLIRVEGN LRVEYLDDRN

TFRHSVVVPC EPPEVGSDCT TIHYNYMCNS SCMGGMNRRP

ILTIITLEDS SGNLLGRNSF EVHVCACPGR DRRTEEENLR

KKGEPHHELP PGSTKRALSN NT

A compound of the disclosure can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the disclosure.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the disclosure can be used, for example, to induce apoptosis, cell cycle arrest, or senescence in a cell. In some embodiments, the cell is a cancer cell. In some embodiments, the cell carries a mutation in p53.

Compounds of the disclosure.

In some embodiments, the compound is of the formula:

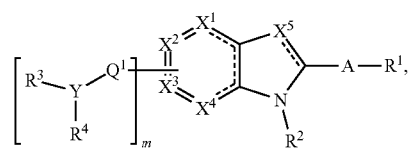

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N, $NR^9$, O, S, C=O, C=S, or a carbon atom connected to $Q^1$;

$X^4$ is $CR^{11}$, $CR^{11}R^{12}$, N, $NR^{11}$, O, S, C=O, C=S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

A is a linking group;

$Q^1$ is C=O, C=S, C=$CR^{14}R^{15}$, C=$NR^{14}$, alkylene, alkenylene, or alkynylene, each of which is independently substituted or unsubstituted, or a bond;

m is 1, 2, 3, or 4;

Y is N, O, or absent;

$R^1$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —$C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, A is alkylene, alkenylene, or alkynylene, each of which is substituted or unsubstituted. In some embodiments, A is alkylene. In some embodiments, A is alkenylene. In some embodiments, A is alkynylene.

In some embodiments, A is aryl, heteroaryl, or heterocyclyl, each of which is substituted or unsubstituted. In some embodiments, A is substituted aryl. In some embodiments, A is substituted heteroaryl. In some embodiments, A is substituted heterocyclyl.

In some embodiments, $R^1$ is alkyl, alkenyl, —$C(O)R^{16}$, —$C(O)OR^{16}$, or —$C(O)NR^{16}R^{17}$, each of which is unsubstituted or substituted. In some embodiments, $R^1$ is substituted alkyl. In some embodiments, $R^1$ is alkyl substituted with $NR^{16}R^{17}$.

In some embodiments, the compound of the formula is:

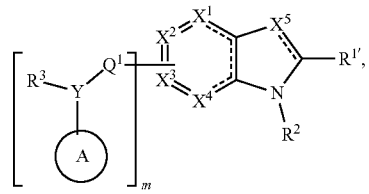

wherein:

each ------- is independently a single bond or a double bond;

$X^1$ is $CR^5$, $CR^5R^6$, N, $NR^5$, O, S, C=O, C=S, or a carbon atom connected to $Q^1$;

$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N, $NR^9$, O, S, C=O, C=S, or a carbon atom connected to $Q^1$;

$X^4$ is $CR^{11}$, $CR^{11}R^{12}$, N, $NR^{11}$, O, S, C=O, C=S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

$Q^1$ is C=O, C=S, C=$CR^{14}R^{15}$, C=$NR^{14}$, alkylene, alkenylene, or alkynylene, each of which is independently substituted or unsubstituted, or a bond;

m is 1, 2, 3, or 4;

Y is N, O, or absent;

ring A is a cyclic group;

$R^{1'}$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, C=O, C=S, —CN, —$SiR^{16}R^{17}R^{18}$, alkyl, alkenyl, alkynyl, aryl, heteroaryl, or heterocyclyl, each of which is independently substituted or unsubstituted, or hydrogen;

$R^3$ is —$C(O)R^{19}$, —$C(O)OR^{19}$, —$C(O)NR^{19}R^{20}$, —$SOR^{19}$, —$SO_2R^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent, each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is $C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, a compound of the invention is a compound of the formula

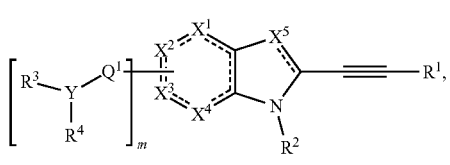

wherein:
  each ------- is independently a single bond or a double bond;
  $X^1$ is $CR^5$, $CR^5R^6$, N, $NR^5$, O, S, C=O, C=S, or a carbon atom connected to $Q^1$;
  $X^2$ is $CR^7$, $CR^7R^8$, N, $NR^7$, O, S, C=O, C=S, or a carbon atom connected to $Q^1$;
  $X^3$ is $CR^9$, $CR^9R^{10}$, N, $NR^9$, O, S, C=O, C=S, or a carbon atom connected to $Q^1$;
  $X^4$ is $CR^{11}$, $CR^{11}R^{12}$, N, $NR^{11}$, O, S, C=O, C=S, or a carbon atom connected to $Q^1$;
  $X^5$ is $CR^{13}$, N, or $NR^{13}$;
wherein at least one of $X^1$, $X^2$, $X^3$, and $X^4$ is a carbon atom connected to $Q^1$;
  $Q^1$ is C=O, C=S, C=$CR^{14}R^{15}$, C=$NR^{14}$, alkylene, alkenylene, or alkynylene, each of which is independently substituted or unsubstituted, or a bond;
  m is 1, 2, 3, or 4;
  Y is N, O, or absent;
  $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
  each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent,
  each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
  each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
  each $R^{21}$ and $R^{22}$ is independently alkyl, alkenyl, alkynyl, aryl, heteroaryl, or heterocyclyl, each of which is independently substituted or unsubstituted, or hydrogen; and
  each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, the compound is of the formula:

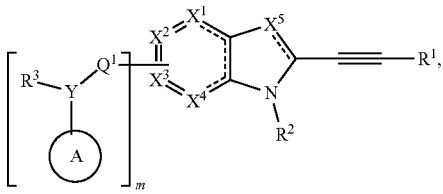

wherein:
  each ------- is independently a single bond or a double bond;
  $X^1$ is $CR^5$, $CR^5R^6$, N, $NR^5$, O, S, C=O, C=S, or a carbon atom connected to $Q^1$;
  $X^2$ is $CR^7$, $CR^7R^8$, N, $NR^7$, O, S, C=O, C=S, or a carbon atom connected to $Q^1$;
  $X^3$ is $CR^9$, $CR^9R^{10}$, N, $NR^9$, O, S, C=O, C=S, or a carbon atom connected to $Q^1$;
  $X^4$ is $CR^{11}$, $CR^{11}R^{12}$, N, $NR^{11}$, O, S, C=O, C=S, or a carbon atom connected to $Q^1$;
  $X^5$ is $CR^{13}$, N, or $NR^{13}$;
wherein at least one of $X^1$, $X^2$, $X^3$, and $X^4$ is a carbon atom connected to $Q^1$;
  $Q^1$ is C=O, C=S, C=$CR^{14}R^{15}$, C=$NR^{14}$, alkylene, alkenylene, or alkynylene, each of which is independently substituted or unsubstituted, or a bond;
  m is 1, 2, 3, or 4;
  Y is N, O, or absent;
  ring A is a cyclic group;
  $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
  $R^3$ is —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent;
  each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
  each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
  each $R^{21}$ and $R^{22}$ is independently alkyl, alkenyl, alkynyl, aryl, heteroaryl, or heterocyclyl, each of which is independently substituted or unsubstituted, or hydrogen; and
  each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, the pattern of dashed bonds is chosen to provide an aromatic system, for example, an indole, an indolene, a pyrrolopyridine, a pyrrolopyrimidine, or a pyrrolopyrazine.

In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, $Q^1$ is a bond. In some embodiments, $Q^1$ is $C_1$-alkylene. In some embodiments, m is 1. In some embodiments, m is 2. In some embodiments, m is 3. In some embodiments, m is 4.

In some embodiments, $R^1$ is alkyl, alkenyl, —C(O)$R^{16}$, —C(O)O$R^{16}$, or —C(O)N$R^{16}R^{17}$, each of which is unsubstituted or substituted. In some embodiments, $R^1$ is substituted alkyl. In some embodiments, $R^1$ is alkyl substituted with $NR^{16}R^{17}$.

In some embodiments, ring A is aryl, heteroaryl, or heterocyclyl, each of which is substituted or unsubstituted. In some embodiments, ring A is substituted aryl. In some embodiments, ring A is aryl substituted with fluoro-. In some embodiments, ring A is aryl substituted with chloro-. In some embodiments, ring A is substituted heteroaryl. In some embodiments, ring A is heteroaryl substituted with fluoro-. In some embodiments, ring A is heteroaryl substituted with chloro-. In some embodiments, ring A is substituted heterocyclyl. In some embodiments, ring A is heterocyclyl substituted with fluoro-. In some embodiments, A is heterocyclyl substituted with chloro-.

In some embodiments, ring A is piperidinyl, piperazinyl, tetahydropyranyl, morpholinyl, or pyrrolidinyl, each of which is independently substituted or unsubstituted. In some embodiments, ring A is piperidinyl, piperazinyl, tetahydropyranyl, morpholinyl, or pyrrolidinyl, each of which is independently substituted with at least halo-. In some embodiments, ring A is piperidinyl substituted with halo-. In some embodiments, ring A is methylpiperidinyl substituted with halo-. In some embodiments, ring A is 3-fluoro-1-methylpiperidinyl. In some embodiments, ring A is 3-fluoro-1-(2-hydroxy-3-methoxypropyl)piperidinyl. In some embodiments, ring A is tetrahydropyranyl substituted with at least halo-.

In some embodiments, each $R^{16}$ and $R^{17}$ is independently alkyl, alkenyl, aryl, heteroaryl, heterocyclyl, each of which is independently substituted or unsubstituted, or hydrogen. In some embodiments, $R^{16}$ is hydrogen or alkyl. In some embodiments, $R^{17}$ is aryl, heteroaryl, or heterocyclyl, each of which is independently substituted or unsubstituted. In some embodiments, $R^{17}$ is substituted aryl. In some embodiments, $R^{17}$ is substituted phenyl. In some embodiments, $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is phenyl substituted with a substituted amide group.

In some embodiments, the compound is of the formula:

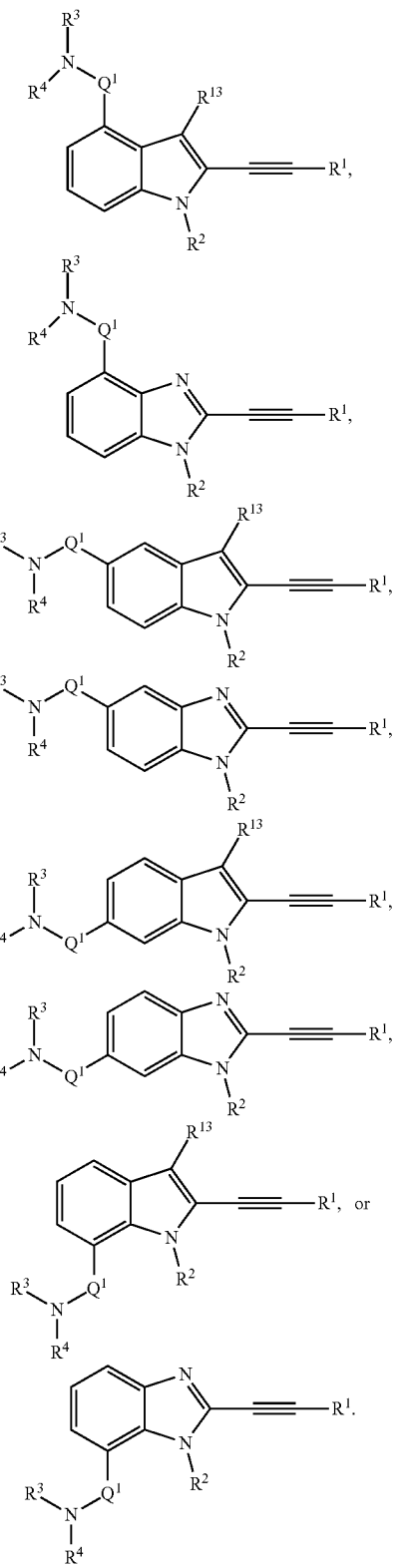

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene or a bond. In some embodiments, $Q^1$ is $C_1$-alkylene. In some embodiments, $Q^1$ is a bond.

In some embodiments, Y is N. In some embodiments, Y is O. In some embodiments, Y is absent.

In some embodiments, $R^2$ is hydrogen or alkyl. In some embodiments, $R^2$ is alkyl. In some embodiments, $R^2$ is substituted $C_1$-$C_5$-alkyl. In some embodiments, $R^2$ is trifluoroethyl. In some embodiments, $R^2$ is cycloalkyl. In some embodiments, $R^2$ is cyclopropyl.

In some embodiments, $R^{13}$ is alkyl, alkenyl, hydrogen, or halogen. In some embodiments, $R^{13}$ is hydrogen.

In some embodiments, $R^2$ is $C_1$-$C_5$-alkyl, and $R^{13}$ is $C_1$-$C_5$-alkyl. In some embodiments, $R^2$ is $C_1$-$C_5$-alkyl, and $R^{13}$ is hydrogen. In some embodiments, $R^2$ is substituted $C_1$-$C_5$-alkylene. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, the compound is of the formula:

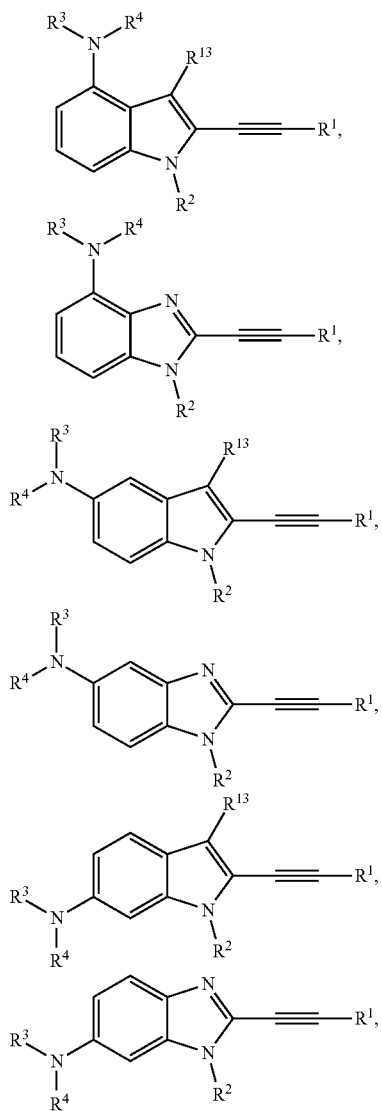

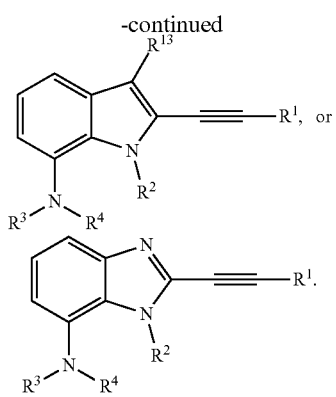

In some embodiments, the compound is of the formula:

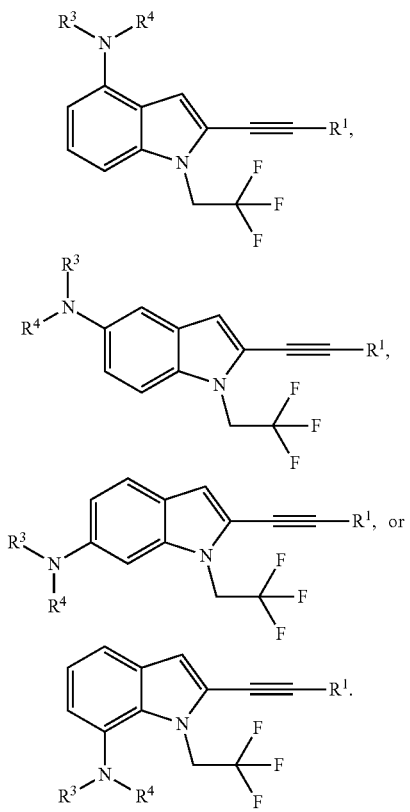

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted. In some embodiments, each $R^3$ and $R^4$ is independently substituted or unsubstituted $C_1$-$C_6$-alkylene. In some embodiments, $R^3$ is H, and $R^4$ is substituted or unsubstituted $C_1$-$C_4$ alkylene. In some embodiments, $R^3$ is H, and $R^4$ is substituted or unsubstituted heterocyclyl. In some embodiments, $R^3$ is H, and $R^4$ is substituted or unsubstituted piperidinyl. In some embodiments, $R^3$ is H, and $R^4$ is substituted or unsubstituted cycloalkyl. In some embodiments, $R^3$ is H, and $R^4$ is cycloalkyl substituted with an amino group. In some embodiments, $R^3$ is H, and $R^4$ is substituted or unsubstituted cyclobutyl. In some embodiments, $R^3$ is H, and $R^4$ is cyclobutyl substituted with an amino group. In some embodiments, $R^3$ is H, and $R^4$ is substituted or unsubstituted cyclohexyl. In some embodiments, $R^3$ is H, and $R^4$ is cyclohexyl substituted with an amino group.

In some embodiments, the compound is of the formula:

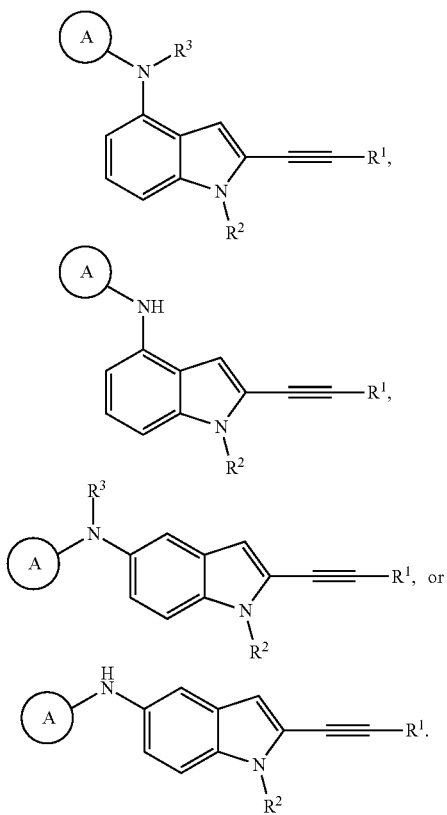

In some embodiments, the compound is of the formula:

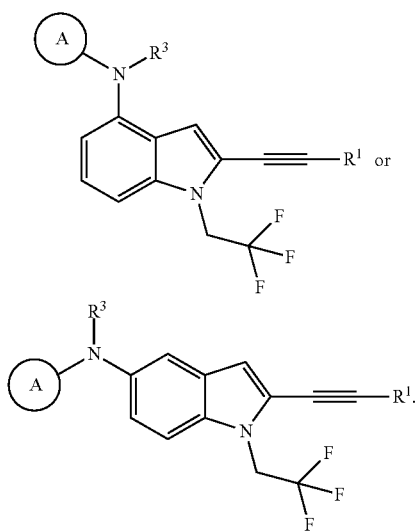

$R^1$ can be a group substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group. In some embodiments, $R^1$ is alkyl, alkenyl, —C(O)$R^{16}$, —C(O)O$R^{16}$, or —C(O)N$R^{16}R^{17}$.

In some embodiments, $R^1$ is substituted or unsubstituted $C_1$-$C_3$ alkyl. In some embodiments, $R^1$ is $C_1$-$C_3$-alkyl substituted with an amine group. In some embodiments, $R^1$ is $C_1$-alkyl substituted with N$R^{16}R^{17}$. In some embodiments, each $R^{16}$ and $R^{17}$ is independently aryl, heteroaryl, or heterocyclyl, each of which is independently substituted or unsubstituted, or hydrogen. In some embodiments, $R^{16}$ is H, and $R^{17}$ is substituted aryl. In some embodiments, $R^{16}$ is H, and $R^{17}$ is substituted phenyl. In some embodiments, $R^{16}$ is H, and $R^{17}$ is phenyl substituted with alkyl, alkoxy, halo, sulfonamide, a sulfone, or a carboxy group. In some embodiments, $R^{16}$ is H, and $R^{17}$ is substituted heteroaryl. In some embodiments, $R^{16}$ is H, and $R^{17}$ is substituted heterocyclyl.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is $C_1$-alkylene, $R^{16}$ is aryl, and $R^{17}$ is alkyl. In some embodiments, $Q^1$ is $C_1$-alkylene, $R^{16}$ is aryl, and $R^{17}$ is hydrogen. In some embodiments, $Q^1$ is $C_1$-alkylene, $R^{16}$ is heteroaryl, and $R^{17}$ is alkyl. In some embodiments, $Q^1$ is $C_1$-alkylene, $R^{16}$ is heteroaryl, and $R^{17}$ is hydrogen. In some embodiments, $Q^1$ is $C_1$-alkylene, $R^{16}$ is substituted heteroaryl, and $R^{17}$ is hydrogen. In some embodiments, $Q^1$ is $C_1$-alkylene, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano.

In some embodiments, $R^2$ is alkyl, and $R^{13}$ is alkyl, each of which is substituted or substituted. In some embodiments, $R^2$ is hydrogen, and $R^{13}$ is unsubstituted or substituted alkyl. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is hydrogen, and $R^{13}$ is alkyl. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen. In some embodiments, $R^3$ is alkyl, alkenyl, alkynyl, aryl, heteroaryl, or heterocyclyl, each of which is independently substituted or unsubstituted, or hydrogen. In some embodiments, $R^3$ is substituted alkyl. In some embodiments, $R^3$ is H.

In some embodiments, $R^3$ is H, and $R^4$ is unsubstituted or substituted alkyl. In some embodiments, $R^3$ is H, and $R^4$ is unsubstituted or substituted cycloalkyl. In some embodiments, $R^3$ is H, and $R^4$ is substituted cyclohexyl. In some embodiments, $R^3$ is H, and $R^4$ is substituted cyclobutyl.

In some embodiments, at least one of $R^3$ and $R^4$ is alkyl, alkylene, alkenyl, alkenylene, alkynyl, aryl, heteroaryl, or heterocyclyl, each of which is substituted at least with halo-. In some embodiments, $R^3$ is hydrogen and $R^4$ is a ring A. In some embodiments, $R^4$ or ring A is cycloalkyl, aryl, heteroaryl, or heterocyclyl, each of which is independently substituted or unsubstituted. In some embodiments, $R^4$ or ring A is substituted or unsubstituted aryl. In some embodiments, $R^4$ or ring A is substituted or unsubstituted phenyl. In some embodiments, $R^4$ or ring A is substituted or unsubstituted cycloalkyl. In some embodiments, $R^4$ or ring A is substituted or unsubstituted cyclopropyl. In some embodiments, $R^4$ or ring A is substituted cyclopropyl. In some embodiments, $R^4$ or ring A is substituted cyclohexyl. In some embodiments, $R^4$ or ring A is cyclohexyl substituted with an amino group.

In some embodiments, $R^3$ is H, and $R^4$ or ring A is unsubstituted or substituted heterocyclyl. In some embodiments, $R^4$ or ring A is heterocyclyl. In some embodiments, $R^4$ or ring A is piperidinyl, piperazinyl, tetahydropyranyl, morpholinyl, or pyrrolidinyl, each of which is independently substituted or unsubstituted. In some embodiments, $R^3$ is H, and $R^4$ or ring A is substituted piperidinyl. In some embodiments, $R^3$ is H, and $R^4$ or ring A is piperidine substituted with alkyl, carboxy, heterocyclyl, or an amide group. In some embodiments, $R^3$ is H, and $R^4$ or ring A is unsubstituted or substituted methyl piperidinyl. In some embodiments, $R^3$ is H, and $R^4$ or ring A is 3-fluoro-1-methylpiperidinyl. In some embodiments, $R^3$ is H, and $R^4$ or ring A is piperidinyl substituted with methoxypropanol. In some embodiments, $R^3$ is H, and $R^4$ or ring A is 3-fluoro-1-(2-hydroxy-3-methoxypropyl)piperidinyl. In some embodiments, $R^3$ is H, and $R^4$ or ring A is unsubstituted or substituted tetrahydropyranyl. In some embodiments, $R^3$ is H, and $R^4$ or ring A is unsubstituted tetrahydropyranyl. In some embodiments, $R^3$ is H, and $R^4$ or ring A is tetrahydropyranyl substituted with alkyl. In some embodiments, $R^3$ is H, and $R^4$ or ring A is tetrahydrothiopyran-1,1-dioxide.

In some embodiments, $R^4$ or ring A is cycloalkyl, aryl, heteroaryl, or heterocyclyl, each of which is substituted at least with halo-. In some embodiments, $R^4$ or ring A is $C_4$-$C_6$-cycloalkyl substituted with at least halo-. In some embodiments, $R^4$ or ring A is cyclohexyl substituted with at least halo-. In some embodiments, $R^4$ or ring A is aryl substituted with at least halo-. In some embodiments, $R^4$ or ring A is phenyl substituted with at least halo-. In some embodiments, $R^4$ or ring A is aryl substituted with fluoro-. In some embodiments, $R^4$ or ring A is phenyl substituted with fluoro-. In some embodiments, $R^4$ or ring A is aryl substituted with chloro-. In some embodiments, $R^4$ or ring A is phenyl substituted with chloro-. In some embodiments, $R^4$ or ring A is heteroaryl substituted with at least halo-. In some embodiments, $R^4$ or ring A is heteroaryl substituted with fluoro-. In some embodiments, $R^4$ or ring A is heteroaryl substituted with chloro-. In some embodiments, $R^4$ or ring A is $C_4$-$C_6$-heterocyclyl substituted with at least halo-. In some embodiments, $R^4$ or ring A is heterocyclyl substituted with fluoro-. In some embodiments, $R^4$ or ring A is heterocyclyl substituted with chloro-.

In some embodiments, $R^4$ or ring A is piperidinyl, piperazinyl, tetahydropyranyl, morpholinyl, or pyrrolidinyl, each of which is independently substituted with at least halo-. In some embodiments, $R^4$ or ring A is piperidinyl substituted with halo-. In some embodiments, $R^4$ or ring A is methylpiperidinyl substituted with halo-. In some embodiments, $R^4$ or ring A is 3-fluoro-1-methylpiperidinyl. In some embodiments, $R^4$ or ring A is 3-fluoro-1-(2-hydroxy-3-methoxypropyl)piperidinyl. In some embodiments, $R^4$ or ring A is tetrahydropyranyl substituted with at least halo-.

In some embodiments, $R^4$ or Ring A is a ring that is:

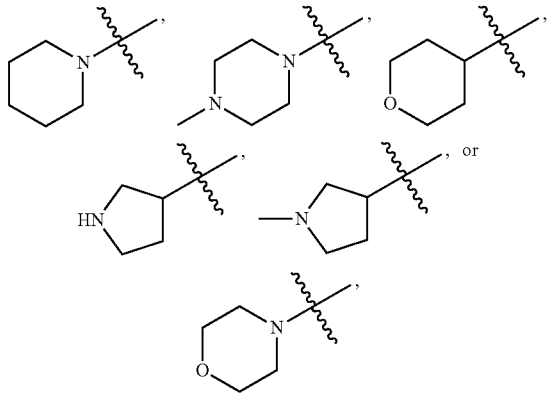

wherein the ring is substituted or unsubstituted. In some embodiments, the ring is substituted with halo-. In some embodiments, the ring is substituted with fluoro. In some embodiments, $R^3$ is H, and $R^4$ is a ring that is

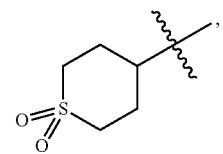 [SMILES: *C1CCS(=O)(=O)CC1]

wherein the ring is substituted or unsubstituted. In some embodiments, the ring is substituted with halo-. In some embodiments, the ring is substituted with fluoro. In some embodiments, $R^3$ is H, and $R^4$ is a ring that is

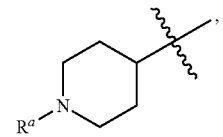

wherein the ring is substituted or unsubstituted. In some embodiments, $R^a$ is alkylene. In some embodiments, $R^a$ is methyl. In some embodiments, the ring is substituted with halo. In some embodiments, the ring is substituted with fluoro. In some embodiments, $R^3$ is H, and $R^4$ is a ring that is

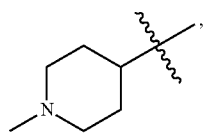 [SMILES: *C1CCN(C)CC1]

wherein the ring is substituted or unsubstituted. In some embodiments, the ring is substituted with halo. In some embodiments, the ring is substituted with fluoro. In some embodiments, $R^3$ is H, and $R^4$ is a ring that is

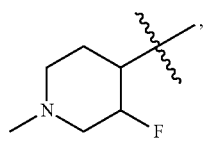 [SMILES: *C1CCN(C)CC1F]

wherein the ring is substituted or unsubstituted.

In some embodiments, the $R^4$ or ring A is substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.

In some embodiments, $R^3$ and $R^4$ together with the nitrogen atom to which $R^3$ and $R^4$ are bound form a ring of a following formula:

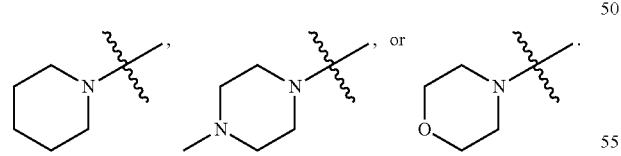

In some embodiments, the compound is of the formula:

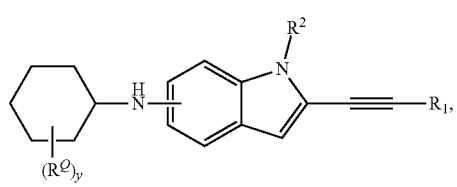

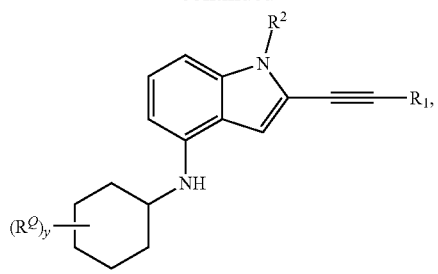

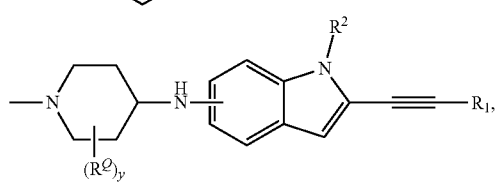

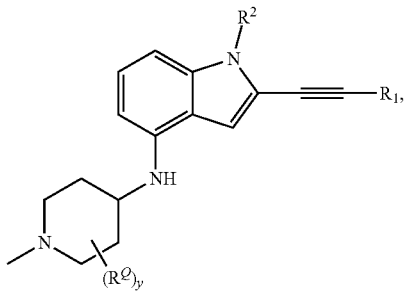

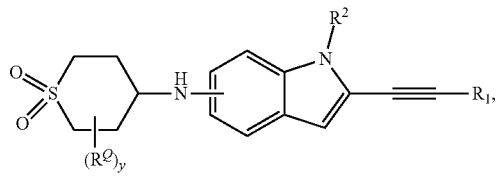

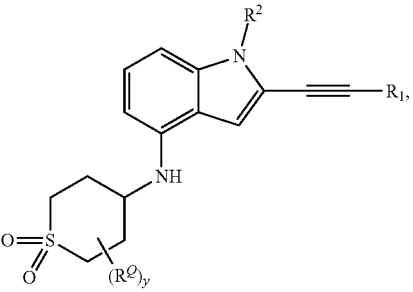

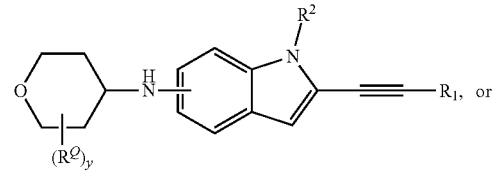

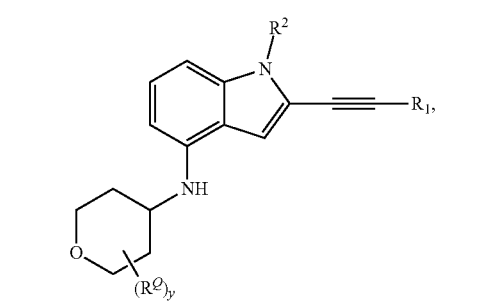

wherein:
R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each R$^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

y is 0, 1, 2, 3, or 4;

each R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted, or hydrogen. In some embodiments, R$^1$ is alkyl, alkylene, alkoxy, —NR$^{21}$R$^{22}$, or aryl, each of which is independently substituted or unsubstituted; halo or hydrogen.

In some embodiments, R$^1$ is substituted C$_1$-C$_5$-alkyl. In some embodiments, R$^1$ is C$_1$-C$_3$-alkyl substituted with NR$^{16}$R$^{17}$. In some embodiments, R$^1$ is methyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, R$^1$ is methyl substituted with NR$^{16}$R$^{17}$, wherein R$^{16}$ is hydrogen, and R$^{17}$ is a substituted carboxyl group. In some embodiments, R$^1$ is methyl substituted with NR$^{16}$R$^{17}$, wherein R$^{16}$ is hydrogen, and R$^{17}$ is substituted aryl. In some embodiments, R$^1$ is methyl substituted with NR$^{16}$R$^{17}$, wherein R$^{16}$ is hydrogen, and R$^{17}$ is substituted phenyl. In some embodiments, R$^1$ is methyl substituted with NR$^{16}$R$^{17}$, wherein R$^{16}$ is hydrogen, and R$^{17}$ is phenyl, substituted with a sulfoxide group, carboxyl group, amide group, amino group, alkyl, alkoxy, hydroxy, halo, cyano, or heterocyclyl, each of which is independently substituted or unsubstituted. In some embodiments, R$^{17}$ is phenyl substituted with methoxy. In some embodiments, R$^{17}$ is phenyl substituted with a substituted sulfoxide group. In some embodiments, R$^{17}$ is phenyl substituted with a carboxyl group. In some embodiments, R$^{17}$ is a substituted amide group. In some embodiments, R$^{17}$ is substituted with methoxy and sulfonamide.

In some embodiments, R$^2$ is hydrogen or alkyl. In some embodiments, R$^2$ is substituted C$_1$-C$_5$-alkylene. In some embodiments, R$^2$ is trifluoroethyl. In some embodiments, R$^{13}$ is alkyl, alkenyl, hydrogen, or halogen. In some embodiments, R$^2$ is alkyl, and R$^{13}$ is alkyl. In some embodiments, R$^2$ is hydrogen, and R$^{13}$ is alkyl. In some embodiments, R$^2$ is methyl, ethyl, propyl, iso-propyl, butyl, or tert-butyl. In some embodiments, R$^{13}$ is methyl, ethyl, propyl, iso-propyl, butyl or tert-butyl. In some embodiments, R$^2$ is hydrogen, and R$^{13}$ is hydrogen.

In some embodiments, the compound is of the formula:

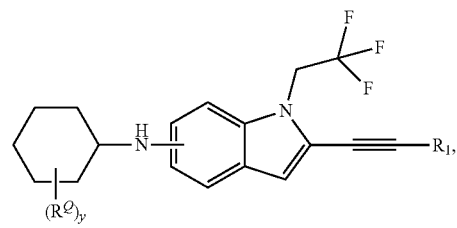

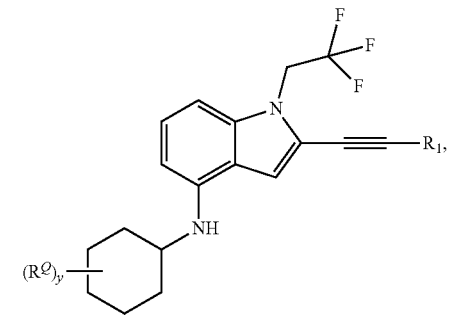

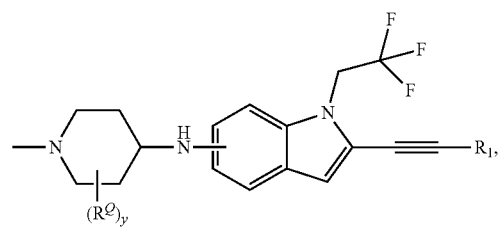

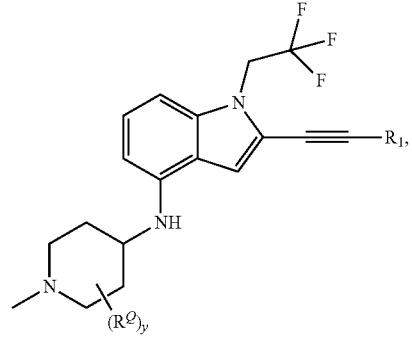

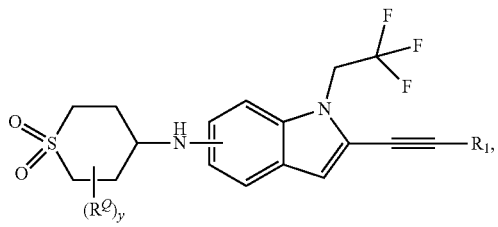

-continued

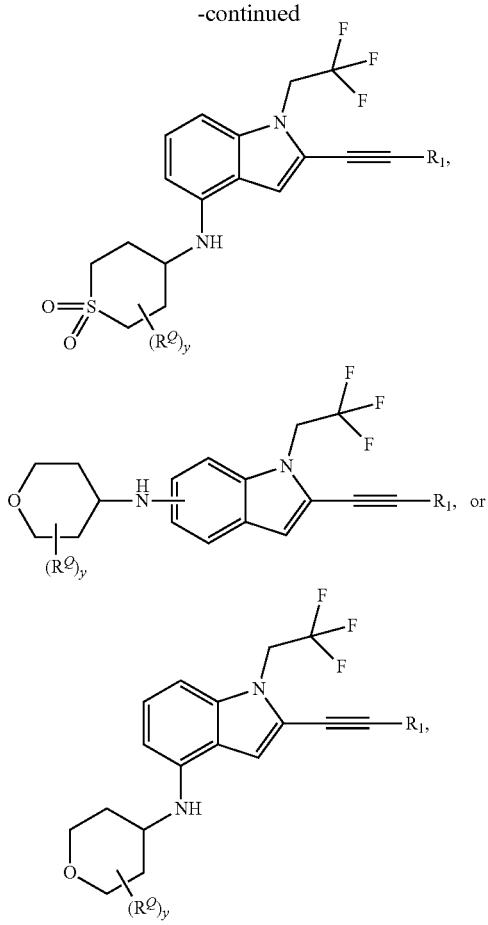

or a pharmaceutically-acceptable salt thereof, wherein the variables are as defined above.

In some embodiments, each $R^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen. In some embodiments, each $R^Q$ is In some embodiments, y is 1. In some embodiments, y is 2. In some embodiments, y is 3. In some embodiments, y is 4.

In some embodiments, $R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —NR$^{21}$R$^{22}$, or aryl, each of which is independently substituted or unsubstituted; halo or hydrogen.

In some embodiments, $R^1$ is substituted alkyl. In some embodiments, $R^1$ is substituted C$_1$-C$_3$-alky 1. In some embodiments, $R^1$ is alkyl substituted with NR$^{16}$R$^{17}$. In some embodiments, $R^1$ is C$_1$-C$_3$-alkyl substituted with NR$^{16}$R$^{17}$. In some embodiments, $R^1$ is methyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with NR$^{16}$R$^{17}$, wherein R$^{16}$ is hydrogen, and R$^{17}$ is a substituted carboxyl group.

In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted.

In some embodiments, the compound is of the formula:

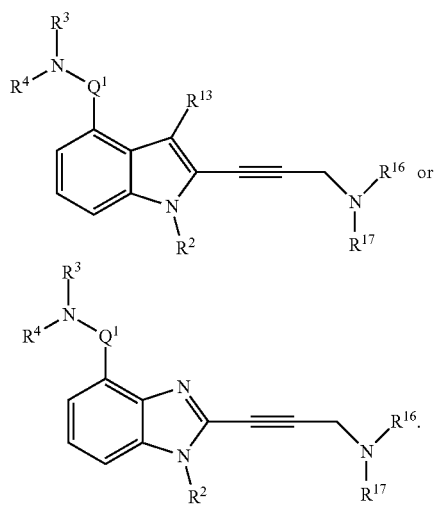

In some embodiments, the compound is of the formula:

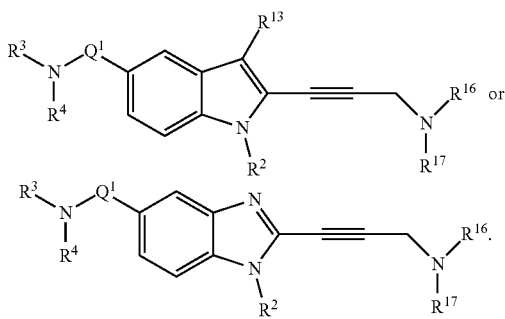

In some embodiments, the compound is of the formula:

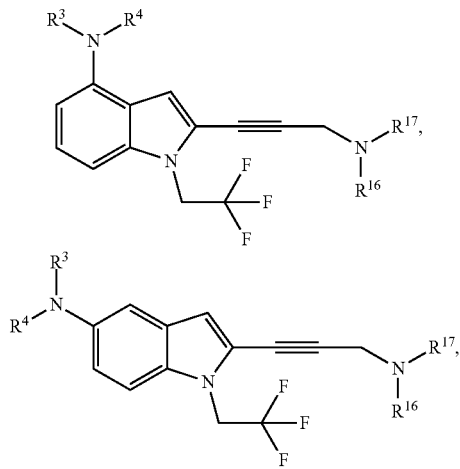

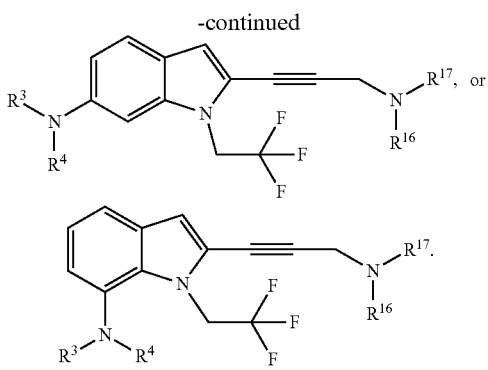

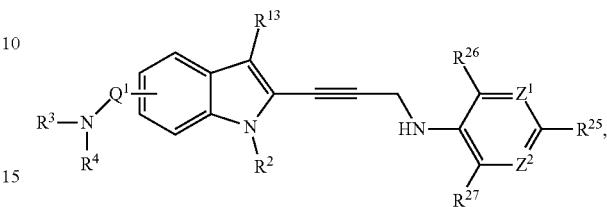

In some embodiments, each $R^{16}$ and $R^{17}$ is independently alkyl, alkenyl, aryl, heteroaryl, heterocyclyl, or hydrogen. In some embodiments, $R^{16}$ is aryl, and $R^{17}$ is alkyl. In some embodiments, $R^{16}$ is aryl, and $R^{17}$ is hydrogen. In some embodiments, $R^{16}$ is heteroaryl, and $R^{17}$ is alkyl. In some embodiments, $R^{16}$ is heteroaryl, and $R^{17}$ is hydrogen. In some embodiments, $R^{16}$ is substituted heteroaryl, and $R^{17}$ is hydrogen. In some embodiments, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{16}$ is hydrogen. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano. In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted. In some embodiments, $R^{16}$ is hydrogen, and $R^{17}$ is substituted phenyl. In some embodiments, $R^{16}$ is hydrogen, and $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is a substituted amide group. In some embodiments, $R^{17}$ is substituted with methoxy and sulfonamide.

In some embodiments, each $R^3$ and $R^4$ is independently unsubstituted or substituted alkyl. In some embodiments, $R^3$ is hydrogen and $R^4$ is —C(O)$R^{19}$, —C(O)O$R^{19}$, alkyl, alkenyl, alkynyl, aryl, heteroaryl, or heterocyclyl, each of which is independently substituted or unsubstituted. In some embodiments, $R^3$ is hydrogen, and $R^4$ is alkyl, aryl, heteroaryl, or heterocyclyl, each of which is independently substituted or unsubstituted. In some embodiments, $R^3$ is H, and $R^4$ is substituted heterocyclyl. In some embodiments, $R^3$ is H, and $R^4$ is substituted or unsubstituted $C_4$-$C_6$-heterocyclyl. In some embodiments, $R^3$ is H, and $R^4$ is substituted alkyl. In some embodiments, $R^3$ is H, and $R^4$ is substituted $C_1$-$C_6$-alkyl. In some embodiments, $R^3$ is H, and $R^4$ is substituted or unsubstituted cycloalkyl. In some embodiments, $R^3$ is H, and $R^4$ is substituted or unsubstituted $C_4$-$C_6$-cycloalkyl. In some embodiments, $R^3$ is H, and $R^4$ is $C_4$-$C_6$-cycloalkyl substituted with an amino group.

In some embodiments, the compound is of the formula:

wherein:
$Q^1$ is C=O, C=S, C=C$R^{14}R^{15}$, C=N$R^{14}$, alkylene, alkenylene, or alkynylene, each of which is independently substituted or unsubstituted, or a bond;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;

each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $Z^1$ and $Z^2$ is independently C$R^{28}$, C$R^{29}$, or N;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen;

each $R^{23}$ and $R^{24}$ is independently alkyl, alkenyl, alkynyl, aryl, heteroaryl, or heterocyclyl, each of which is independently substituted or unsubstituted, or hydrogen; and each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group, or a pharmaceutically-acceptable salt thereof.

In some embodiments, $Z^1$ is N. In some embodiments, $Z^1$ and $Z^2$ are N. In some embodiments, each R and R is independently a halogen. In some embodiments, R is

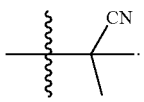

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

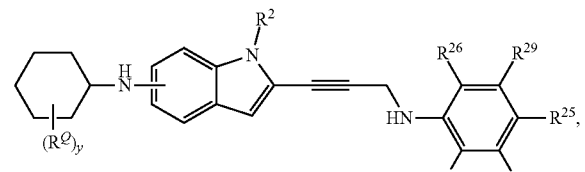

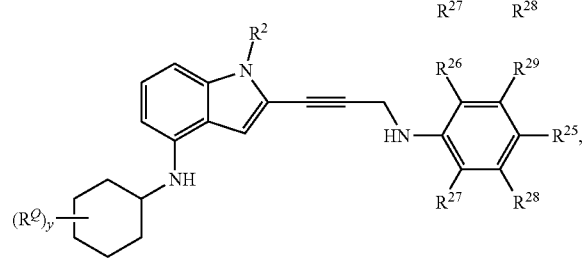

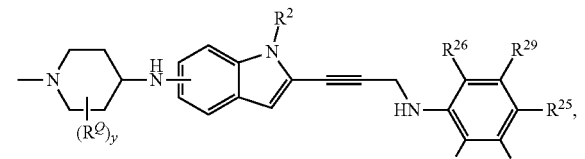

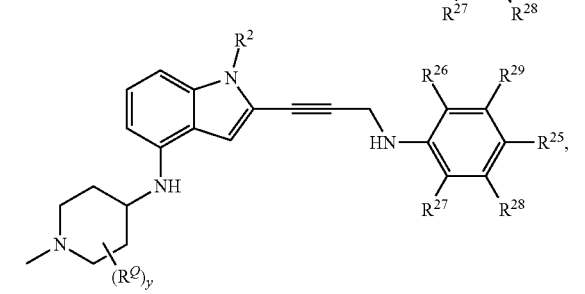

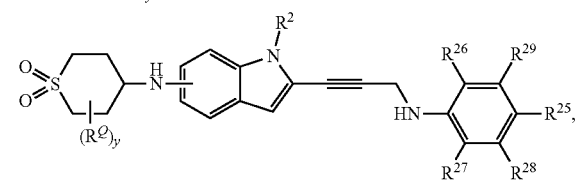

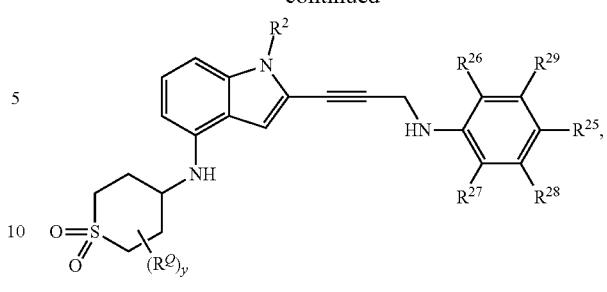

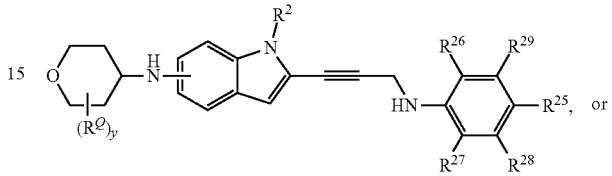

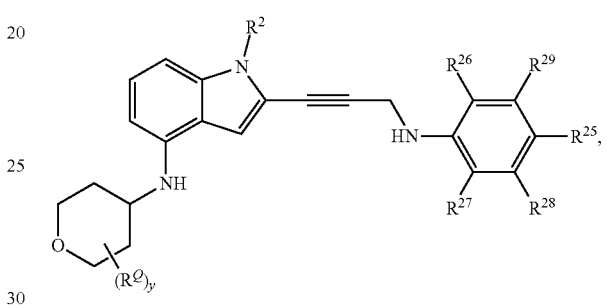

wherein:
- $R^2$ is —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^Q$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted;
- y is 0, 1, 2, 3, or 4;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group.

or a pharmaceutically-acceptable salt thereof.

In some embodiments, the compound is of the formula:

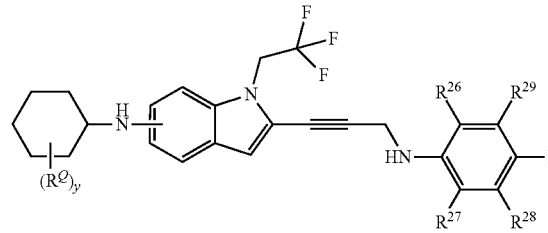

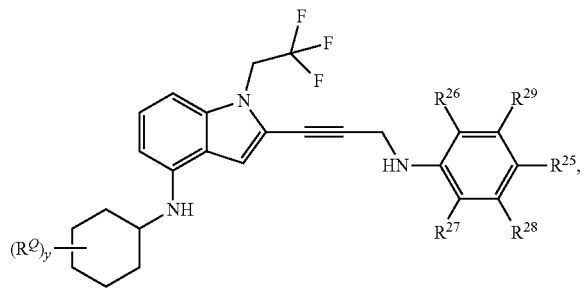

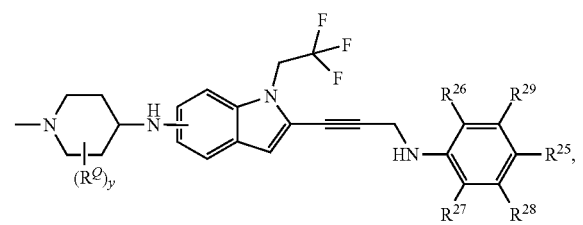

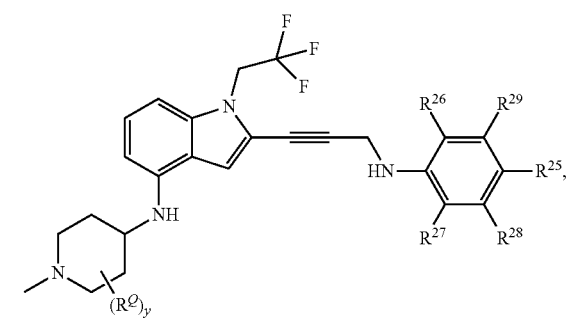

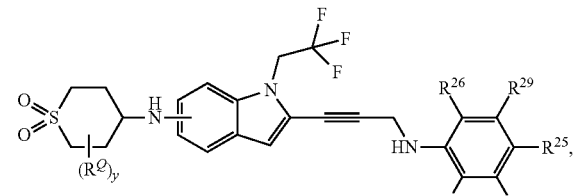

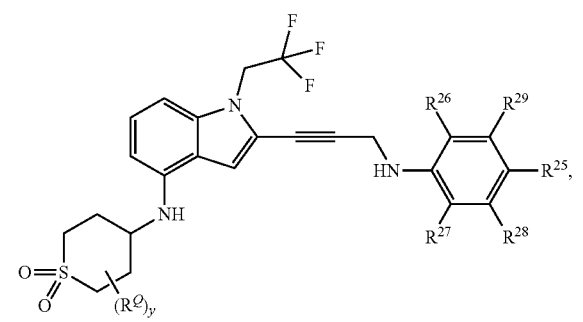

-continued

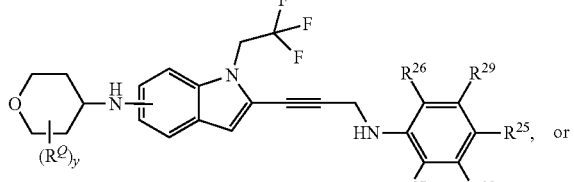

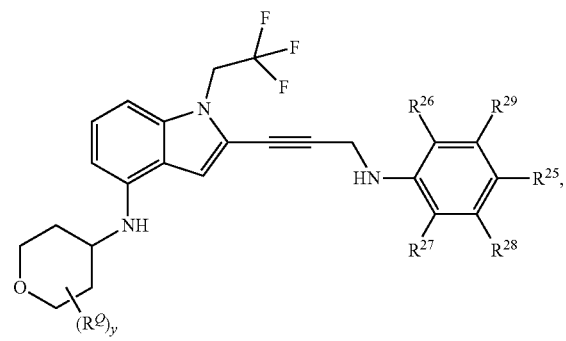

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

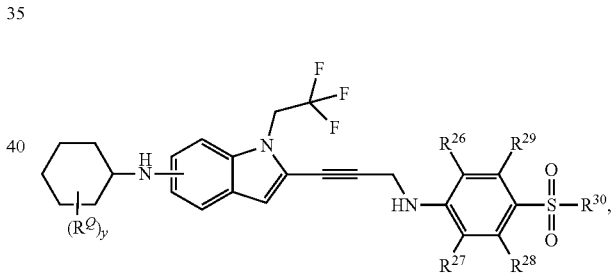

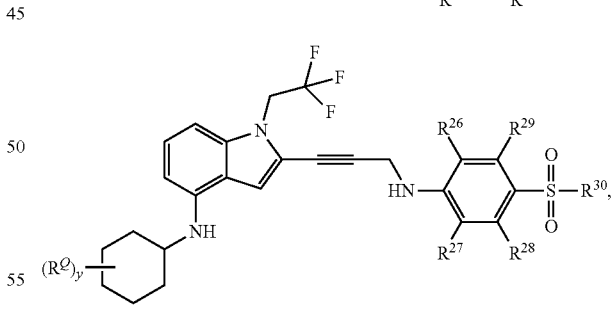

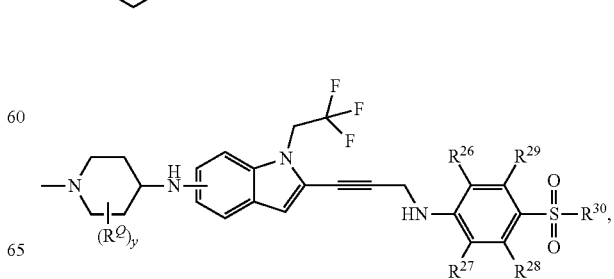

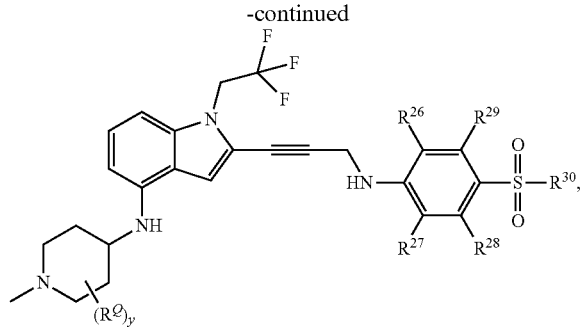

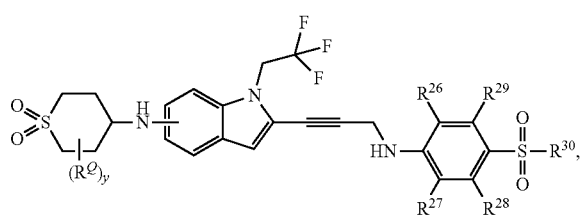

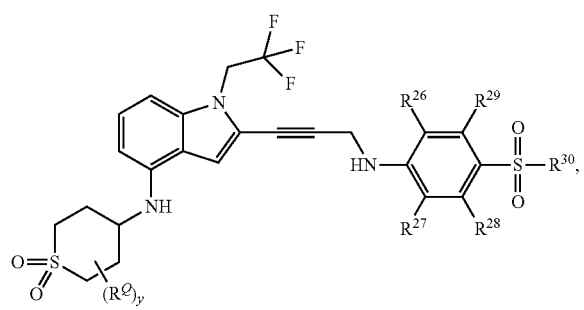

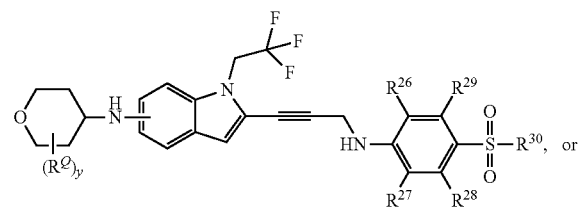

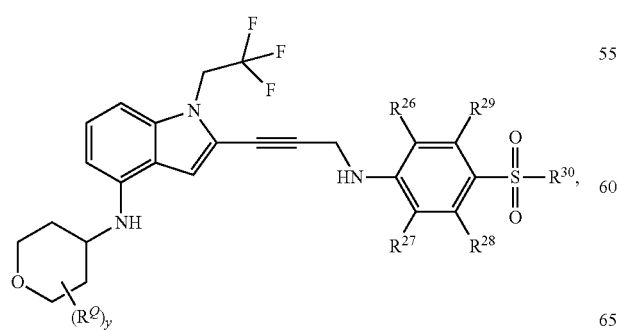

wherein:

each $R^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted;

y is 0, 1, 2, 3, or 4;

each $R^{21}$ and $R^{22}$ is independently alkyl, alkenyl, alkynyl, aryl, heteroaryl, or heterocyclyl, each of which is independently substituted or unsubstituted, or hydrogen;

each $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, haloalkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group; and $R^{30}$ is alkyl or an amino group, each of which is substituted or unsubstituted, or a pharmaceutically-acceptable salt thereof.

In some embodiments, $R^{30}$ is methyl. In some embodiments, $R^{30}$ is NH$_2$. In some embodiments, $R^{30}$ is NHMe. In some embodiments, $R^{30}$ is NMe$_2$.

In some embodiments, the compound is of the formula:

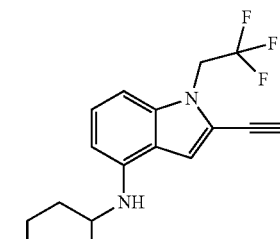 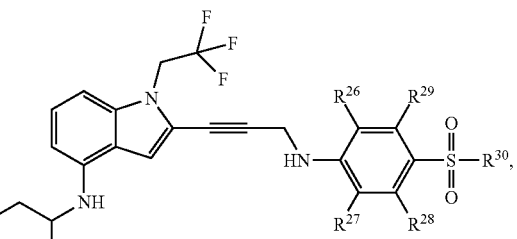

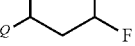

wherein $R^{30}$ is alkyl or an amino group, each of which is unsubstituted or substituted. In some embodiments, $R^{30}$ is methyl.

Non-limiting examples of compounds of the current disclosure include the following:
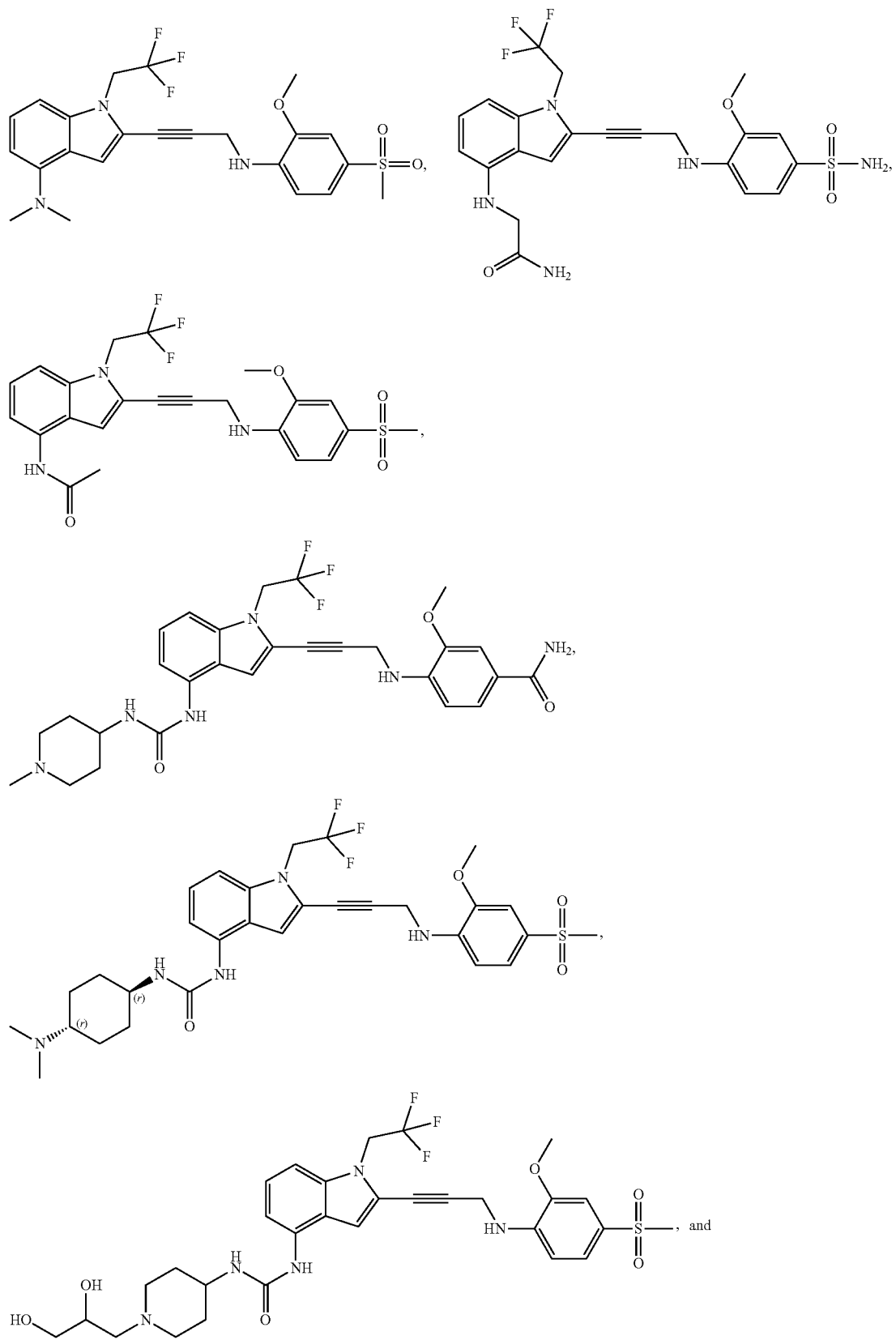

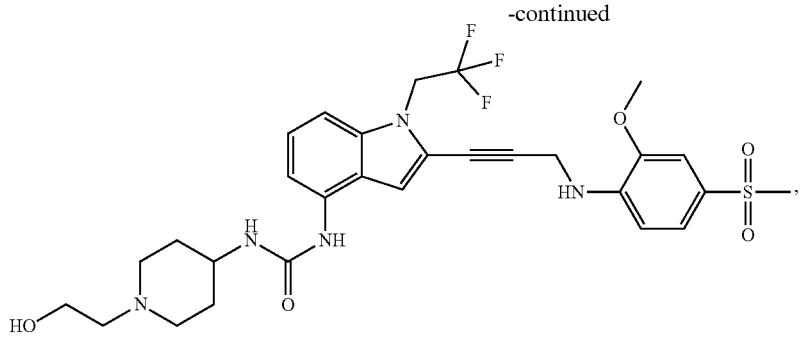
or a pharmaceutically-acceptable salt thereof.
Non-limiting examples of compounds of the current disclosure include the following:
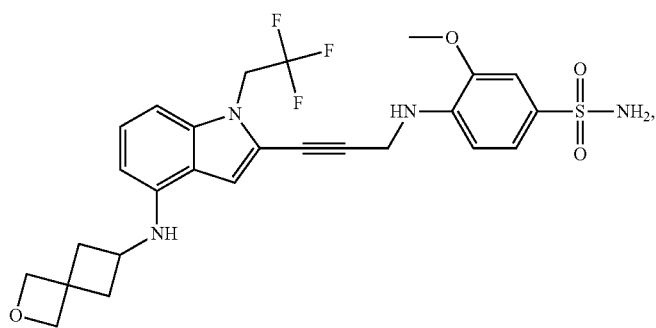
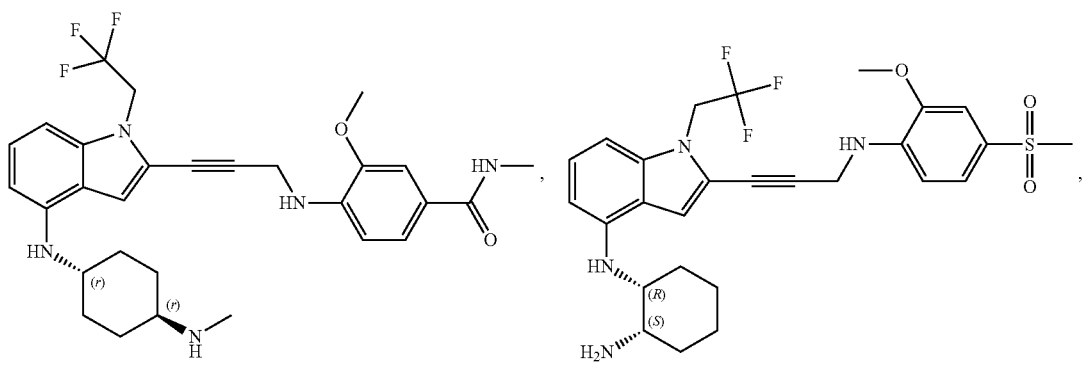
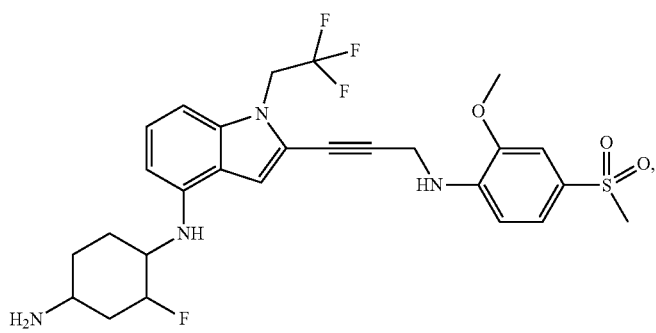

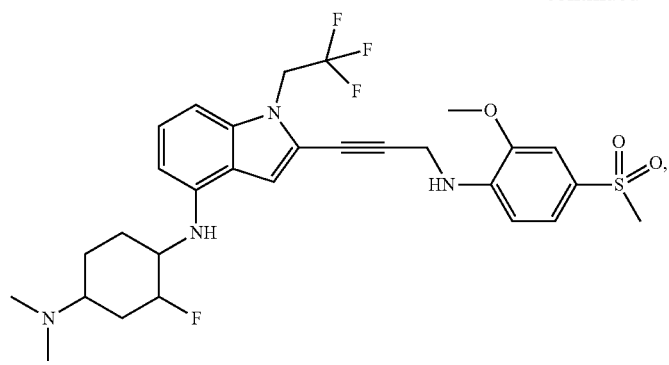
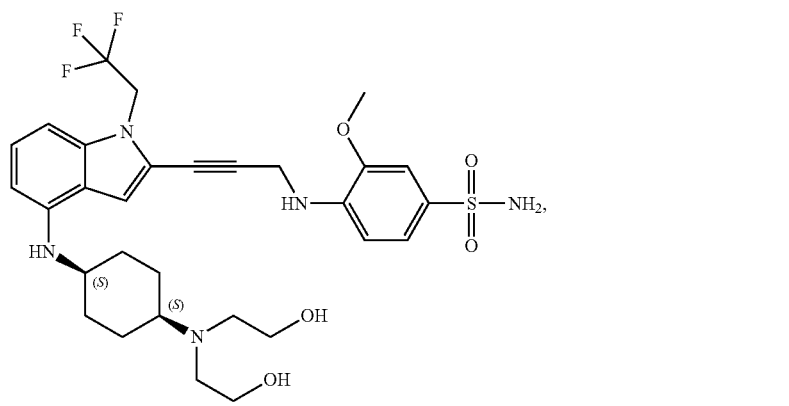
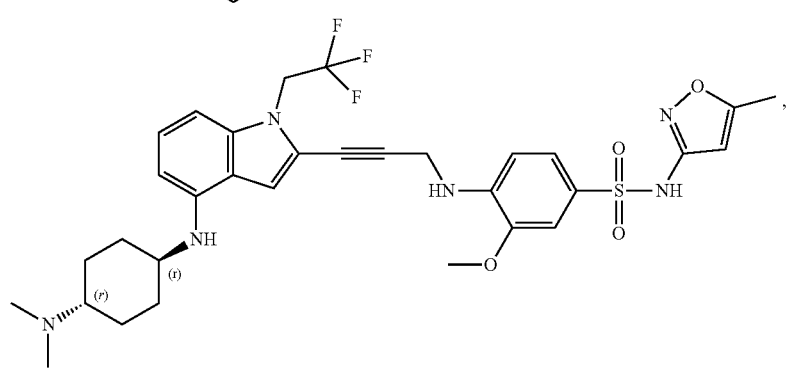
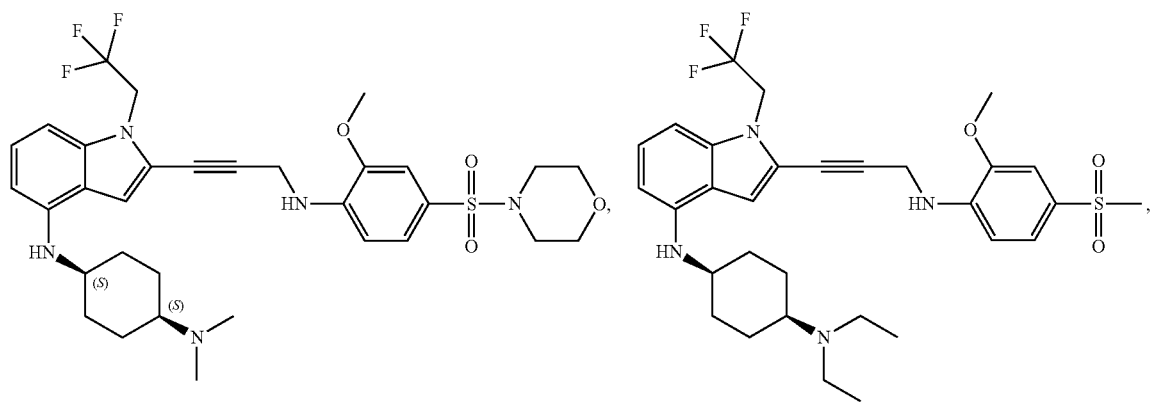

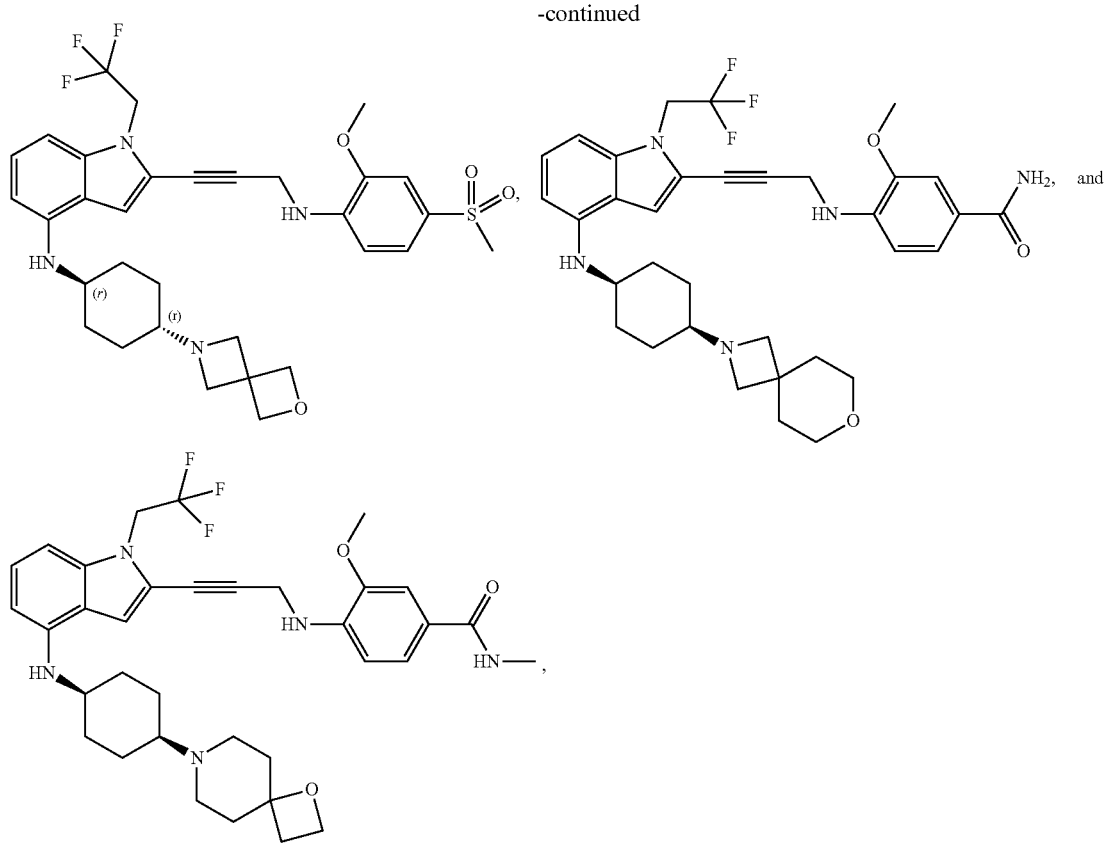
or a pharmaceutically-acceptable salt thereof.
Non-limiting examples of compounds of the current disclosure include the following:
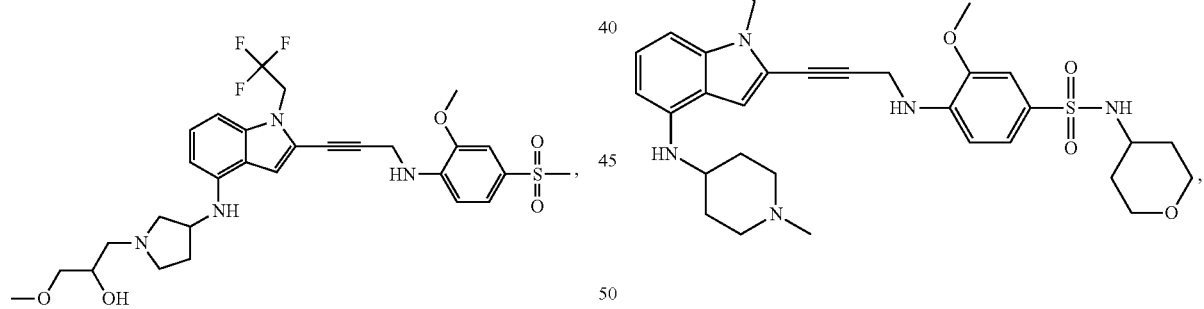
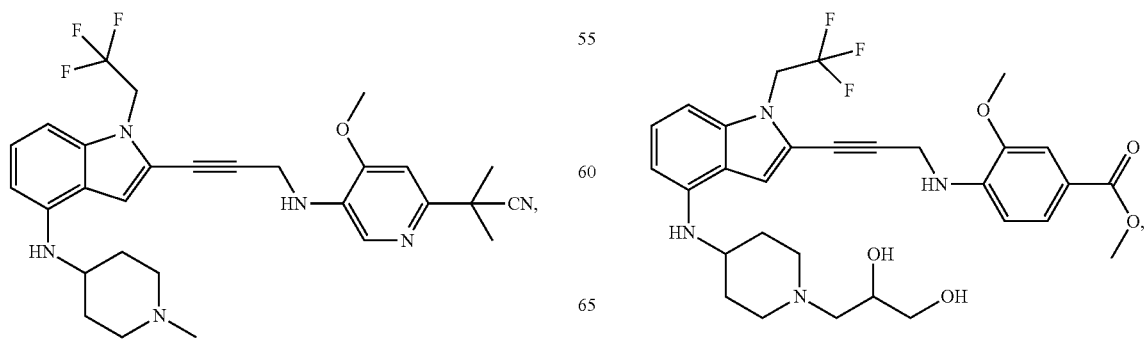

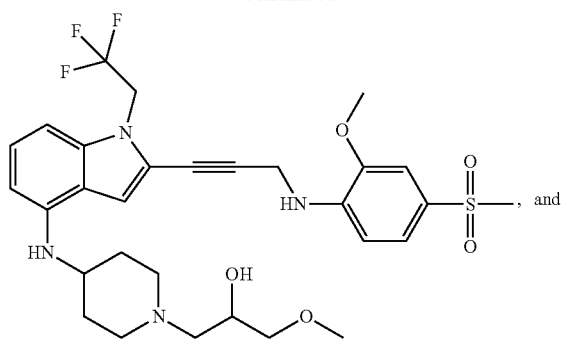
, and
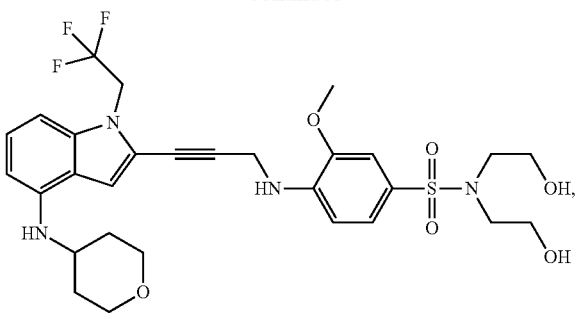
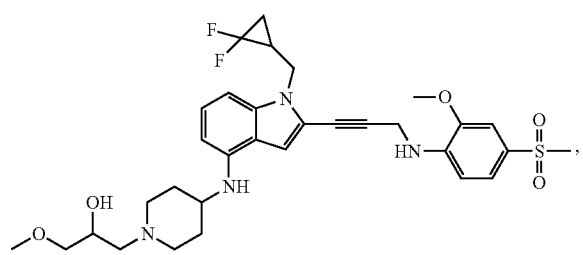
or a pharmaceutically-acceptable salt thereof.
Non-limiting examples of compounds of the current disclosure include the following:
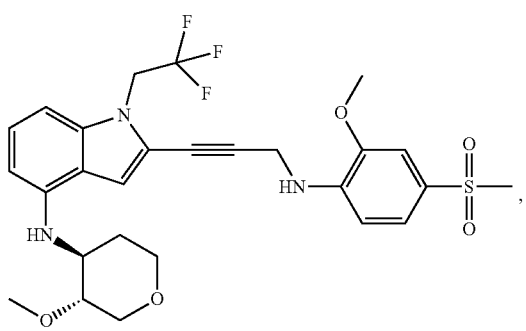
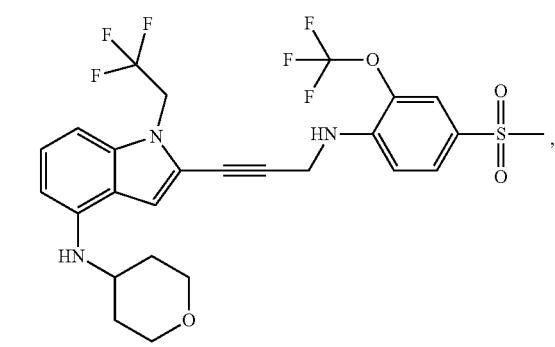
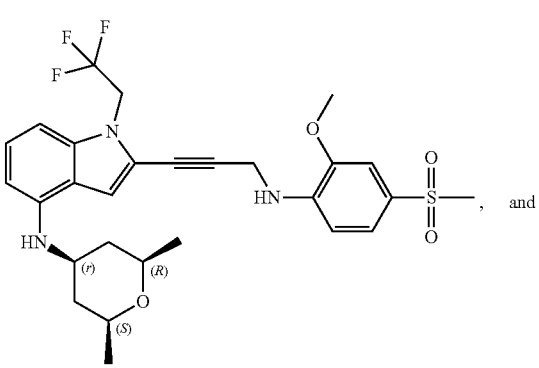
, and
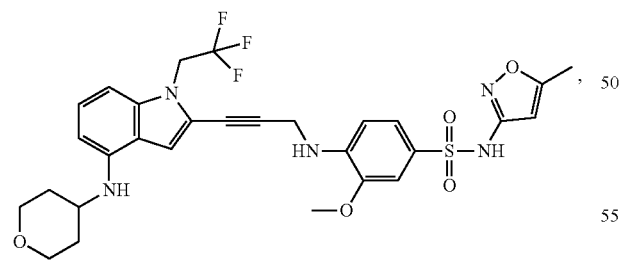
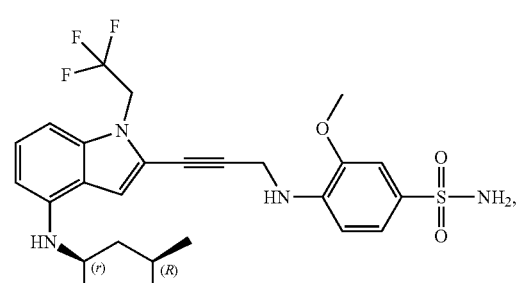
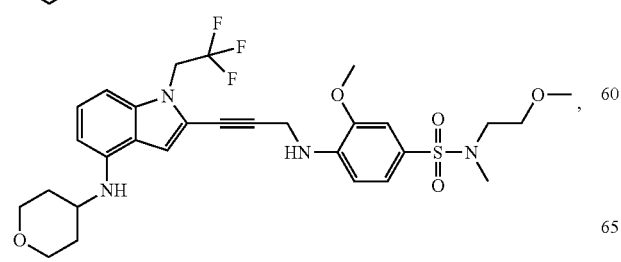
or a pharmaceutically-acceptable salt thereof.

Non-limiting examples of compounds of the current disclosure include the following:
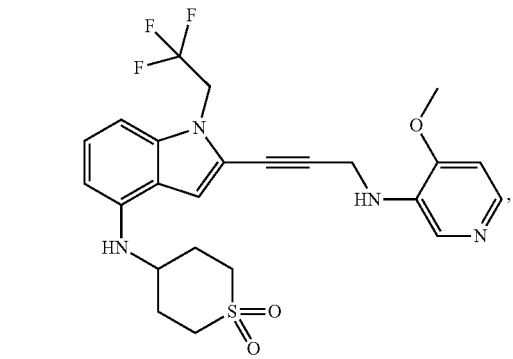
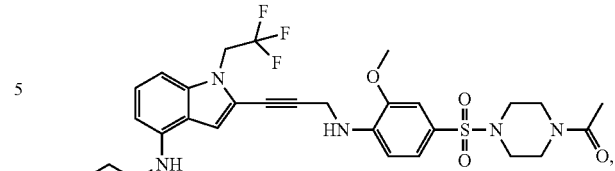
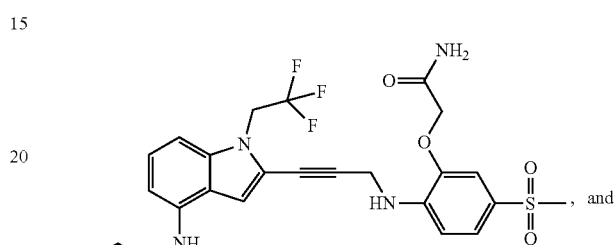
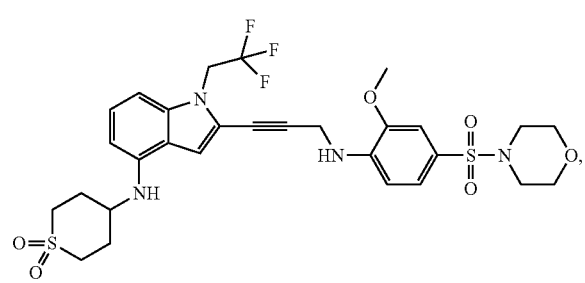
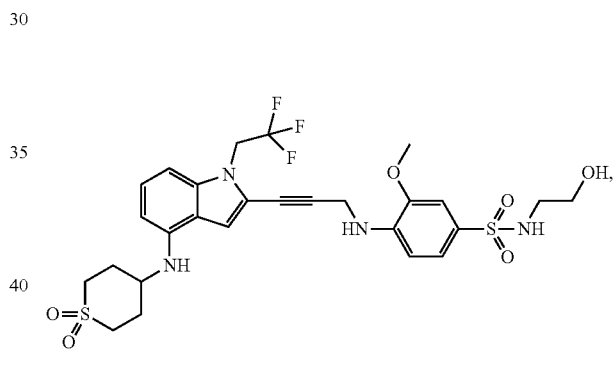
or a pharmaceutically-acceptable salt thereof.
Non-limiting examples of compounds of the current disclosure include the following:
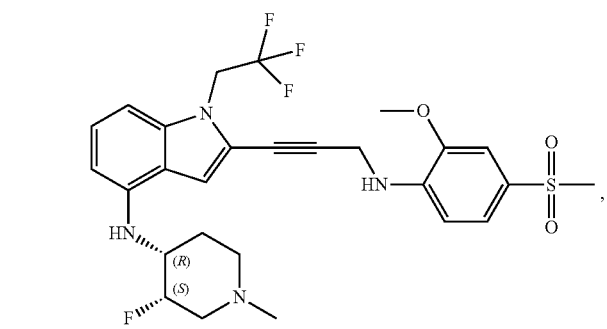
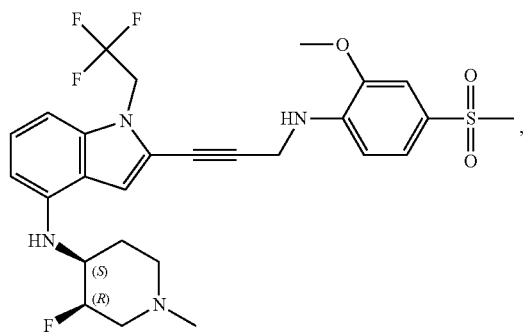

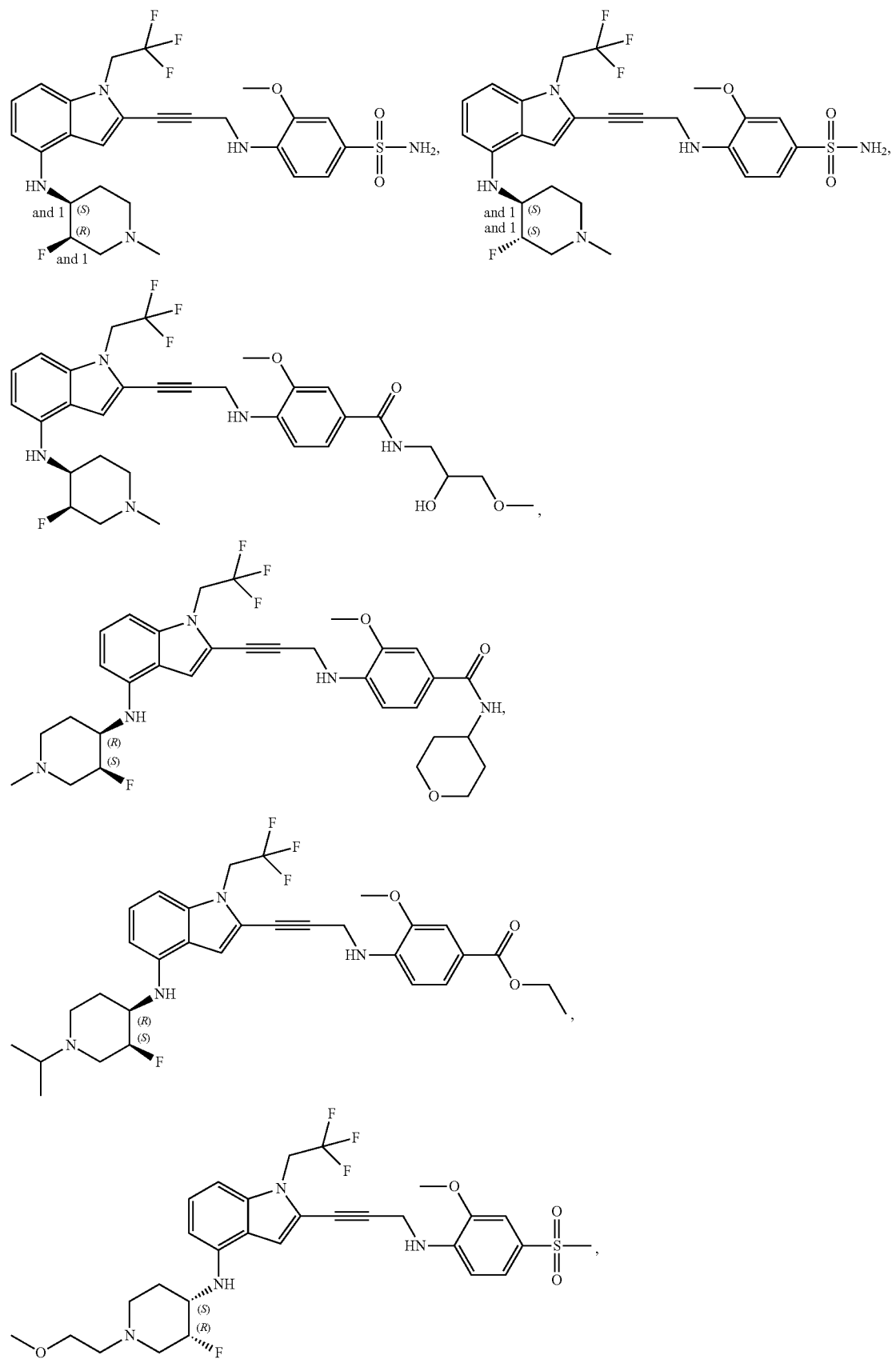

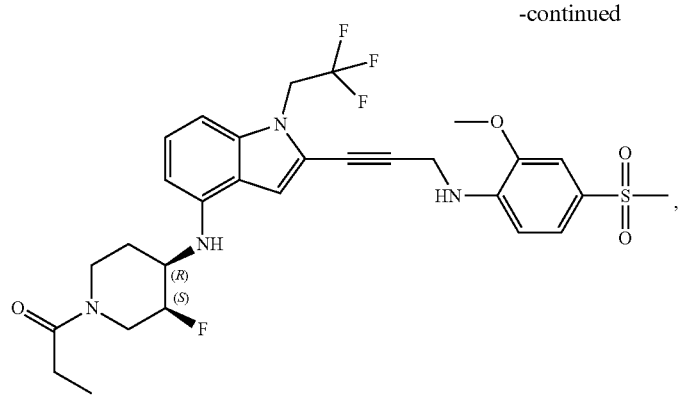
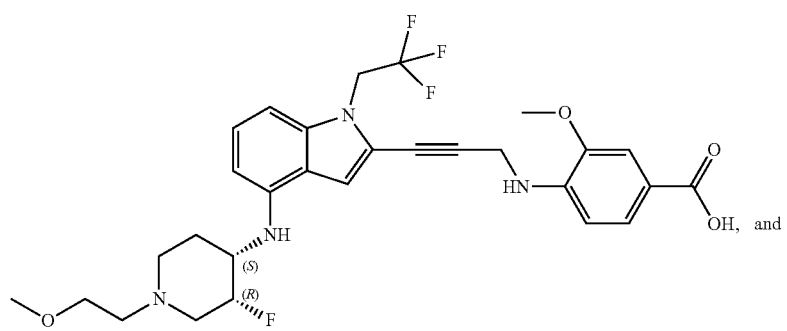
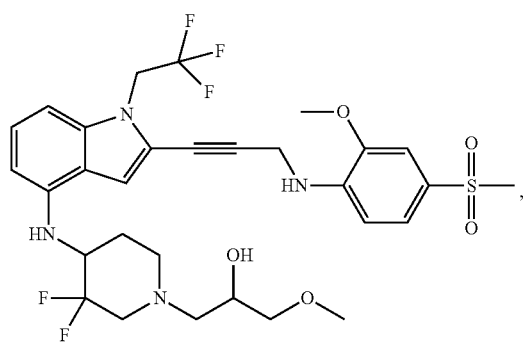
or a pharmaceutically-acceptable salt thereof.
Non-limiting examples of compounds of the current disclosure include the following:
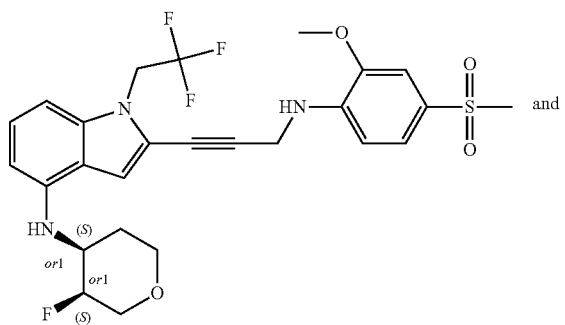
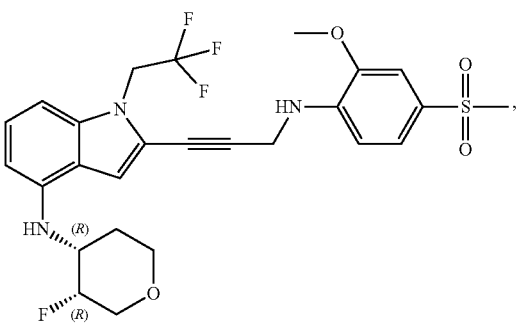
or a pharmaceutically-acceptable salt thereof.-

Non-limiting examples of compounds of the current disclosure include the following:
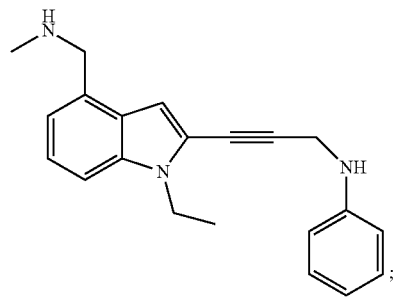
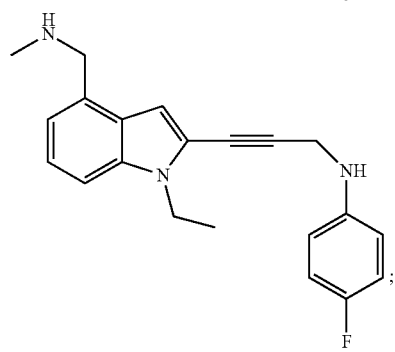
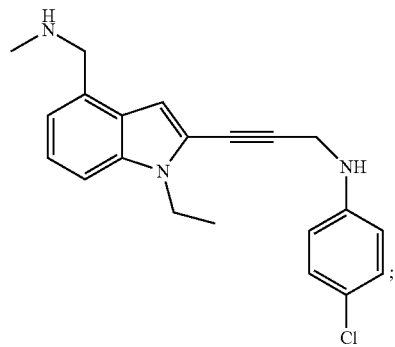
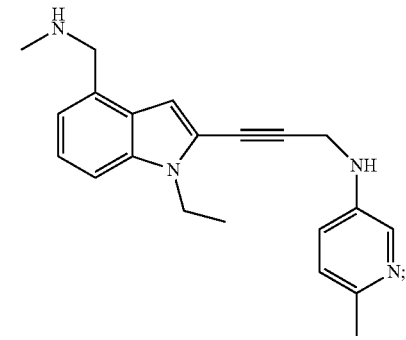
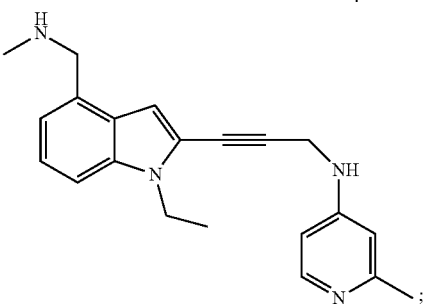
-continued
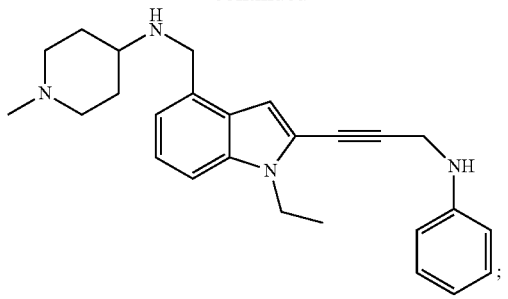
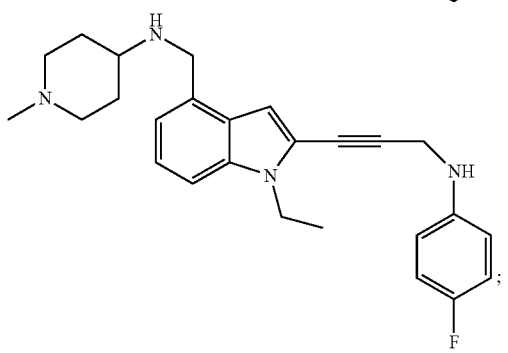
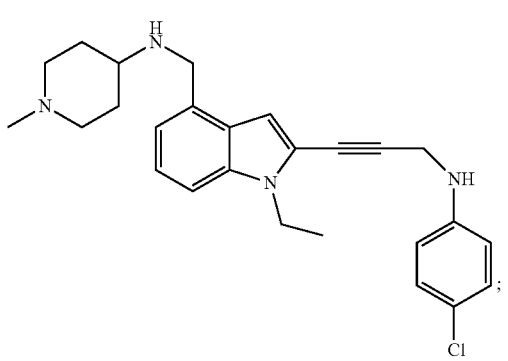
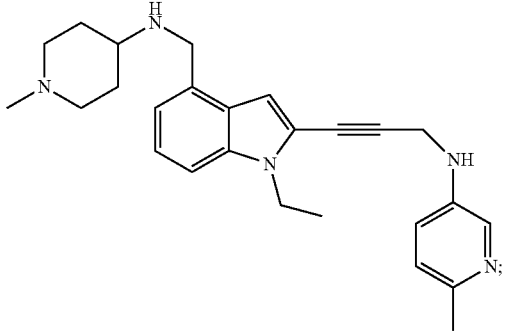
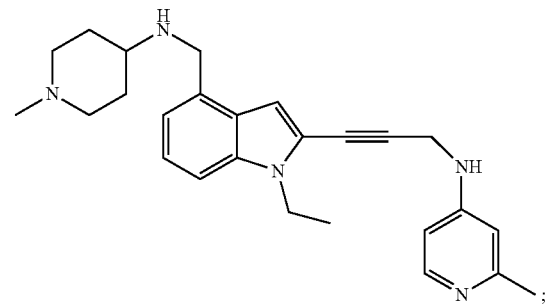

51
-continued
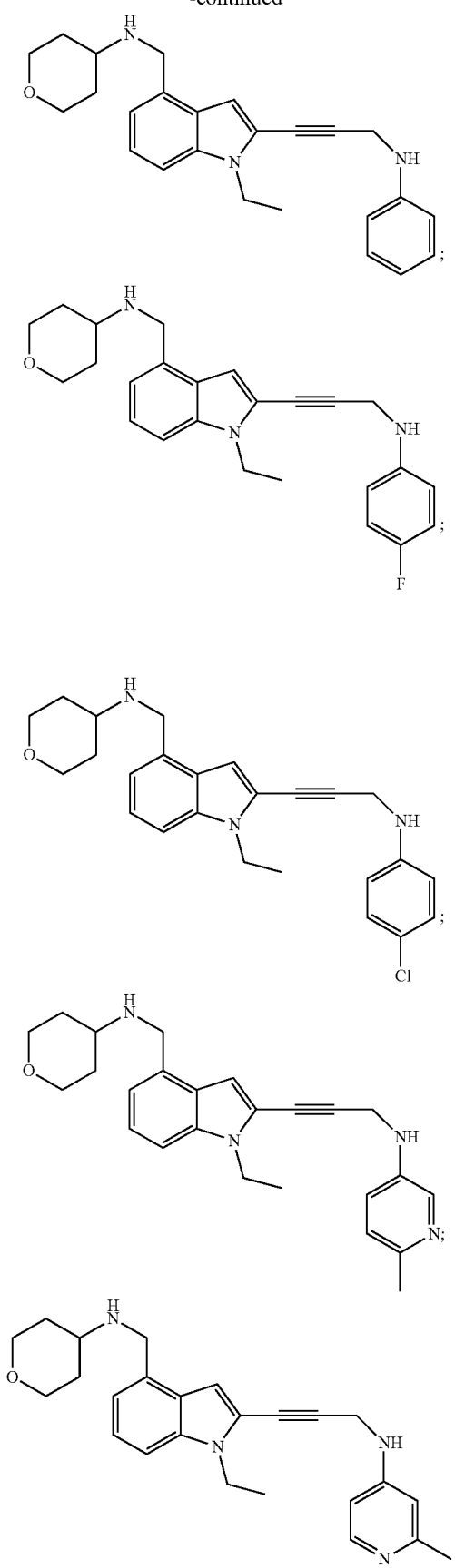
52
-continued
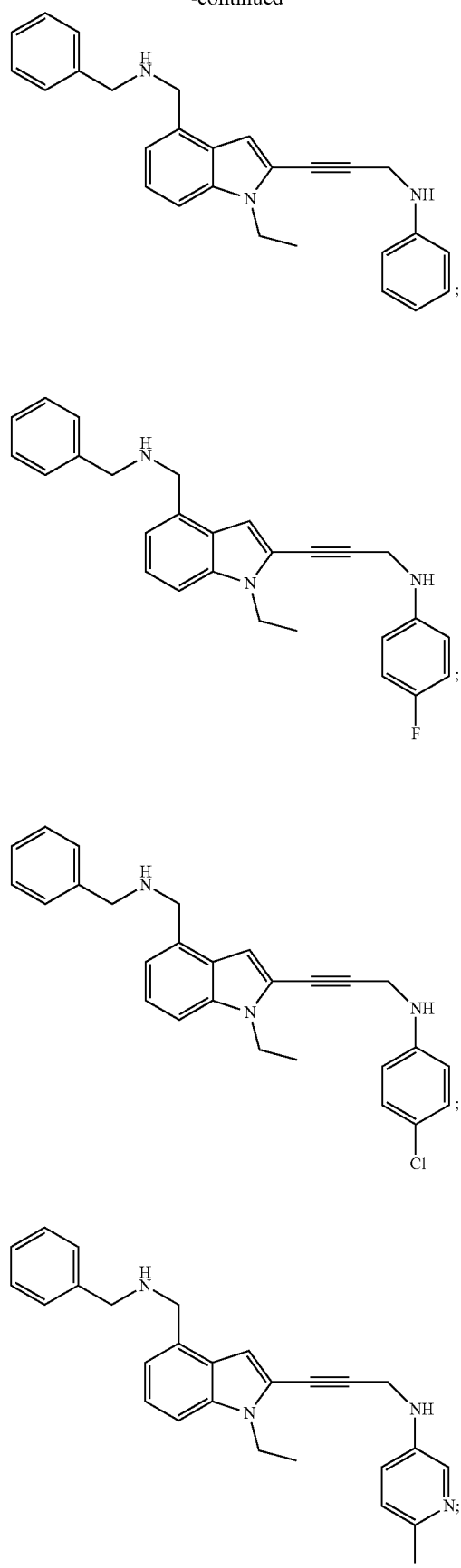

53
-continued
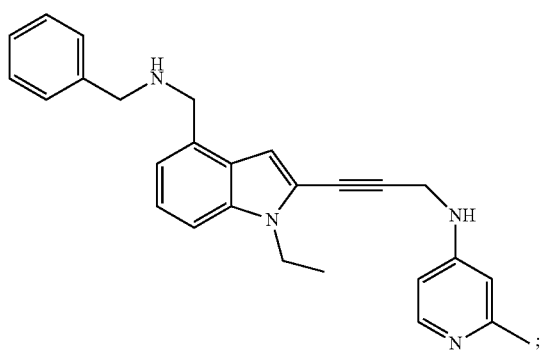
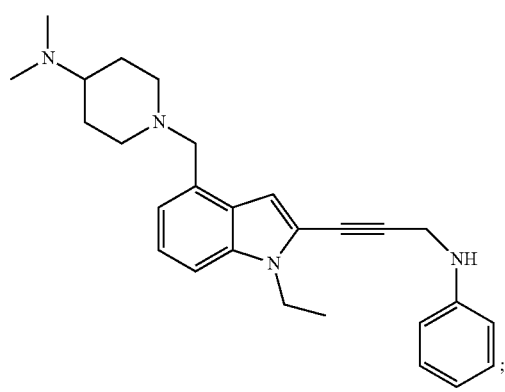
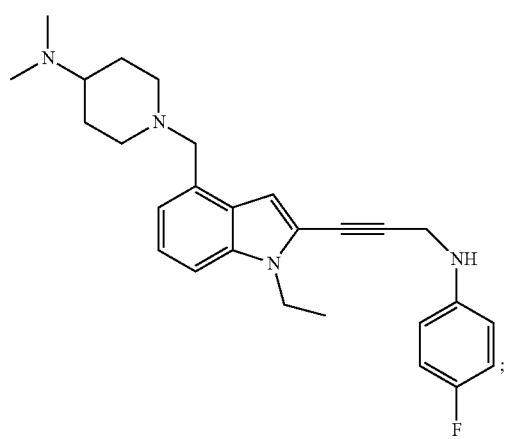
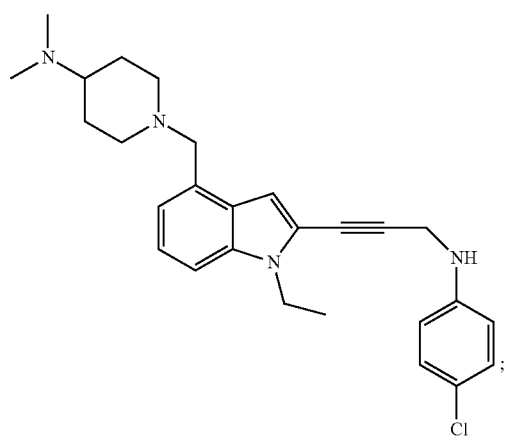
54
-continued
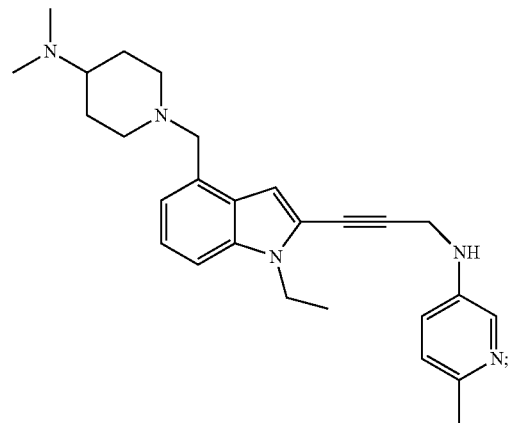
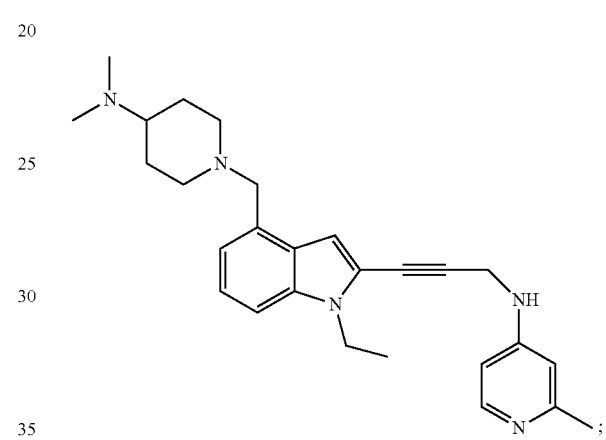
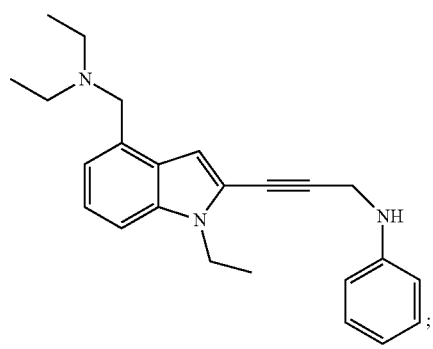
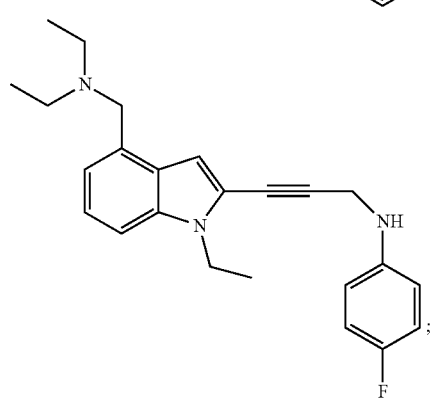

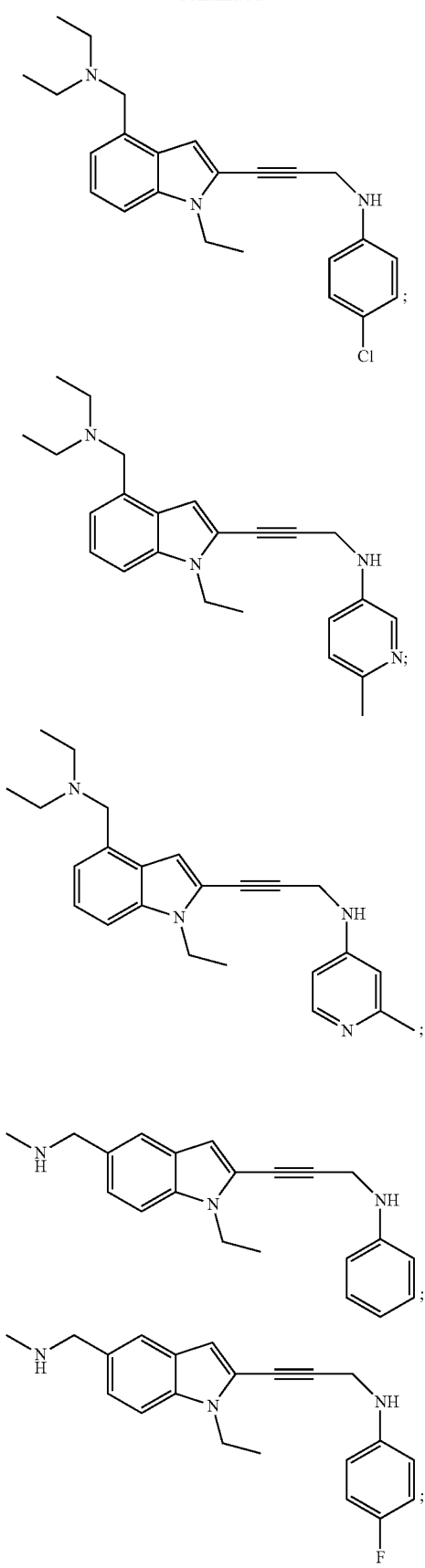
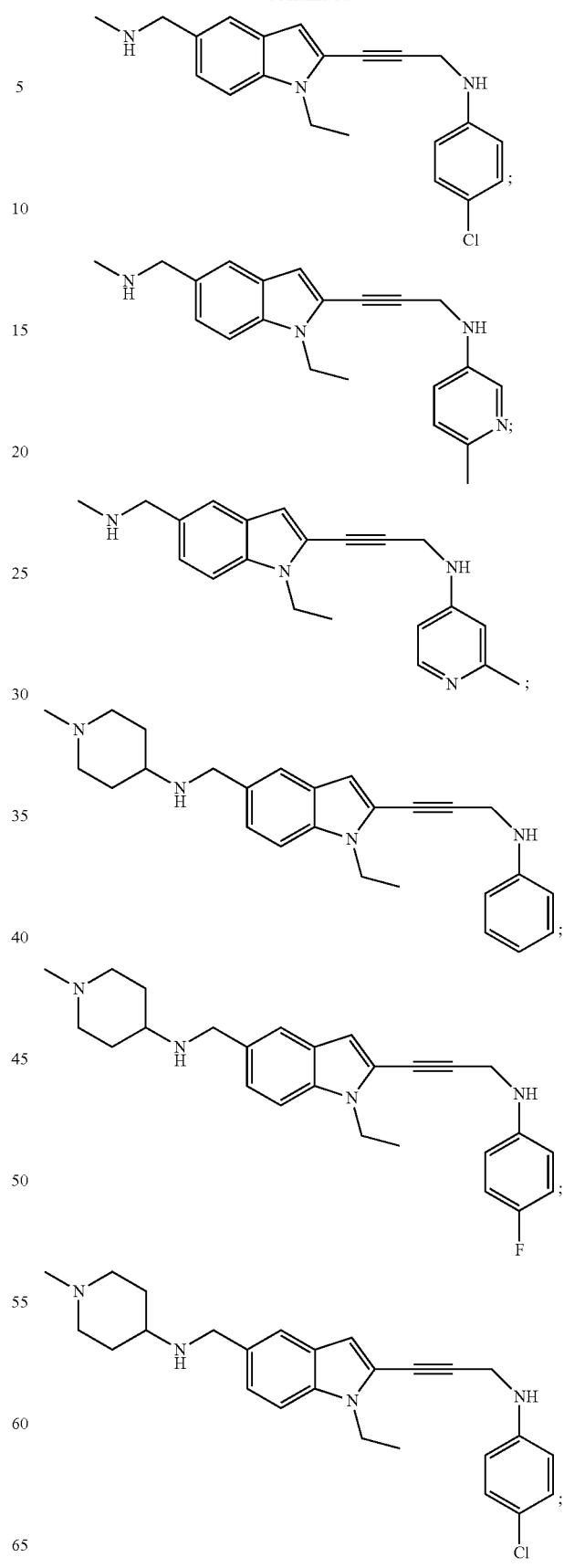

57
-continued
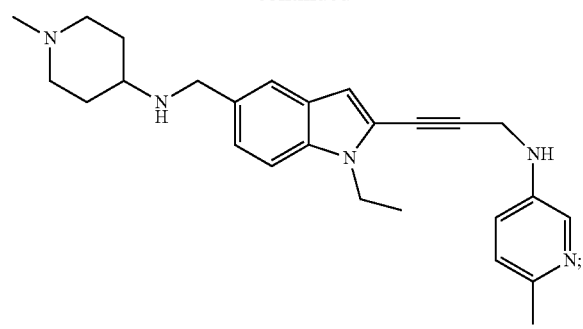
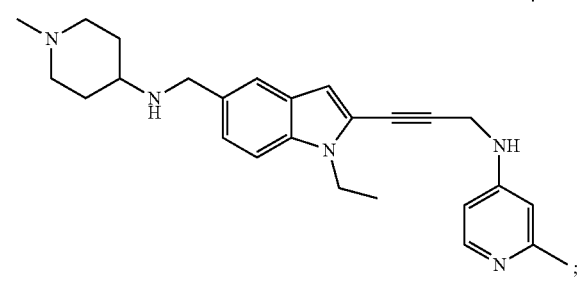
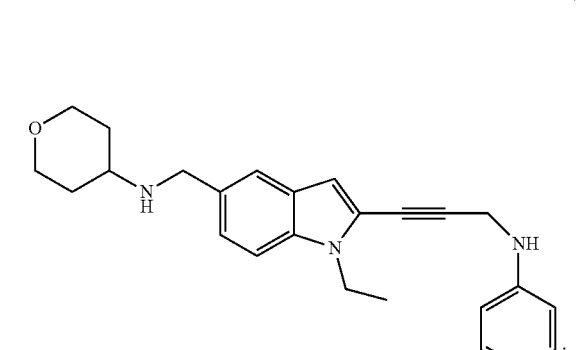
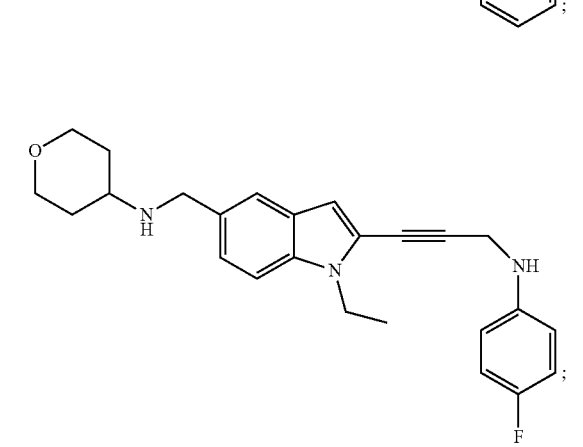
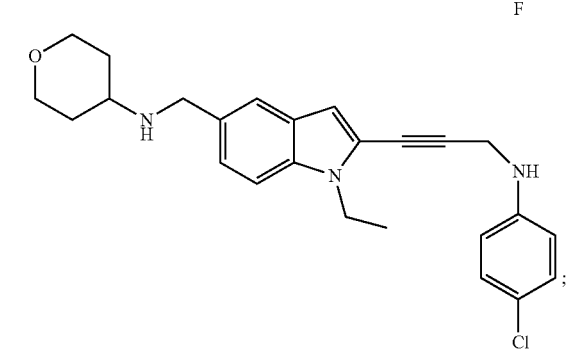
58
-continued
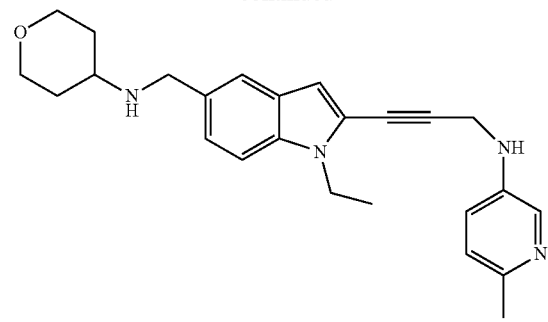
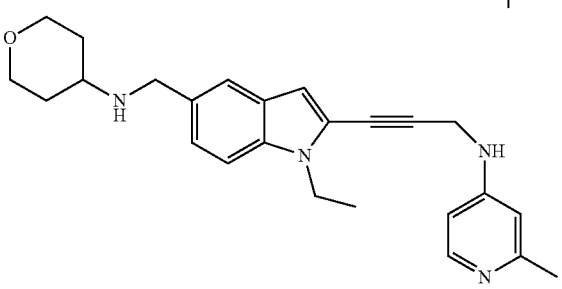
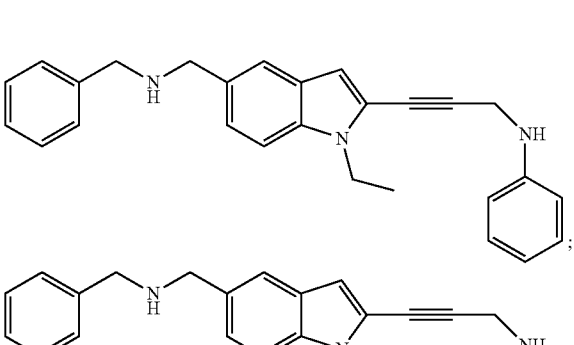
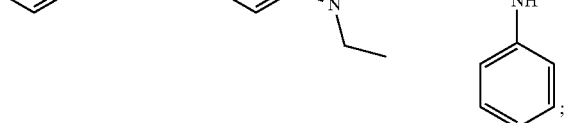
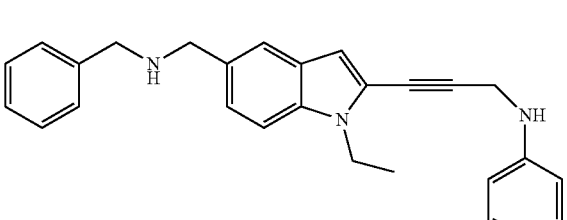
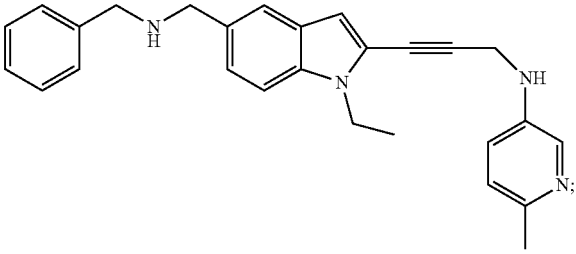

59
-continued
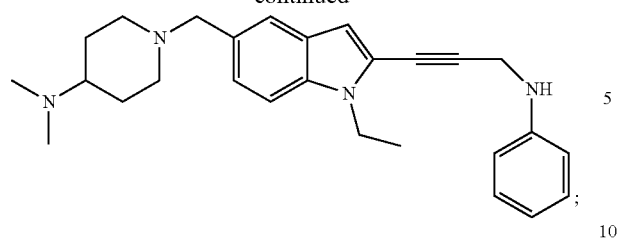
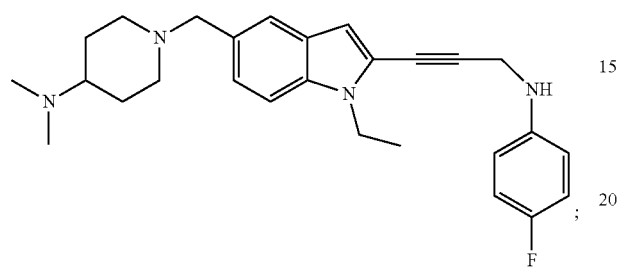
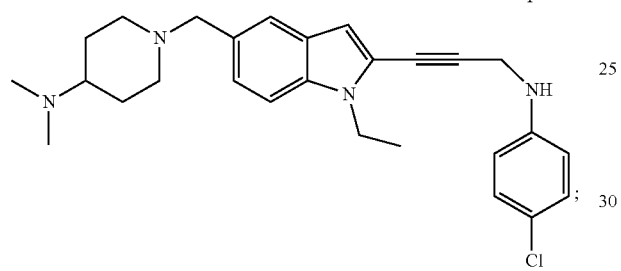
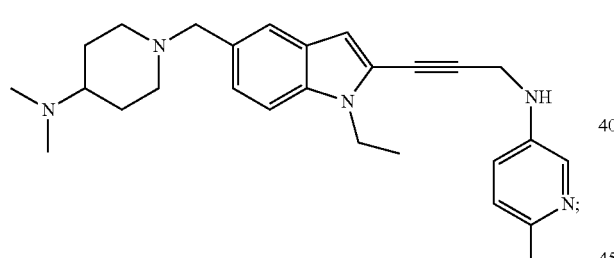
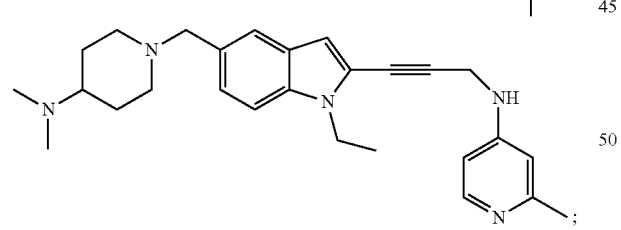
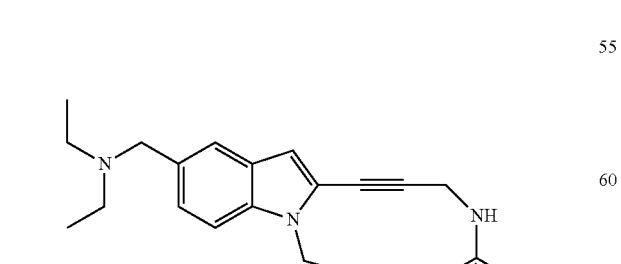
60
-continued
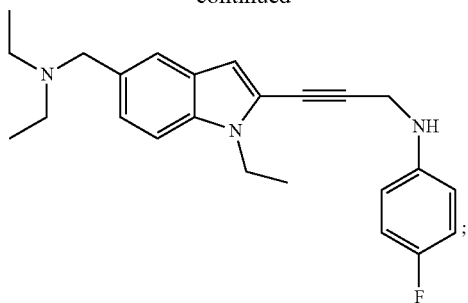
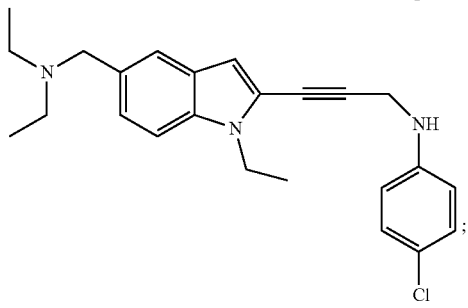 [SMILES: CCN(CC)Cc1ccc2c(c1)nc(C#CCNc1ccc(F)cc1)n2CC]
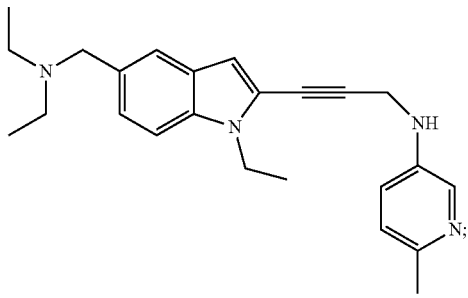
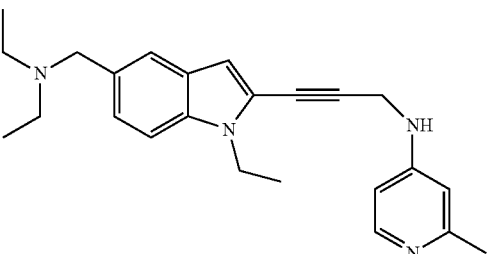
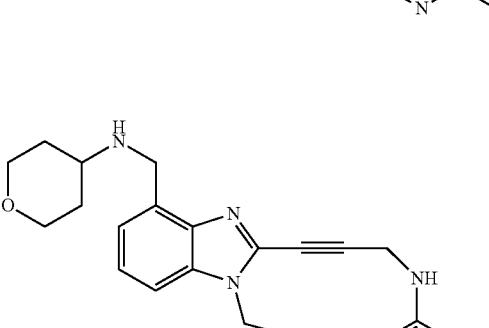
; and -continued
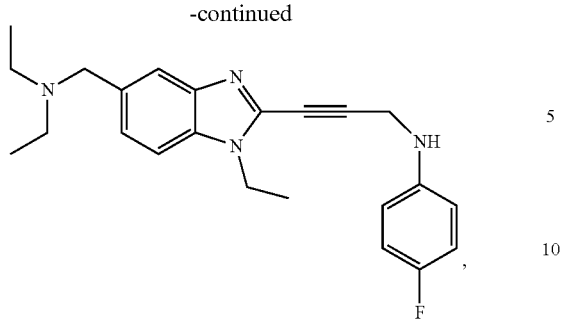
or a pharmaceutically-acceptable salt of any of the foregoing.
Non-limiting examples of compounds of the current disclosure include the following:
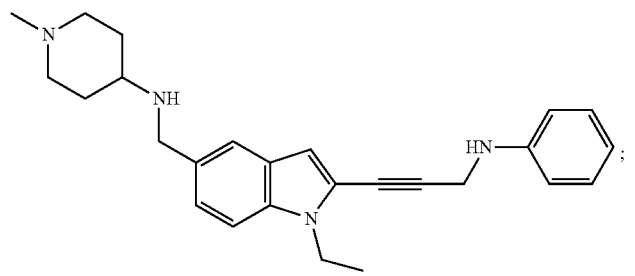
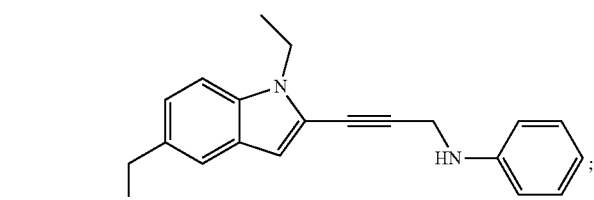
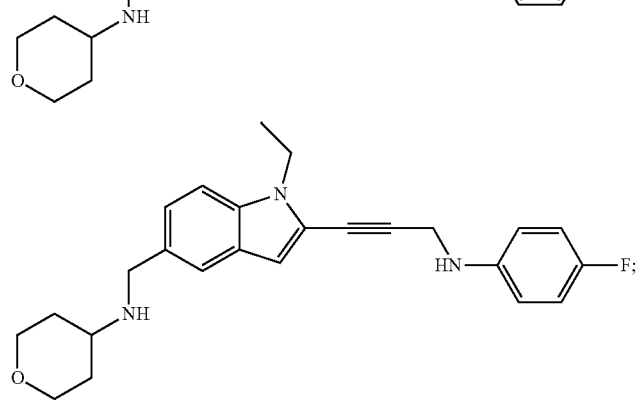
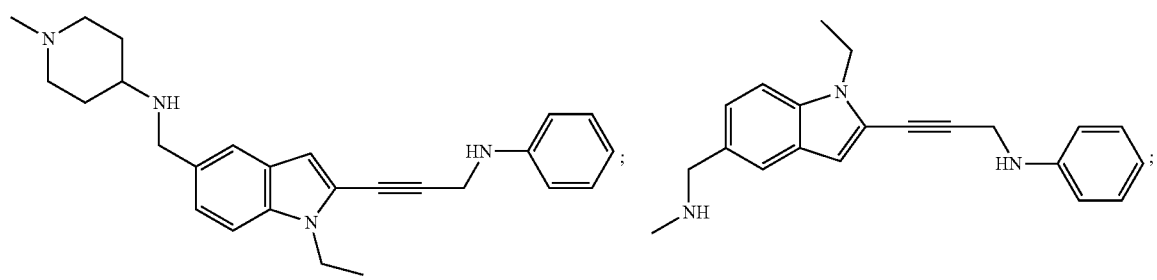

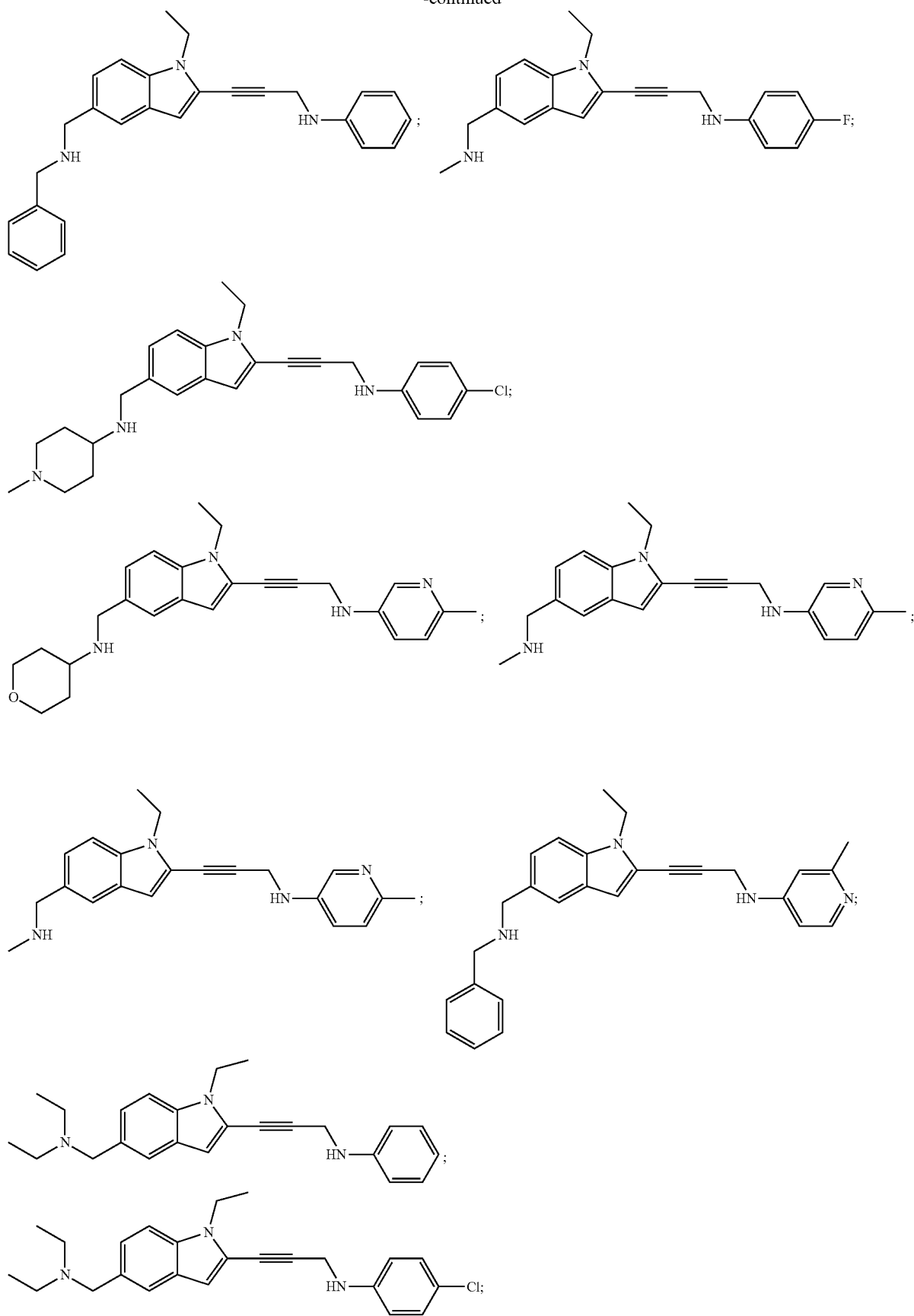

-continued
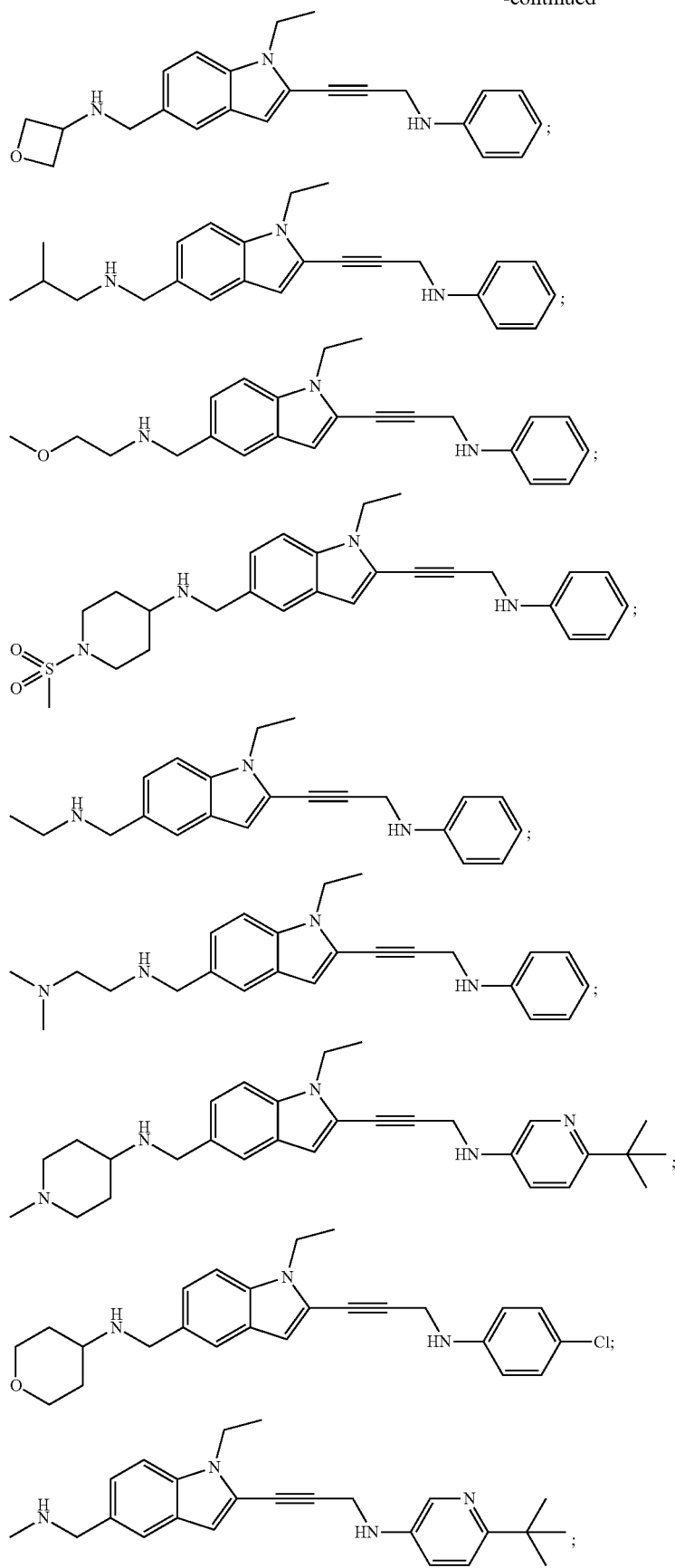

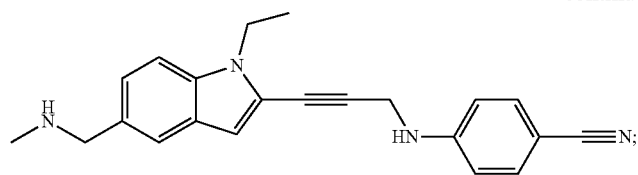
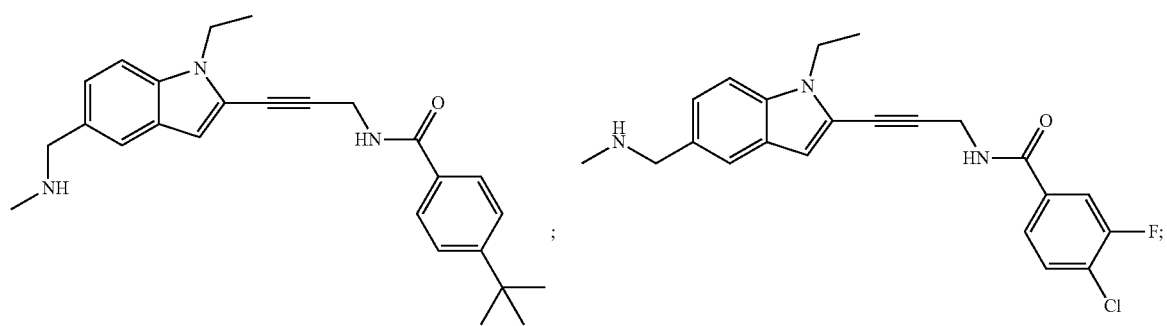
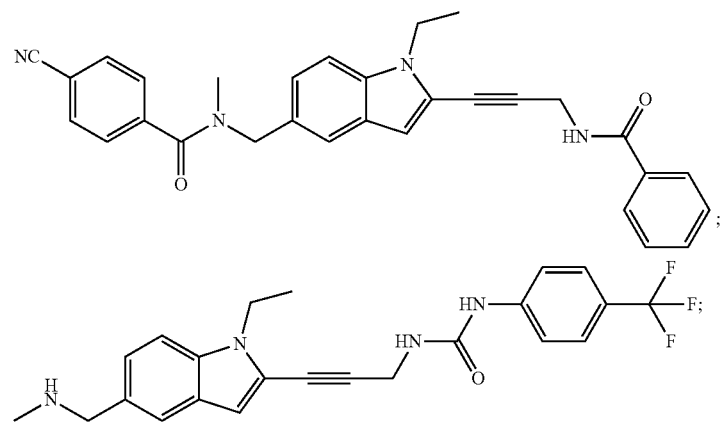
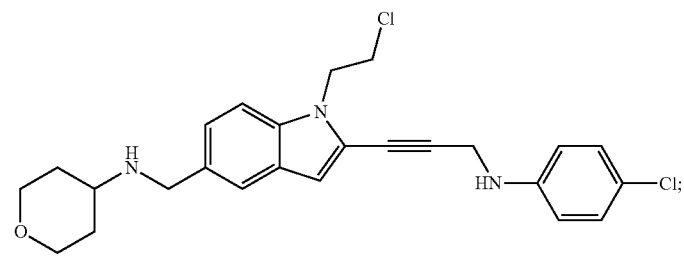
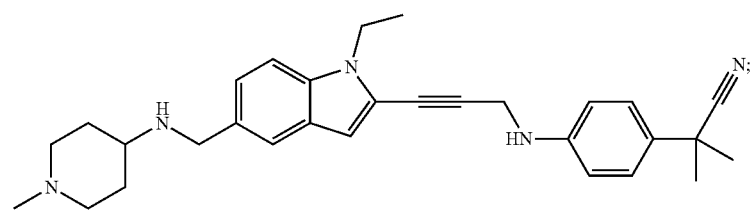

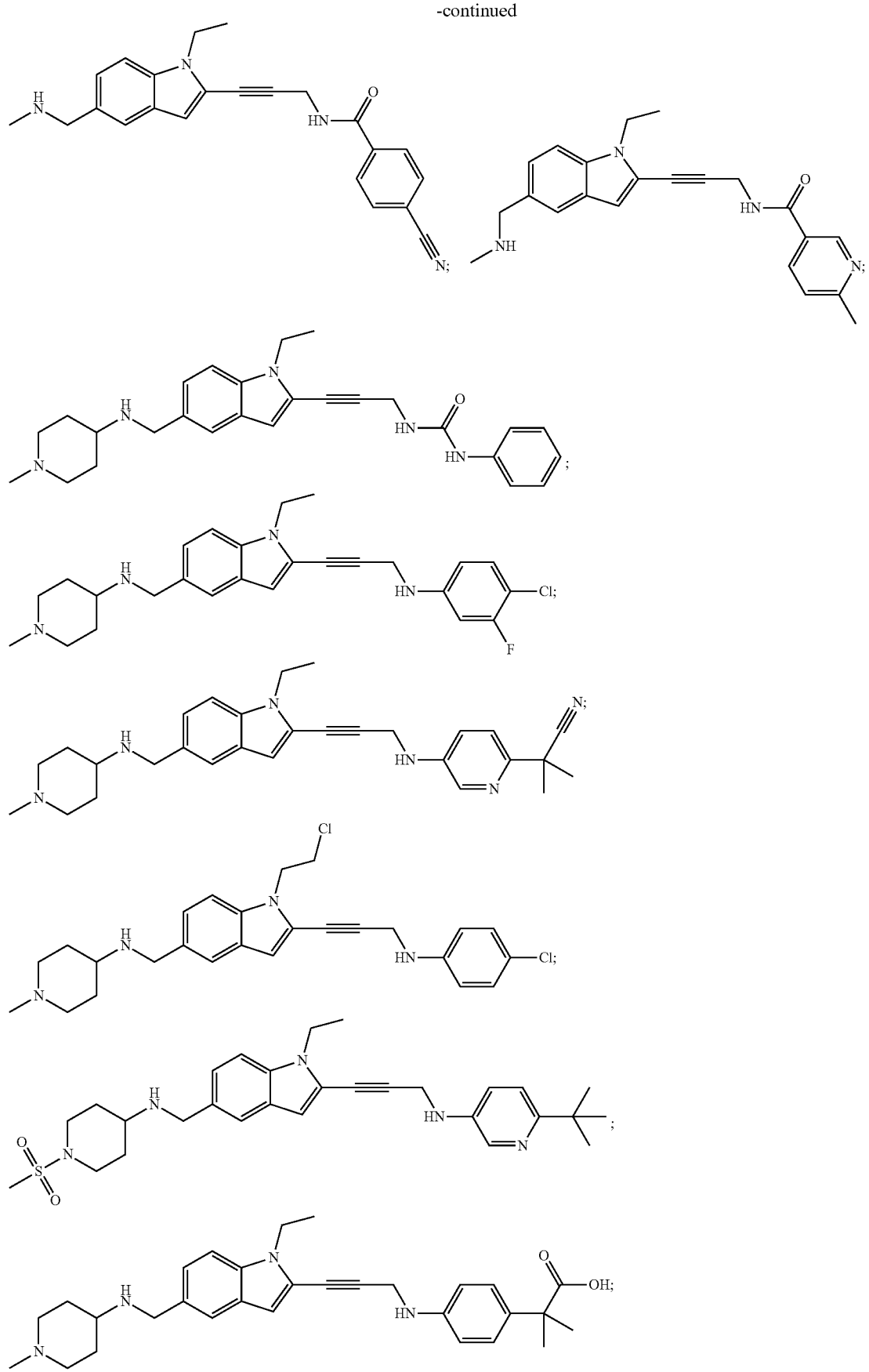

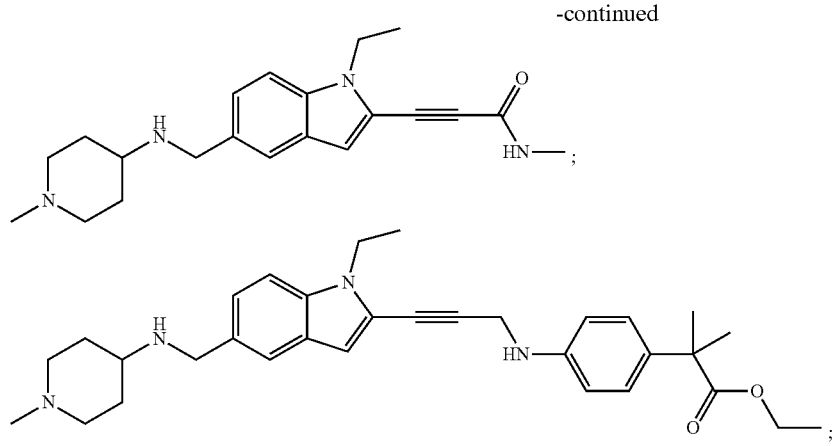
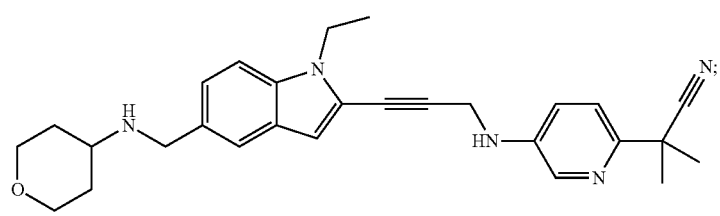
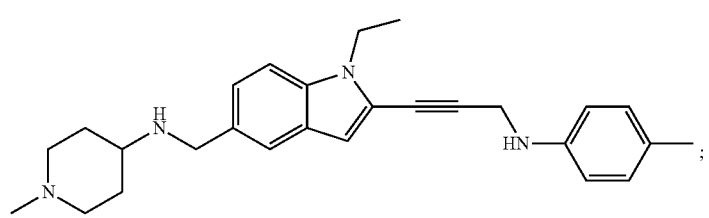
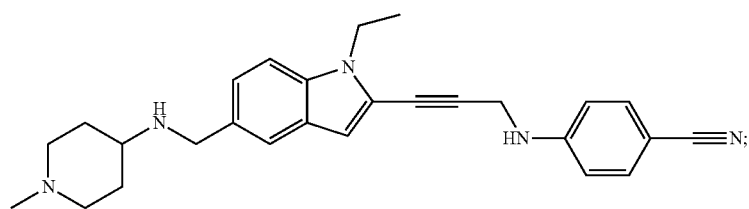
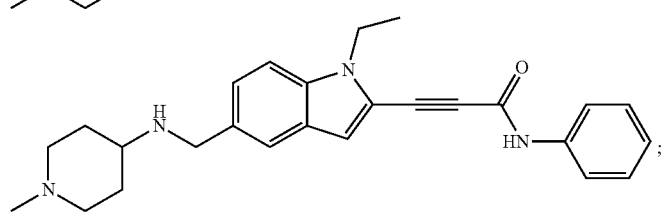
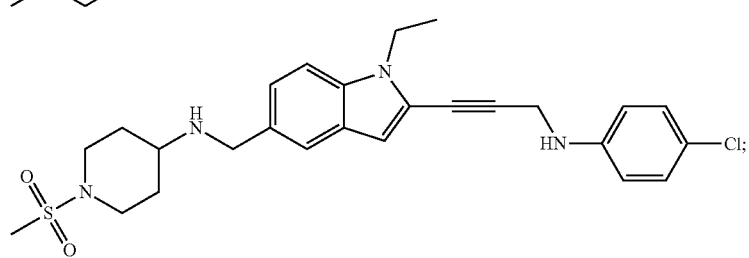

-continued
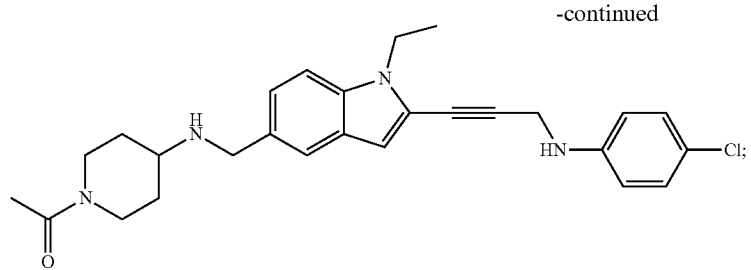
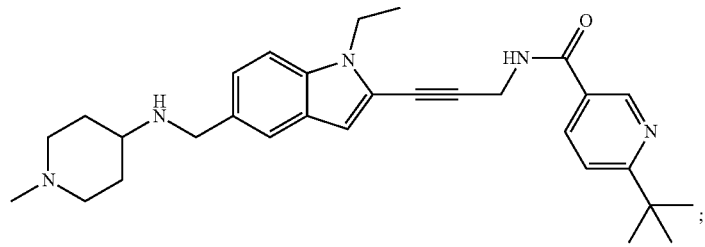
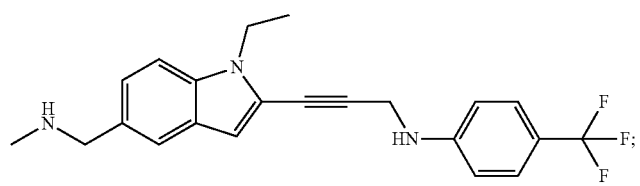
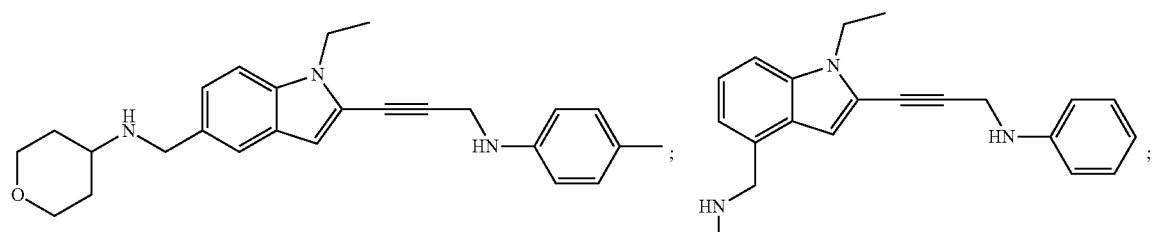
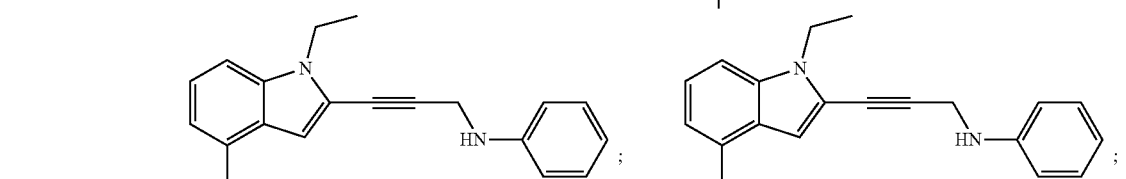
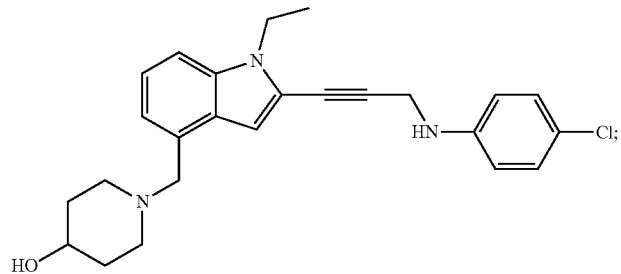

-continued
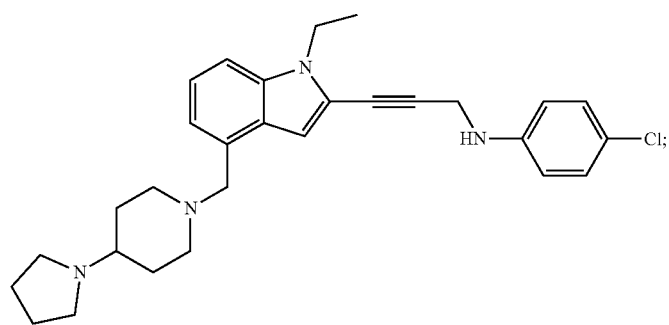
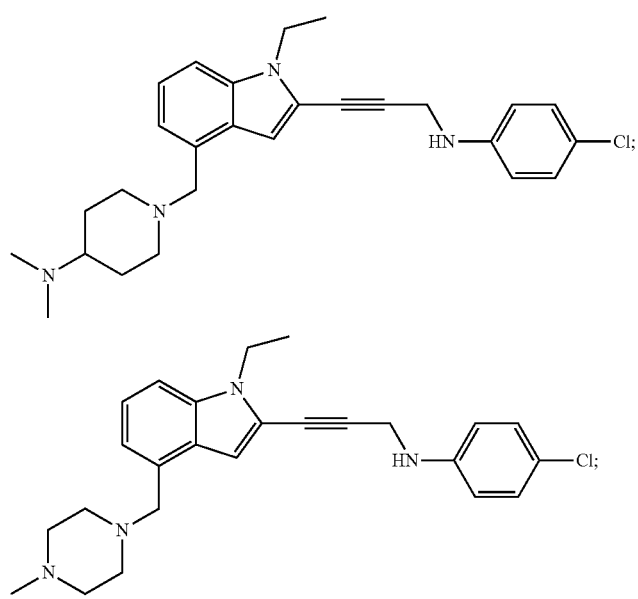
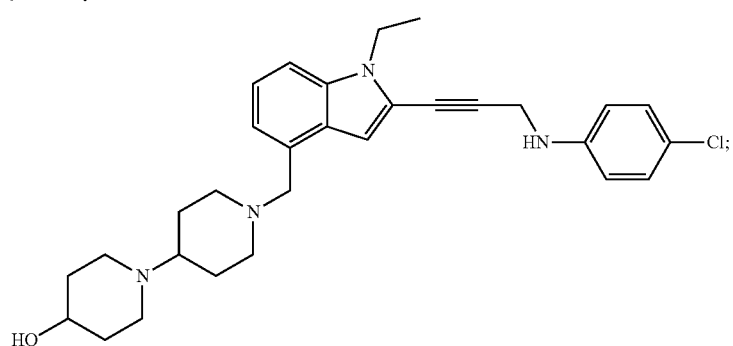
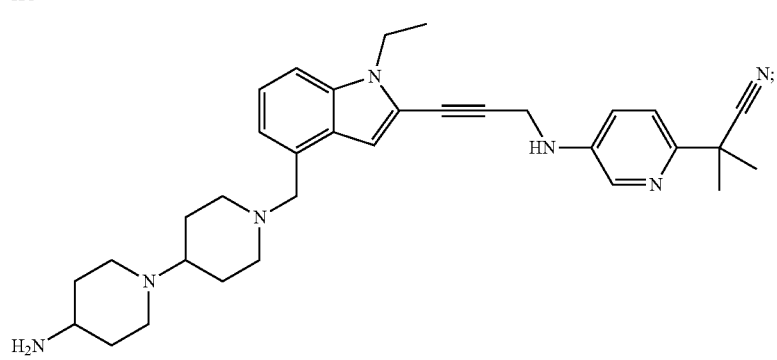

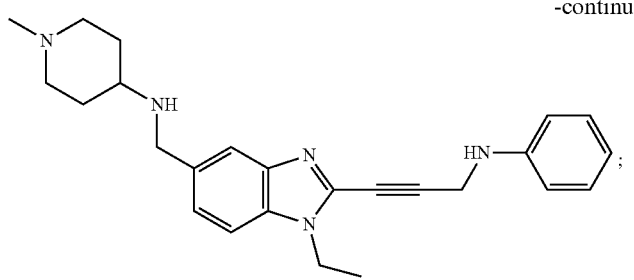
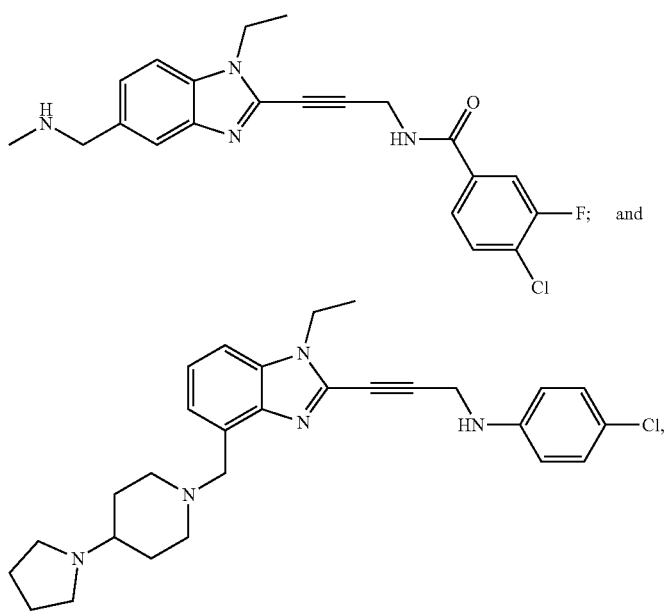
or a pharmaceutically-acceptable salt of any of the foregoing.
Non-limiting examples of compounds of the current disclosure include the following:
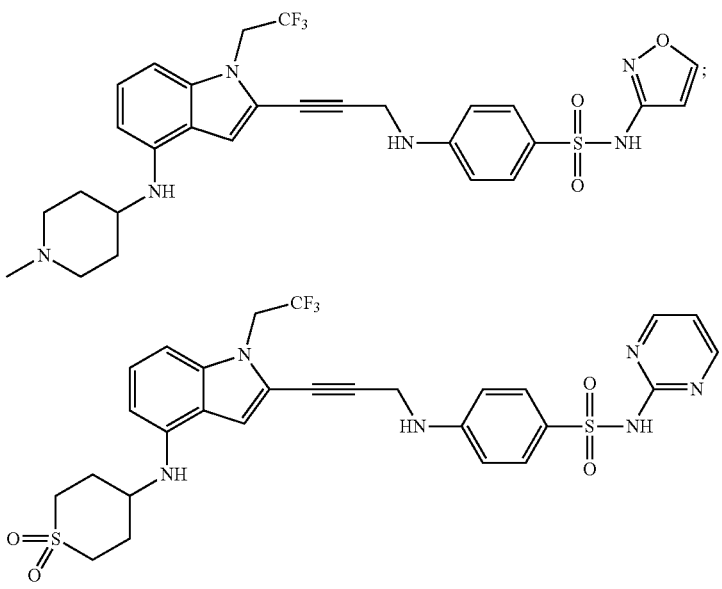

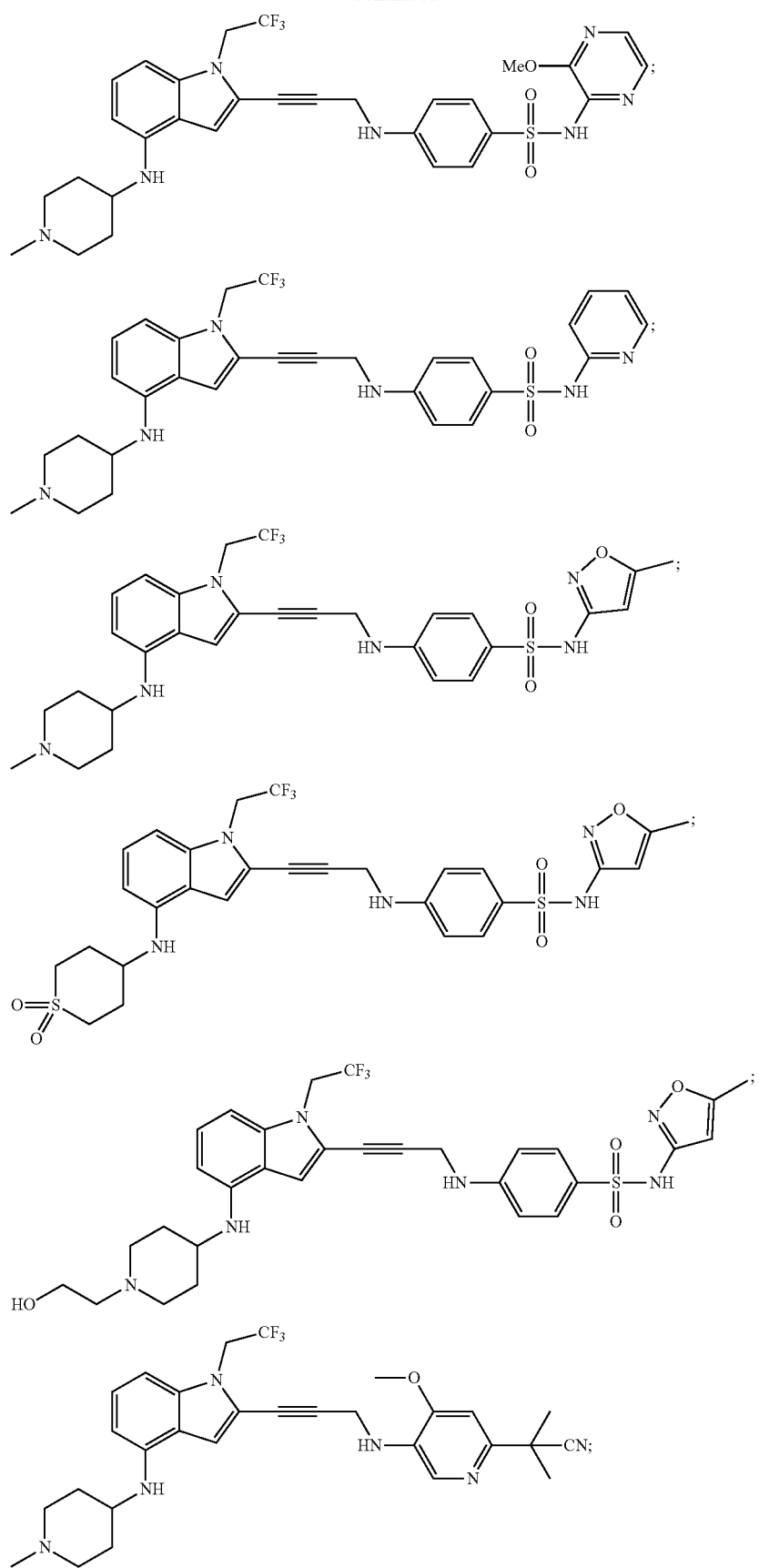

-continued
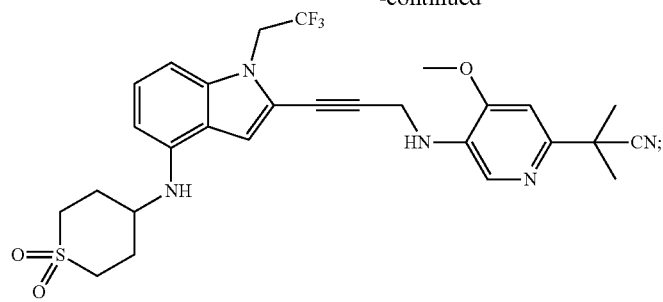
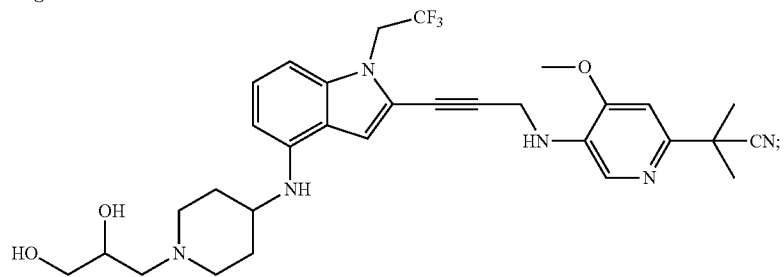
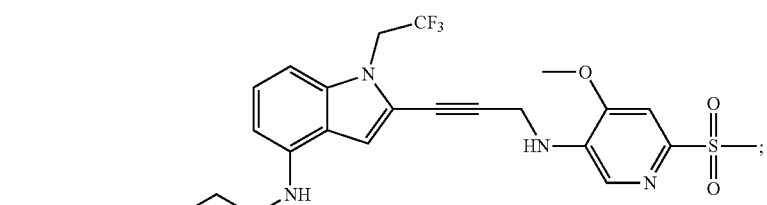
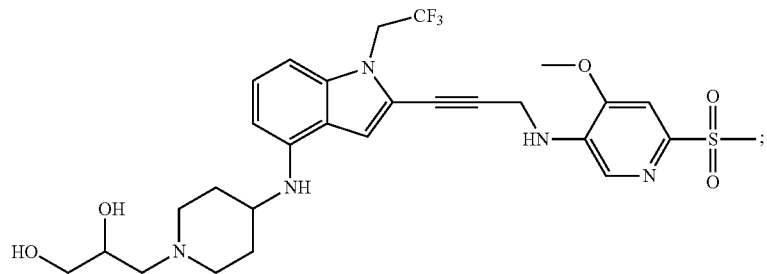
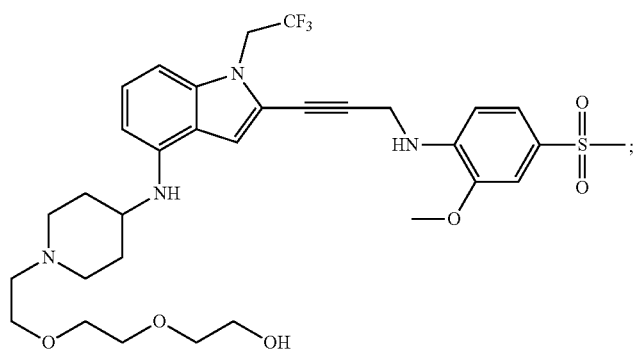

-continued
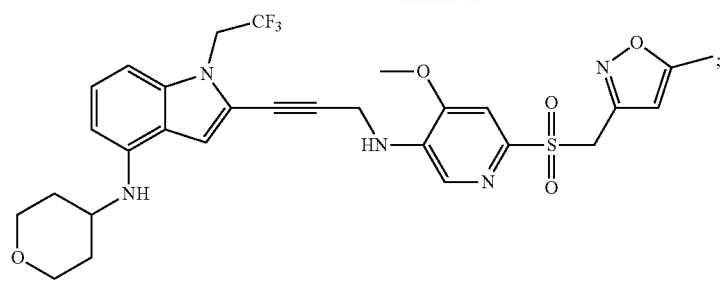
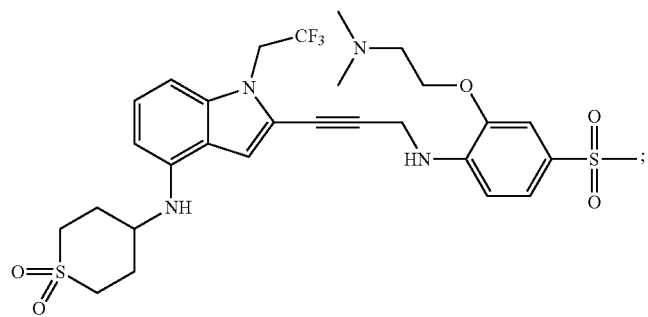
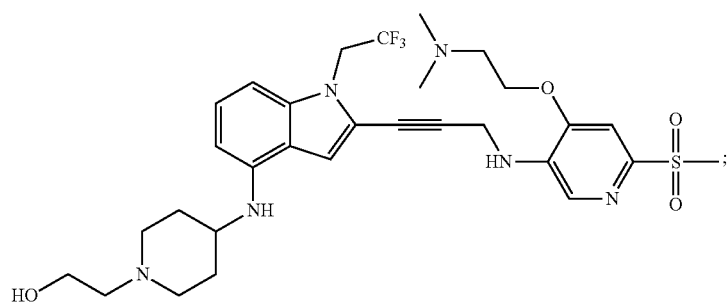
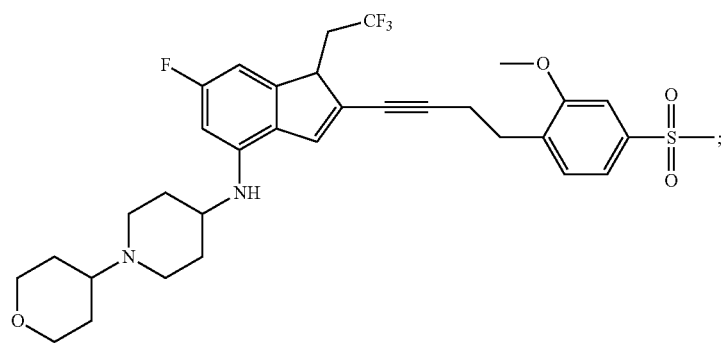
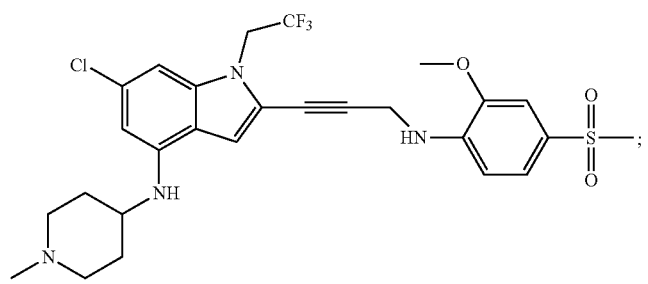

-continued
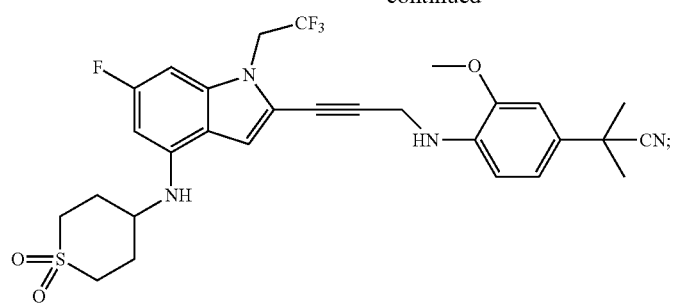
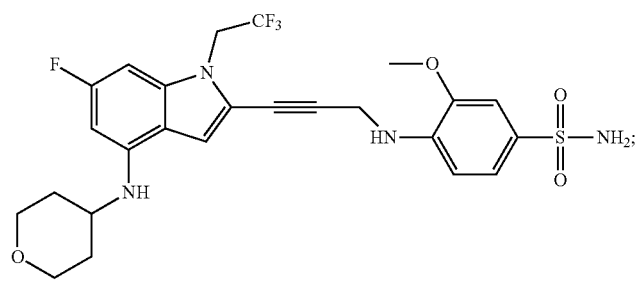
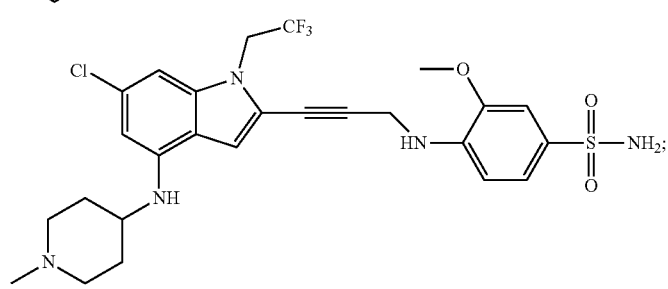
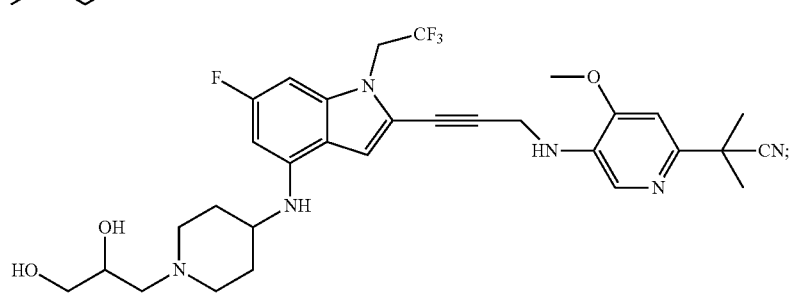
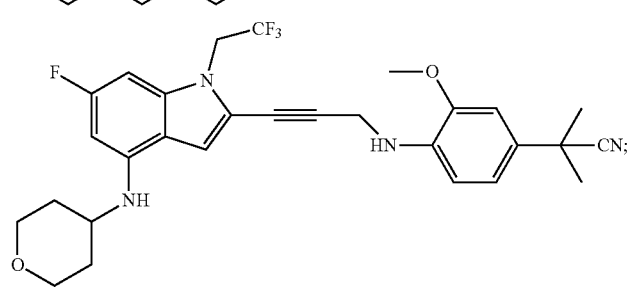
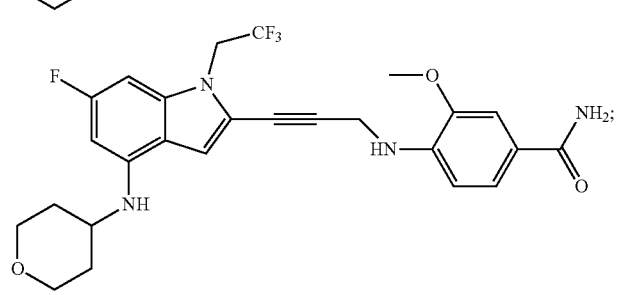

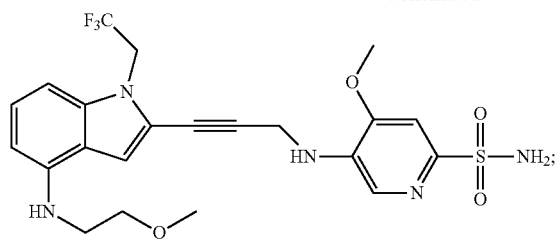
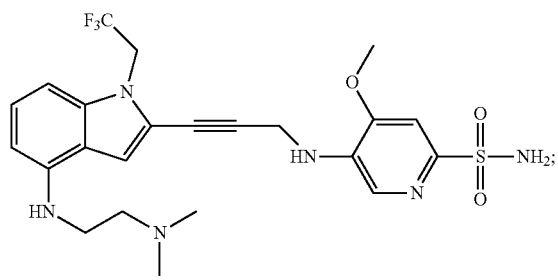
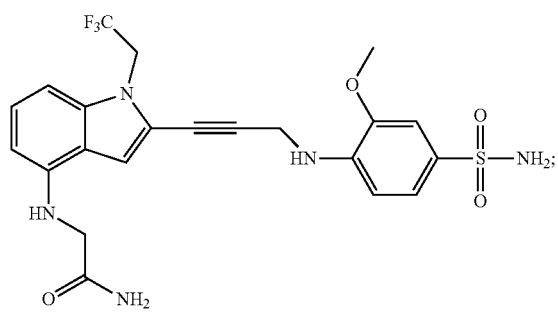
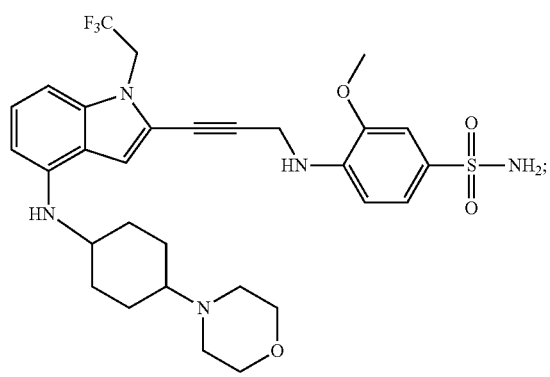
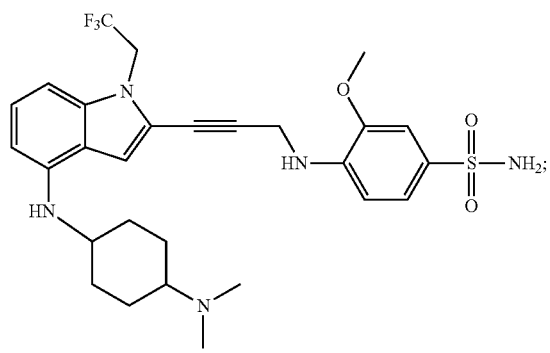

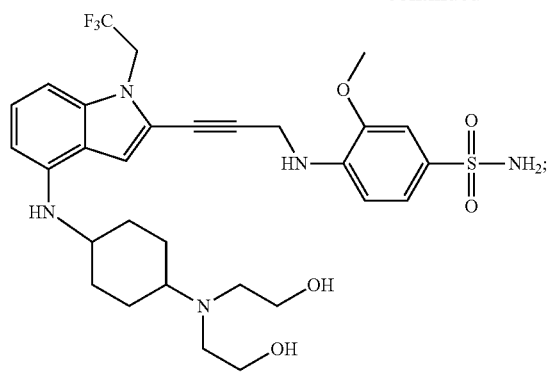
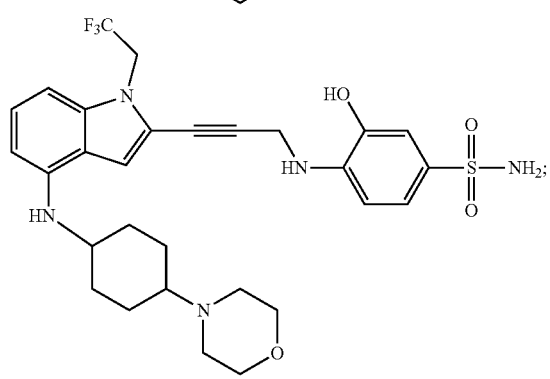
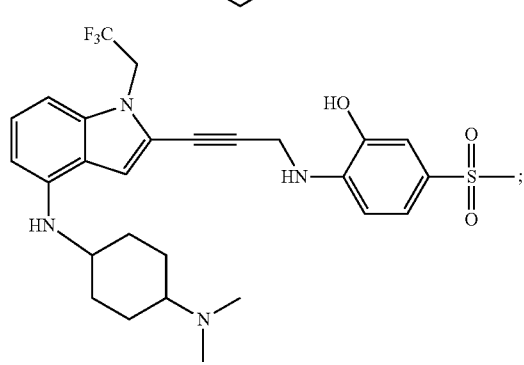
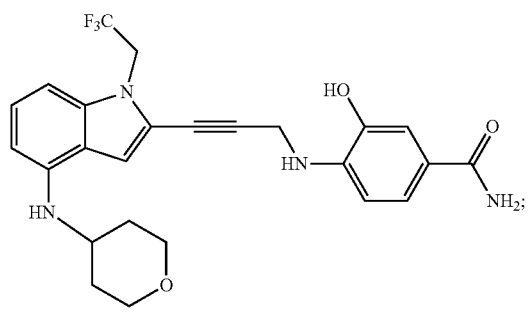
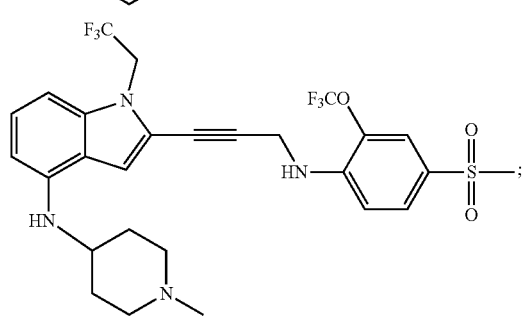

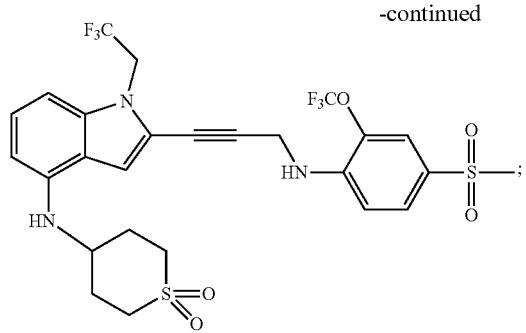
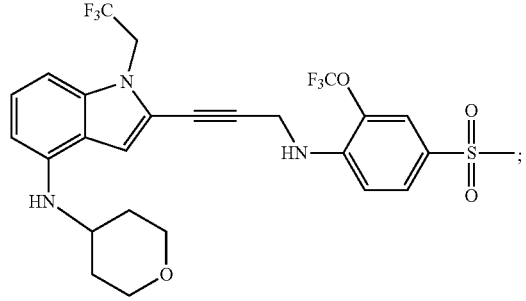
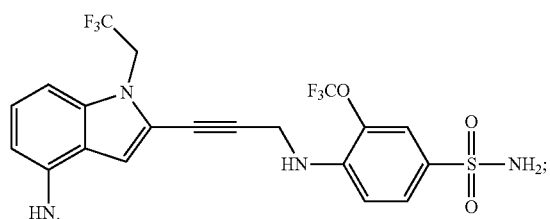
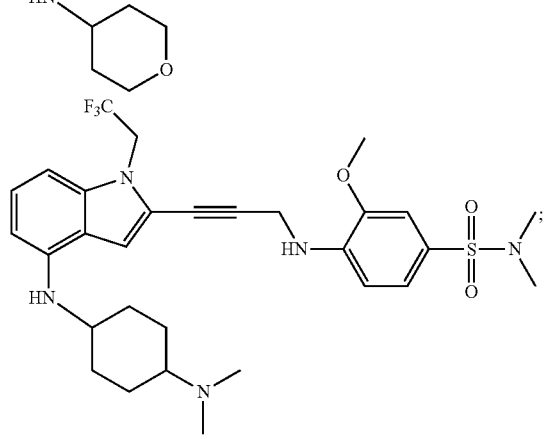
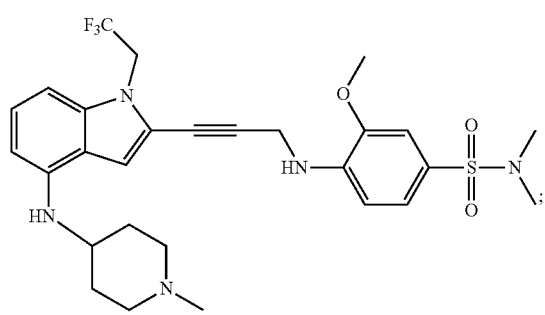

-continued
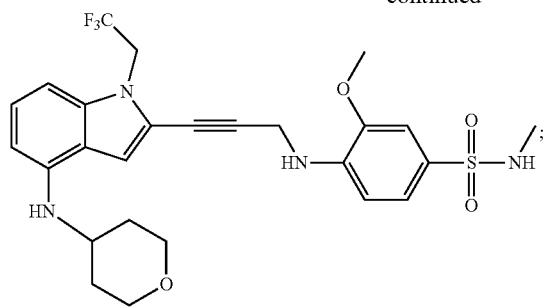
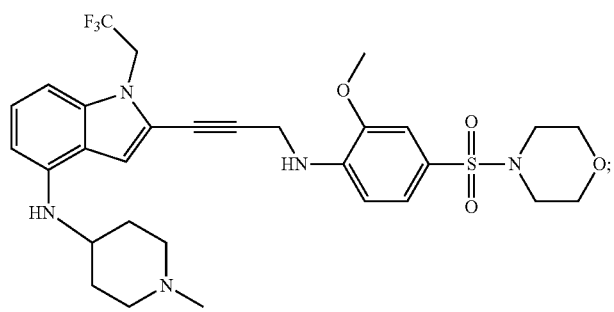
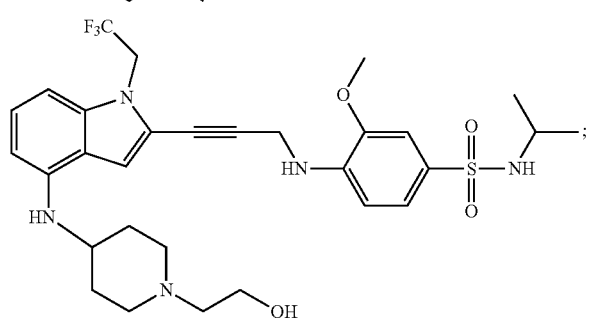
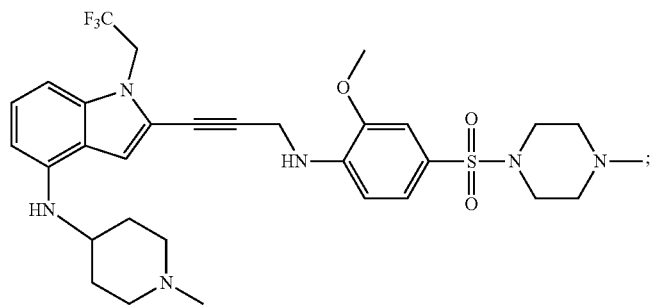
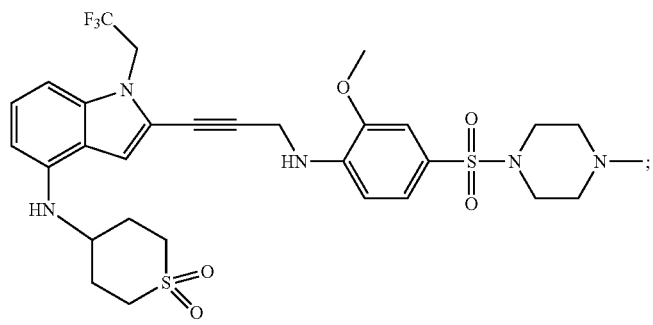

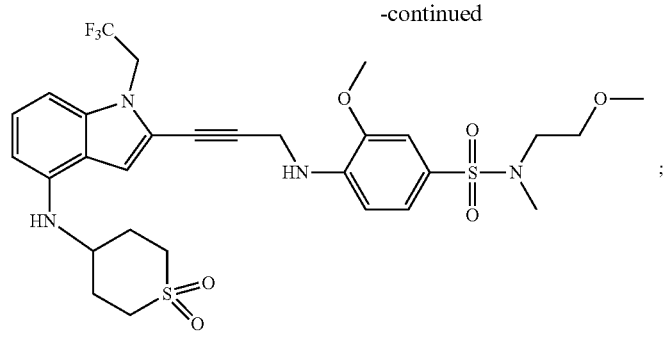
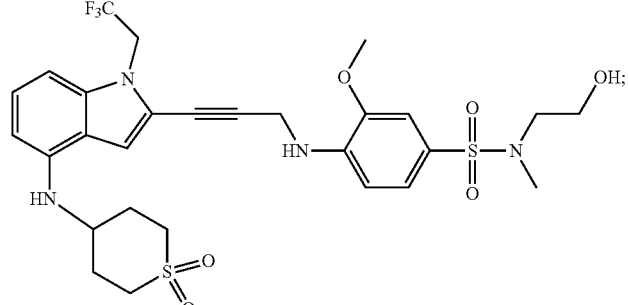
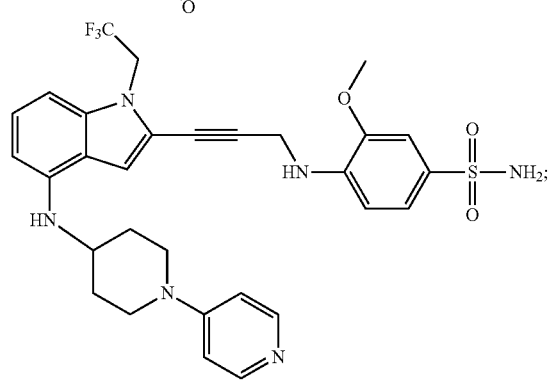
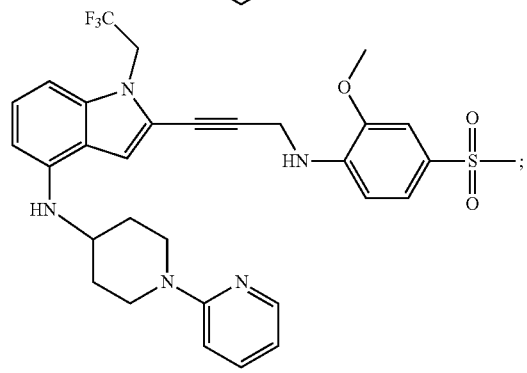
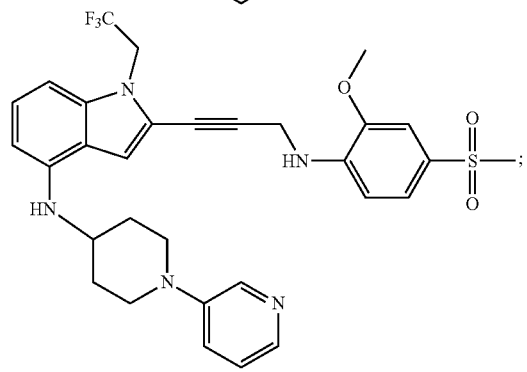

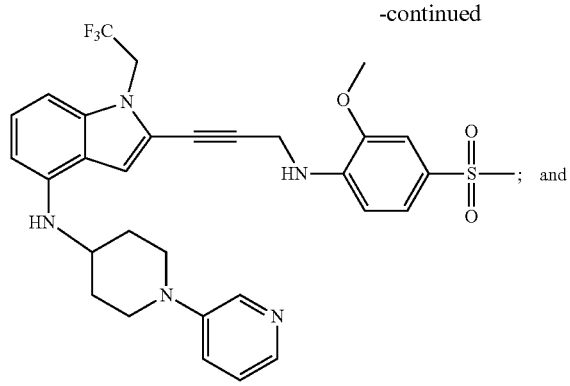
; and
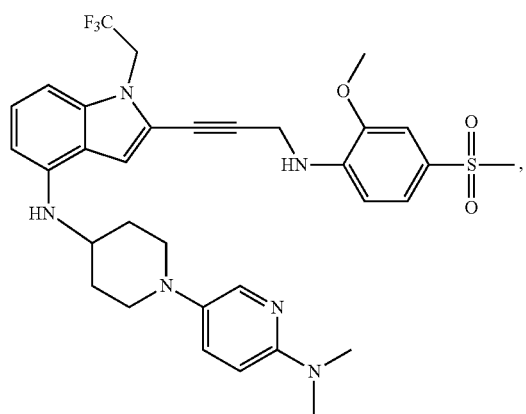 [SMILES: COc1cc(S(C)(=O)=O)ccc1NCC#Cc1cc2c(NC3CCN(c4ccc(N(C)C)nc4)CC3)cccc2n1CC(F)(F)F]
or a pharmaceutically-acceptable salt of any of the forgoing.
Non-limiting examples of compounds of the current disclosure include the following:
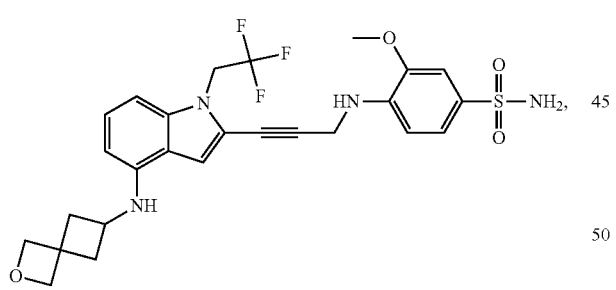
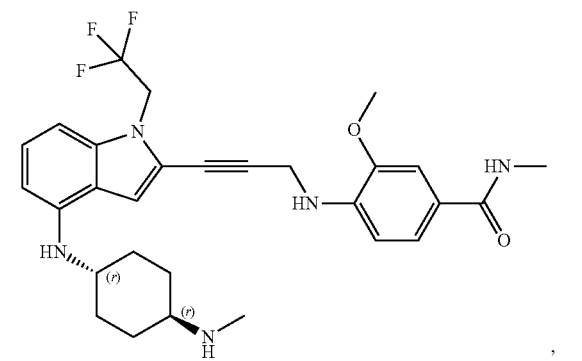
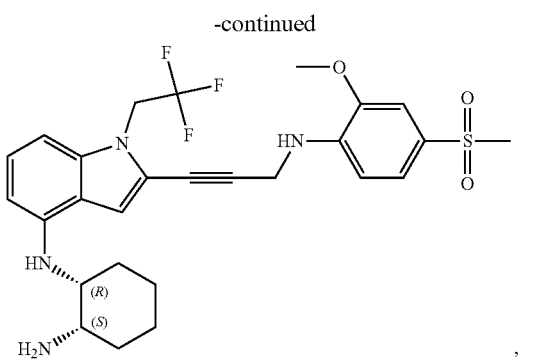
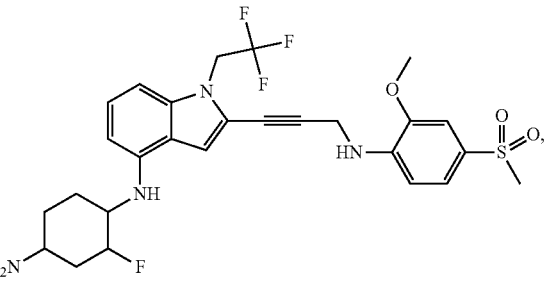

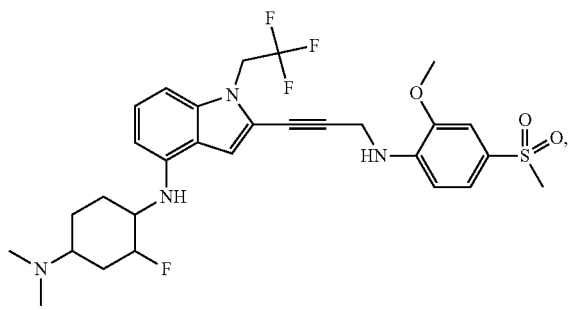
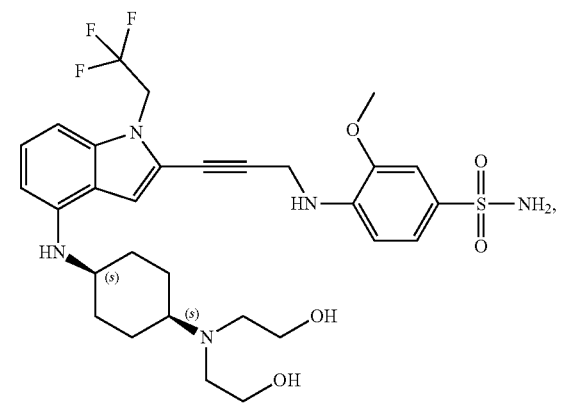
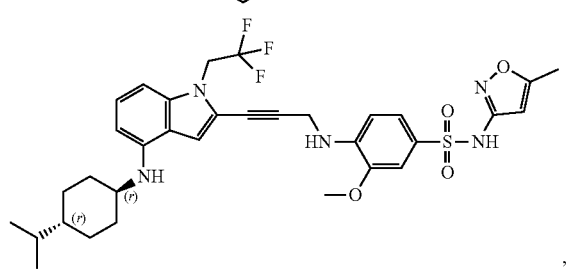
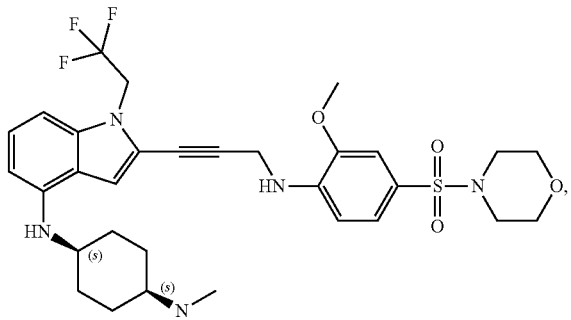
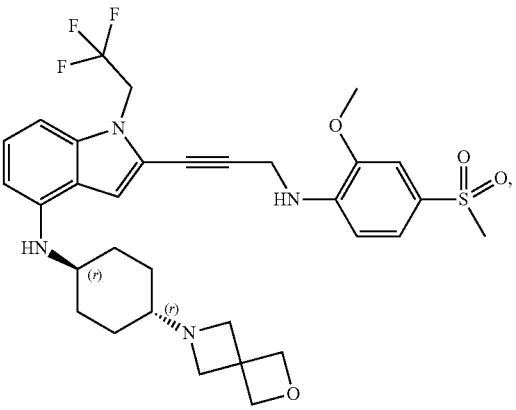
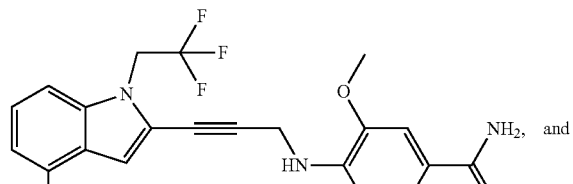
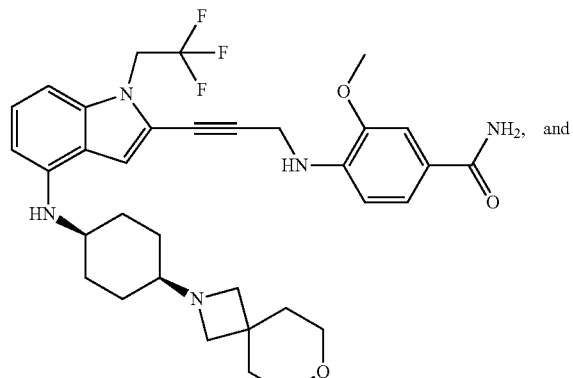
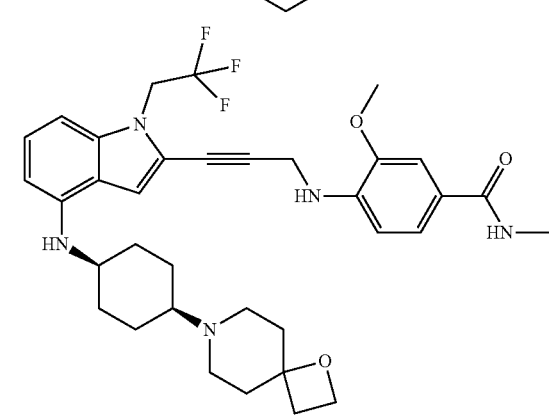
or a pharmaceutically-acceptable salt thereof.
Non-limiting examples of compounds of the current disclosure include the following:
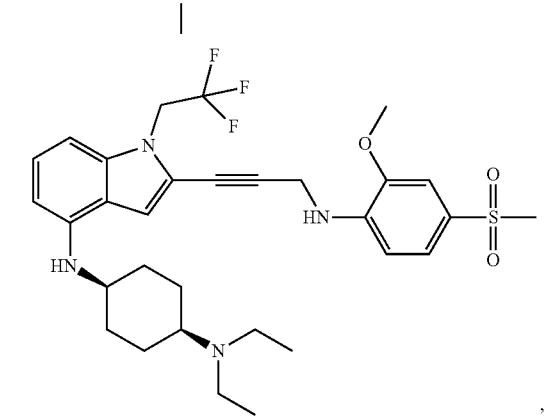
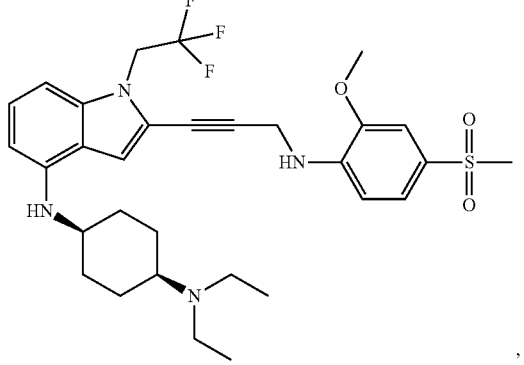
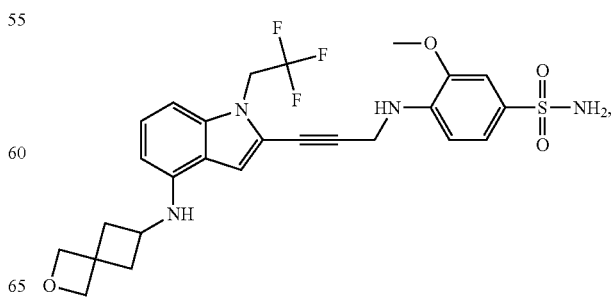

101
-continued
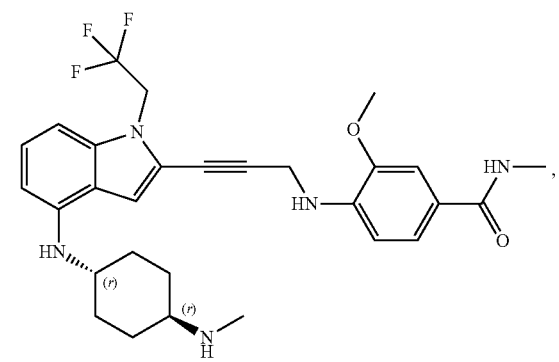
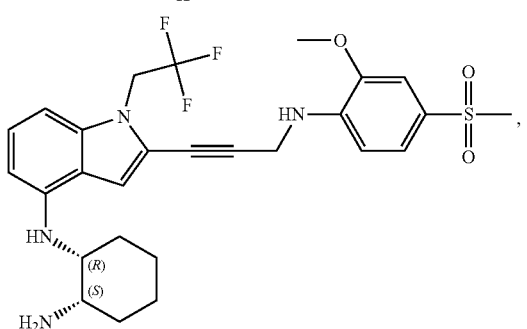
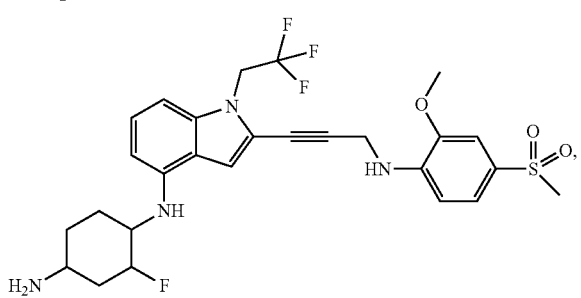
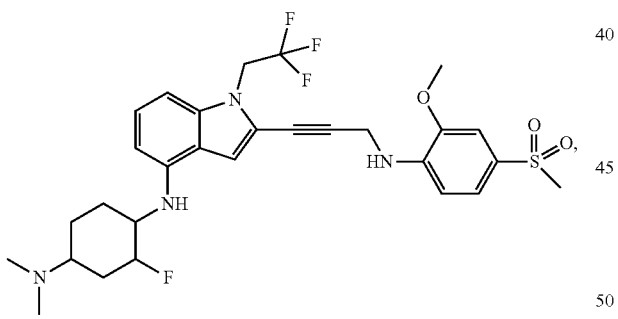
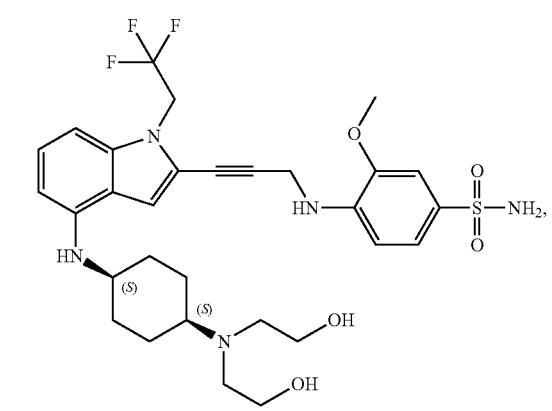
102
-continued
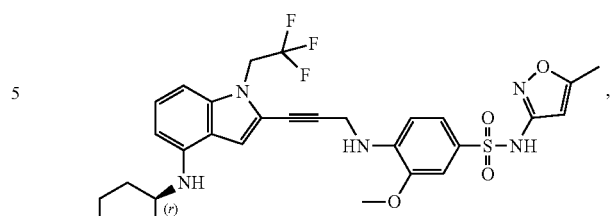
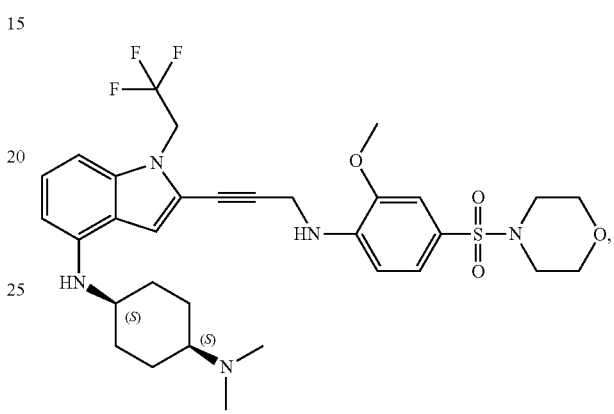
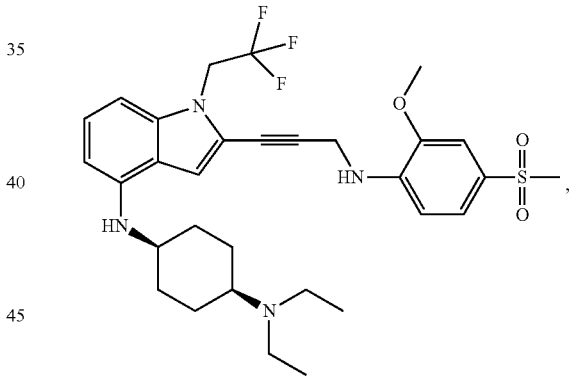
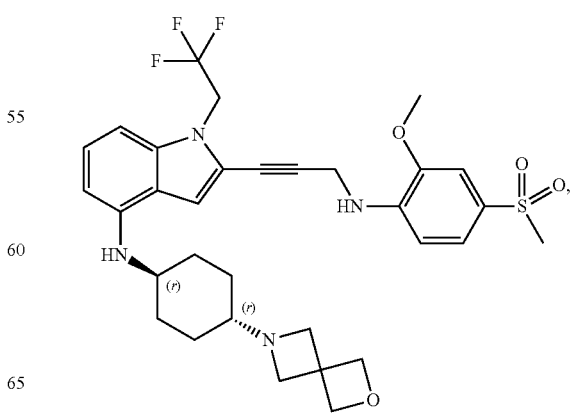

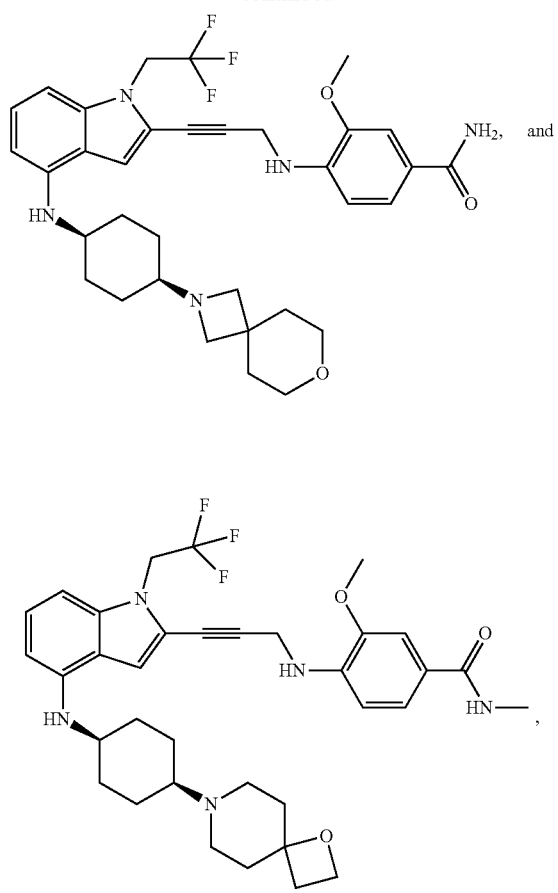
or a pharmaceutically-acceptable salt thereof.
Non-limiting examples of compounds of the current disclosure include the following:
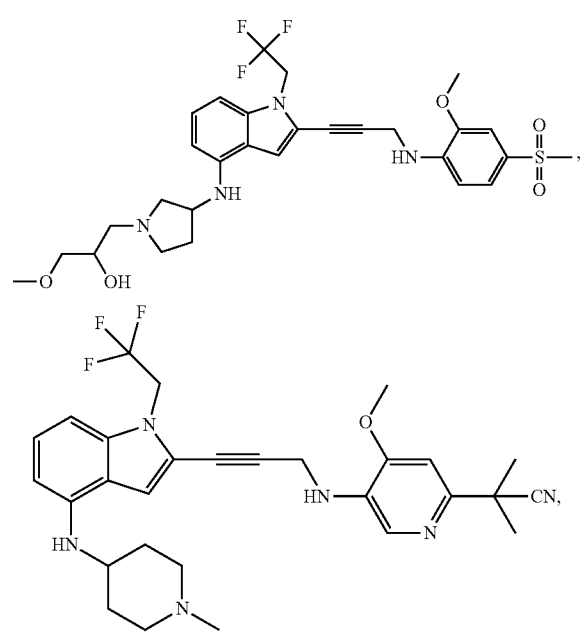
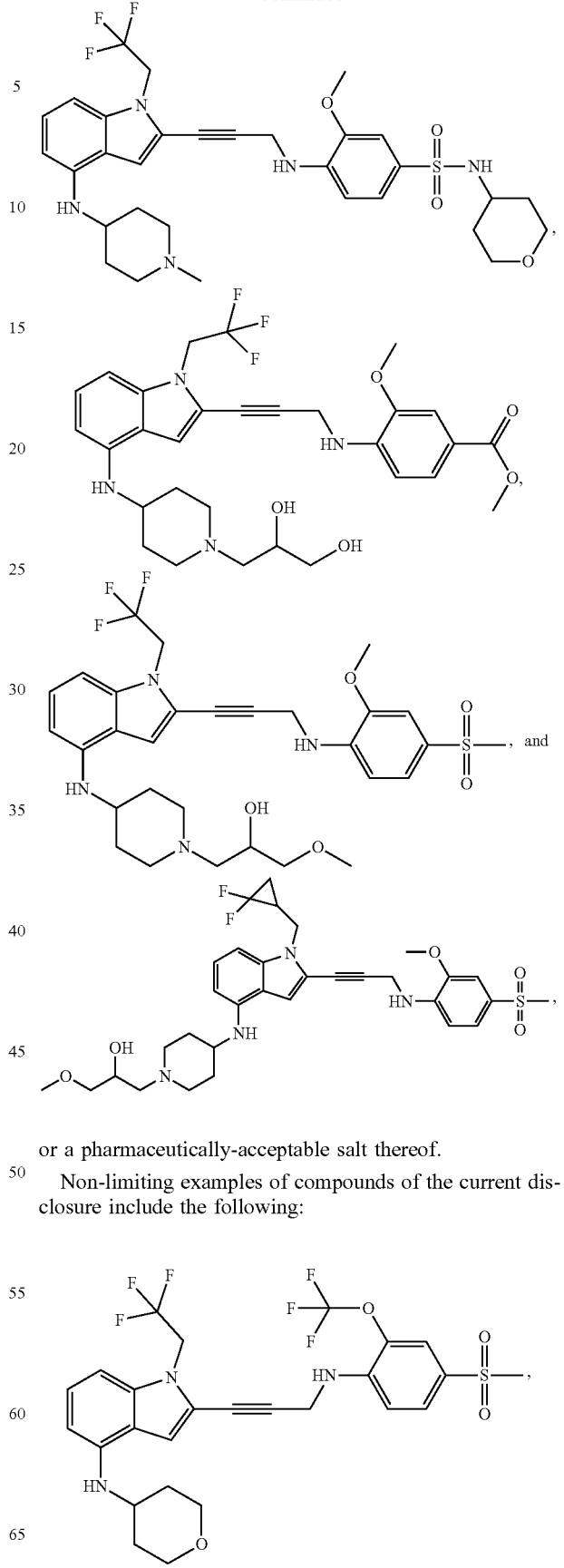
or a pharmaceutically-acceptable salt thereof.
Non-limiting examples of compounds of the current disclosure include the following:

105
-continued
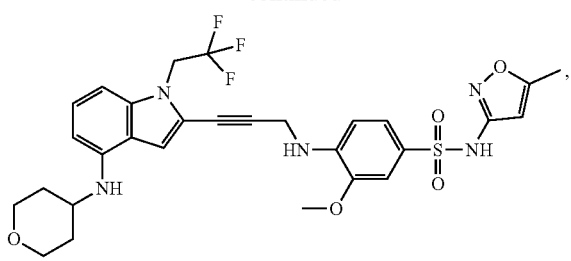
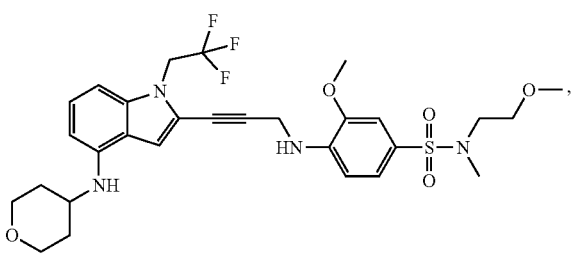
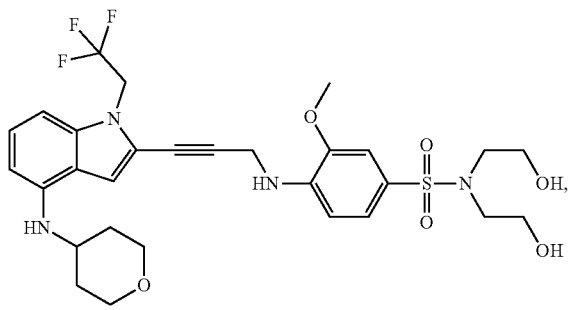
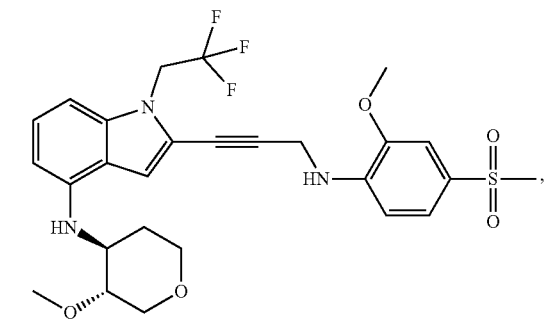
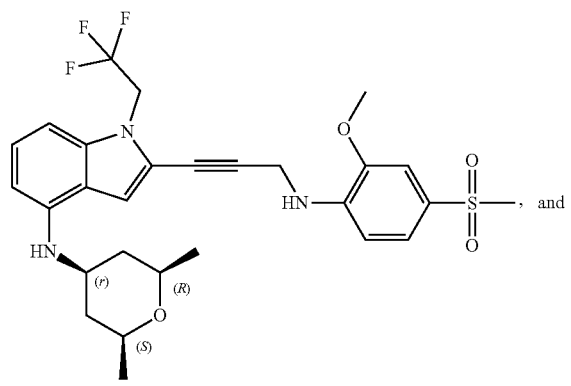
106
-continued
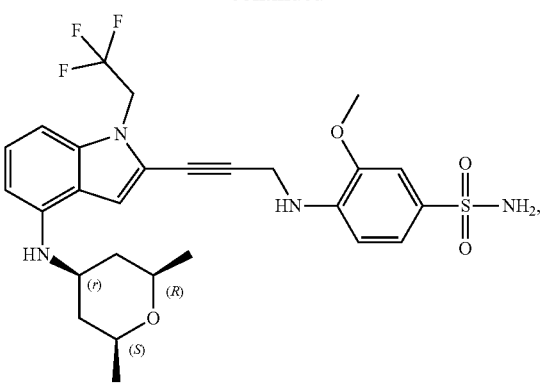
or a pharmaceutically-acceptable salt thereof.
Non-limiting examples of compounds of the current disclosure include the following:
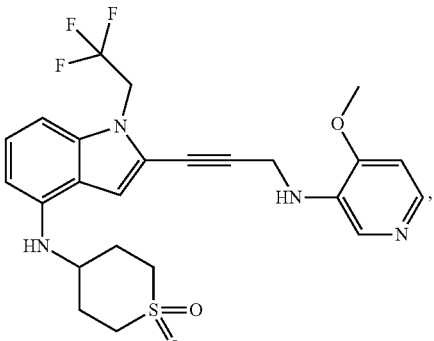
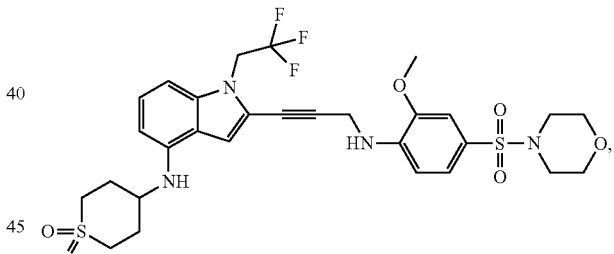
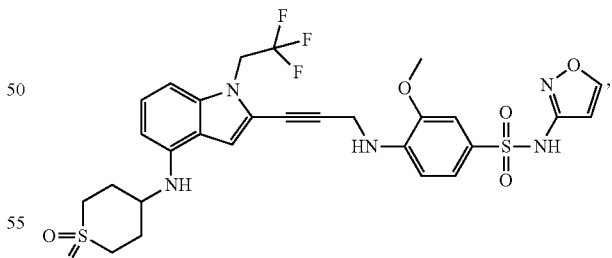
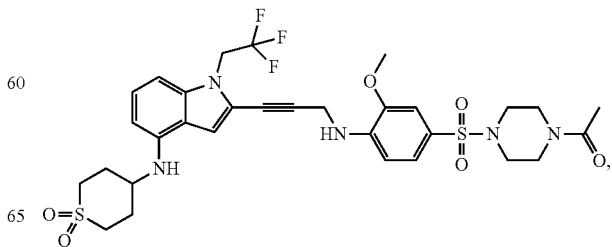

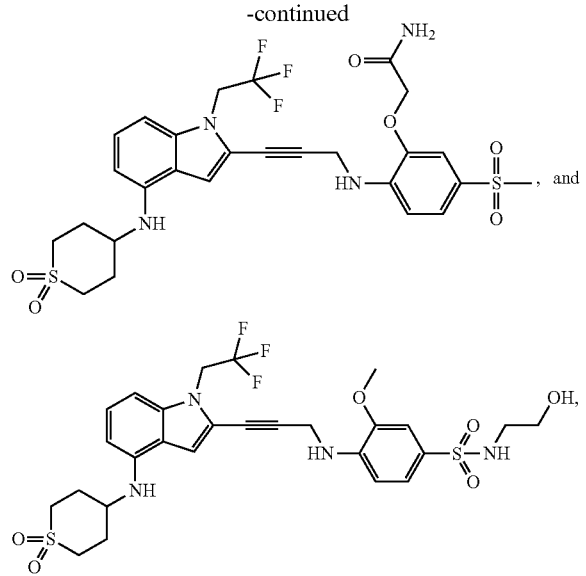
or a pharmaceutically-acceptable salt thereof.
Non-limiting examples of compounds of the current disclosure include the following:
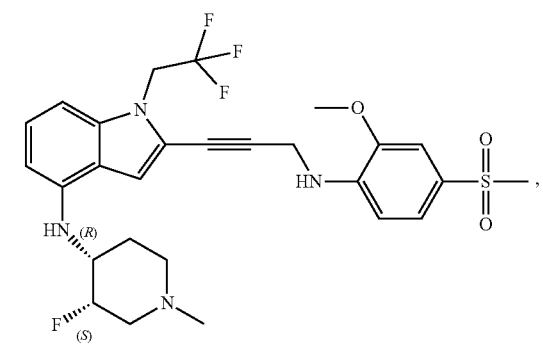
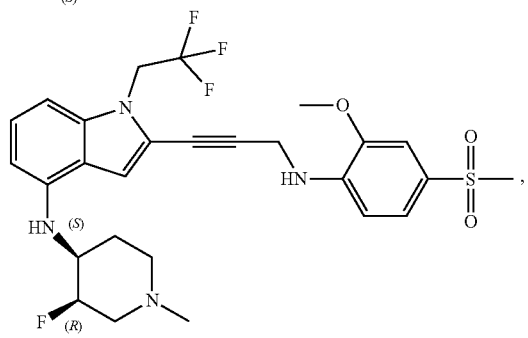
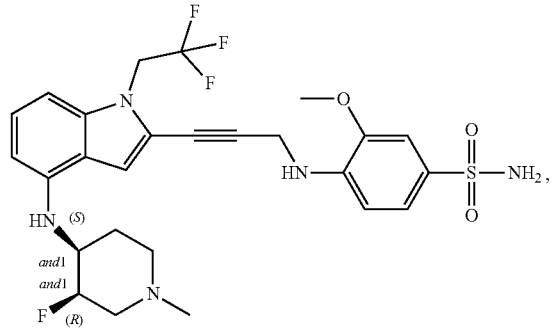
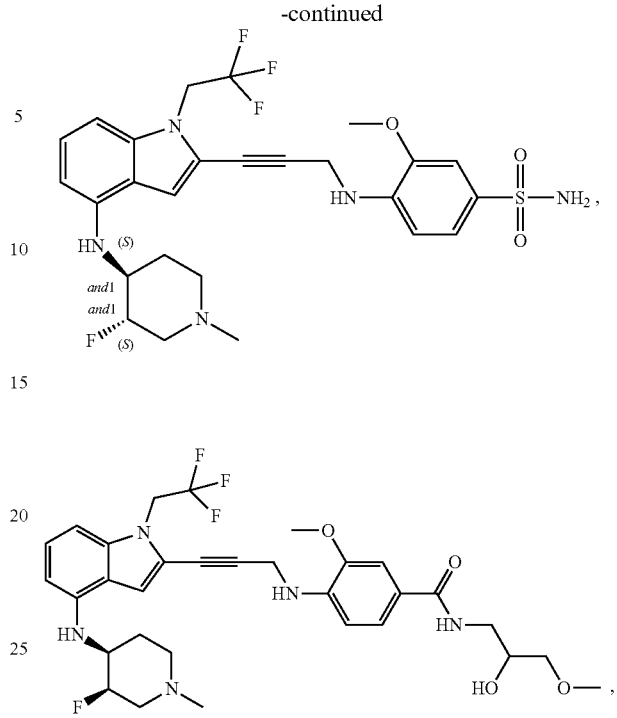

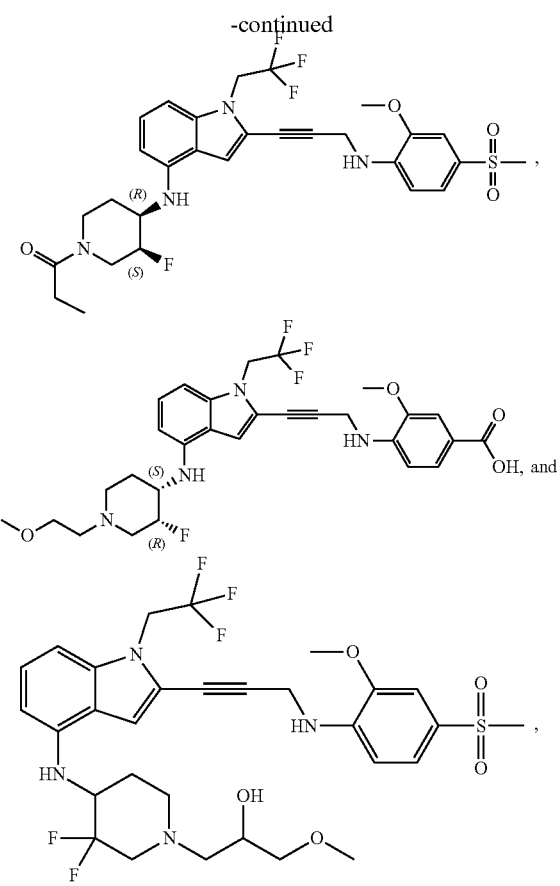

or a pharmaceutically-acceptable salt thereof.

Non-limiting examples of compounds of the current disclosure include the following:

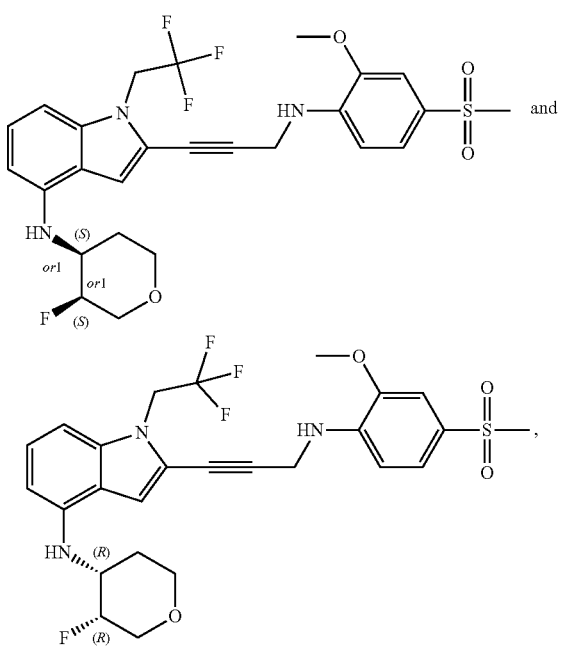

or a pharmaceutically-acceptable salt thereof.

In some embodiments, the disclosure provides a compound comprising: an indole group, wherein the indole group comprises: a) a haloalkyl group at a 1-position of the indole group; b) a first substituent at a 2-position of the indole group, wherein the first substituent is a cyclic group; and c) a second substituent, wherein the second substituent is substituted with at least halo-; or a pharmaceutically-acceptable salt thereof.

In some embodiments, the cyclic group is aryl, heteroaryl, or heterocyclyl, each of which is substituted or unsubstituted. In some embodiments, the cyclic group is unsubstituted aryl. In some embodiments, the cyclic group is substituted aryl. In some embodiments, the cyclic group is substituted phenyl. In some embodiments, the cyclic group is substituted or unsubstituted heteroaryl. In some embodiments, the heteroaryl is an aromatic 5-membered or 6-membered monocyclic ring. In some embodiments, the heteroaryl is thiazolyl, thiadiazolyl, pyrazolyl, thiophenyl, or oxadiazolyl. In some embodiments, the heteroaryl is pyridinyl or pyrimidinyl.

In some embodiments, the second substituent is at a 4-position of the indole group. In some embodiments, the second substituent is a second cyclic group that is substituted or unsubstituted. In some embodiments, the second cyclic group is heterocyclyl. In some embodiments, the heterocyclyl is piperidinyl. In some embodiments, the heterocyclyl is tetrahydropyranyl. In some embodiments, the heterocyclyl is substituted with fluoro-. In some embodiments, the heterocyclyl is substituted with chloro-. In some embodiments, the haloalkyl group is trifluoroethyl.

In some embodiments, the disclosure provides a compound, the compound comprising an indole group, wherein the indole group comprises: a) a substituted or unsubstituted non-cyclic group at a 3-position of the indole group; and b) a substituted or unsubstituted cyclic group at a 2-position of the indole group, wherein the compound increases a stability of a biologically-active conformation of a p53 mutant relative to a stability of a biologically-active conformation of the p53 mutant in an absence of the compound, or a pharmaceutically-acceptable salt thereof.

In some embodiments, the non-cyclic group is hydrogen. In some embodiments, the non-cyclic group is halo-. In some embodiments, the cyclic group is aryl, heteroaryl, heterocyclyl, or cycloalkylene, each of which is substituted or unsubstituted. In some embodiments, the cyclic group is aryl or heteroaryl, each of which is substituted or unsubstituted. In some embodiments, the cyclic group is substituted aryl. In some embodiments, the cyclic group is substituted phenyl. In some embodiments, the cyclic group is phenyl substituted with alkyl, cycloalkyl, alkoxy, an amine group, a carboxyl group, a carboxylic acid group, a carbamide group, or an amide group, each of which is substituted or unsubstituted; cyano, halo-, or hydrogen.

In some embodiments, the cyclic group is substituted heteroaryl. In some embodiments, the cyclic group is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, the cyclic group is pyridinyl, pyrimidinyl, thiadiazolyl, thiazolyl, pyrazolyl, thiophenyl, or oxadiazolyl, In some embodiments, the cyclic group is 1,3,5-thiadiazol-2-yl. In some embodiments, the cyclic group is 1,3,4-oxadiazol-2-yl or 1,2,4-oxadiazol-2-yl. In some embodiments, the cyclic group is pyridinyl.

In some embodiments, the indole group further comprises a substituent at a 4-position of the indole group. In some embodiments, the substituent is an amino group that is substituted or unsubstituted. In some embodiments, the amino group is substituted with a second cyclic group. In some embodiments, the second cyclic group is a heterocyclyl group substituted with at least halo-. In some embodiments, the heterocyclyl group is substituted with at least fluoro-. In some embodiments, the heterocyclyl group is substituted with at least chloro-. In some embodiments, the heterocyclyl group is piperidinyl. In some embodiments, the heterocyclyl group is tetrahydropyranyl.

Non-limiting examples of compounds of the disclosure include compounds of any of the following formulae:

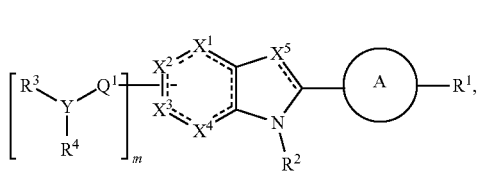

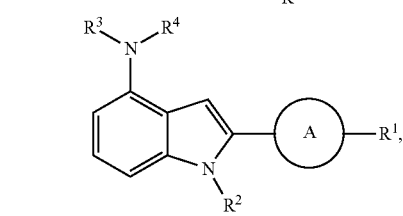

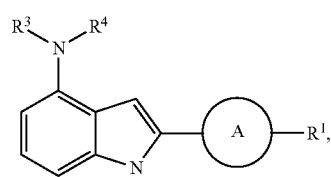

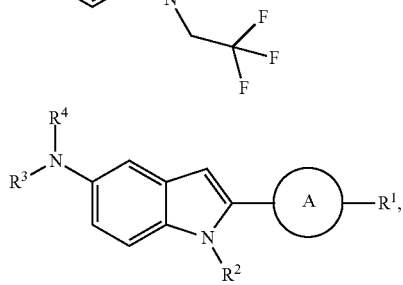

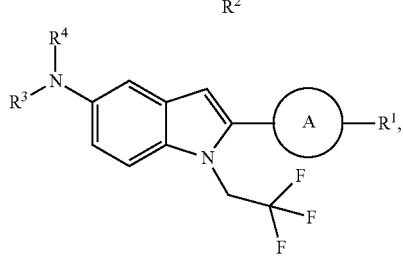

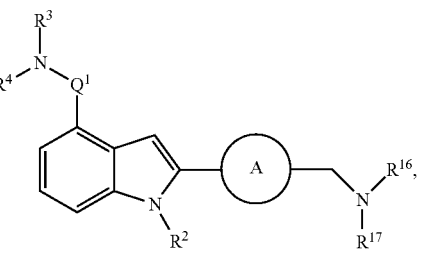

-continued

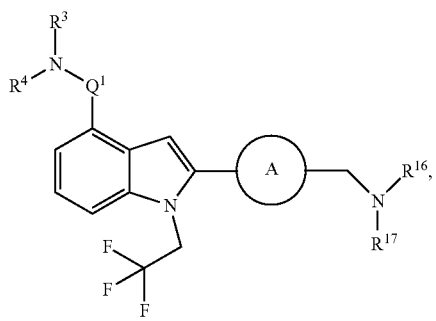

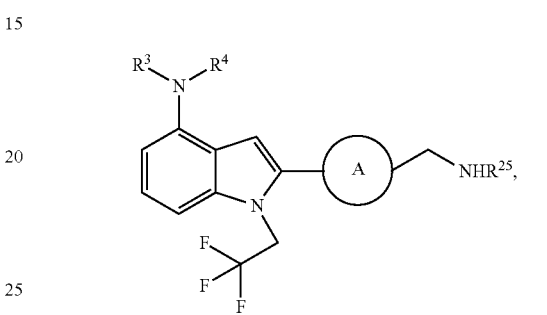

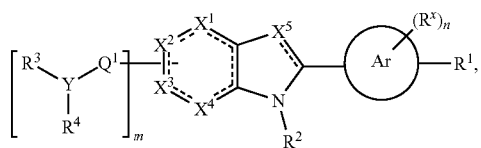

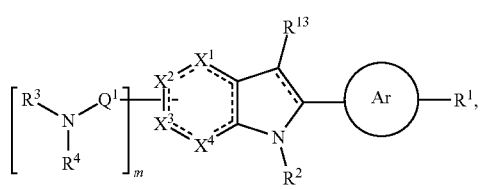

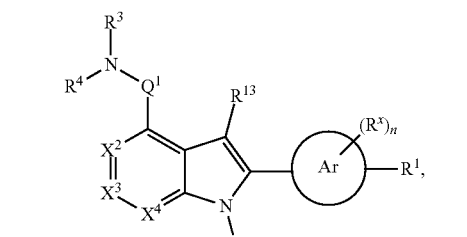

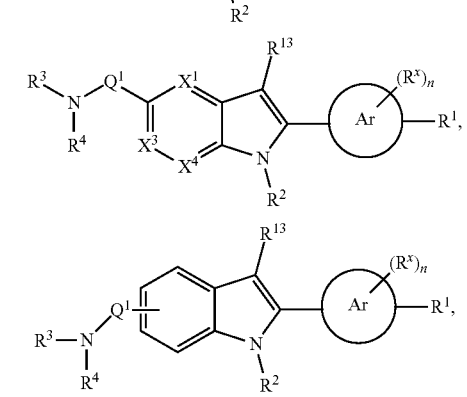

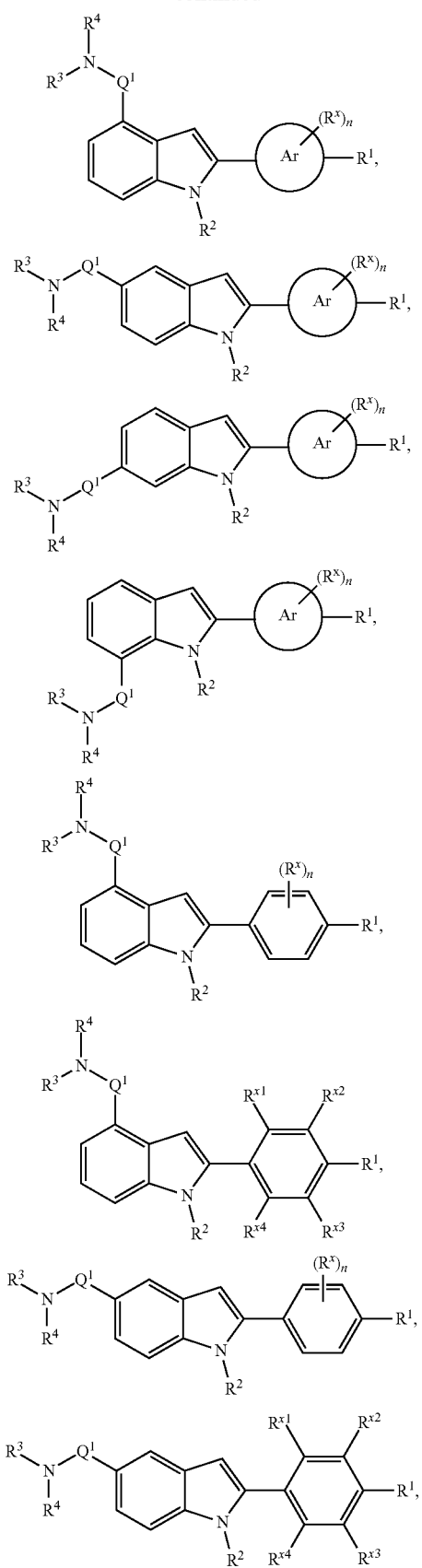
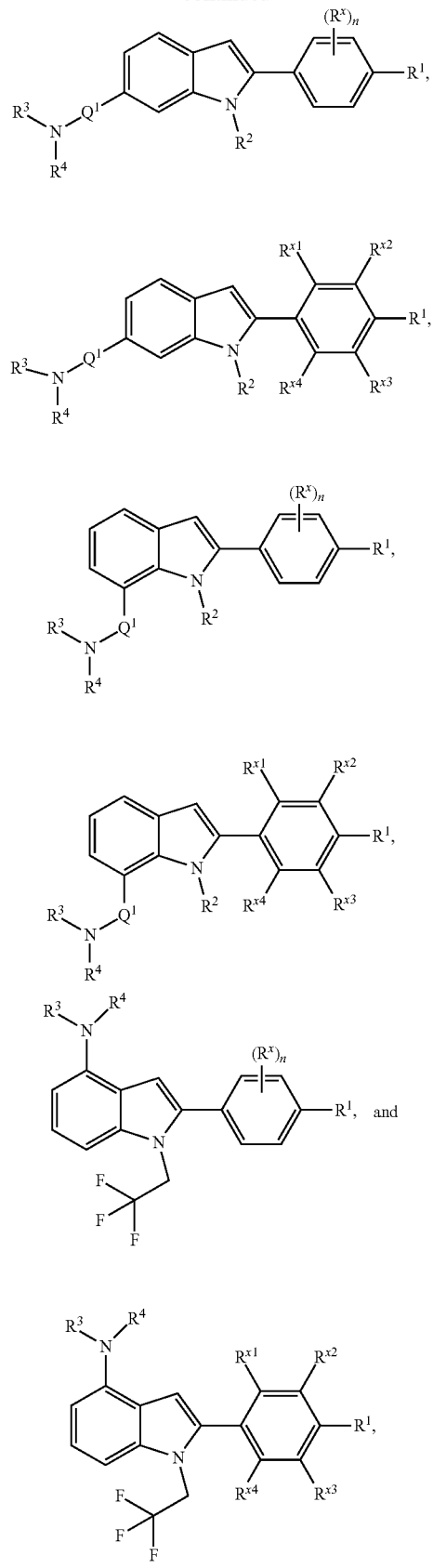
or a pharmaceutically-acceptable salt thereof.-

In some embodiments, the disclosure provides a compound of the formula:

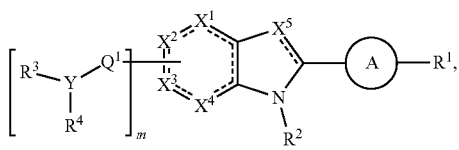

each ------- is independently a single bond or a double bond;

X$^1$ is CR$^5$, CR$^5$R$^6$, N, NR$^5$, O, S, C=O, C=S, or a carbon atom connected to Q$^1$;

X$^2$ is CR$^7$, CR$^7$R$^8$, N, NR$^7$, O, S, C=O, C=S, or a carbon atom connected to Q$^1$;

X$^3$ is CR$^9$, CR$^9$R$^{10}$, N, NR$^9$, O, S, C=O, C=S, or a carbon atom connected to Q$^1$;

X$^4$ is CR$^{11}$, CR$^{11}$R$^{12}$, N, NR$^{11}$, O, S, C=O, C=S, or a carbon atom connected to Q$^1$;

X$^5$ is CR$^{13}$, N, or NR$^{13}$;

wherein at least one of X$^1$, X$^2$, X$^3$, and X$^4$ is a carbon atom connected to Q$^1$;

A is a substituted or unsubstituted ring;

Q$^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

each R$^2$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, A is substituted or unsubstituted aryl, heteroaryl, heterocyclyl, cycloalkylene. In some embodiments, A is a 6-carbon monocyclic or 10-carbon bicyclic aromatic ring system wherein 0, 1, 2, 3, or 4 atoms of each ring are optionally substituted. In some embodiments, A is naphthyl. In some embodiments, A is indazolyl.

In some embodiments, A is substituted aryl. In some embodiments, A is substituted phenyl. In some embodiments, A is phenyl substituted with alkyl, cycloalkyl, alkoxy, an amine group, a carboxyl group, a carboxylic acid group, a carbamide group, or an amide group, each of which is substituted or unsubstituted; cyano, halogen, or hydrogen. In some embodiments, A is phenyl substituted with alkyl, wherein alkyl is substituted. In some embodiments, A is phenyl substituted with alkyl, wherein alkyl is substituted with an amino group that is substituted or unsubstituted. In some embodiments, A is phenyl substituted with an amine group that is substituted or unsubstituted. In some embodiments, A is phenyl substituted with a carboxyl group that is substituted or unsubstituted. In some embodiments, A is phenyl substituted with cyano. In some embodiments, A is phenyl substituted with halo-.

In some embodiments, A is substituted or unsubstituted heterocyclyl. In some embodiments, A is substituted heterocyclyl.

In some embodiments, A is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, A is an aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S. In some embodiments, A is an aromatic 5-membered, 6-membered, 7-membered, or 8-membered monocyclic ring system comprising 1, 2, or 3 heteroatoms, and the aromatic 5-membered, 6-membered, 7-membered, or 8-membered monocyclic ring system is substituted. In some embodiments, A is an 8-membered, 9-membered, 10-membered, 11-membered, or 12-membered bicyclic ring system having 1, 2, 3, 4, 5, or 6 heteroatoms, and the 8-membered, 9-membered, 10-membered, 11-membered, or 12-membered bicyclic ring system is substituted.

In some embodiments, A is pyridinyl, pyrimidinyl, thiadiazolyl, thiazolyl, pyrazolyl, thiophenyl, or oxadiazolyl, each of which is independently substituted or unsubstituted. In some embodiments, A is 1,3,5-thiadiazol-2-yl. In some embodiments, A is 1,3,4-oxadiazol-2-yl or 1,2,4-oxadiazol-2-yl. In some embodiments, A is 1,3,4-oxadiazol-2-yl.

In some embodiments, m is 1. In some embodiments, m is 2. In some embodiments, Q$^1$ is alkylene, alkenylene, or alkynylene, each of which is independently substituted or unsubstituted, or a bond. In some embodiments, Q$^1$ is a bond. In some embodiments, Y is N.

In some embodiments, R$^2$ is hydrogen. In some embodiments, R$^2$ is substituted or unsubstituted alkyl. In some embodiments, R$^2$ is trifluoroethyl. In some embodiments, R$^2$ is cycloalkyl.

In some embodiments, R$^1$ is —C(O)R$^{16}$, —C(O)OR$^{16}$, —C(O)NR$^{16}$R$^{17}$, —OR$^{16}$, —NR$^{16}$R$^{17}$, —NR$^{16}$C(O)R$^{16}$, —OC(O)R$^{16}$, alkyl, alkoxy, aryl, heteroaryl, or heterocyclyl, each of which is independently substituted or unsubstituted; cyano, halo, or halogen. In some embodiments, R$^1$ is —NR$^{16}$R$^{17}$. In some embodiments, R$^1$ is substituted alkyl.

In some embodiments, each R$^3$ and R$^4$ is independently aryl, heteroaryl, or heterocyclyl, each of which is independently substituted or unsubstituted; or hydrogen. In some embodiments, R$^3$ is hydrogen, and R$^4$ is heterocyclyl substituted at least with halo-. In some embodiments, R$^4$ is heterocyclyl substituted with fluoro. In some embodiments, $R^4$ is heterocyclyl substituted with chloro.

In some embodiments, $R^{13}$ is alkyl, alkenyl, hydrogen, or halogen. In some embodiments, $R^{13}$ is hydrogen.

In some embodiments, the compound has the formula:

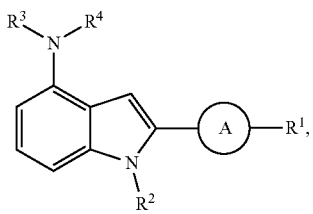

or a pharmaceutically-acceptable salt thereof, wherein the variable are as defined above.

In some embodiments, the compound has the formula:

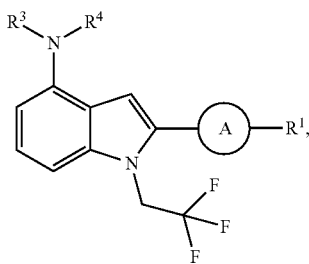

or a pharmaceutically-acceptable salt thereof, wherein the variables are as defined above.

In some embodiments, the compound has the formula:

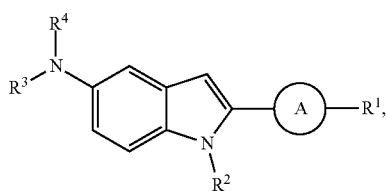

or a pharmaceutically-acceptable salt thereof, wherein the variables are as defined above.

In some embodiments, the compound has the formula:

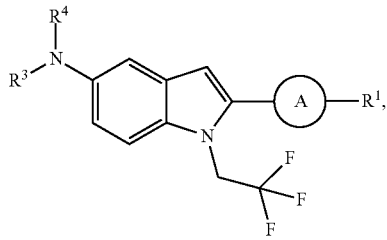

or a pharmaceutically-acceptable salt thereof, wherein the variables are as defined above.

In some embodiments, the disclosure provides a compound of the formula:

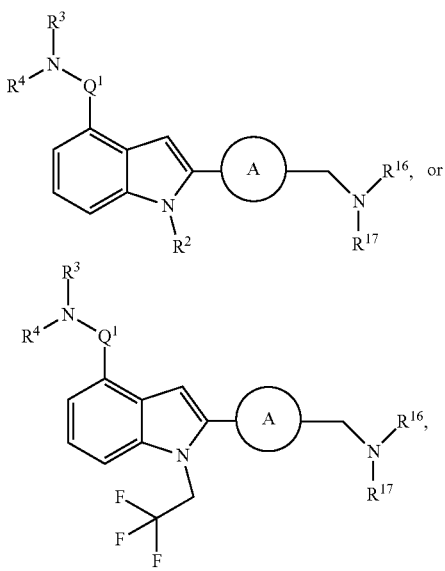

or a pharmaceutically-acceptable salt thereof, wherein the variables are as defined above.

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

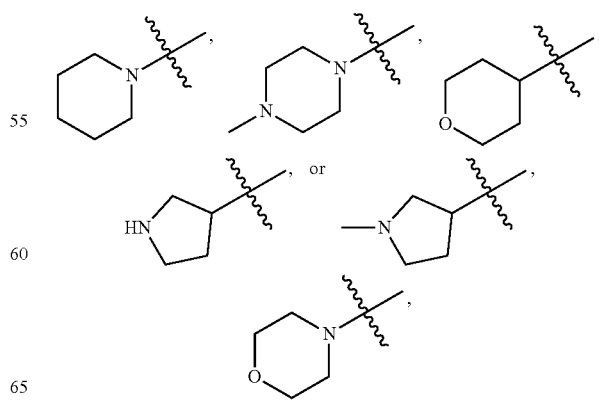

wherein the ring is substituted or unsubstituted. In some embodiments, R³ is H, and R⁴ is a ring that is

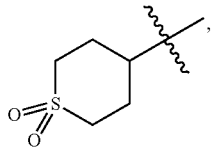

wherein the ring is substituted or unsubstituted. In some embodiments, R³ is H, and R⁴ is a ring that is

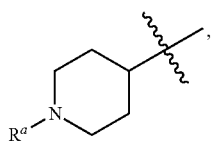

wherein the ring is substituted or unsubstituted. In some embodiments, R$^a$ is alkylene. In some embodiments, R$^a$ is methyl. In some embodiments, R³ is H, and R⁴ is a ring that is

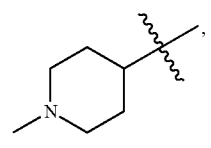 [SMILES: *C1CCN(C)CC1]

wherein the ring is substituted or unsubstituted. In some embodiments, R³ is H, and R⁴ is a ring that is

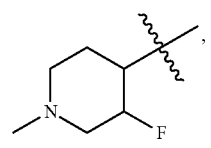 [SMILES: *C1CCN(C)CC1F]

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

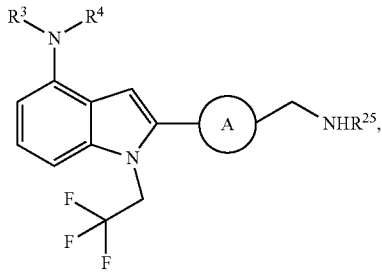

wherein $R^{25}$ is —C(O)$R^{16}$, —C(O)N$R^{16}R^{17}$, alkyl, alkenyl, alkynyl, aryl, heteroaryl, or heterocyclyl, each of which is independently substituted or unsubstituted, or hydrogen. In some embodiments, $R^{25}$ is aryl that is substituted or unsubstituted. In some embodiments, $R^{25}$ is substituted phenyl. In some embodiments, $R^{25}$ is —C(O)$R^{16}$, wherein $R^{16}$ is alkyl, aryl, heteroaryl, or heterocyclyl. In some embodiments, $R^{25}$ is —C(O)$R^{16}$, wherein $R^{16}$ is substituted phenyl.

In some embodiments, the disclosure provides a compound of the formula:

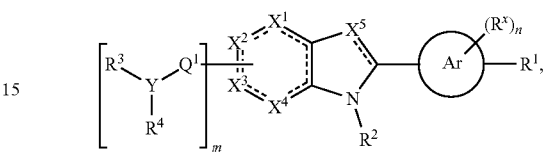

each ------- is independently a single bond or a double bond;

$X^1$ is $CR^5$, $CR^5R^6$, N, $NR^5$, O, S, C=O, C=S, or a carbon atom connected to $Q^1$;

$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N, $NR^9$, O, S, C=O, C=S, or a carbon atom connected to $Q^1$;

$X^4$ is $CR^{11}$, $CR^{11}R^{12}$, N, $NR^{11}$, O, S, C=O, C=S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

Ar is unsubstituted or substituted aryl;

$Q^1$ is C=O, C=S, C=$CR^{14}R^{15}$, C=$NR^{14}$, alkylene, alkenylene, or alkynylene, each of which is independently substituted or unsubstituted, or a bond;

m is 1, 2, 3, or 4;

n is 0, 1, 2, 3, or 4;

Y is N, O, or absent;

each $R^x$ and $R^1$ is independently C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;

each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

The pattern of dashed bonds can be chosen to provide an aromatic system, for example, an indole, an indolene, a pyrrolopyridine, a pyrrolopyrimidine, or a pyrrolopyrazine. In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, Ar is a 6-carbon monocyclic or 10-carbon bicyclic aromatic ring system wherein 0, 1, 2, 3, or 4 atoms of each ring are optionally substituted. In some embodiments, Ar is phenyl. In some embodiments, Ar is naphthyl. In some embodiments, Ar is indazolyl.

$R^1$ can be —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen. In some embodiments, $R^1$ is methyl, cyclohexyl, methylene, methoxy, or benzyl. In some embodiments, $R^1$ is fluoro or chloro. In some embodiments, $R^1$ is phenyl. In some embodiments, $R^1$ is hydrogen.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with N$R^{16}R^{17}$. In some embodiments, $R^1$ is alkyl substituted with —C(O)N$R^{16}R^{17}$. In some embodiments, $R^1$ is methyl substituted with —C(O)N$R^{16}R^{17}$. In some embodiments, $R^1$ is alkyl substituted with —C(O)O$R^{16}$. In some embodiments, $R^1$ is methyl substituted with COOH.

In some embodiments, m is 1, 2, 3, or 4. In some embodiments, m is 1. In some embodiments, $X^3$ is carbon atom connected to $Q^1$, and m is 1. In some embodiments, n is 1, 2, or 3. In some embodiments, n is 1. In some embodiments, n is 2. In some embodiments, n is 0.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is $C_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

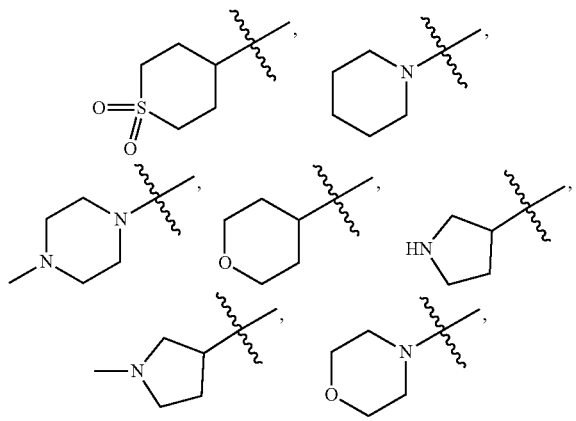

wherein the ring is substituted or unsubstituted. In some embodiments, $R^3$ is H, and $R^4$ is a ring that is

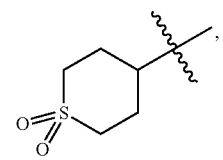 [SMILES: *C1CCS(=O)(=O)CC1]

wherein the ring is substituted or unsubstituted. In some embodiments, $R^3$ is H, and $R^4$ is a ring that is

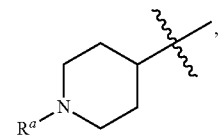

wherein the ring is substituted or unsubstituted. In some embodiments, $R^a$ is alkylene. In some embodiments, $R^a$ is methyl. In some embodiments, $R^3$ is H, and $R^4$ is a ring that is

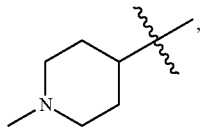 [SMILES: *C1CCN(C)CC1]

wherein the ring is substituted or unsubstituted. In some embodiments, $R^3$ is H, and $R^4$ is a ring that is

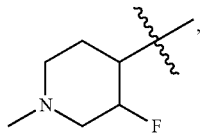 [SMILES: *C1CCN(C)CC1F]

wherein the ring is substituted or unsubstituted. In some embodiments, $R^3$ is H, and R is a ring that is

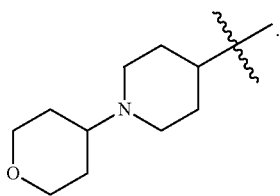 [SMILES: *C1CCN(C2CCOCC2)CC1]

In some embodiments, the disclosure provides a compound of the formula:

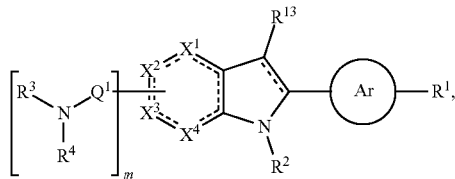

wherein the variables are as defined above.

In some embodiments, the disclosure provides a compound of the formula:

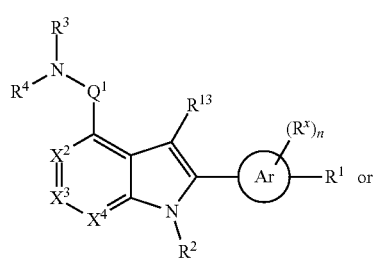

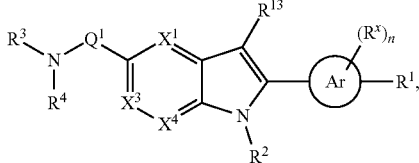

wherein:

$X^1$ is $CR^5$, $CR^5R^6$, N, $NR^5$, O, S, C=O, C=S, or a carbon atom connected to $Q^1$;

$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N, $NR^9$, O, S, C=O, C=S, or a carbon atom connected to $Q^1$;

$X^4$ is $CR^{11}$, $CR^{11}R^{12}$, N, $NR^{11}$, O, S, C=O, C=S, or a carbon atom connected to $Q^1$;

Ar is unsubstituted or substituted aryl;

$Q^1$ is C=O, C=S, C=$CR^{14}R^{15}$, C=$NR^{14}$, alkylene, alkenylene, or alkynylene, each of which is independently substituted or unsubstituted, or a bond;

n is 0, 1, 2, 3, or 4;

each $R^x$ and $R^1$ is independently $C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;

each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted, or hydrogen or halogen;

each $R^{19}$ and $R^{20}$ is —$C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

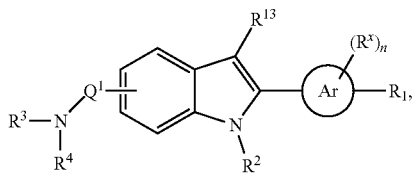

wherein the variables are as defined above.

In some embodiments, Ar is a 6-carbon monocyclic or 10-carbon bicyclic aromatic ring system wherein 0, 1, 2, 3, or 4 atoms of each ring are optionally substituted. In some embodiments, Ar is phenyl. In some embodiments, Ar is naphthyl. In some embodiments, Ar is indazolyl.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with $NR^{16}R^{17}$. In some embodiments, $R^1$ is alkyl substituted with $—C(O)NR^{16}R^{17}$. In some embodiments, $R^1$ is methyl substituted with $—C(O)NR^{16}R^{17}$. In some embodiments, $R^1$ is alkyl substituted with $—C(O)OR^{16}$. In some embodiments, $R^1$ is methyl substituted with COOH.

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is $C_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is $—C(O)R^{19}$, $—C(O)OR^{19}$, alkyl, alkenyl, alkynyl, aryl, heteroaryl, or heterocyclyl, each of which is independently substituted or unsubstituted, or hydrogen, and $R^4$ is $—C(O)R^{19}$, $—C(O)OR^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is $—C(O)R^{19}$, $—C(O)OR^{19}$, $—C(O)NR^{19}R^{20}$, $—SOR^{19}$, $—SO_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

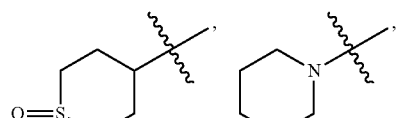

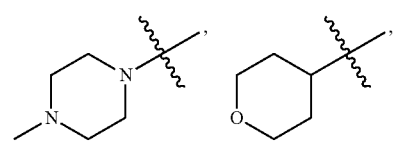

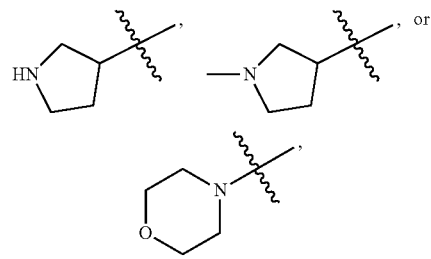

wherein the ring is substituted or unsubstituted. In some embodiments, $R^3$ is H, and $R^4$ is a ring that is

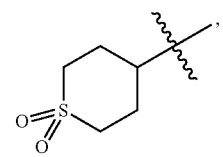

wherein the ring is substituted or unsubstituted. In some embodiments, $R^3$ is H, and $R^4$ is a ring that is

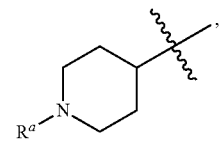

wherein the ring is substituted or unsubstituted. In some embodiments, $R^a$ is alkylene. In some embodiments, $R^a$ is methyl. In some embodiments, $R^3$ is H, and $R^4$ is a ring that is

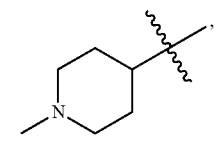 [SMILES: *C1CCN(C)CC1]

wherein the ring is substituted or unsubstituted. In some embodiments, $R^3$ is H, and $R^4$ is a ring that is

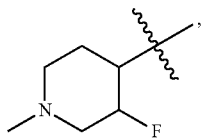 [SMILES: *C1CCN(C)CC1F]

wherein the ring is substituted or unsubstituted. In some embodiments, $R^3$ is H, and $R^4$ is a ring that is

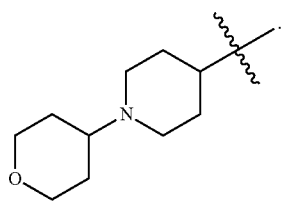 [SMILES: *C1CCN(C2CCOCC2)CC1]

In some embodiments, the disclosure provides a compound of the formula:

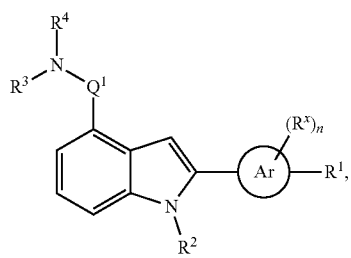

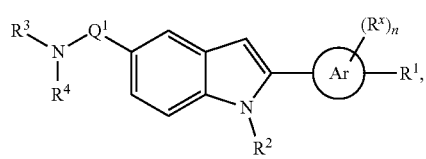

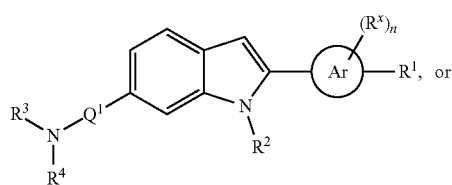

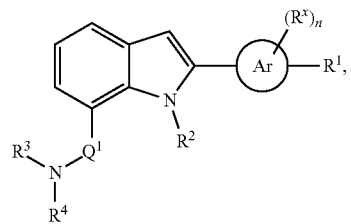

or a pharmaceutically-acceptable salt thereof, wherein the variables are as defined above.

In some embodiments, the disclosure provides a compound of the formula:

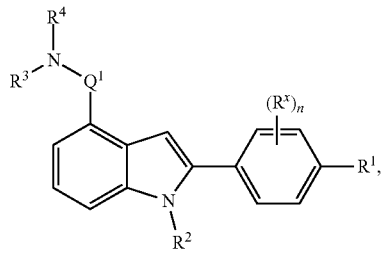

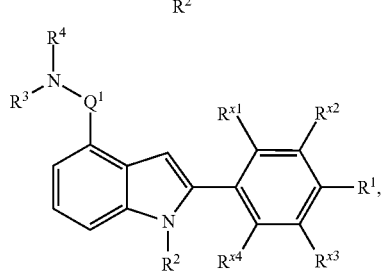

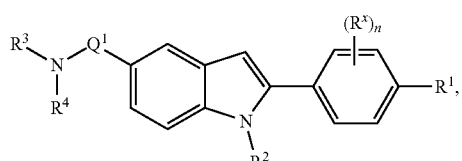

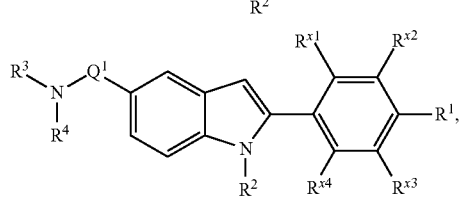

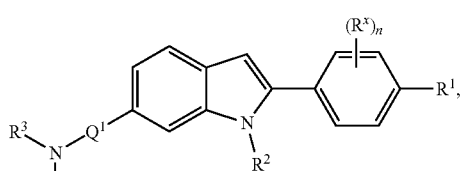

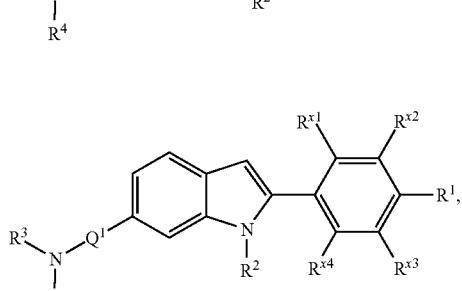

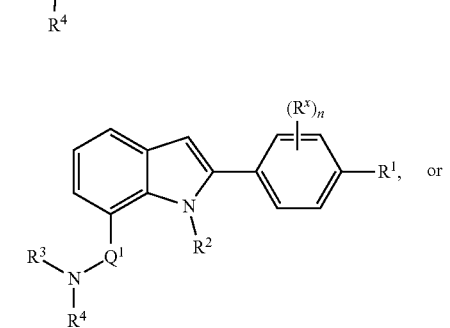

-continued

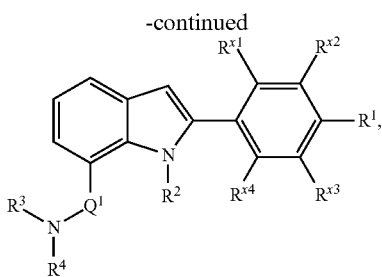

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- each $R^1$, $R^x$, $R^{x1}$, $R^{x2}$, $R^{x3}$, and $R^{x4}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;
- each $R^3$ and $R^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- n is 0, 1, 2, 3, or 4;
- each $R^2$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with NR$^{16}$R$^{17}$. In some embodiments, $R^1$ is methyl substituted with NR$^{16}$R$^{17}$, wherein $R^{16}$ is hydrogen, and $R^{17}$ is alkyl, aryl, heteroaryl, an amino group, a carboxyl group, or an ester group, any of which is substituted or unsubstituted. In some embodiments, $R^1$ is methyl substituted with NR$^{16}$R$^{17}$, wherein $R^{16}$ is hydrogen, and $R^{17}$ is substituted or unsubstituted alkyl, aryl, or heteroaryl. In some embodiments, $R^1$ is methyl substituted with NR$^{16}$R$^{17}$, wherein $R^{16}$ is hydrogen, and $R^{17}$ is substituted or unsubstituted phenyl. In some embodiments, $R^1$ is methyl substituted with NR$^{16}$R$^{17}$, wherein $R^{16}$ is hydrogen, and $R^{17}$ is substituted or unsubstituted pyridinyl.

In some embodiments, $R^1$ is —C(O)NR$^{16}$R$^{17}$. In some embodiments, $R^1$ is —C(O)NR$^{16}$R$^{17}$, wherein $R^{16}$ and $R^{17}$ are hydrogen. In some embodiments, $R^1$ is —C(O)NR$^{16}$R$^{17}$, wherein $R^{16}$ is hydrogen, and $R^{17}$ alkyl. In some embodiments, $R^1$ is —C(O)NR$^{16}$R$^{17}$, wherein $R^{16}$ is hydrogen, and $R^{17}$ methyl. In some embodiments, $R^1$ is —C(O)OR$^{16}$. In some embodiments, $R^1$ is —C(O)OH. In some embodiments, $R^1$ is methyl. In some embodiments, $R^1$ is halogen. In some embodiments, $R^1$ is chloro or fluoro.

In some embodiments, n is 0, 1, 2, or 3. In some embodiments, n is 1. In some embodiments, n is 2. In some embodiments, n is 0.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is C$_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen, and $R^4$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

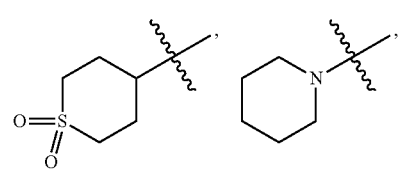

-continued

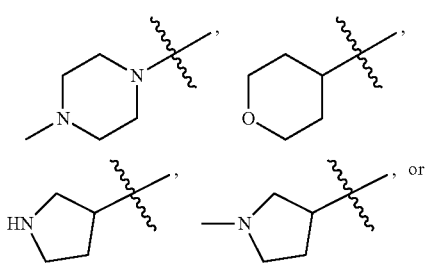

wherein the ring is substituted or unsubstituted. In some embodiments, $R^3$ is H, and $R^4$ is a ring that is

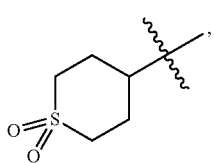

wherein the ring is substituted or unsubstituted. In some embodiments, $R^3$ is H, and $R^4$ is a ring that is

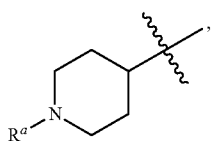

wherein the ring is substituted or unsubstituted. In some embodiments, $R^a$ is alkylene. In some embodiments, $R^a$ is methyl. In some embodiments, $R^3$ is H, and $R^4$ is a ring that is

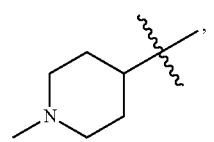 [SMILES: *C1CCN(C)CC1]

wherein the ring is substituted or unsubstituted. In some embodiments, $R^3$ is H, and $R^4$ is a ring that is

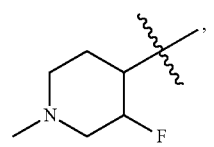 [SMILES: *C1CCN(C)CC1F]

wherein the ring is substituted or unsubstituted. In some embodiments, $R^3$ is H, and $R^4$ is a ring that is

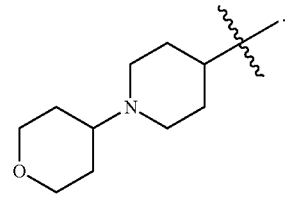 [SMILES: *C1CCN(C2CCOCC2)CC1]

In some embodiments, the disclosure provides a compound of the formula:

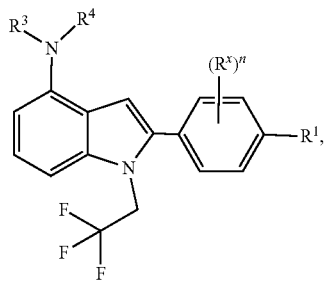

or a pharmaceutically-acceptable salt thereof, wherein the variables are as defined above.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, haloalkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with $NR^{16}R^{17}$. In some embodiments, $R^1$ is methyl substituted with $NR^{16}R^{17}$, wherein $R^{16}$ is hydrogen, and $R^{17}$ is alkyl, aryl, heteroaryl, an amino group, a carboxyl group, or an ester group, any of which is substituted or unsubstituted. In some embodiments, $R^1$ is methyl substituted with $NR^{16}R^{17}$, wherein $R^{16}$ is hydrogen, and $R^{17}$ is substituted or unsubstituted alkyl, aryl, or heteroaryl. In some embodiments, $R^1$ is methyl substituted with $NR^{16}R^{17}$, wherein $R^{16}$ is hydrogen, and $R^{17}$ is substituted or unsubstituted phenyl. In some embodiments, $R^1$ is methyl substituted with $NR^{16}R^{17}$, wherein $R^{16}$ is hydrogen, and $R^{17}$ is substituted or unsubstituted pyridinyl.

In some embodiments, $R^1$ is —C(O)NR$^{16}$R$^{17}$. In some embodiments, $R^1$ is —C(O)NR$^{16}$R$^{17}$, wherein $R^{16}$ and $R^{17}$ are hydrogen. In some embodiments, $R^1$ is —C(O)NR$^{16}$R$^{17}$, wherein $R^{16}$ is hydrogen, and $R^{17}$ alkyl. In some embodiments, $R^1$ is —C(O)NR$^{16}$R$^{17}$, wherein $R^{16}$ is hydrogen, and $R^{17}$ methyl. In some embodiments, $R^1$ is —C(O)OR$^{16}$. In some embodiments, $R^1$ is —C(O)OH. In some embodiments, $R^1$ is methyl. In some embodiments, $R^1$ is halogen. In some embodiments, $R^1$ is chloro or fluoro.

In some embodiments, n is 1, 2, or 3. In some embodiments, n is 1. In some embodiments, n is 2. In some embodiments, n is 0.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^3$ is H, and $R^4$ is a ring that is:

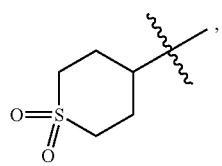 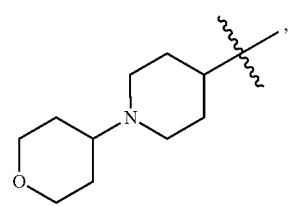

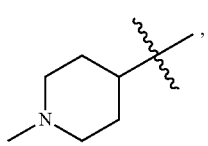

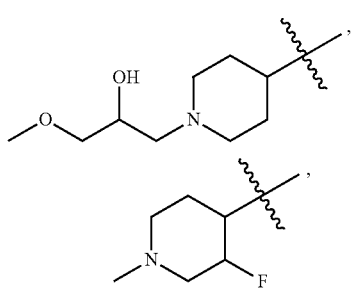 or

In some embodiments, $R^3$ is H, and $R^4$ is a ring that is

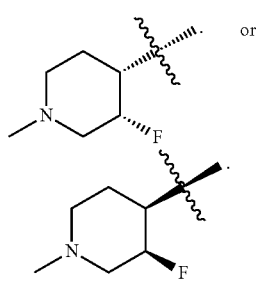

In some embodiments, $R^3$ is H, and $R^4$ is a ring that is

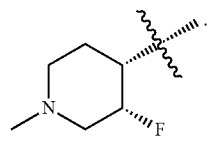 [SMILES: *[C@H]1CCN(C)C[C@H]1F]

Non-limiting examples of compounds of the disclosure include compounds of any of the following formulae:

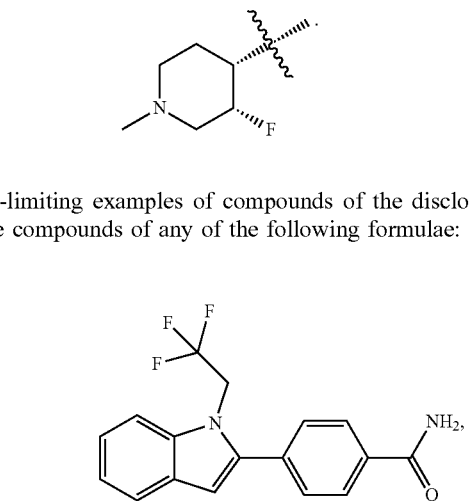

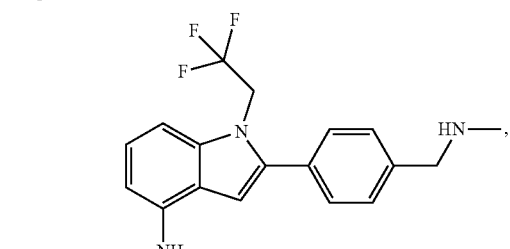

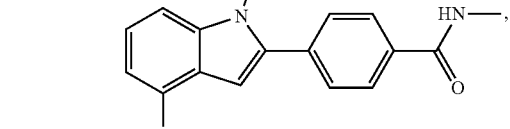

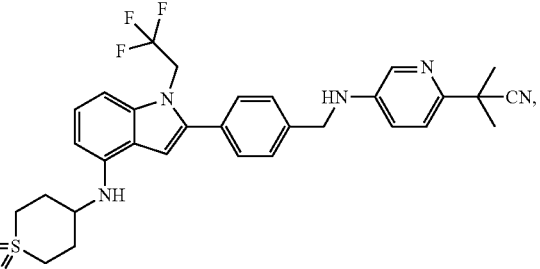

135
-continued
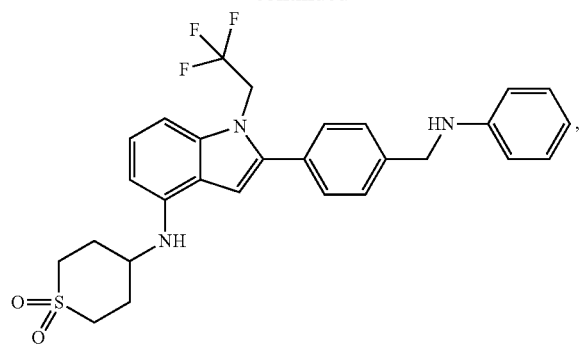
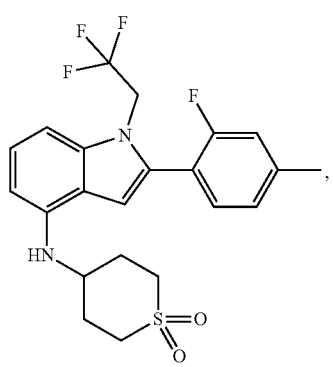
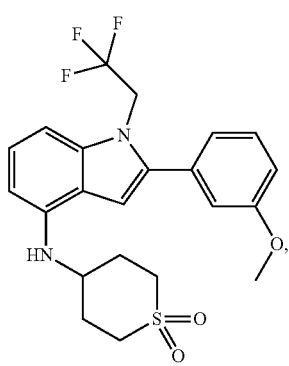
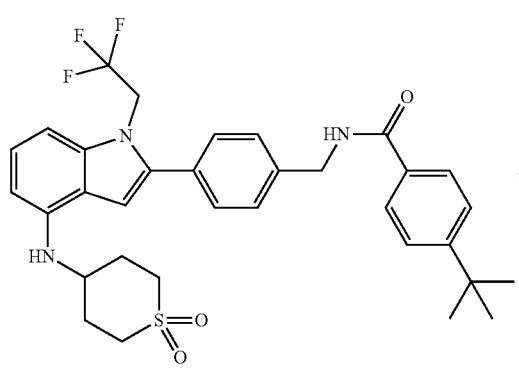
136
-continued
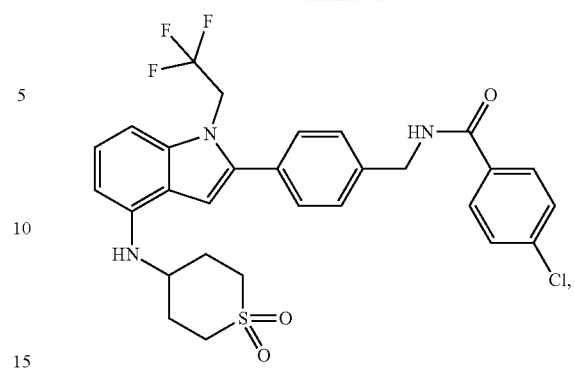
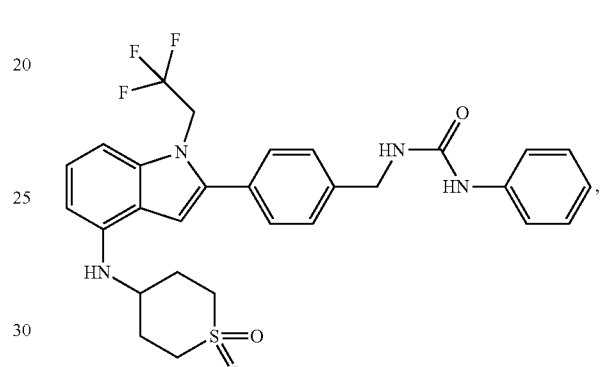
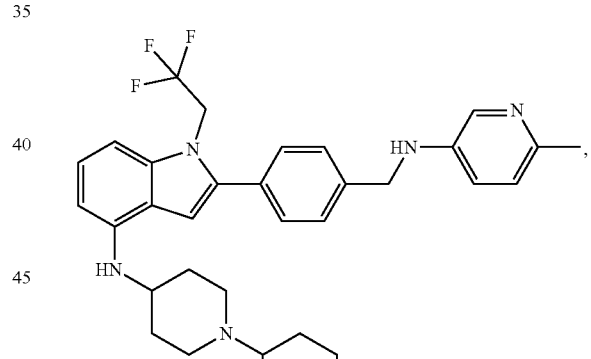
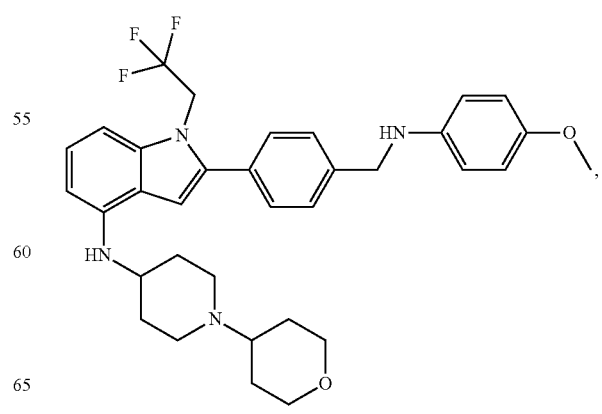

-continued

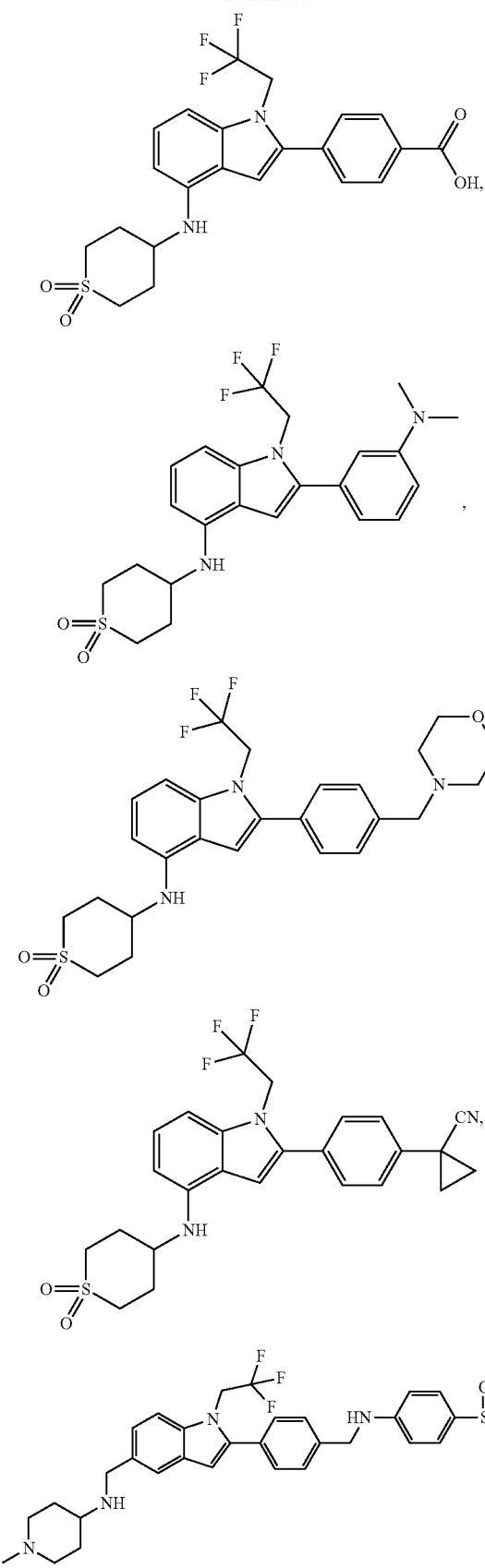

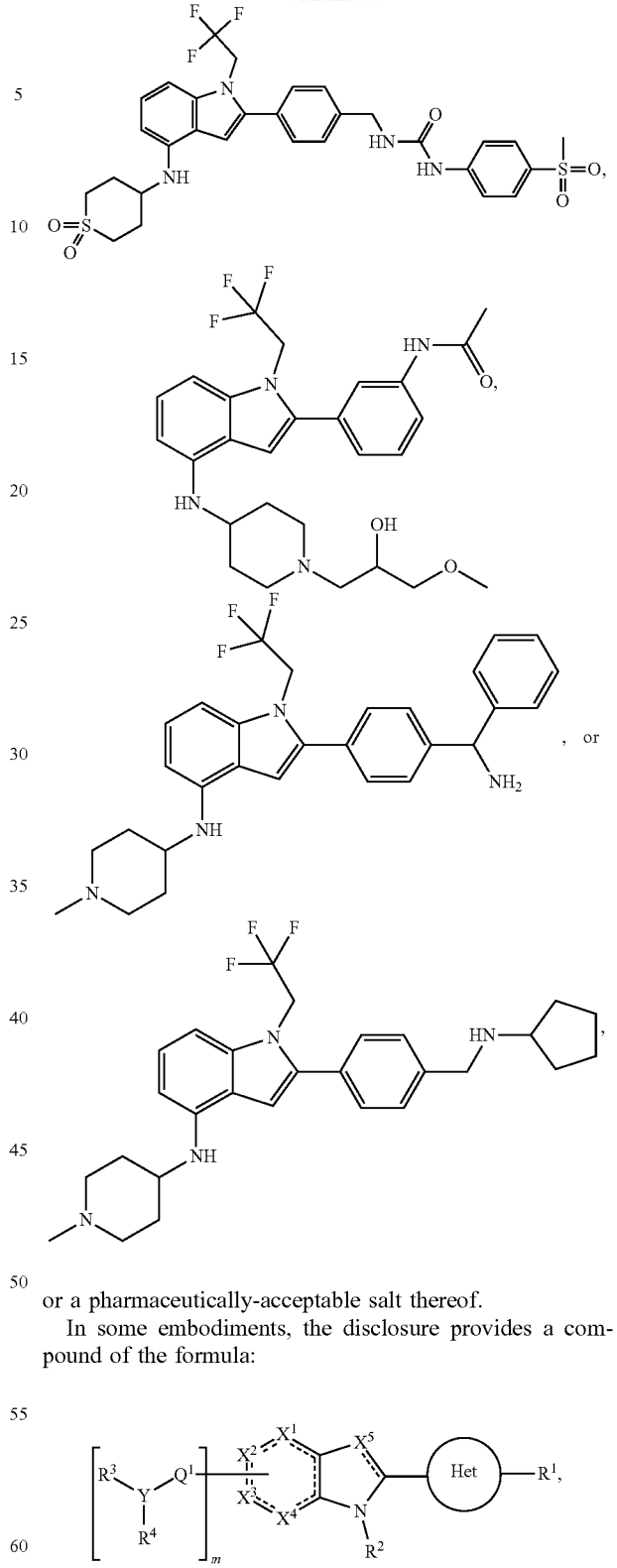

or a pharmaceutically-acceptable salt thereof.

In some embodiments, the disclosure provides a compound of the formula:

$$\left[ R^3 \diagdown_Y \diagdown_{Q^1} \diagdown_{R^4} \right]_m \begin{matrix} X^2 \diagdown X^1 \diagdown X^5 \\ \vdots \\ X^3 \diagdown X^4 \diagdown N \\ R^2 \end{matrix} - \text{Het} - R^1,$$

wherein:

each ======= is independently a single bond or a double bond;

$X^1$ is $CR^5$, $CR^5R^6$, N, $NR^5$, O, S, C=O, C=S, or a carbon atom connected to $Q^1$;

X² is CR⁷, CR⁷R⁸, N, NR⁷, O, S, C=O, C=S, or a carbon atom connected to Q¹;

X³ is CR⁹, CR⁹R¹⁰, N, NR⁹, O, S, C=O, C=S, or a carbon atom connected to Q¹;

X⁴ is CR¹¹, CR¹¹R¹², N, NR¹¹, O, S, C=O, C=S, or a carbon atom connected to Q¹;

X⁵ is CR¹³, N, or NR¹³;

wherein at least one of X¹, X², X³, and X⁴ is a carbon atom connected to Q¹;

Het is substituted or unsubstituted heteroaryl;

Q¹ is C=O, C=S, C=CR¹⁴R¹⁵, C=NR¹⁴, alkylene, alkenylene, or alkynylene, each of which is independently substituted or unsubstituted, or a bond;

m is 1, 2, 3, or 4;

Y is N, O, or absent;

R¹ is —C(O)R¹⁶, —C(O)OR¹⁶, —C(O)NR¹⁶R¹⁷, —OR¹⁶, —SR¹⁶, —NR¹⁶R¹⁷, —NR¹⁶C(O)R¹⁶, —OC(O)R¹⁶, —SiR¹⁶R¹⁷R¹⁸, alkyl, alkenyl, alkynyl, alkoxy, aryl, heteroaryl, heterocyclyl, or halo, each of which is independently substituted or unsubstituted, or hydrogen;

each R³ and R⁴ is independently —C(O)R¹⁹, —C(O)OR¹⁹, —C(O)NR¹⁹R²⁰, —SOR¹⁹, —SO₂R¹⁹, alkyl, alkenyl, alkynyl, aryl, heteroaryl, or heterocyclyl, each of which is independently substituted or unsubstituted, or hydrogen, or R³ and R⁴ together with the nitrogen atom to which R³ and R⁴ are bound form a ring, wherein the ring is substituted or unsubstituted, or R³ is absent;

each R², R⁵, R⁶, R⁷, R⁸, R⁹, R¹⁰, R¹¹, R¹², R¹³, R¹⁴, R¹⁵, R¹⁶, R¹⁷, and R¹⁸ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;

each R¹⁹ and R²⁰ is —C(O)R²³, —C(O)OR²³, —C(O)NR²³R²⁴, —OR²³, —SR²³, —NR²³R²⁴, —NR²³C(O)R²⁴, —OC(O)R²³, alkyl, alkenyl, alkynyl, aryl, heteroaryl, or heterocyclyl, each of which is independently substituted or unsubstituted, or hydrogen or halogen;

each R²¹ and R²² is independently alkyl, alkenyl, alkynyl, aryl, heteroaryl, or heterocyclyl, each of which is independently substituted or unsubstituted, or hydrogen; and each R²³ and R²⁴ is independently alkyl, alkenyl, alkynyl, aryl, heteroaryl, or heterocyclyl, each of which is independently substituted or unsubstituted, or hydrogen, or a pharmaceutically-acceptable salt thereof.

The pattern of dashed bonds can be chosen to provide an aromatic system, for example, an indole, an indolene, a pyrrolopyridine, a pyrrolopyrimidine, or a pyrrolopyrazine. In some embodiments, X¹ is CR⁵, CR⁵R⁶, or a carbon atom connected to Q¹. In some embodiments, X² is CR⁷, CR⁷R⁸, or a carbon atom connected to Q¹. In some embodiments, X³ is CR⁹, CR⁹R¹⁰, or a carbon atom connected to Q¹. In some embodiments, X⁴ is CR¹¹, CR¹¹R¹², or a carbon atom connected to Q¹. In some embodiments, X⁵ is CR¹³, N, or NR¹³. In some embodiments, X¹ is a carbon atom connected to Q¹. In some embodiments, X² is a carbon atom connected to Q¹. In some embodiments, X³ is a carbon atom connected to Q¹. In some embodiments, X⁴ is a carbon atom connected to Q¹. In some embodiments, X⁵ is N.

In some embodiments, Het is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, Het is an aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S. In some embodiments, Het is an aromatic 5-membered, 6-membered, 7-membered, or 8-membered monocyclic ring system comprising 1, 2, or 3 heteroatoms, and the aromatic 5-membered, 6-membered, 7-membered, or 8-membered monocyclic ring system is substituted. In some embodiments, Het is an 8-membered, 9-membered, 10-membered, 11-membered, or 12-membered bicyclic ring system having 1, 2, 3, 4, 5, or 6 heteroatoms, and the 8-membered, 9-membered, 10-membered, 11-membered, or 12-membered bicyclic ring system is substituted.

In some embodiments, Het is pyridinyl, pyrimidinyl, thiadiazolyl, thiazolyl, pyrazolyl, thiophenyl, or oxadiazolyl, each of which is independently substituted or unsubstituted. In some embodiments, Het is 1,3,5-thiadiazol-2-yl. In some embodiments, Het is 1,3,4-oxadiazol-2-yl or 1,2,4-oxadiazol-2-yl. In some embodiments, Het is 1,3,4-oxadiazol-2-yl.

In some embodiments, R¹ is —C(O)R¹⁶, —C(O)OR¹⁶, —C(O)NR¹⁶R¹⁷, —OR¹⁶, —SR¹⁶, —NR¹⁶R¹⁷, —NR¹⁶C(O)R¹⁶, —OC(O)R¹⁶, —SiR¹⁶R¹⁷R¹⁸, alkyl, alkenyl, alkynyl, alkoxy, aryl, heteroaryl, or heterocyclyl, each of which is independently substituted or unsubstituted, or hydrogen. In some embodiments, R¹ is alkyl, alkylene, alkoxy, —NR²¹R²², or aryl, each of which is independently substituted or unsubstituted; halo or hydrogen. In some embodiments, R¹ is methyl, cyclohexyl, methylene, methoxy, or benzyl. In some embodiments, R¹ is fluoro or chloro. In some embodiments, R¹ is phenyl. In some embodiments, R¹ is hydrogen.

In some embodiments, R¹ is a substituted alkyl or alkylene. R¹ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, R¹ is substituted alkyl. In some embodiments, R¹ is alkyl substituted with NR¹⁶R¹⁷. In some embodiments, R¹ is methyl substituted with NR¹⁶R¹⁷, wherein each R¹⁶ and R¹⁷ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, R¹ is methyl substituted with NR¹⁶R¹⁷, wherein R¹⁶ is hydrogen, and R¹⁷ is a substituted carboxyl group.

In some embodiments, m is 1, 2, 3, or 4. In some embodiments, m is 1. In some embodiments, X¹ is carbon atom connected to Q¹, and m is 1. In some embodiments, X² is carbon atom connected to Q¹, and m is 1.

In some embodiments, Q¹ is C=O, C=S, C=CR¹⁴R¹⁵, C=NR¹⁴, alkylene, alkenylene, or alkynylene, each of which is independently substituted or unsubstituted, or a bond. In some embodiments, Q¹ is alkylene, alkenylene, or alkynylene. In some embodiments, Q¹ is C₁-alkylene. In some embodiments, each R¹⁶ and R¹⁷ is independently alkyl, alkenyl, aryl, heteroaryl, heterocyclyl, or hydrogen. In some embodiments, $Q^1$ is a bond.

In some embodiments, $Q^1$ is $C_1$-alkylene, $R^{16}$ is aryl, and $R^{17}$ is alkyl. In some embodiments, $Q^1$ is $C_1$-alkylene, $R^{16}$ is aryl, and $R^{17}$ is hydrogen. In some embodiments, $Q^1$ is $C_1$-alkylene, $R^{16}$ is heteroaryl, and $R^{17}$ is alkyl. In some embodiments, $Q^1$ is $C_1$-alkylene, $R^{16}$ is heteroaryl, and $R^{17}$ is hydrogen. In some embodiments, $Q^1$ is $C_1$-alkylene, $R^{16}$ is substituted heteroaryl, and $R^{17}$ is hydrogen. In some embodiments, $Q^1$ is $C_1$-alkylene, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano.

In some embodiments, $R^2$ is hydrogen or alkyl. In some embodiments, $R^2$ is substituted alkyl. In some embodiments, $R^2$ is trifluoroethyl. In some embodiments, $R^{13}$ is alkyl, alkenyl, hydrogen, or halogen. In some embodiments, $R^{13}$ is methyl, ethyl, propyl, iso-propyl, butyl or tert-butyl. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen; and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

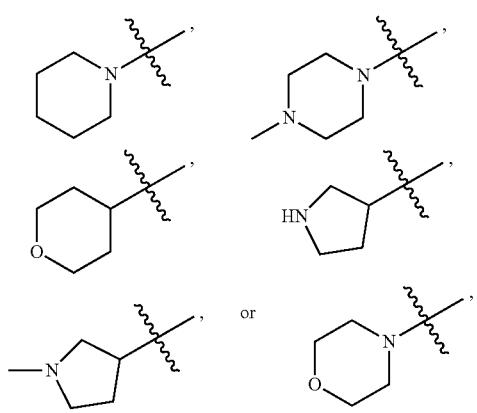

wherein the ring is substituted or unsubstituted. In some embodiments, $R^3$ is H, and $R^4$ is a ring that is

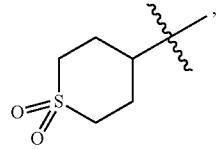 [SMILES: *C1CCS(=O)(=O)CC1]

wherein the ring is substituted or unsubstituted. In some embodiments, $R^3$ is H, and $R^4$ is a ring that is

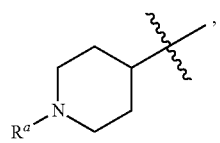

wherein the ring is substituted or unsubstituted. In some embodiments, $R^a$ is alkylene. In some embodiments, $R^a$ is methyl. In some embodiments, $R^3$ is H, and $R^4$ is a ring that is

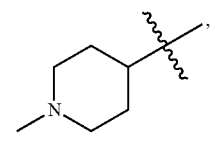 [SMILES: *C1CCN(C)CC1]

wherein the ring is substituted or unsubstituted. In some embodiments, $R^3$ is H, and $R^4$ is a ring that is

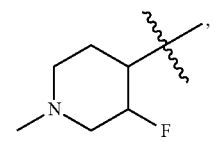 [SMILES: *C1CCN(C)CC1F]

wherein the ring is substituted or unsubstituted.

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.-

In some embodiments, the disclosure provides a compound of the formula:

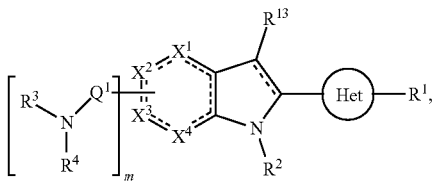

or a pharmaceutically-acceptable salt thereof, wherein the variables are as defined above.

In some embodiments, the disclosure provides a compound of the formula:

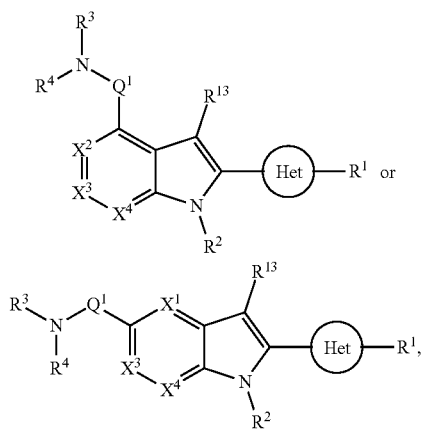

or a pharmaceutically-acceptable salt thereof, wherein the variables are as defined above.

In some embodiments, the compound is of the formula:

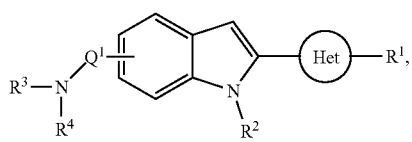

or a pharmaceutically-acceptable salt thereof, wherein the variables are as defined above.

In some embodiments, the disclosure provides a compound of the formula:

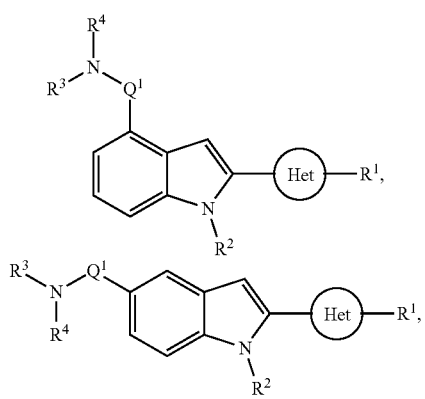

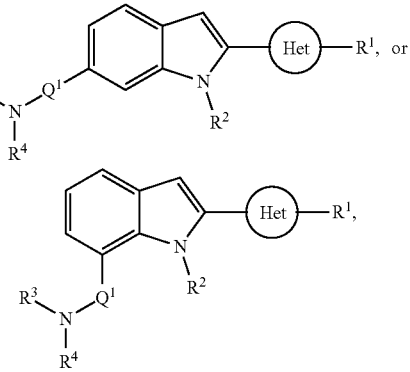

or a pharmaceutically-acceptable salt thereof, wherein the variables are as defined above.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen.

In some embodiments, $R^1$ is substituted alkyl. In some embodiments, $R^1$ is alkyl substituted with N$R^{16}R^{17}$. In some embodiments, $R^1$ is methyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with N$R^{16}R^{17}$, wherein $R^{16}$ is hydrogen, and $R^{17}$ is a substituted carboxyl group.

In some embodiments, $R^2$ is hydrogen or alkyl. In some embodiments, $R^2$ is substituted alkyl. In some embodiments, $R^2$ is trifluoroethyl.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

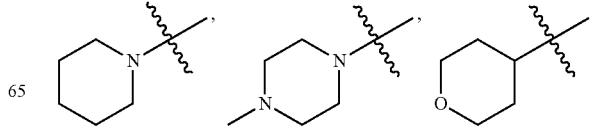

-continued

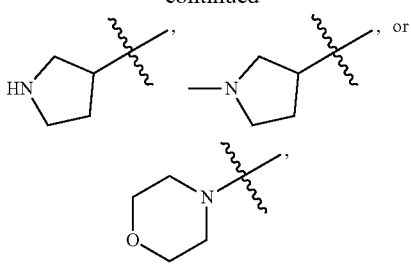

wherein the ring is substituted or unsubstituted. In some embodiments, $R^3$ is H, and $R^4$ is a ring that is

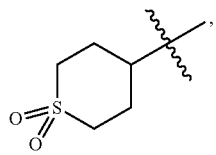

wherein the ring is substituted or unsubstituted. In some embodiments, $R^3$ is H, and $R^4$ is a ring that is

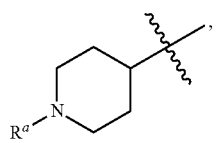

wherein the ring is substituted or unsubstituted. In some embodiments, $R^a$ is alkylene. In some embodiments, $R^a$ is methyl. In some embodiments, $R^3$ is H, and $R^4$ is a ring that is

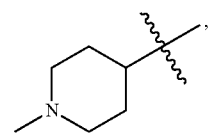 [SMILES: *C1CCN(C)CC1]

wherein the ring is substituted or unsubstituted. In some embodiments, $R^3$ is H, and $R^4$ is a ring that is

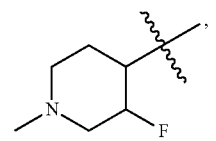 [SMILES: *C1CCN(C)CC1F]

wherein the ring is substituted or unsubstituted.

In some embodiments, the disclosure provides a compound of the formula:

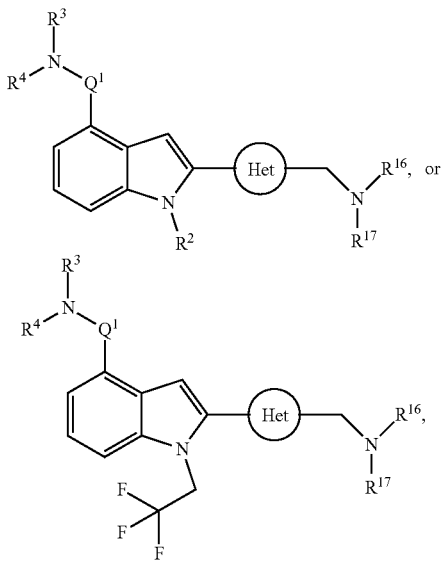

or a pharmaceutically-acceptable salt thereof, wherein the variables are as defined above.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

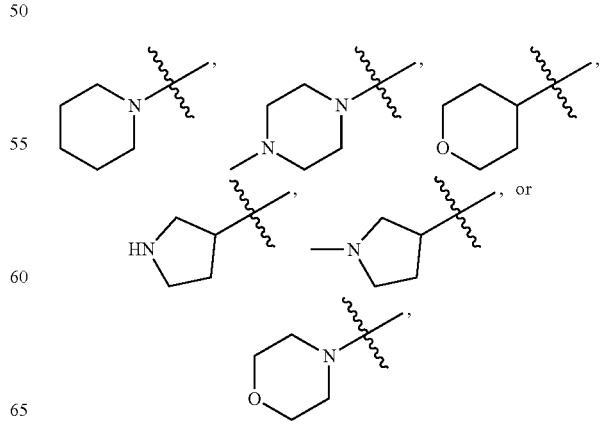

wherein the ring is substituted or unsubstituted. In some embodiments, $R^3$ is H, and $R^4$ is a ring that is

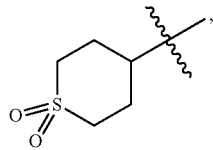 [SMILES: *C1CCS(=O)(=O)CC1]

wherein the ring is substituted or unsubstituted. In some embodiments, $R^3$ is H, and $R^4$ is a ring that is

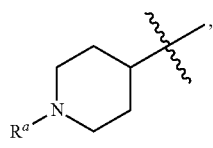

wherein the ring is substituted or unsubstituted. In some embodiments, $R^a$ is alkylene. In some embodiments, $R^a$ is methyl. In some embodiments, $R^3$ is H, and $R^4$ is a ring that is

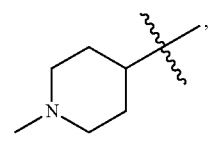 [SMILES: *C1CCN(C)CC1]

wherein the ring is substituted or unsubstituted. In some embodiments, $R^3$ is H, and $R^4$ is a ring that is

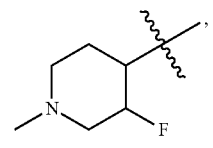 [SMILES: *C1CCN(C)CC1F]

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

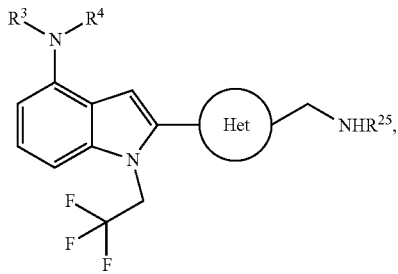

wherein $R^{25}$ is —C(O)$R^{16}$, —C(O)N$R^{16}R^{17}$, alkyl, alkenyl, alkynyl, aryl, heteroaryl, or heterocyclyl, each of which is independently substituted or unsubstituted, or hydrogen. In some embodiments, $R^{25}$ is aryl that is substituted or unsubstituted. In some embodiments, $R^{25}$ is substituted phenyl. In some embodiments, $R^{25}$ is —C(O)$R^{16}$, wherein $R^{16}$ is alkyl, aryl, heteroaryl, or heterocyclyl. In some embodiments, $R^{25}$ is —C(O)$R^{16}$, wherein $R^{16}$ is substituted phenyl; or a pharmaceutically-acceptable salt thereof, In some embodiments, the compound is of the formula:

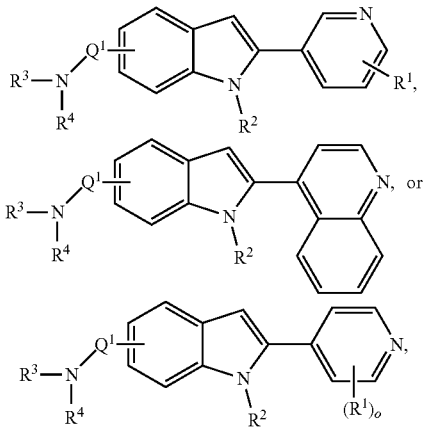

wherein:
$Q^1$ is C=O, C=S, C=C$R^{14}R^{15}$, C=N$R^{14}$, alkylene, alkenylene, or alkynylene, each of which is independently substituted or unsubstituted, or a bond;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

the variables are as defined above, and wherein o is 1, 2, 3, or 4.

In some embodiments, the compound is of the formula:

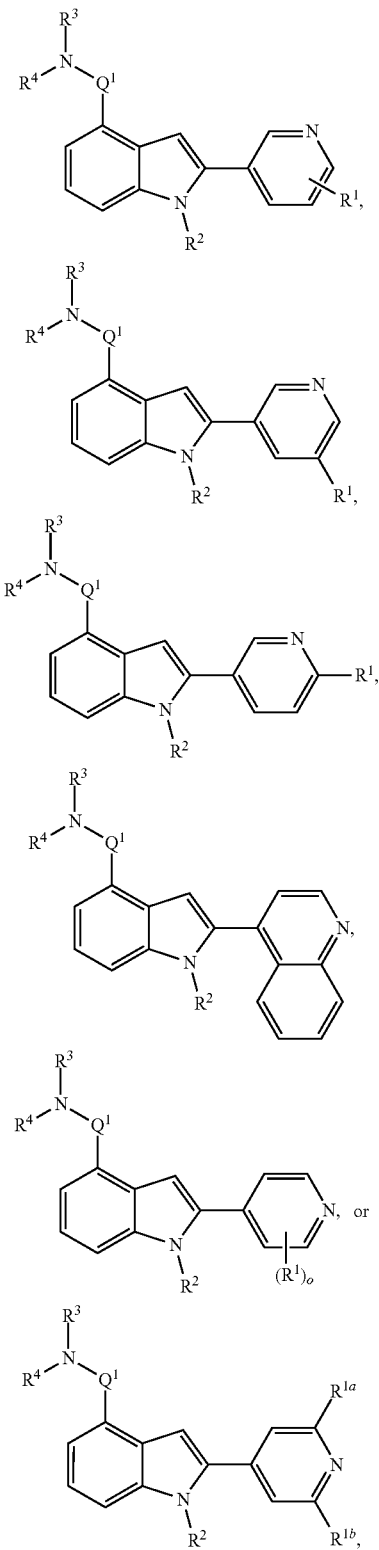

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- each $R^1$, $R^{1a}$, and $R^{1b}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- o is 0, 1, 2, 3, or 4;
- each $R^2$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, each $R^{1a}$ and $R^{1b}$ is independently alkyl, alkoxy, aryl, heteroaryl, heterocyclyl, or NR$^{16}$R$^{17}$. In some embodiments, $R^{1a}$ is unsubstituted phenyl, and $R^{1b}$ is amino.

In some embodiments, the compound is of the formula:

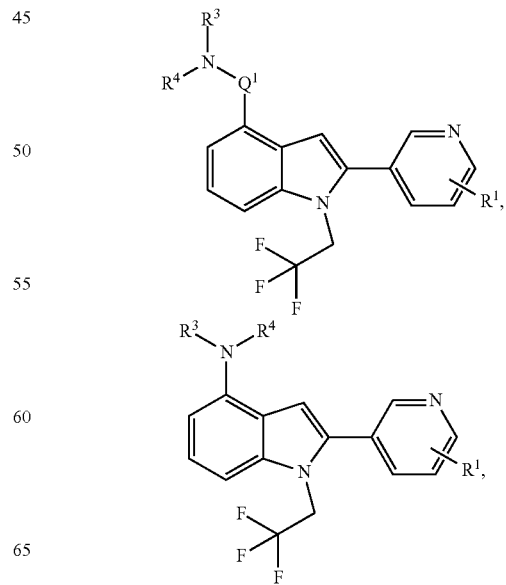

-continued
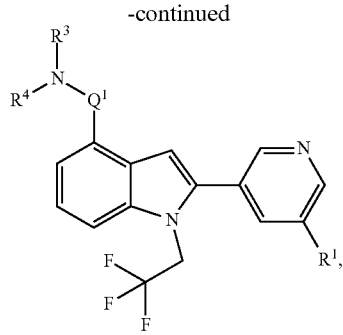
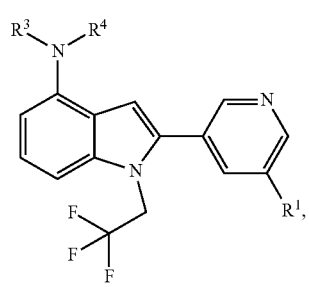
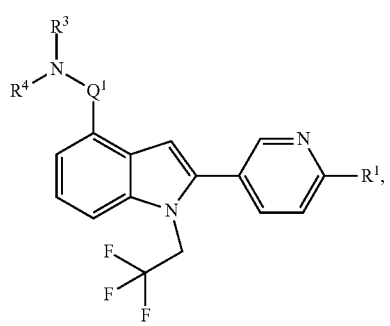
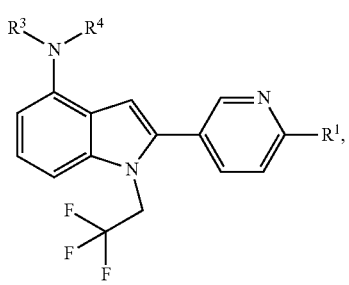
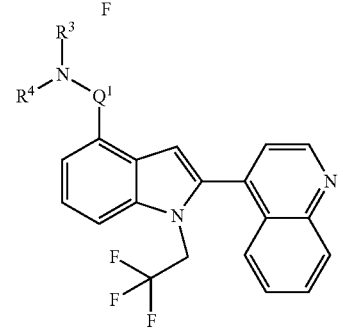
-continued
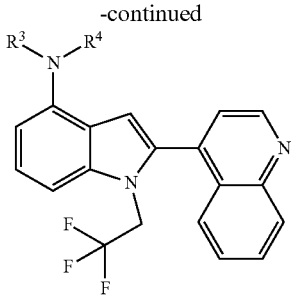
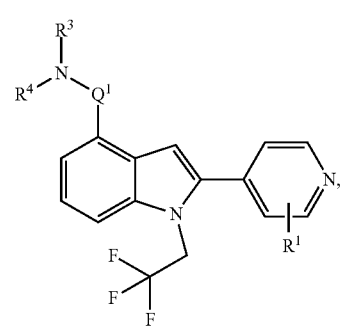
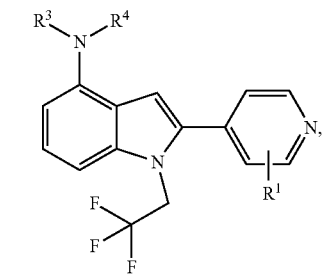
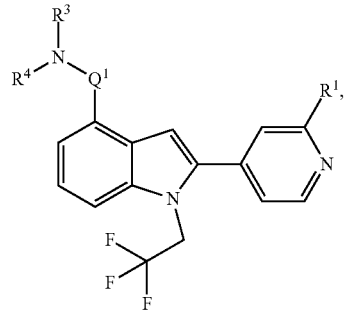
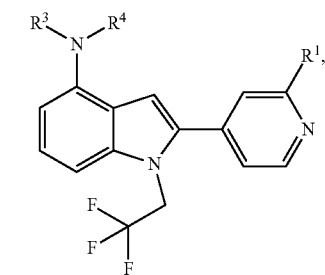

-continued

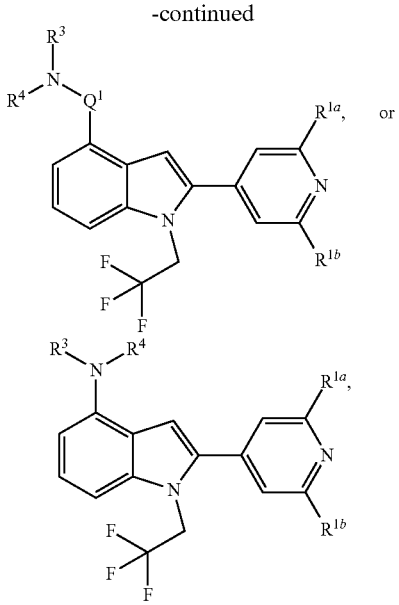

or a pharmaceutically-acceptable salt thereof, wherein the variables are as defined above.

In some embodiments, $R^1$ is —C(O)NR$^{16}$R$^{17}$, alkyl, alkenyl, alkynyl, alkoxy, aryl, heteroaryl, heterocyclyl, or halo, each of which is independently substituted or unsubstituted, or hydrogen. In some embodiments, $R^1$ is alkyl, alkoxy, aryl, or halo. In some embodiments, $R^1$ is methoxy, methyl, or phenyl. In some embodiments, each $R^{1a}$ and $R^{1b}$ is independently alkyl, alkoxy, aryl, heteroaryl, heterocyclyl, or NR$^{16}$R$^{17}$. In some embodiments, $R^{1a}$ is unsubstituted phenyl, and $R^{1b}$ is amino.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

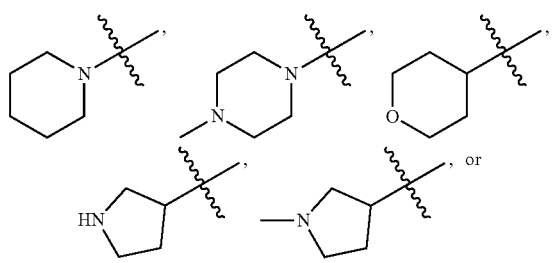

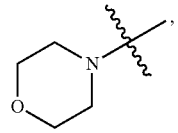

wherein the ring is substituted or unsubstituted. In some embodiments, $R^3$ is H, and $R^4$ is a ring that is

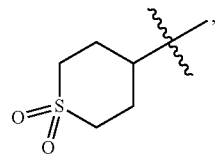 [SMILES: *C1CCS(=O)(=O)CC1]

wherein the ring is substituted or unsubstituted. In some embodiments, $R^3$ is H, and $R^4$ is a ring that is

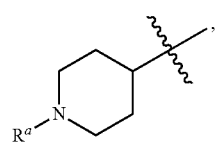

wherein the ring is substituted or unsubstituted. In some embodiments, $R^a$ is alkylene. In some embodiments, $R^a$ is methyl. In some embodiments, $R^3$ is H, and $R^4$ is a ring that is

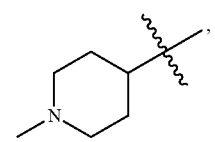 [SMILES: *C1CCN(C)CC1]

wherein the ring is substituted or unsubstituted. In some embodiments, $R^3$ is H, and $R^4$ is a ring that is

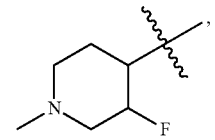

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

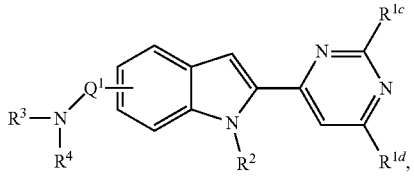

wherein:
- $Q^1$ is C=O, C=S, $C=CR^{14}R^{15}$, $C=NR^{14}$, alkylene, alkenylene, or alkynylene, each of which is independently substituted or unsubstituted, or a bond;
- each $R^{1c}$ and $R^{1d}$ is independently —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- each $R^2$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, each $R^{1c}$ and $R^{1d}$ is independently —O$R^{16}$, —N$R^{16}R^{17}$, —N$R^{16}$C(O)$R^{16}$, alkyl, alkenyl, alkynyl, alkoxy, aryl, heteroaryl, or heterocyclyl, each of which is independently substituted or unsubstituted, or hydrogen. In some embodiments, the compound is of the formula:

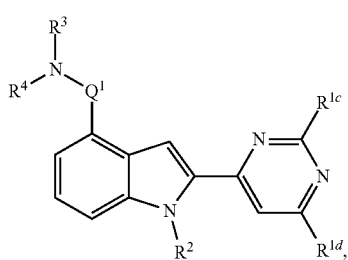

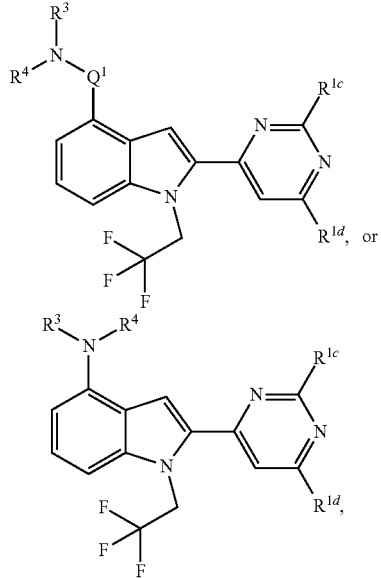

or a pharmaceutically-acceptable salt thereof, wherein the variables are as defined above.

In some embodiments, each $R^{1c}$ and $R^{1d}$ is independently C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^{1c}$ is amino, and $R^{1d}$ is phenyl. In some embodiments, $R^{1c}$ is amino, and $R^{1d}$ is cycloalkenyl.

In some embodiments, the compound is of the formula:

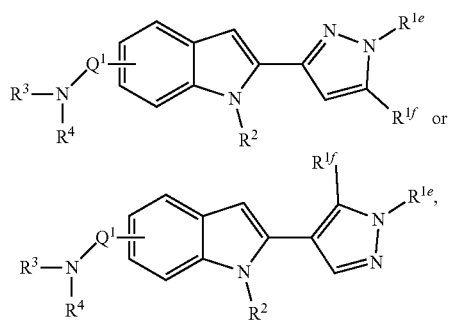

wherein:
- $Q^1$ is C=O, C=S, $C=CR^{14}R^{15}$, $C=NR^{14}$, alkylene, alkenylene, or alkynylene, each of which is independently substituted or unsubstituted, or a bond;
- each $R^{1e}$ and $R^{1f}$ is independently —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

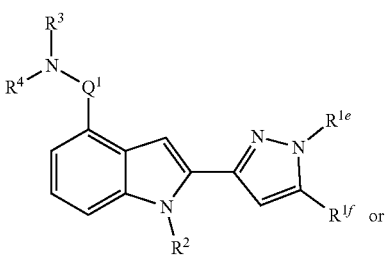

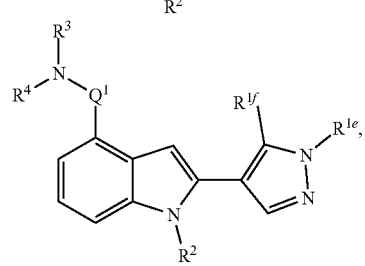

or a pharmaceutically-acceptable salt thereof, wherein the variables are as defined above.

In some embodiments, the compound is of the formula:

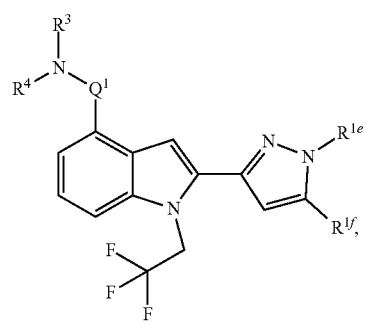

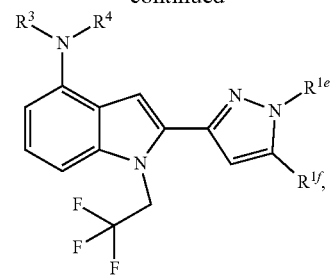

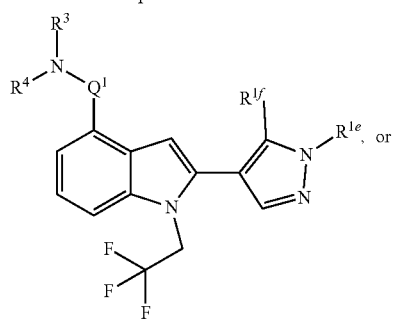

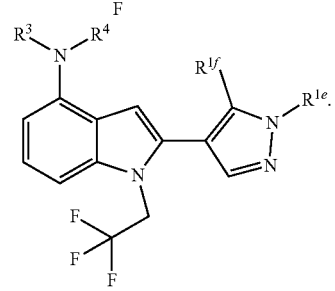

or a pharmaceutically-acceptable salt thereof, wherein the variables are as defined above.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

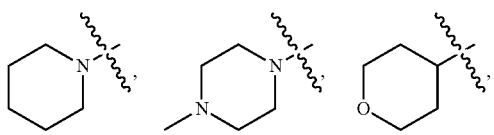

-continued

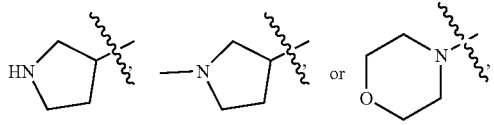

wherein the ring is substituted or unsubstituted. In some embodiments, $R^3$ is H, and $R^4$ is a ring that is

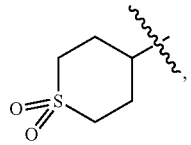

wherein the ring is substituted or unsubstituted. In some embodiments, $R^3$ is H, and $R^4$ is a ring that is

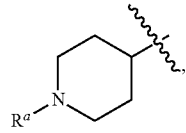

wherein the ring is substituted or unsubstituted. In some embodiments, $R^a$ is alkylene. In some embodiments, $R^a$ is methyl. In some embodiments, $R^3$ is H, and $R^4$ is a ring that is

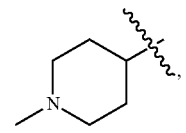

wherein the ring is substituted or unsubstituted. In some embodiments, $R^3$ is H, and $R^4$ is a ring that is

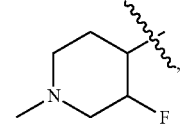

wherein the ring is substituted or unsubstituted.

In some embodiments, each $R^{1e}$ and $R^{1f}$ is independently alkyl, $NR^{16}R^{17}$, aryl, heteroaryl, or heterocyclyl, each of which is independently substituted or unsubstituted, or hydrogen. In some embodiments, $R^{1e}$ is substituted alkyl, and $R^{1f}$ is hydrogen. In some embodiments, $R^{1e}$ is hydrogen, and $R^{1f}$ is $NR^{16}R^{17}$, wherein each $R^{16}$ and $R^{17}$ is independently alkyl, alkenyl, aryl, heteroaryl, or heterocyclyl, each of which is independently substituted or unsubstituted, or hydrogen. In some embodiments, $R^{1e}$ is hydrogen, and $R^{1f}$ is $NR^{16}R^{17}$, wherein $R^{16}$ is hydrogen, and $R^{17}$ is alkyl. In some embodiments, $R^{1e}$ is hydrogen, and $R^{1f}$ is $NR^{16}R^{17}$, wherein $R^{16}$ is hydrogen, and $R^{17}$ is phenyl. In some embodiments, $R^{1e}$ is hydrogen, and $R^{1f}$ is amino.

In some embodiments, the compound is of the formula:

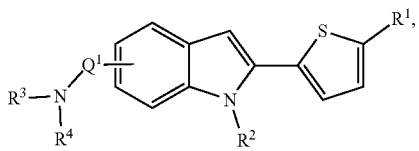

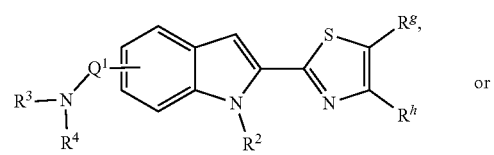

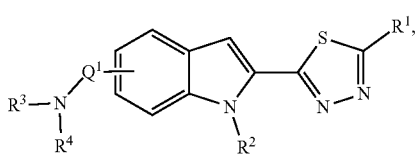

wherein:
Q$^1$ is C═O, C═S, C═CR$^{14}$R$^{15}$, C═NR$^{14}$, alkylene, alkenylene, or alkynylene, each of which is independently substituted or unsubstituted, or a bond;

each R$^1$, R$^{1g}$, and R$^{1h}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

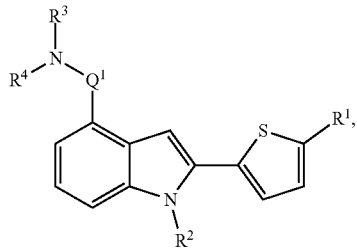

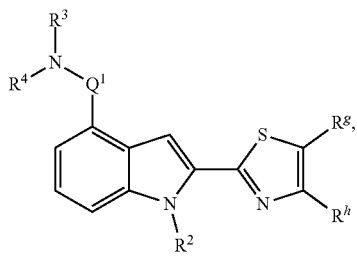

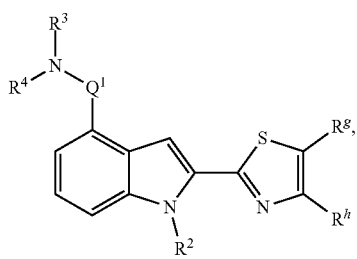

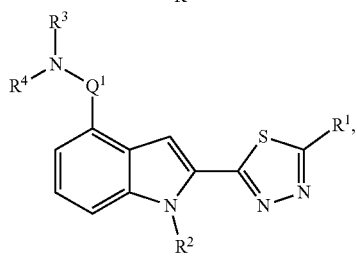

or a pharmaceutically-acceptable salt thereof, wherein the variables are as defined above.

In some embodiments, the compound is of the formula:

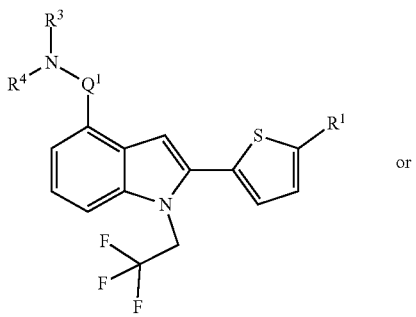

or

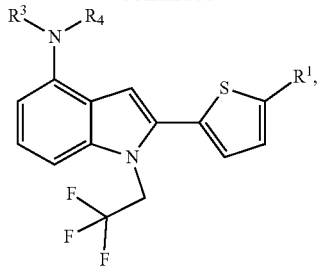

or a pharmaceutically-acceptable salt thereof, wherein the variables are as defined above.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

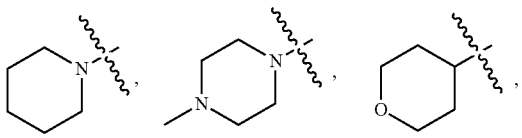

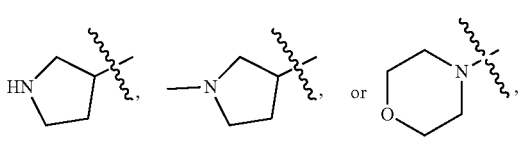

wherein the ring is substituted or unsubstituted. In some embodiments, $R^3$ is H, and $R^4$ is a ring that is

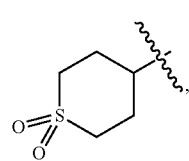

wherein the ring is substituted or unsubstituted. In some embodiments, $R^3$ is H, and $R^4$ is a ring that is

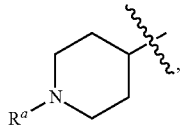

wherein the ring is substituted or unsubstituted. In some embodiments, $R^a$ is alkylene. In some embodiments, $R^a$ is methyl. In some embodiments, $R^3$ is H, and $R^4$ is a ring that is

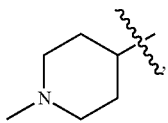

wherein the ring is substituted or unsubstituted. In some embodiments, $R^3$ is H, and $R^4$ is a ring that is

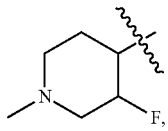

wherein the ring is substituted or unsubstituted.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^1$ is substituted alkyl. In some embodiments, $R^1$ is alkyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group. In some embodiments, $R^{16}$ is hydrogen, and $R^{17}$ is carboxyl substituted with alkyl or aryl. In some embodiments, $R^{16}$ is hydrogen, and $R^{17}$ is carboxyl substituted with cycloalkyl or phenyl. In some embodiments, $R^{16}$ and $R^{17}$ are hydrogen.

In some embodiments, the compound is of the formula:

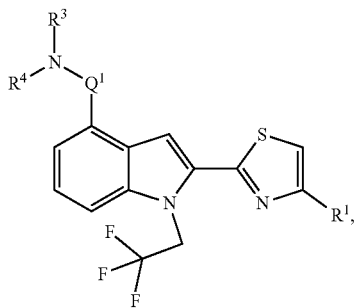

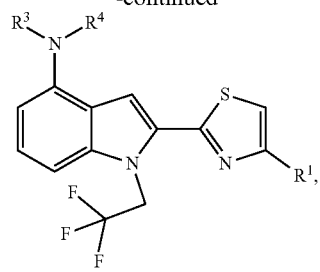

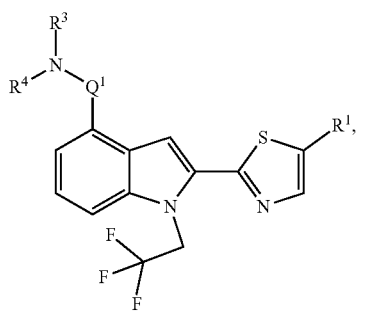

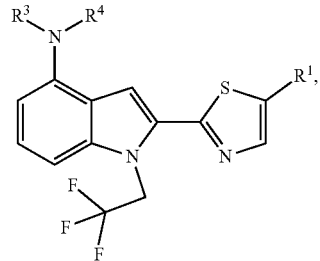

or a pharmaceutically-acceptable salt thereof, wherein the variables are as defined above.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^1$ is substituted alkyl. In some embodiments, $R^1$ is alkyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group. In some embodiments, $R^{16}$ is hydrogen, and $R^{17}$ is carboxyl substituted with alkyl or aryl. In some embodiments, $R^{16}$ is hydrogen, and $R^{17}$ is carboxyl substituted with cycloalkyl or phenyl. In some embodiments, $R^{16}$ and $R^{17}$ are hydrogen.

In some embodiments, the compounds if of the formula:

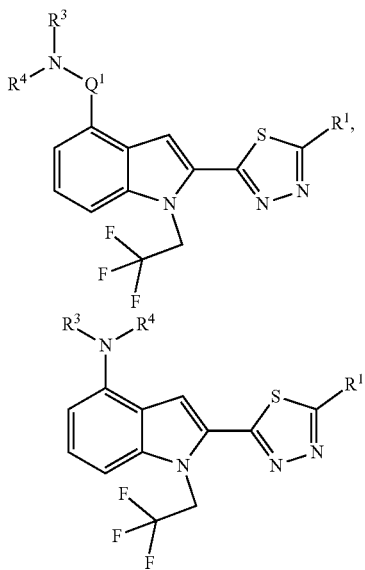

or

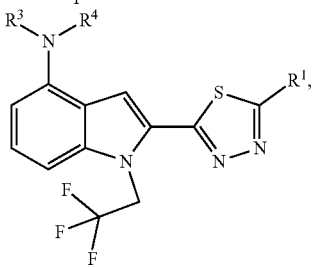

or a pharmaceutically-acceptable salt thereof, wherein the variables are as defined above.

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

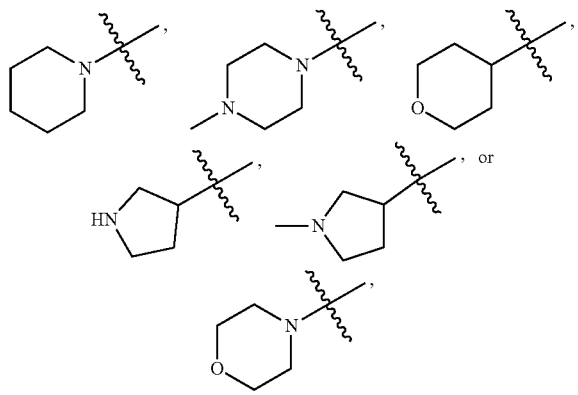

wherein the ring is substituted or unsubstituted. In some embodiments, $R^3$ is H, and $R^4$ is a ring that is

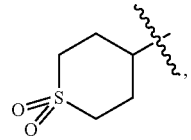

wherein the ring is substituted or unsubstituted. In some embodiments, $R^3$ is H, and $R^4$ is a ring that is

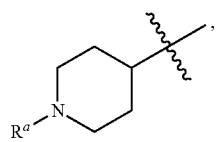

wherein the ring is substituted or unsubstituted. In some embodiments, $R^a$ is alkylene. In some embodiments, $R^a$ is methyl. In some embodiments, $R^3$ is H, and $R^4$ is a ring that is

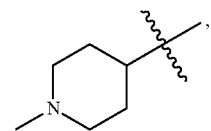 [SMILES: *C1CCN(C)CC1]

wherein the ring is substituted or unsubstituted. In some embodiments, $R^3$ is H, and $R^4$ is a ring that is

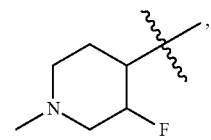 [SMILES: *C1CCN(C)CC1F]

wherein the ring is substituted or unsubstituted.

In some embodiments, $R^1$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments $R^1$ is substituted alkyl. In some embodiments, $R^1$ is alkyl substituted with $NR^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is aryl, heteroaryl, carboxyl, or hydrogen. In some embodiments, $R^{16}$ is hydrogen, and $R^{17}$ is carboxyl substituted with aryl, heteroaryl, cycloalkyl, or alkyl. In some embodiments, $R^{16}$ and $R^{17}$ are hydrogen.

In some embodiments, the compound is of the formula:

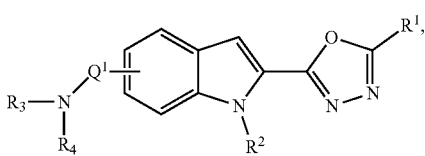

-continued

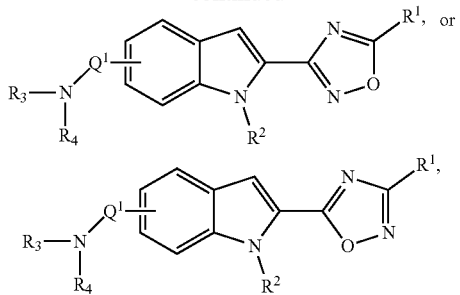

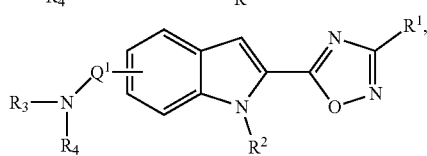

wherein:
- $Q^1$ is C=O, C=S, C=$CR^{14}R^{15}$, C=$NR^{14}$, alkylene, alkenylene, or alkynylene, each of which is independently substituted or unsubstituted, or a bond;
- $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- each $R^2$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

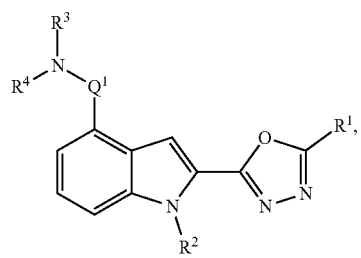

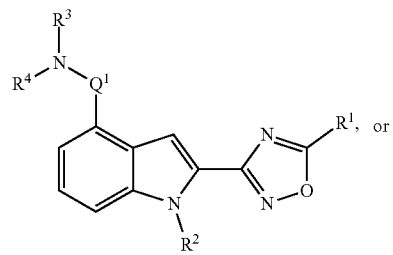

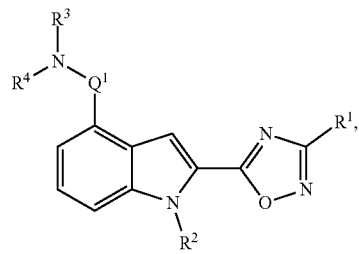

or a pharmaceutically-acceptable salt thereof, wherein the variables are as defined above.

In some embodiments, the compound is of the formula:

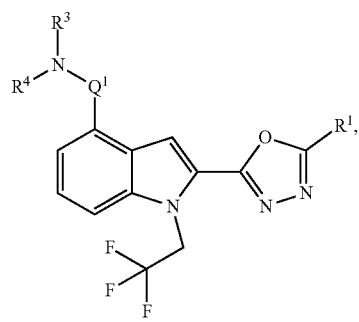

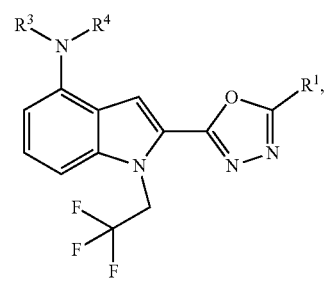

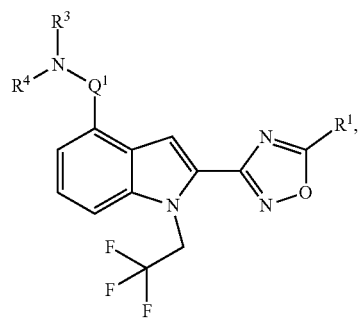

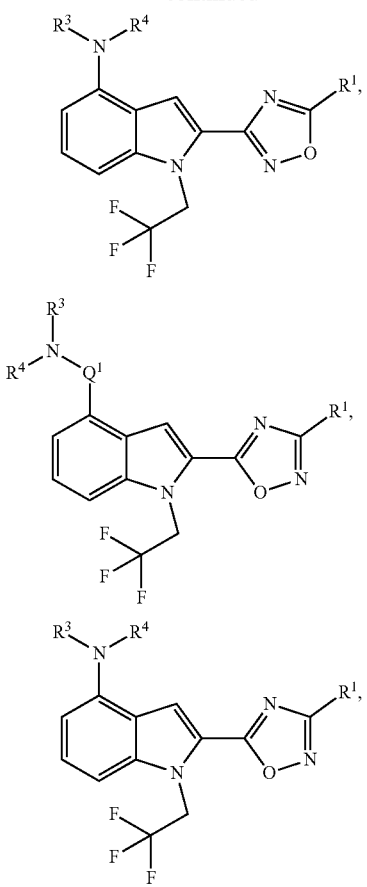

or a pharmaceutically-acceptable salt thereof, wherein the variables are as defined above.

In some embodiments, the compound is of the formula:

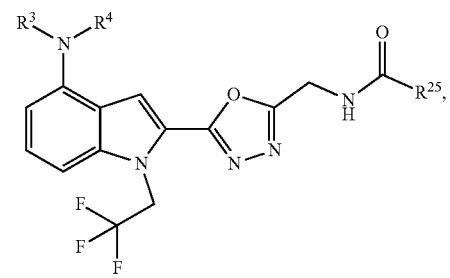

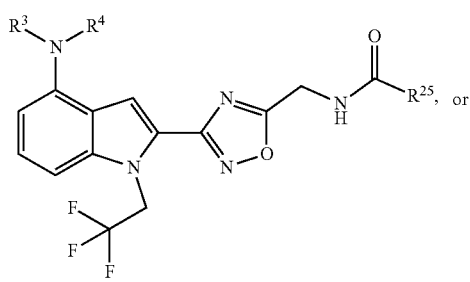

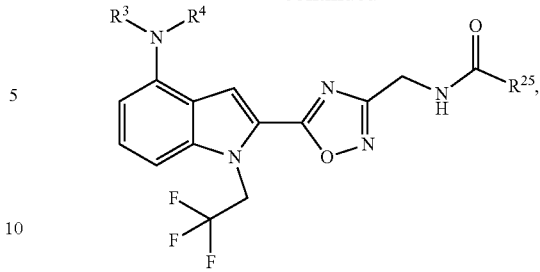

wherein:

Q$^1$ is C=O, C=S, C=CR$^{14}$R$^{15}$, C=NR$^{14}$, alkylene, alkenylene, or alkynylene, each of which is independently substituted or unsubstituted, or a bond;

each R$^{1c}$ and R$^{1d}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

each R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, R$^{25}$ is alkyl, alkenyl, alkynyl, aryl, heteroaryl, or heterocyclyl, each of which is independently substituted or unsubstituted, or hydrogen;

or a pharmaceutically-acceptable salt thereof.

In some embodiments, R$^{25}$ is heterocyclyl, cycloalkyl, aryl, each of which is substituted or unsubstituted. In some embodiments, R$^{25}$ is phenyl or cyclopropyl, each of which is substituted or unsubstituted. In some embodiments, R$^{25}$ is substituted cyclopropyl. In some embodiments, R$^{25}$ is heteroaryl or heterocyclyl, each of which is substituted or unsubstituted. In some embodiments, R$^{25}$ is thiophenyl, indolenyl, or pyrrolyl, each of which is substituted or unsubstituted.

Non-limiting examples of compounds of the disclosure include compounds of any of the following formulae:
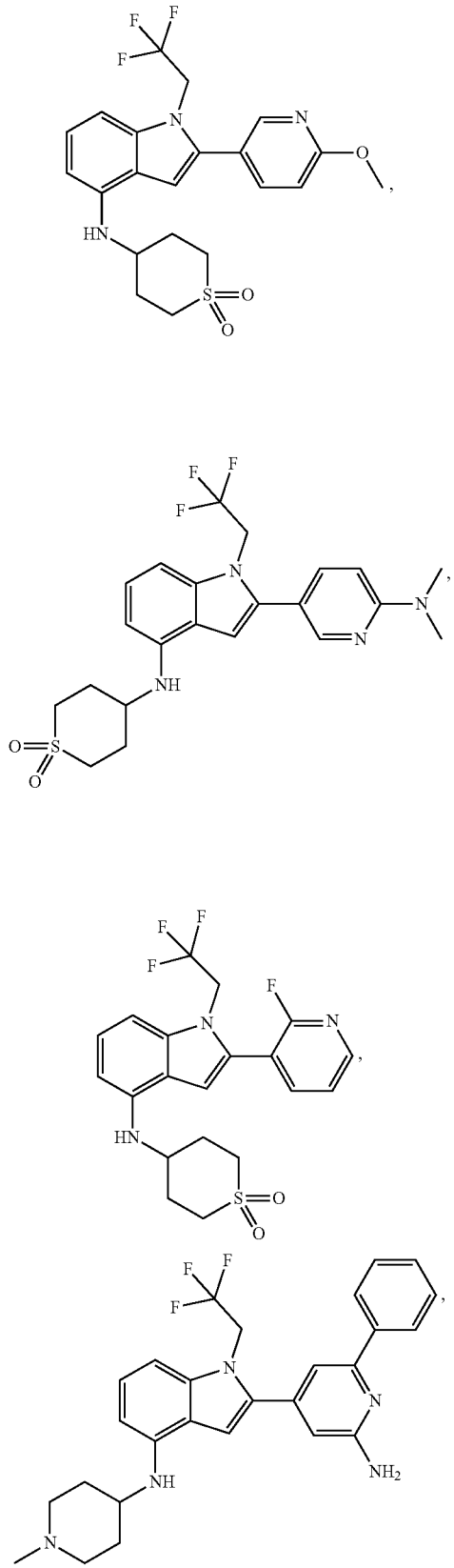
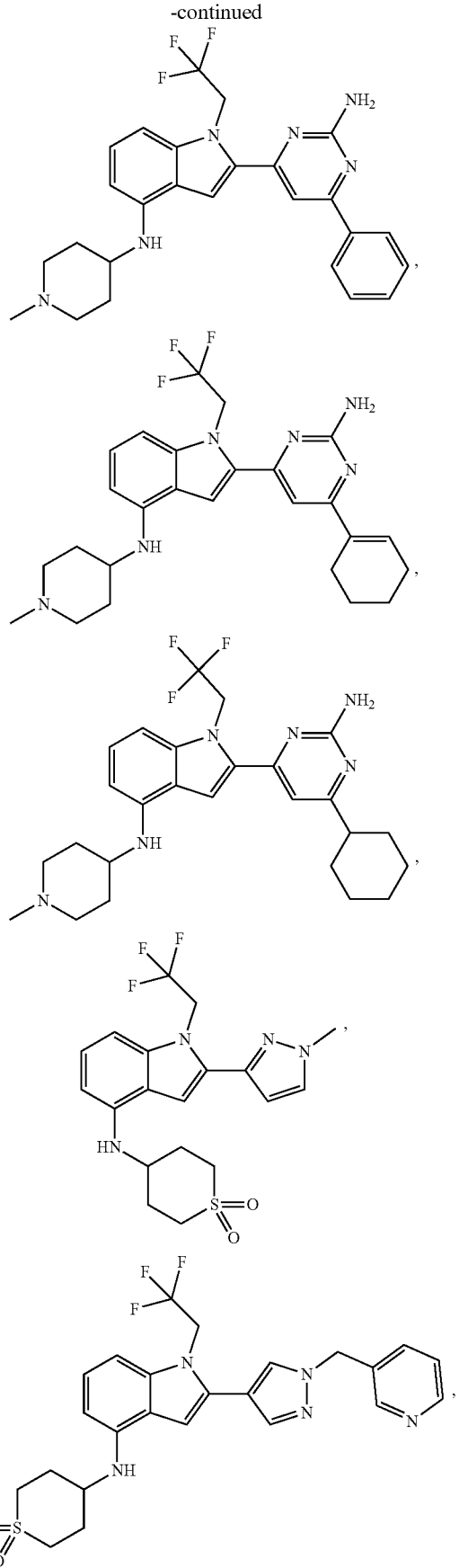

173
-continued
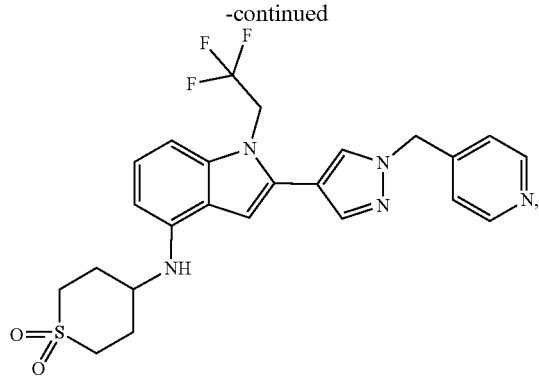
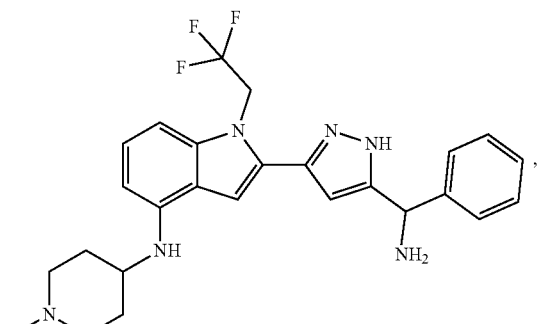
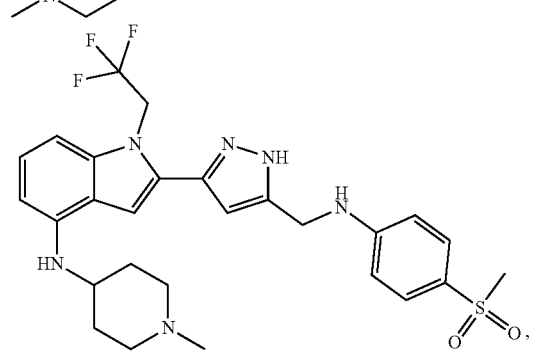
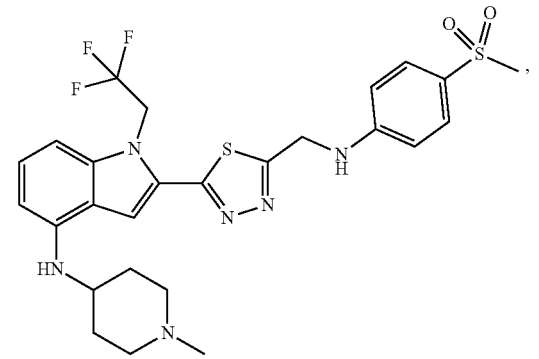
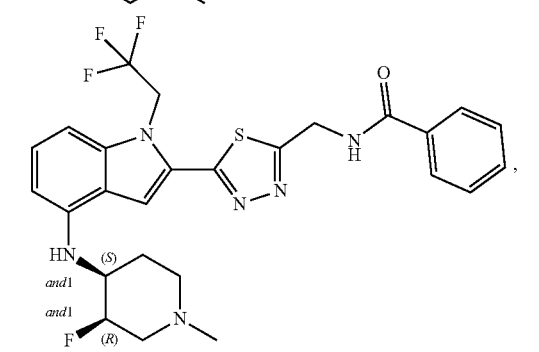
174
-continued
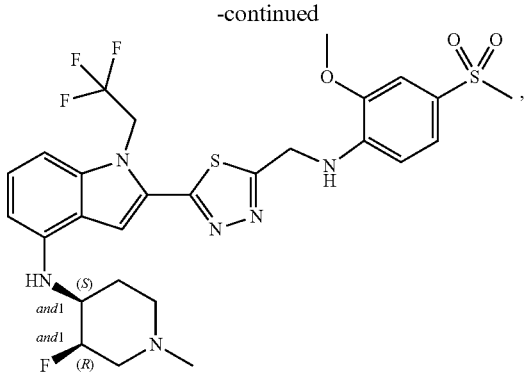
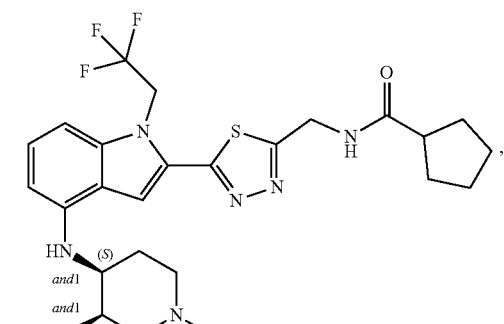
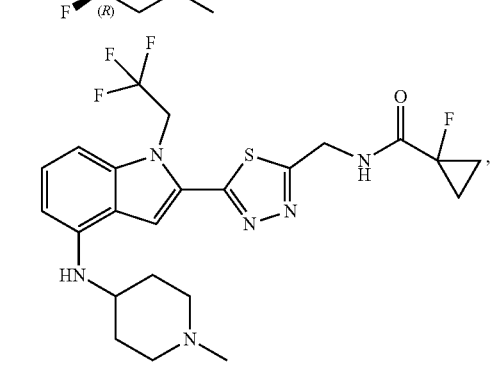
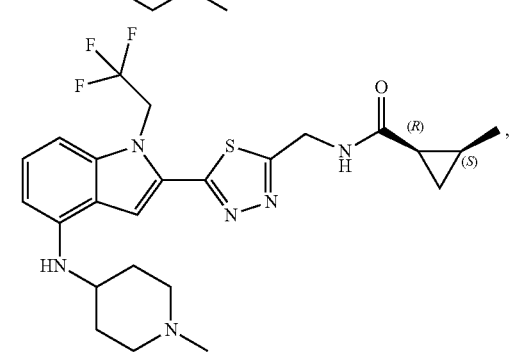
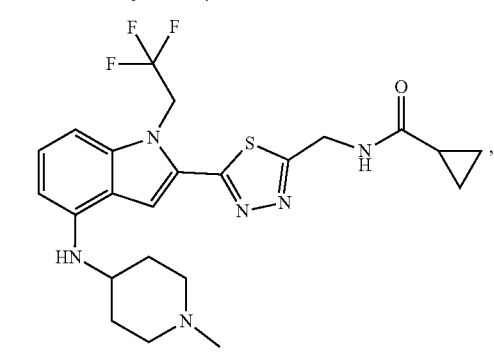

175
-continued
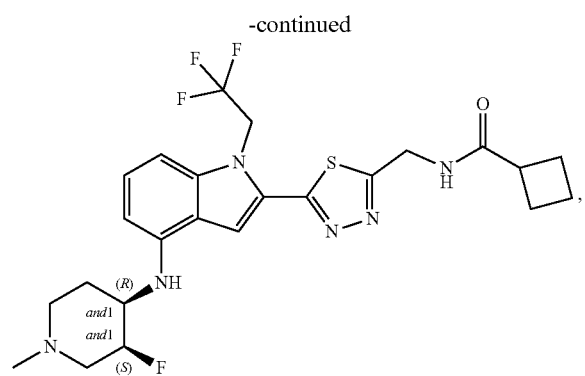
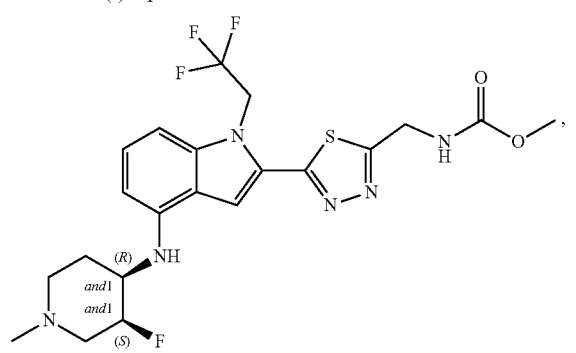
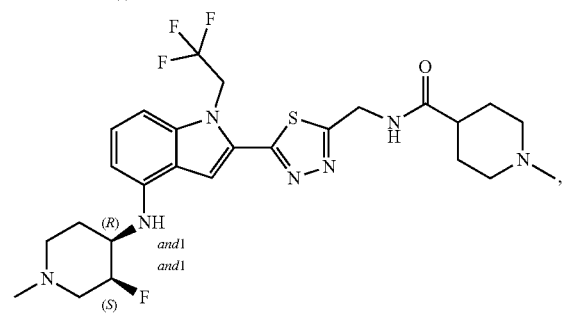
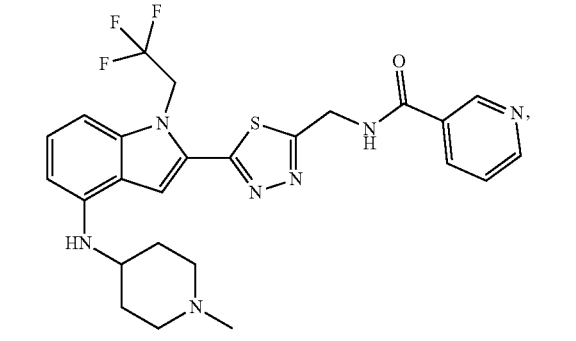
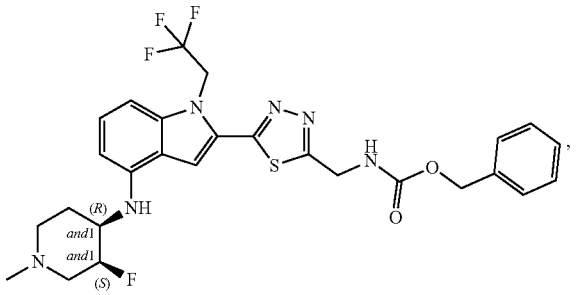
176
-continued
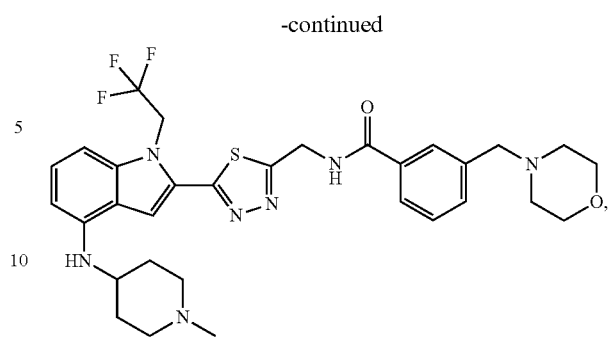
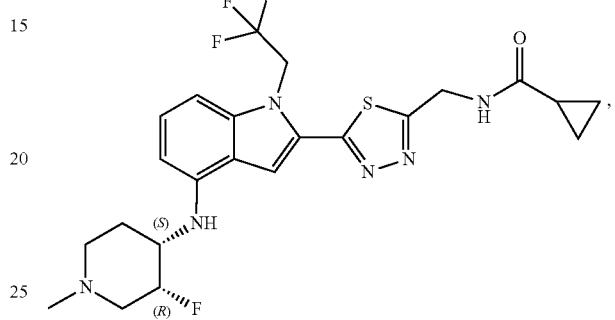
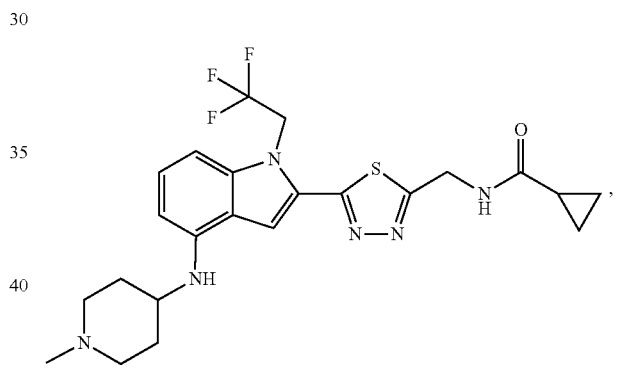
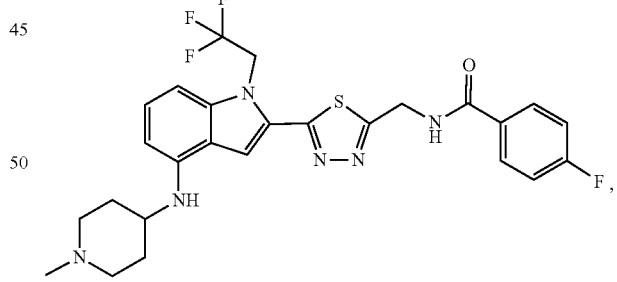
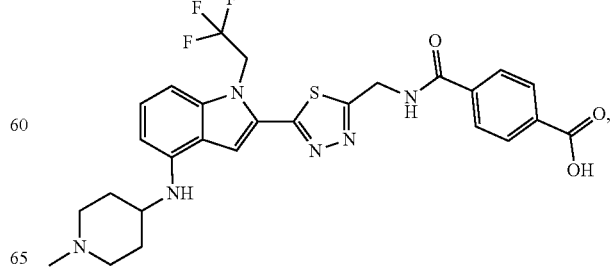

-continued
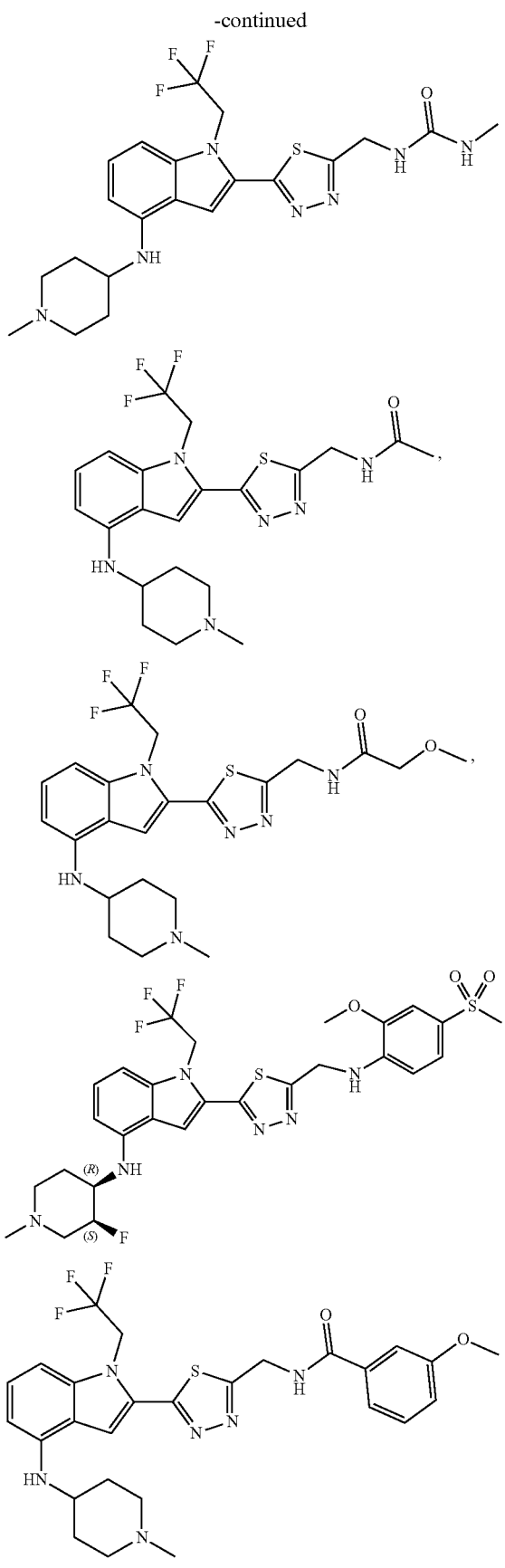
-continued
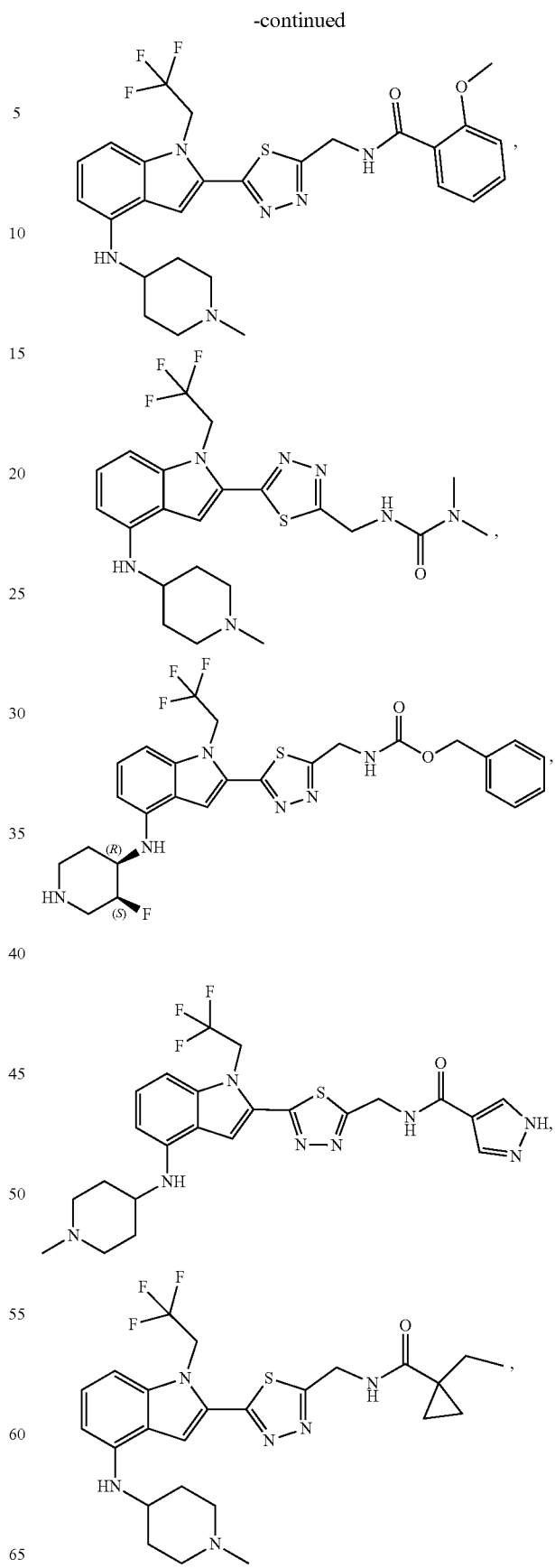

179
-continued
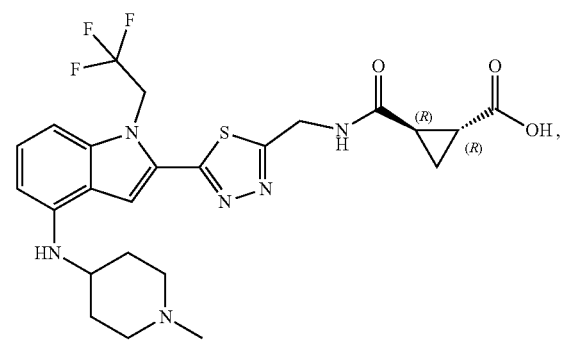
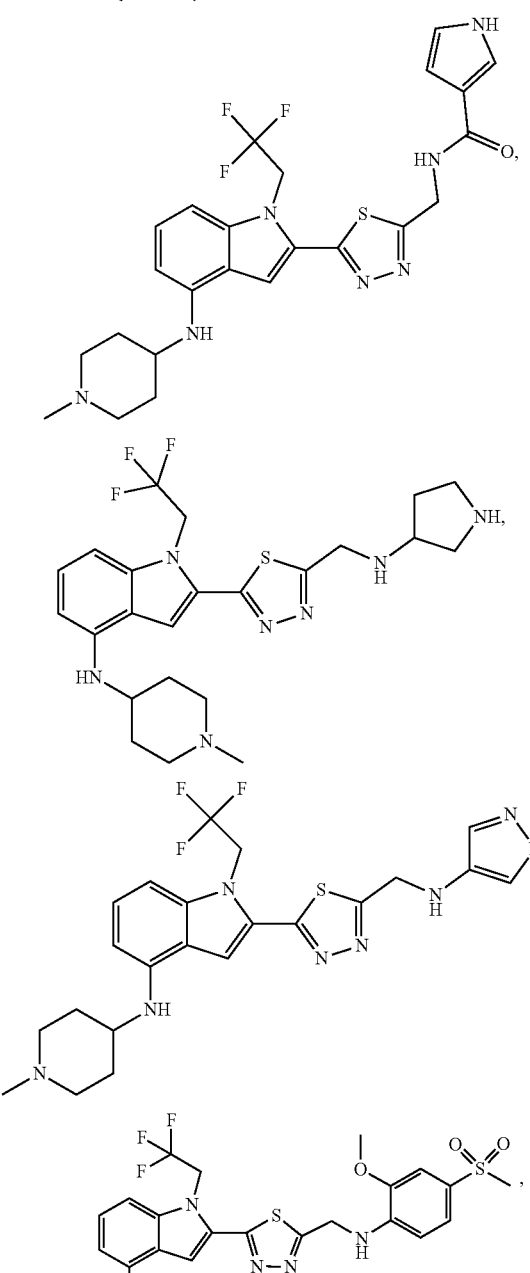
180
-continued
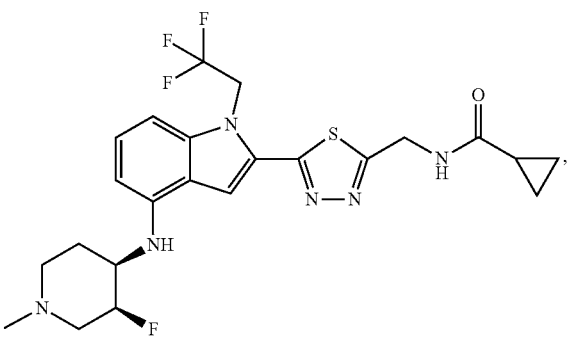
or a pharmaceutically-acceptable salt thereof.
Non-limiting examples of compounds of the disclosure include compounds of any of the following formulae:
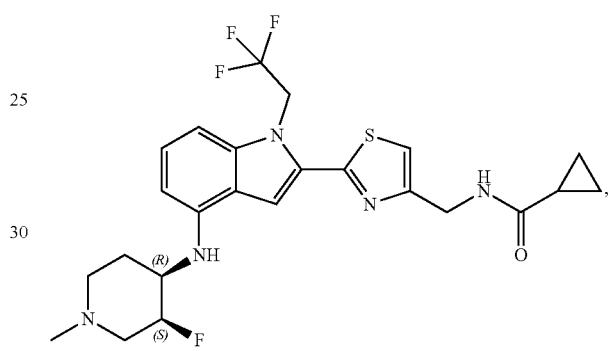
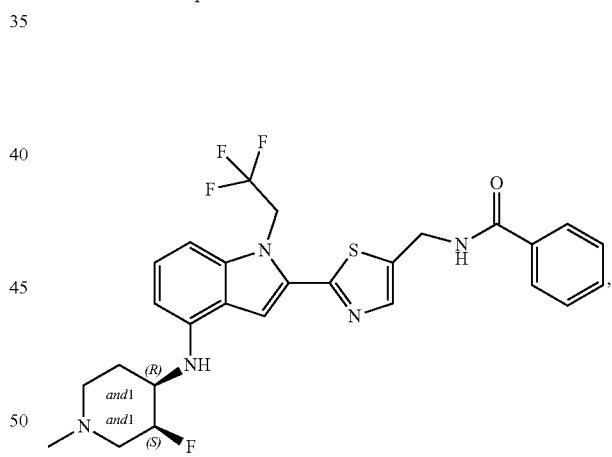
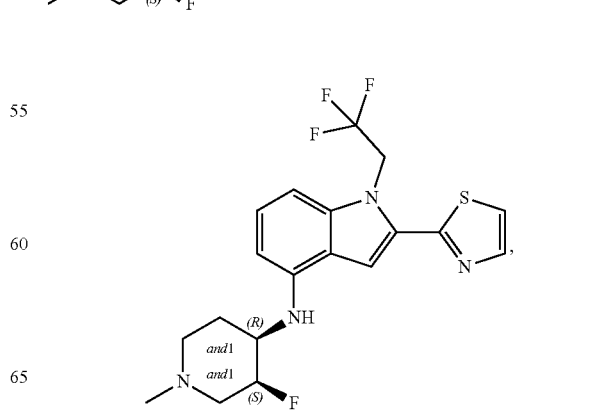

181
-continued
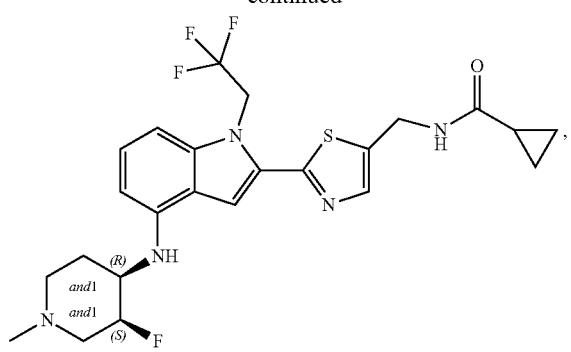
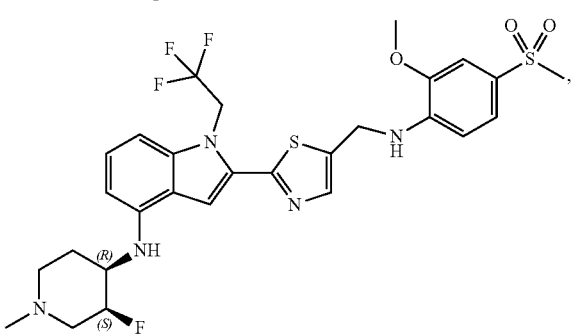
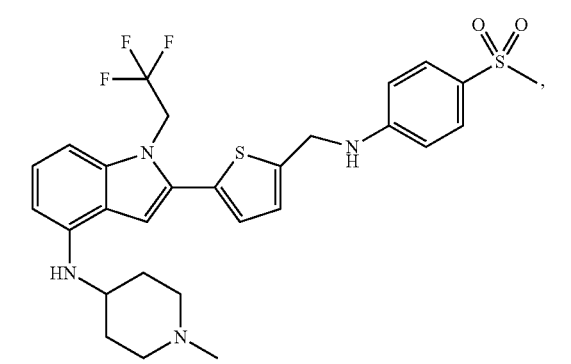
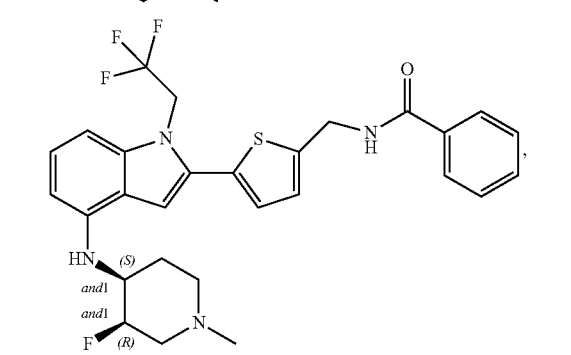
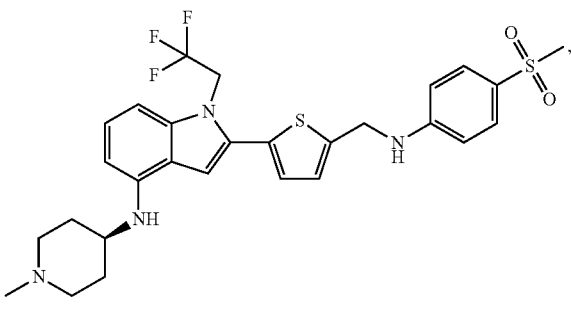
182
-continued
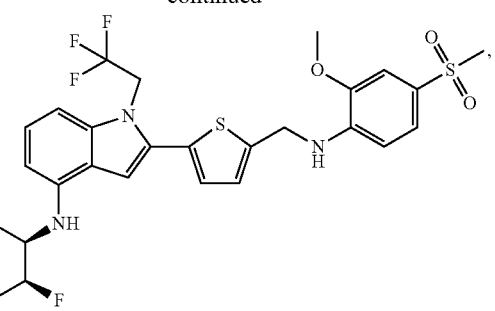
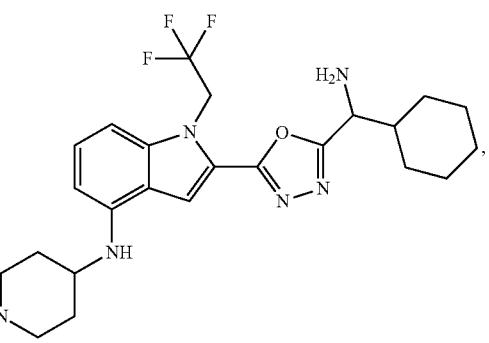
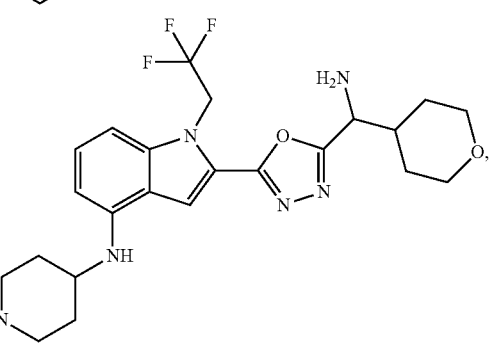
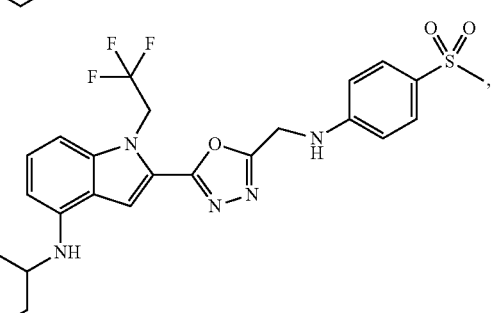
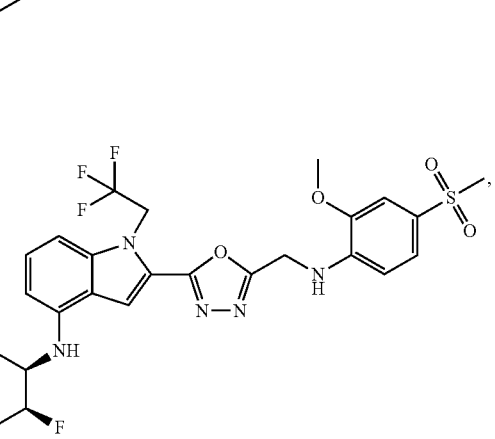

183
-continued
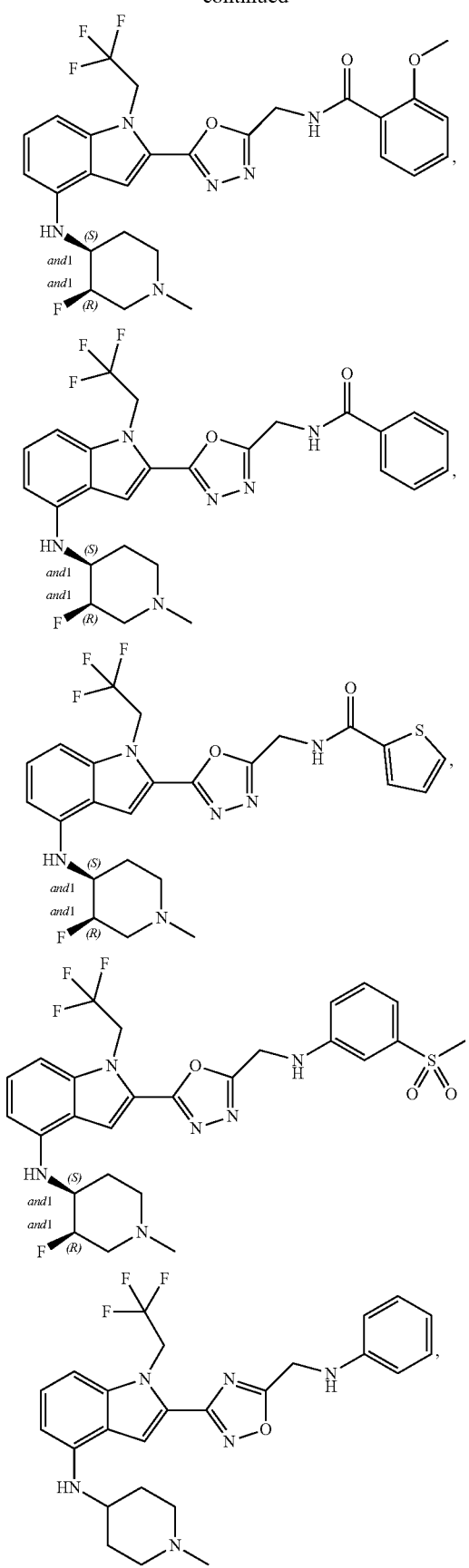
184
-continued
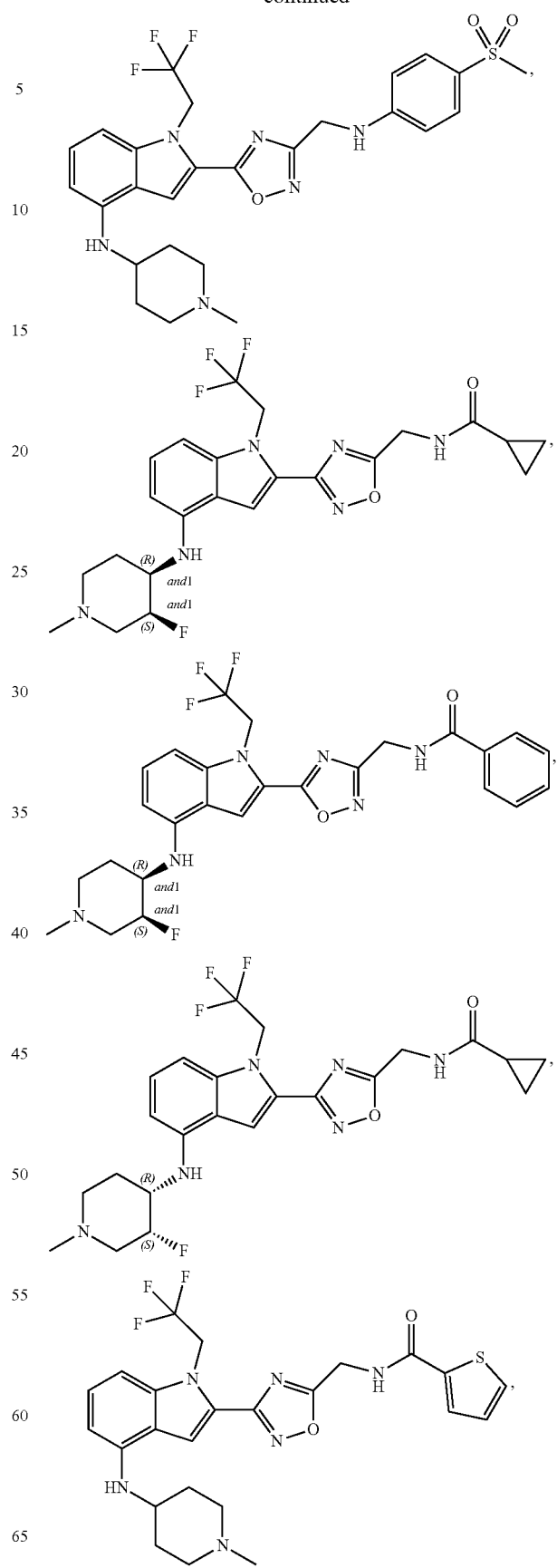

-continued
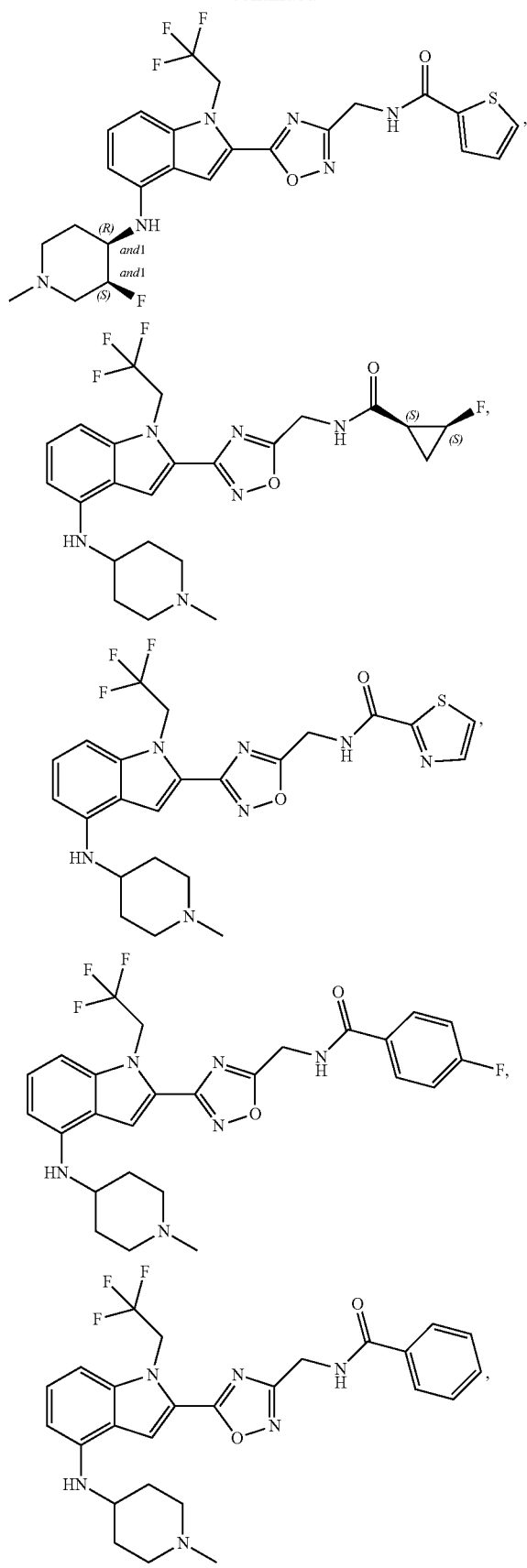
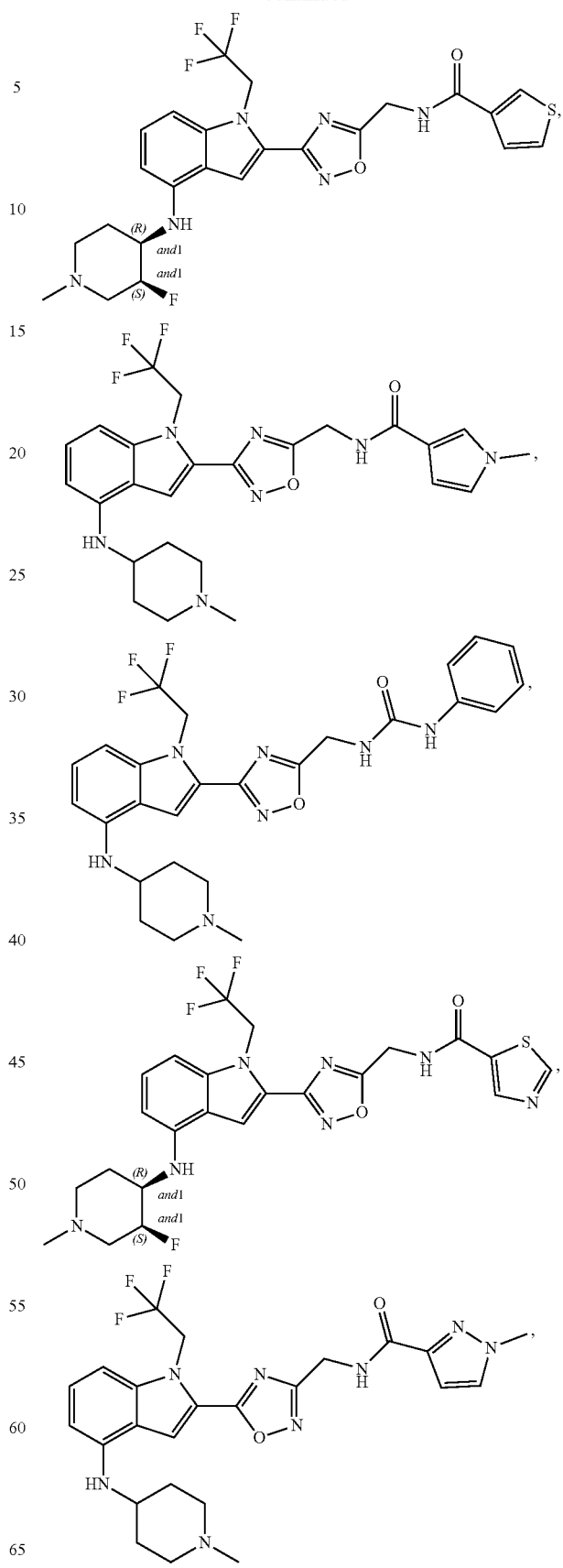

187
-continued
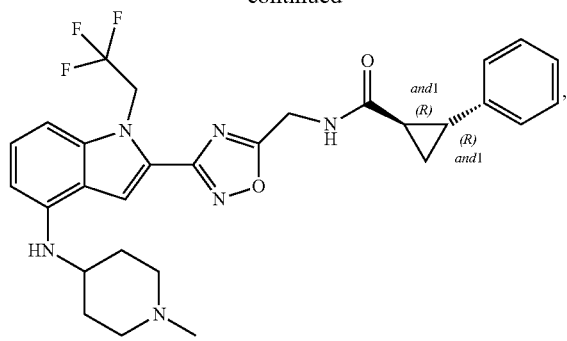
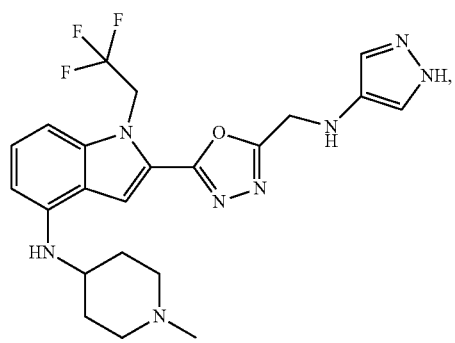
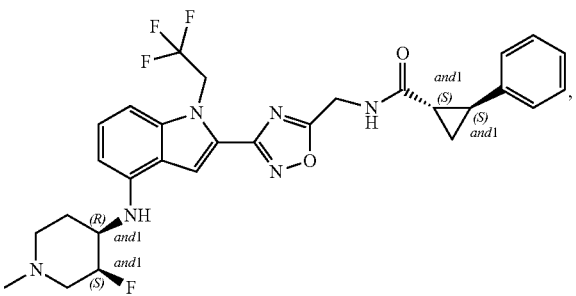
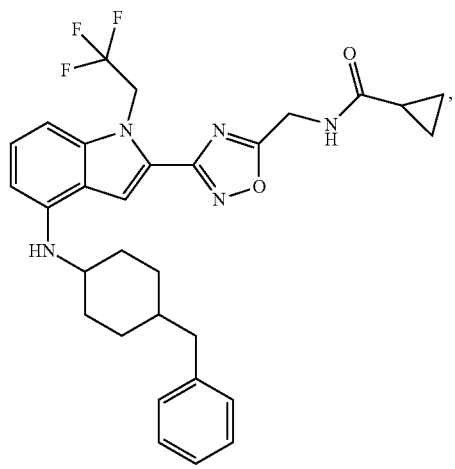
188
-continued
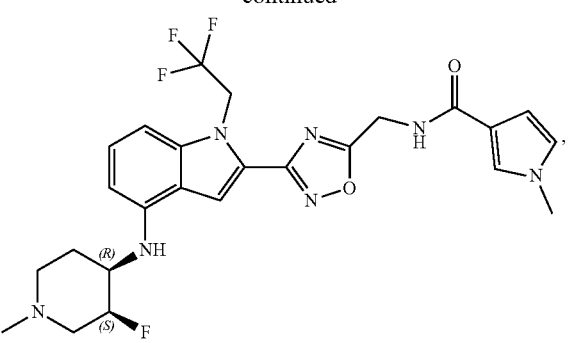
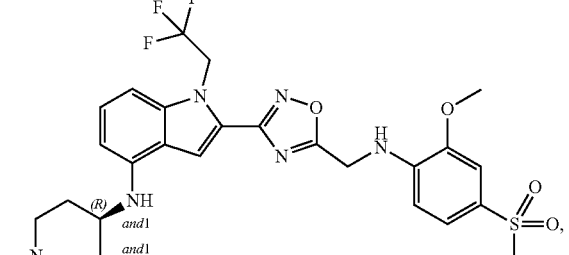
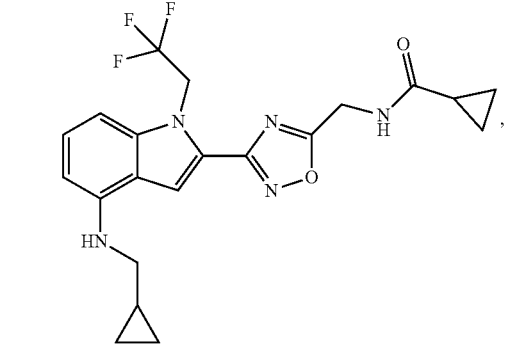
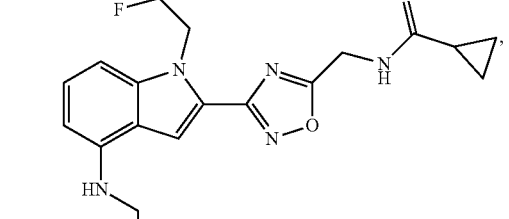
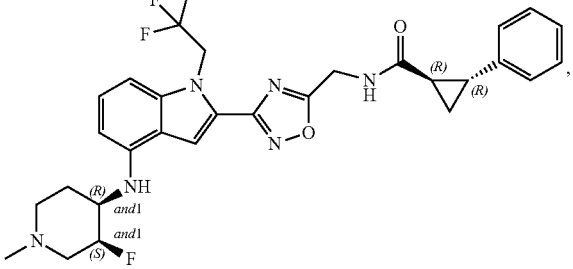

189
-continued
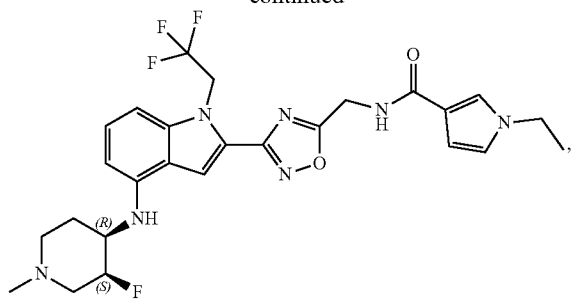
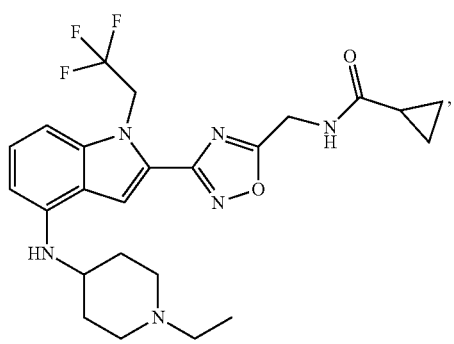
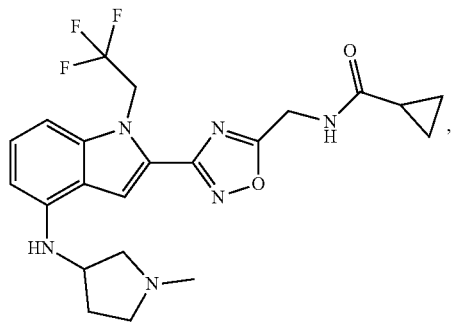
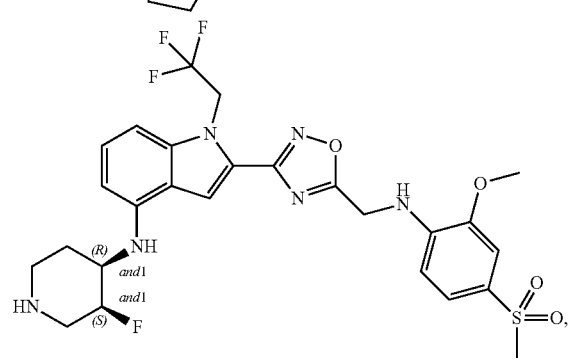
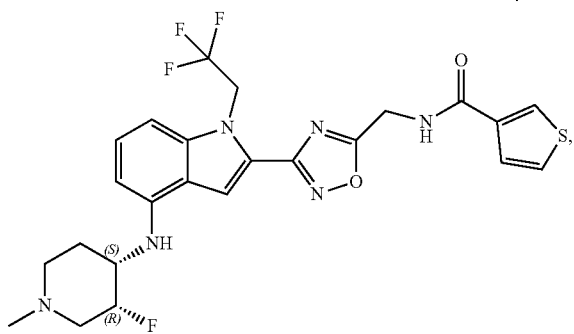
190
-continued
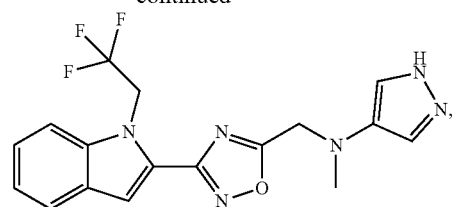
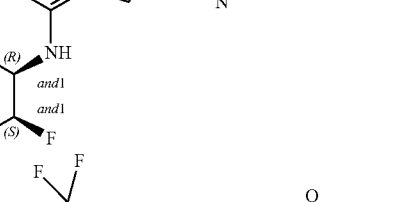
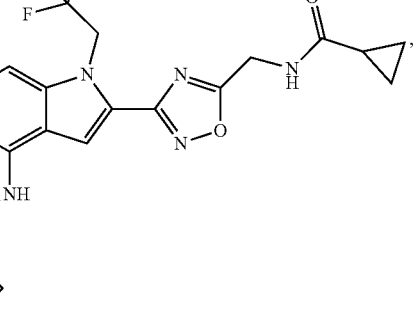
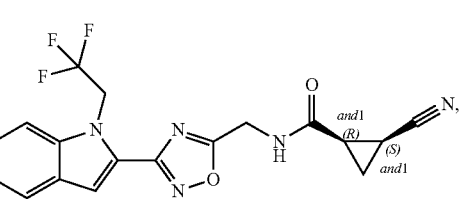
or
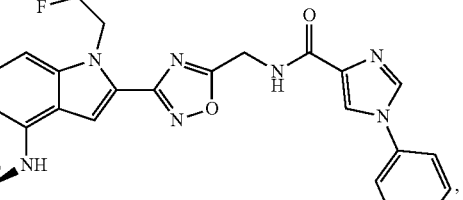
or a pharmaceutically-acceptable salt thereof.

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, or C50 group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxy ethyl, 1,2-difluoroethyl, and 3-carboxy propyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxy cyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, or C50 group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, or C50 group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4] triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the disclosure can be used to treat cancer in a subject. A compound of the disclosure can, for example, slow the proliferation of cancer cell lines, or kill cancer cells. Non-limiting examples of cancer that can be treated by a compound of the disclosure include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

In some embodiments, the compounds of the disclosure show non-lethal toxicity.

Pharmaceutically-Acceptable Salts.

The disclosure provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Disclosure.

A pharmaceutical composition of the disclosure can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the disclosure can be applied topically to the skin, or a body cavity, for example, oral, vaginal, bladder, cranial, spinal, thoracic, or pelvic cavity of a subject. The compounds of the disclosure can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound of the disclosure can be present in a composition in an amount of from about 500 mg to about 2000 mg. In some embodiments, a compound of the disclosure can be present in a composition in an amount of from about 1000 mg to about 1500 mg. In some embodiments, a compound of the disclosure can be present in a composition in an amount of about 500 mg. In some embodiments, a compound of the disclosure can be present in a composition in an amount of about 1000 mg. In some embodiments, a compound of the disclosure can be present in a composition in an amount of about 1500 mg. In some embodiments, a compound of the disclosure can be present in a composition in an amount of about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Companion Diagnostic Methods.

Disclosed herein are methods of detecting mutant p53 in a cell, the method comprising performing an assay to determine a mutational status of a gene in the cell that modulates the p53 pathway. In some embodiments, the methods of the disclosure further comprise, after the performing, contacting the cell with a compound that binds a p53 mutant. Also disclosed herein are methods of inducing apoptosis in a cell, the method comprising performing an assay to determine a mutational status of a gene in the cell that modulates the p53 pathway. In some embodiments, the method further comprises, after the performing, contacting the cell with a compound that binds a p53 mutant.

In some embodiments, the methods of the disclosure can be used to demonstrate that treatment with an anti-cancer agent has an anti-tumor efficacious effect. In some embodiments, the methods of the disclosure can be used to demonstrate that treatment with a compound of the disclosure has an anti-tumor efficacious effect. In some embodiments, a liquid companion diagnostics assay can be used to demonstrate a reduction or disappearance of tumor DNA found in a blood sample of a subject. In some embodiments, methods of the disclosure can be used to determine a mutational status of a gene in a cell of sample that modulates the p53 pathway to determine the likelihood the subject will respond to an anti-cancer agent that targets the mutational status of the gene.

Further disclosed herein are methods of treating a condition in a subject in need thereof, the method comprising: a) performing an assay to determine a mutational status of a gene in the subject that modulates the p53 pathway; and b) administering to the subject a therapeutically-effective amount of a compound that binds a mutant p53. In some embodiments, the assay shows that the cell has mutant p53, and shows that the cell can be treated with a compound of the disclosure to reactivate the mutant p53. In some embodiments, the assay shows that the subject has a mutant p53 that modulates the p53 pathway, and shows that the subject can be administered with a compound of the disclosure.

Further disclosed herein are methods of treating a condition in a subject in need thereof, the method comprising: administering to the subject a therapeutically-effective amount of a compound that binds a p53 mutant, wherein the subject has been previously determined to have a mutation in a TP53 gene that encodes the p53 mutant in the subject based on an assay performed on a biological sample of the subject, wherein the compound does not contain arsenic, antimony, or bismuth.

Also disclosed herein is a method of treating a condition in a subject in need thereof, the method comprising: a) based on a result of an assay performed on a biological sample of the subject, determining that the subject harbors a mutation in a TP53 gene that encodes a p53 mutant; b) based on the result of the assay, administering to the subject a therapeutically-effective amount of a small molecule compound, wherein the small molecule compound does not contain arsenic, antimony, or bismuth.

The mutational status of a gene in a subject can be, for example, a single nucleotide polymorphism (SNP), a mutated gene sequence (MUT), loss of gene expression without gene mutation (LOE), wild-type gene sequence (WT), or a entire gene deletion (NULL).

In some embodiments, the methods of the disclosure further comprise obtaining the biological sample of the subject. In some embodiments, the methods of the disclosure further comprise performing the assay on the biological sample of the subject to detect the mutation in the TP53 gene that encodes the p53 mutant in the subject. In some embodiments, the administering of the therapeutically-effective amount of the small molecule compound to the subject reduces a likelihood of denaturation of the p53 mutant in the subject. In some embodiments, the administering of the therapeutically-effective amount of the small molecule compound to the subject reactivates a p53 pathway in the subject. In some embodiments, the administering of the therapeutically-effective amount of the small molecule compound to the subject increases anti-cancer activity of the p53 mutant in the subject.

In some embodiments, the small molecule compound increases an ability of the p53 mutant to bind DNA. In some embodiments, the small molecule compound induces a conformational change in the p53 mutant. In some embodiments, the small molecule compound selectively binds the p53 mutant as compared to a wild type p53. In some embodiments, the small molecule compound increases stability of a biologically-active conformation of the p53 mutant relative to the stability of the biologically-active conformation of the p53 mutant in absence of the small molecule compound.

In some embodiments, the mutation in the TP53 gene deactivates a p53 pathway in the subject. In some embodiments, the subject has a cancer, wherein the cancer expresses the p53 mutant. In some embodiments, the mutation is at amino acid 220. In some embodiments, the p53 mutant is a p53 Y220C. In some embodiments, the p53 mutant has a reduced ability to bind to DNA in the subject as compared to wild-type p53. In some embodiments, the TP53 gene contains a frameshift mutation. In some embodiments, the TP53 gene contains a splice site mutation. In some embodiments, the TP53 gene contains an insertion mutation. In some embodiments, the TP53 gene contains a deletion mutation. In some embodiments, the TP53 gene contains a substitution mutation. In some embodiments, the TP53 gene contains a copy number variation. In some embodiments, the TP53 gene contains a copy number loss. In some embodiments, the TP53 gene contains a single nucleotide polymorphism.

In some embodiments, the assay is DNA sequencing. In some embodiments, the assay is next-generation DNA sequencing. In some embodiments, the assay is RNA sequencing.

In some embodiments, the biological sample is a liquid biopsy. In some embodiments, the biological sample is a blood sample. In some embodiments, the biological sample is circulating tumor DNA. In some embodiments, the biological sample is cell free DNA. In some embodiments, the biological sample is a solid tumor sample.

Clinical Trials.

To determine the suitability of a compound disclosed herein for treatment of humans, clinical trials are performed. For example, patients diagnosed with cancer and in need of treatment are selected and separated in treatment and one or more groups, wherein the treatment group is administered a compound disclosed herein, while the control groups receive a placebo or a known anti-cancer drug. The treatment safety and efficacy of the compound disclosed herein can thus be evaluated by performing comparisons of the patient groups with respect to factors such as survival and quality-of-life. In this example, the patient group treated with a compound disclosed herein show improved long-term survival compared to a patient control group treated with a placebo.

Results from genetic and biomarker tests and additional tests of the biological samples for biomarkers relevant to the safety and efficacy of the compounds disclosed herein can be investigated for possible correlation with patient outcome.

For example, clinical activity or response can be evaluated by standard imaging assessments, such as computed tomography (CT), magnetic resonance imaging (MRI), and bone scans. In addition, [18F]-fluorodeoxyglucose and [18F]-fluorothymidine positron emission tomography (FDG-PET and FLT-PET, respectively), or other techniques considered clinically appropriate for the patient's specific disease type can be used. CT-imaging can be performed, for example, at the end of Cycle 2, and every 2 cycles (e.g., Cycles 4 and 6) thereafter for DR-A and after the last infusion in Cycle 3 and every 3 cycles (e.g., Cycles 6 and 9) thereafter in DR-B. Anti-cancer cell activity can be assessed using IWG (2014) (Appendix H) criteria for patients with lymphomas. Additionally, for patients with an FDG-avid lymphoma, FDG-PET imaging can be performed at baseline and post-baseline as outlined in IWG 2014. FLT-PET imaging can be performed at baseline for patients with cancer cell commonly showing sufficient uptake of FLT tracer, e.g., patients with lymphoma. For example, DR-A assigned patients who demonstrate a standard uptake value (SUV) of >5 at baseline can have a repeat FLT image one day after their last infusion of study medication in Cycle 1, i.e., Day 16. For example, DR-B patients who demonstrate a standard uptake value (SUV) of >5 at baseline can have a repeat FLT image one day after their last infusion of study medication in Cycle 1, i.e., Day 12.

Biological Samples.

A biological sample can be a fluid or other material derived from the body of a normal or diseased subject, such as blood, serum, plasma, lymph, urine, saliva, tears, cerebrospinal fluid, milk, amniotic fluid, bile, ascites fluid, pus, and the like. In some embodiments, a biological sample is an organ or tissue extract and culture fluid in which any cells or tissue preparation from a subject has been incubated. The biological samples can be any samples from which genetic material can be obtained. Biological samples can also include solid or liquid cancer cell samples or specimens. The cancer cell sample can be a cancer cell tissue sample. The cancer cell sample can be a primary cancer sample, a metastatic cancer sample, or a recurrent cancer sample. In some embodiments, the cancer cell tissue sample can be obtained from surgically excised tissue. Exemplary sources of biological samples include fine needle aspiration, core needle biopsy, vacuum assisted biopsy, incisional biopsy, excisional biopsy, punch biopsy, shave biopsy or skin biopsy. In some cases, the biological samples comprise fine needle aspiration samples. In some embodiments, the biological samples comprise tissue samples, including, for example, excisional biopsy, incisional biopsy, or other biopsy. The biological samples can comprise a mixture of two or more sources; for example, fine needle aspirates and tissue samples. Tissue samples and cellular samples can also be obtained without invasive surgery, for example by punctuating the chest wall or the abdominal wall or from masses of breast, thyroid or other sites with a fine needle and withdrawing cellular material (fine needle aspiration biopsy). In some embodiments, a biological sample is a bone marrow aspirate sample. A biological sample can be obtained by methods known in the art such as the biopsy methods provided herein, swabbing, scraping, phlebotomy, or any other suitable method.

The biological samples obtained can be used in fresh, frozen, or fixed (e.g., formaldehyde fixed-paraffin embedded) form, depending on the nature of the sample, the assay used, and the convenience of the practitioner. Although fresh, frozen and fixed materials are suitable for various RNA and protein assays, generally, fresh tissues can be preferred for ex vivo measurements of activity.

Fixed tissue samples can also be employed. Tissue obtained by biopsy is often fixed, usually by formalin, formaldehyde, or gluteraldehyde, for example, or by alcohol immersion. Fixed biological samples are often dehydrated and embedded in paraffin or other solid supports. Non-embedded, fixed tissue, as well as fixed and embedded tissue, can be used in the present methods. Solid supports for embedding fixed tissue can be removed with organic solvents to enable subsequent rehydration of preserved tissue.

In some cases, an assay described herein includes a step of cell or tissue culture. For example, cells from a biopsy can be disaggregated using enzymes (such as collagenase and hyaluronidase) and or physical disruption (e.g., repeated passage through a 25-gauge needle) to dissociate the cells, collected by centrifugation, and resuspended in desired buffer or culture medium for culture, immediate analysis, or further processing.

Subject/Patient Population.

In some embodiments, a subject treated for cancer in accordance with the methods provided herein is a human, who has or is diagnosed with a cancer. In other embodiments, a subject treated for cancer using methods provided herein is a human, predisposed or susceptible to a cancer. In some embodiments, a subject treated for using methods provided herein is a human, at risk of developing a cancer.

In some embodiments, a subject treated for cancer in accordance with the methods provided herein is a human, who has or is diagnosed with a cancer, determined to carry a p53 deactivating mutation and/or lacking wild-type p53. In other embodiments, a subject treated for cancer in accordance with the methods provided herein is a human, predisposed or susceptible to a cancer, determined to carry a p53 deactivating mutation and/or lacking wild-type p53. In some embodiments, a subject treated for cancer using methods provided herein is a human, at risk of developing a cancer, determined to carry a p53 deactivating mutation and/or lacking wild-type p53.

A p53 deactivating mutation is a mutation that leads to loss of (or a decrease in) the in vitro apoptotic activity of p53. Non-limiting examples of p53 deactivating mutations include mutations at Val143, His168, Arg175, Tyr220, Gly245, Arg248, Arg249, Phe270, Arg273, and Arg282. For example, Y220C, Y220S, Y220H, R248Q, R248W, R273C, and R273H. Additional non-limiting examples of p53 deactivating mutations include E62_W91del, V122X, C135S, V143A, Q144P, W146X, V157F, R158H, Y163N, H168Y, V173L, R175H, R175L, R175P, R175Q, R175S, P219H, Y234C, Y234H, M237I, S240R, G245C, G245S, M246I, R249S, I255N, V272M, R273L, V274F, G279E, R280K, D281H, R282W, R306P, P300_L308del, P300_Y327del, D324_I332del, R337C, and L344P, wherein X is any amino acid.

Accordingly, in some embodiments, a subject treated for cancer using methods provided herein is a human, at risk of developing, who has, or is diagnosed with a cancer that is determined to harbor a p53 deactivating mutation.

In some embodiments, a subject treated for cancer in accordance with the methods provided herein is a human, who has or is diagnosed with a cancer, determined to lack a dominant p53 deactivating mutation. Dominant p53 deactivating mutation or dominant negative mutation, as used herein, is a mutation wherein the mutated p53 inhibits or disrupt the activity of the wild-type p53 gene.

In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with the cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer. In various embodiments, a patient with cancer is refractory when the number of CTCs or MNBCs associated with the cancer has not decreased or has increased. In various embodiments, a patient with cancer is refractory when one or more cancer cells metastasize and/or spread to another organ.

In some embodiments, a subject treated for cancer using methods provided herein is a human that has proven refractory to therapies other than treatment with the a compound disclosed herein, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring cancer cells despite treatment with existing therapies.

In some embodiments, the subject is a human who has had at least one unsuccessful prior treatment and/or therapy of the cancer.

Methods of Detecting Wild-Type p53 and/or p53 Mutations.

In some embodiments, a subject with at least one p53-deactivating mutation is a candidate for cancer treatment with a compound of the disclosure. Cancer cells from patient groups should be assayed to determine p53-deactivating mutations and/or expression of wild-type p53 prior to treatment with a compound of the disclosure.

The activity of the p53 pathway can be determined by the mutational status of genes involved in the p53 pathways, including, for example, AKT1, AKT2, AKT3, ALK, BRAF, CDK4, CDKN2A, DDR2, EGFR, ERBB2 (HER2), FGFR1, FGFR3, GNA11, GNQ, GNAS, KDR, KIT, KRAS, MAP2K1 (MEK1), MET, HRAS, NOTCH1, NRAS, NTRK2, PIK3CA, NF1, PTEN, RAC1, RBI, NTRK3, STK11, PDC3R1, TSC1, TSC2, RET, TP53, and VHL. Genes that modulate the activity of p53 can also be assessed, including, for example, kinases: ABL1, JAK1, JAK2, JAK3; receptor tyrosine kinases: FLT3 and KIT; receptors: CSF3R, IL7R, MPL, and NOTCH1; transcription factors: BCOR, CEBPA, CREBBP, ETV6, GATA1, GATA2. MLL, KZF1, PAX5, RUNX1, STAT3, WT1, and TP53; epigenetic factors: ASXL1, DNMT3A, EZH2, KDM6A (UTX), SUZ12, TET2, PTPN11, SF3B1, SRSF2, U2AF35, and ZRSR2; RAS proteins: HRAS, KRAS, and NRAS; adaptors CBL and CBL-B; FBXW7, IDH1, IDH2, and NPM1.

Cancer cell samples can be obtained, for example, from solid or liquid tumors via primary or metastatic tumor resection (e.g., pneumonectomy, lobetomy, wedge resection, and craniotomy) primary or metastatic disease biopsy (e.g., transbronchial or needle core), pleural or ascites fluid (e.g., FFPE cell pellet), bone marrow aspirate, bone marrow clot, and bone marrow biopsy, or macro-dissection of tumor rich areas (solid tumors).

To detect the p53 wild-type gene or a p53-deactivating mutation in a tissue, cancerous tissue can be isolated from surrounding normal tissues. For example, the tissue can be isolated from paraffin or cryostat sections. Cancer cells can also be separated from normal cells by flow cytometry. If the cancer cells tissue is highly contaminated with normal cells, detection of mutations can be more difficult.

Various methods and assays for analyzing wild-type p53 and/or p53 mutations are suitable for use in the disclosure. Non-limiting examples of assays include polymerase chain reaction (PCR), quantitative PCR (qPCR), real-time PCR (RT-PCR), Sanger sequencing, restriction fragment length polymorphism (RFLP), microarray, Southern Blot, northern blot, western blot, eastern Blot, H&E staining, microscopic assessment of tumors, massively parallel sequencing (MPS), next-generation DNA sequencing (NGS) (e.g., extraction, purification, quantitiation, and amplification of DNA, library preparation), immunohistochemistry (IHC), protein quantification, chromogenic in situ hybridization (CISH), and fluorescent in situ hybridization (FISH).

A microarray allows a researcher to investigate multiple DNA sequences attached to a surface, for example, a DNA chip made of glass or silicon, or a polymeric bead or resin. The DNA sequences are hybridized with fluorescent or luminescent probes. The microarray can indicate the presence of oligonucleotide sequences in a sample based on hybridization of sample sequences to the probes, followed by washing and subsequent detection of the probes. Quantification of the fluorescent or luminescent signal indicates the presence of known oligonucleotide sequences in the sample.

PCR allows rapid amplification of DNA oligomers, and can be used to identify an oligonucleotide sequence in a sample. PCR experiments involve contacting an oligonucleotide sample with a PCR mixture containing primers complementary to a target sequence, one or more DNA polymerase enzymes, deoxynucleotide triphosphate (dNTP) building blocks, including dATP, dGTP, dTTP, and dCTP, suitable buffers, salts, and additives. If a sample contains an oligonucleotide sequence complementary to a pair of primers, the experiment amplifies the sample sequence, which can be collected and identified.

In some embodiments, an assay comprises amplifying a biomolecule from the cancer sample. The biomolecule can be a nucleic acid molecule, such as DNA or RNA. In some embodiments, the assay comprises circularization of a nucleic acid molecule, followed by digestion of the circularized nucleic acid molecule.

In some embodiments, the assay comprises contacting an organism, or a biochemical sample collected from an organism, such as a nucleic acid sample, with a library of oligonucleotides, such as PCR primers. The library can contain any number of oligonucleotide molecules. The oligonucleotide molecules can bind individual DNA or RNA motifs, or any combination of motifs described herein. The motifs can be any distance apart, and the distance can be known or unknown. In some embodiments, two or more oligonucleotides in the same library bind motifs a known distance apart in a parent nucleic acid sequence. Binding of the primers to the parent sequence can take place based on the complementarity of the primers to the parent sequence. Binding can take place, for example, under annealing, or under stringent conditions.

In some embodiments, the results of an assay are used to design a new oligonucleotide sequence for future use. In some embodiments, the results of an assay are used to design a new oligonucleotide library for future use. In some embodiments, the results of an assay are used to revise, refine, or update an existing oligonucleotide library for future use. For example, an assay can reveal that a previously-undocumented nucleic acid sequence is associated with the presence of a target material. This information can be used to design or redesign nucleic acid molecules and libraries.

In some embodiments, one or more nucleic acid molecules in a library comprise a barcode tag. In some embodiments, one or more of the nucleic acid molecules in a library comprise type I or type II restriction sites suitable for circularization and cutting an amplified sample nucleic acid sequence. Such primers can be used to circularize a PCR product and cut the PCR product to provide a product nucleic acid sequence with a sequence that is organized differently from the nucleic acid sequence native to the sample organism.

After a PCR experiment, the presence of an amplified sequence can be verified. Non-limiting examples of methods for finding an amplified sequence include DNA sequencing, whole transcriptome shotgun sequencing (WTSS, or RNA-seq), mass spectrometry (MS), microarray, pyrosequencing, column purification analysis, polyacrylamide gel electrophoresis, and index tag sequencing of a PCR product generated from an index-tagged primer.

In some embodiments, more than one nucleic acid sequence in the sample organism is amplified. Non-limiting examples of methods of separating different nucleic acid sequences in a PCR product mixture include column purification, high performance liquid chromatography (HPLC), HPLC/MS, polyacrylamide gel electrophoresis, and size exclusion chromatography.

The amplified nucleic acid molecules can be identified by sequencing. Nucleic acid sequencing can be performed on automated instrumentation. Sequencing experiments can be done in parallel to analyze tens, hundreds, or thousands of sequences simultaneously. Non-limiting examples of sequencing techniques follow.

In pyrosequencing, DNA is amplified within a water droplet containing a single DNA template bound to a primer-coated bead in an oil solution. Nucleotides are added to a growing sequence, and the addition of each base is evidenced by visual light.

Ion semiconductor sequencing detects the addition of a nucleic acid residue as an electrical signal associated with a hydrogen ion liberated during synthesis. A reaction well containing a template is flooded with the four types of nucleotide building blocks, one at a time. The timing of the electrical signal identifies which building block was added, and identifies the corresponding residue in the template.

DNA nanoball uses rolling circle replication to amplify DNA into nanoballs. Unchained sequencing by ligation of the nanoballs reveals the DNA sequence.

In a reversible dyes approach, nucleic acid molecules are annealed to primers on a slide and amplified. Four types of fluorescent dye residues, each complementary to a native nucleobase, are added, the residue complementary to the next base in the nucleic acid sequence is added, and unincorporated dyes are rinsed from the slide. Four types of reversible terminator bases (RT-bases) are added, and non-incorporated nucleotides are washed away. Fluorescence indicates the addition of a dye residue, thus identifying the complementary base in the template sequence. The dye residue is chemically removed, and the cycle repeats.

Detection of point mutations can be accomplished by molecular cloning of the p53 allele(s) present in the cancer cell tissue and sequencing that allele(s). Alternatively, PCR can be used to amplify p53 gene sequences directly from a genomic DNA preparation from the cancer cell tissue. The DNA sequence of the amplified sequences can then be determined. Specific deletions of p53 genes can also be detected. For example, restriction fragment length polymorphism (RFLP) probes for the p53 gene or surrounding marker genes can be used to score loss of a p53 allele.

Loss of wild-type p53 genes can also be detected on the basis of the loss of a wild-type expression product of the p53 gene. Such expression products include both the mRNA as well as the p53 protein product. Point mutations can be detected by sequencing the mRNA directly or via molecular cloning of cDNA made from the mRNA. The sequence of the cloned cDNA can be determined using DNA sequencing techniques. The cDNA can also be sequenced via PCR.

Alternatively, mismatch detection can be used to detect point mutations in the p53 gene or the mRNA product. The method can involve the use of a labeled riboprobe that is complementary to the human wild-type p53 gene. The riboprobe and either mRNA or DNA isolated from the cancer cell tissue are annealed (hybridized) together and subsequently digested with the enzyme RNase A which is able to detect some mismatches in a duplex RNA structure. If a mismatch is detected by RNase A, the enzyme cleaves at the site of the mismatch. Thus, when the annealed RNA preparation is separated on an electrophoretic gel matrix, if a mismatch has been detected and cleaved by RNase A, an RNA product is seen that is smaller than the full-length duplex RNA for the riboprobe and the p53 mRNA or DNA. The riboprobe need not be the full length of the p53 mRNA or gene but can be a segment of either. For example, if the riboprobe comprises only a segment of the p53 mRNA or gene, a number of these probes can be used to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA which might contain a mutation can be amplified using PCR (see below) before hybridization.

DNA sequences of the p53 gene from the cancer cell tissue which have been amplified by use of PCR can also be screened using allele-specific probes. These probes are nucleic acid oligomers, each of which contains a region of the p53 gene sequence harboring a known mutation. For example, one oligomer can be about 30 nucleotides in length, corresponding to a portion of the p53 gene sequence. At the position coding for the 175th codon of p53 gene the oligomer encodes an alanine, rather than the wild-type codon valine. By use of a battery of such allele-specific probes, the PCR amplification products can be screened to identify the presence of a previously identified mutation in the p53 gene. Hybridization of allele-specific probes with amplified p53 sequences can be performed, for example, on a nylon filter. Hybridization to a particular probe indicates the presence of the same mutation in the cancer cell tissue as in the allele-specific probe.

The identification of p53 gene structural changes in cancer cells can be facilitated through the application of a diverse series of high resolution, high throughput microarray platforms. Essentially two types of array include those that carry PCR products from cloned nucleic acids (e.g., cDNA, BACs, cosmids) and those that use oligonucleotides. The methods can provide a way to survey genome wide DNA copy number abnormalities and expression levels to allow correlations between losses, gains, and amplifications in cancer cells with genes that are over- and under-expressed in the same samples. The gene expression arrays that provide estimates of mRNA levels in cancer cells have given rise to exon-specific arrays that can identify both gene expression levels, alternative splicing events and mRNA processing alterations.

Oligonucleotide arrays can be used to interrogate single nucleotide polymorphisms (SNPs) throughout the genome for linkage and association studies and these have been adapted to quantify copy number abnormalities and loss of heterozygosity events. DNA sequencing arrays can allow resequencing of chromosome regions and whole genomes.

SNP-based arrays or other gene arrays or chips can determine the presence of wild-type p53 allele and the structure of mutations. A single nucleotide polymorphism (SNP), a variation at a single site in DNA, is the most frequent type of variation in the genome. For example, there are an estimated 5-10 million SNPs in the human genome. SNPs can be synonymous or nonsynonymous substitutions. Synonymous SNP substitutions do not result in a change of amino acid in the protein due to the degeneracy of the genetic code, but can affect function in other ways. For example, a seemingly silent mutation in gene that codes for a membrane transport protein can slow down translation, allowing the peptide chain to misfold and produce a less functional mutant membrane transport protein. Nonsynonymous SNP substitutions can be missense substitutions or nonsense substitutions. Missense substitutions occur when a single base change results in change in amino acid sequence of the protein and malfunction thereof leads to disease. Nonsense substitutions occur when a point mutation results in a premature stop codon, or a nonsense codon in the transcribed mRNA, which results in a truncated and usually, nonfunctional, protein product. As SNPs are highly conserved throughout evolution and within a population, the map of SNPs serves as an excellent genotypic marker for research. SNP array is a useful tool to study the whole genome.

In addition, SNP array can be used for studying the Loss Of Heterozygosity (LOH). LOH is a form of allelic imbalance that can result from the complete loss of an allele or from an increase in copy number of one allele relative to the other. While other chip-based methods (e.g., comparative genomic hybridization can detect only genomic gains or deletions), SNP array has the additional advantage of detecting copy number neutral LOH due to uniparental disomy (UPD). In UPD, one allele or whole chromosome from one parent are missing leading to reduplication of the other parental allele (uni-parental=from one parent, disomy=duplicated). In a disease setting this occurrence can be pathologic when the wild-type allele (e.g., from the mother) is missing and instead two copies of the heterozygous allele (e.g., from the father) are present. This usage of SNP array has a huge potential in cancer diagnostics as LOH is a prominent characteristic of most human cancers. SNP array technology have shown that cancers (e.g., gastric cancer, liver cancer, etc.) and hematologic malignancies (ALL, MDS, CML, etc.) have a high rate of LOH due to genomic deletions or UPD and genomic gains. In the present disclosure, using high density SNP array to detect LOH allows identification of pattern of allelic imbalance to determine the presence of wild-type p53 allele.

Examples of p53 gene sequence and SNP arrays include p53 Gene Chip (Affymetrix, Santa Clara, CA), AmpliChip® p53 microarray (Roche Molecular Systems, Pleasanton, CA), GeneChip Mapping arrays (Affymetrix, Santa Clara, CA), SNP Array 6.0 (Affymetrix, Santa Clara, CA), BeadArrays (Illumina, San Diego, CA), etc.

Mutations of wild-type p53 genes can also be detected on the basis of the mutation of a wild-type expression product of the p53 gene. Such expression products include both the mRNA as well as the p53 protein product itself. Point mutations can be detected by sequencing the mRNA directly or via molecular cloning of cDNA made from the mRNA. The sequence of the cloned cDNA can be determined using DNA sequencing techniques. The cDNA can also be sequenced via the polymerase chain reaction (PCR). A panel of monoclonal antibodies could be used in which each of the epitopes involved in p53 functions are represented by a monoclonal antibody. Loss or perturbation of binding of a monoclonal antibody in the panel can indicate mutational alteration of the p53 protein and thus of the p53 gene itself. Mutant p53 genes or gene products can also be detected in body samples, including, for example, serum, stool, urine, and sputum. The same techniques discussed above for detection of mutant p53 genes or gene products in tissues can be applied to other body samples.

Loss of wild-type p53 genes can also be detected by screening for loss of wild-type p53 protein function. Although all of the functions which the p53 protein undoubtedly possesses have yet to be elucidated, at least two specific functions are known. Protein p53 binds to the SV40 large T antigen as well as to the adenovirus E1B antigen. Loss of the ability of the p53 protein to bind to either or both of these antigens indicates a mutational alteration in the protein which reflects a mutational alteration of the gene itself. Alternatively, a panel of monoclonal antibodies could be used in which each of the epitopes involved in p53 functions are represented by a monoclonal antibody. Loss or perturbation of binding of a monoclonal antibody in the panel would indicate mutational alteration of the p53 protein and thus of the p53 gene itself. Any method for detecting an altered p53 protein can be used to detect loss of wild-type p53 genes.

Determination of a p53 deactivating mutation and/or lack of or reduced expression of wild-type p53 in the subject with cancer can be performed before, during, or after the administration of a compound disclosed herein. In some embodiments, the determination of the lack of a p53 deactivating mutation and/or expression of wild-type p53 is performed before the first administration of the compound to the subject, for example about 5 years-about 1 month, about 4 years-about 1 month, about 3 years-1 month, about 2 years-about 1 month, about 1 years-about 1 month, about 5 years-about 1 week, about 4 years-about 1 week, about 3 years-about 1 month, about 2 years-about 1 week, about 1 year-about 1 week, about 5 years-about 1 day, about 4 years-about 1 day, about 3 years-about 1 day, about 2 years-about 1 day, about 1 year-about 1 day, about 15 months-about 1 month, about 15 months-about 1 week, about 15 months-about 1 day, about 12 months-about 1 month, about 12 months-about 1 week, about 12 months-about 1 day, about 6 months-1 about month, about 6 months-about 1 week, about 6 months-about 1 day, about 3 months-1 about month, about 3 months-about 1 week, or about 3 months-about 1 day prior to the first administration of the compound to the subject. In some examples, the confirmation of the lack of the p53 deactivating mutation and/or expression of wild-type p53 is performed up to 6 years, 5 years, 4 years, 3 years, 24 months, 23 months, 22 months, 21 months, 20 months, 19 months, 18 months, 17 months, 16 months, 15 months, 14 months, 13 months, 12 months, 11 months, 10 months, 9 months, 8 months, 7 months, 6 months, 5 months, 4 months, 3 months, 2 months, 1 months, 4 weeks (28 days), 3 weeks (21 days), 2 weeks (14 days), 1 week (7 days), 6 days, 5 days, 4 days, 3 days, 2 days, or 1 day before the first administration of the compound to the subject. In some examples the confirmation of the lack of the p53 deactivating mutation is performed within 1 month of the first administration of the compound to the subject. In some examples the confirmation of the lack of the p53 deactivating mutation is performed within 21 days of the first administration of the compound to the subject.

EXAMPLES

Example 1: Compounds of the Disclosure

Indole compounds with alkynyl, aryl, and heteroaryl linkers were prepared. Alkynyl-linked indole compounds are shown in TABLE 1. Aryl-linked indole compounds are shown in TABLE 2. Heteroaryl-linked indole compounds are shown in TABLE 3. The disclosure provides these compounds and a pharmaceutically-acceptable salt thereof.

TABLE 1

Alkynyl indole compounds of the disclosure.

| Mol # | IUPAC name |
|---|---|
| 1. | 1-Anilino-3-{1-ethyl-5-[(1-methyl-4-piperidylamino)methyl]-1H-indol-2-yl}-2-propyne |
| 2. | 1-Anilino-3-{1-ethyl-5-[(methylamino)methyl]-1H-indol-2-yl}-2-propyne |
| 3. | 1-Anilino-3-{1-ethyl-5-[(tetrahydro-2H-pyran-4-ylamino)methyl]-1H-indol-2-yl}-2-propyne |
| 4. | 1-Anilino-3-[5-(benzylaminomethyl)-1-ethyl-1H-indol-2-yl]-2-propyne |
| 5. | 3-{1-Ethyl-5-[(methylamino)methyl]-1H-indol-2-yl}-1-(p-fluorophenylamino)-2-propyne |
| 6. | 3-{1-Ethyl-5-[(tetrahydro-2H-pyran-4-ylmino)methyl]-1H-indol-2-yl}-1-(p-fluorophenylamino)-2-propyne |
| 7. | 1-(p-Chlorophenylamino)-3-{1-ethyl-5-[(1-methyl-4-piperidylamino)methyl]-1H-indol-2-yl}-2-propyne |
| 8. | 3-{1-Ethyl-5-[(tetrahydro-2H-pyran-4-ylamino)methyl]-1H-indol-2-yl}-1-(6-methyl-3-pyridylamino)-2-propyne |
| 9. | 3-{1-Ethyl-5-[(methylamino)methyl]-1H-indol-2-yl}-1-(6-methyl-3-pyridylamino)-2-propyne |
| 10. | 3-{1-Ethyl-5-[(1-methyl-4-piperidylamino)methyl]-1H-indol-2-yl}-1-(2-methyl-4-pyridylamino)-2-propyne |
| 11. | 3-[5-(Benzylaminomethyl)-1-ethyl-1H-indol-2-yl]-1-(2-methyl-4-pyridylamino)-2-propyne |
| 12. | N-(3-{5-[(Diethylamino)methyl]-1-ethyl-1H-indol-2-yl}prop-2-yn-1-yl)aniline |
| 13. | 4-Chloro-N-(3-{5-[(diethylamino)methyl]-1-ethyl-1H-indol-2-yl}prop-2-yn-1-yl)aniline |
| 14. | N-({1-Ethyl-2-[3-(phenylamino)prop-1-yn-1-yl]-1H-indol-5-yl}methyl)oxetan-3-amine |

TABLE 1-continued

Alkynyl indole compounds of the disclosure.

| Mol # | IUPAC name |
|---|---|
| 15. | N-[3-(1-Ethyl-5-{[(2-methylpropyl)amino]methyl}-1H-indol-2-yl)prop-2-yn-1-yl]aniline |
| 16. | N-[3-(1-Ethyl-5-{[(2-methoxyethyl)amino]methyl}-1H-indol-2-yl)prop-2-yn-1-yl]aniline |
| 17. | N-({1-ethyl-2-[3-(phenylamino)prop-1-yn-1-yl]-1H-indol-5-yl}methyl)-1-methanesulfonylpiperidin-4-amine |
| 18. | N-(3-{1-Ethyl-5-[(ethylamino)methyl]-1H-indol-2-yl}prop-2-yn-1-yl)aniline |
| 19. | N-{3-[5-({[2-(Dimethylamino)ethyl]amino}methyl)-1-ethyl-1H-indol-2-yl]prop-2-yn-1-yl}aniline |
| 20. | 6-tert-Butyl-N-[3-(1-ethyl-5-{[(1-methylpiperidin-4-yl)amino]methyl}-1H-indol-2-yl)prop-2-yn-1-yl]pyridin-3-amine |
| 21. | N-[(2-{3-[(4-Chlorophenyl)amino]prop-1-yn-1-yl}-1-ethyl-1H-indol-5-yl)methyl]oxan-4-amine |
| 22. | 6-tert-Butyl-N-(3-{1-ethyl-5-[(methylamino)methyl]-1H-indol-2-yl}prop-2-yn-1-yl)pyridin-3-amine |
| 23. | 4-[(3-{1-Ethyl-5-[(methylamino)methyl]-1H-indol-2-yl}prop-2-yn-1-yl)amino]benzonitrile |
| 24. | 4-tert-Butyl-N-(3-{1-ethyl-5-[(methylamino)methyl]-1H-indol-2-yl}prop-2-yn-1-yl)benzamide |
| 25. | 4-Chloro-N-(3-{1-ethyl-5-[(methylamino)methyl]-1H-indol-2-yl}prop-2-yn-1-yl)-3-fluorobenzamide |
| 26. | 4-Cyano-N-({1-ethyl-2-[3-(phenylformamido)prop-1-yn-1-yl]-1H-indol-5-yl}methyl)-N-methylbenzamide |
| 27. | 3-(3-{1-Ethyl-5-[(methylamino)methyl]-1H-indol-2-yl}prop-2-yn-1-yl)-1-[4-(trifluoromethyl)phenyl]urea |
| 28. | N-{[1-(2-Chloroethyl)-2-{3-[(4-chlorophenyl)amino]prop-1-yn-1-yl}-1H-indol-5-yl]methyl}oxan-4-amine |
| 29. | 2-(4-{[3-(1-Ethyl-5-{[(1-methylpiperidin-4-yl)amino]methyl}-1H-indol-2-yl)prop-2-yn-1-yl]amino}phenyl)-2-methylpropanenitrile |
| 30. | 4-Cyano-N-(3-{1-ethyl-5-[(methylamino)methyl]-1H-indol-2-yl}prop-2-yn-1-yl)benzamide |
| 31. | N-(3-{1-Ethyl-5-[(methylamino)methyl]-1H-indol-2-yl}prop-2-yn-1-yl)-6-methylpyridine-3-carboxamide |
| 32. | 3-[3-(1-Ethyl-5-{[(1-methylpiperidin-4-yl)amino]methyl}-1H-indol-2-yl)prop-2-yn-1-yl]-1-phenylurea |
| 33. | N-[(2-{3-[(4-Chloro-3-fluorophenyl)amino]prop-1-yn-1-yl}-1-ethyl-1H-indol-5-yl)methyl]-1-methylpiperidin-4-amine |
| 34. | 2-(5-{[3-(1-Ethyl-5-{[(1-methylpiperidin-4-yl)amino]methyl}-1H-indol-2-yl)prop-2-yn-1-yl]amino}pyridin-2-yl)-2-methylpropanenitrile |
| 35. | N-{[1-(2-Chloroethyl)-2-{3-[(4-chlorophenyl)amino]prop-1-yn-1-yl}-1H-indol-5-yl]methyl}-1-methylpiperidin-4-amine |
| 36. | 6-tert-Butyl-N-[3-(1-ethyl-5-{[(1-methanesulfonylpiperidin-4-yl)amino]methyl}-1H-indol-2-yl)prop-2-yn-1-yl]pyridin-3-amine |
| 37. | 2-(4-{[3-(1-Ethyl-5-{[(1-methylpiperidin-4-yl)amino]methyl}-1H-indol-2-yl)prop-2-yn-1-yl]amino}phenyl)-2-methylpropanoic acid |
| 38. | 3-(1-Ethyl-5-{[(1-methylpiperidin-4-yl)amino]methyl}-1H-indol-2-yl)-N-methylprop-2-ynamide |
| 39. | Ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate |
| 40. | 2-(5-{[3-(1-Ethyl-5-{[(oxan-4-yl)amino]methyl}-1H-indol-2-yl)prop-2-yn-1-yl]amino}pyridin-2-yl)-2-methylpropanenitrile |
| 41. | N-[(1-Ethyl-2-{3-[(4-methylphenyl)amino]prop-1-yn-1-yl}-1H-indol-5-yl)methyl]-1-methylpiperidin-4-amine |
| 42. | 4-{[3-(1-Ethyl-5-{[(1-methylpiperidin-4-yl)amino]methyl}-1H-indol-2-yl)prop-2-yn-1-yl]amino}benzonitrile |
| 43. | 3-(1-Ethyl-5-{[(1-methylpiperidin-4-yl)amino]methyl}-1H-indol-2-yl)-N-phenylprop-2-ynamide |
| 44. | N-[(2-{3-[(4-Chlorophenyl)amino]prop-1-yn-1-yl}-1-ethyl-1H-indol-5-yl)methyl]-1-methanesulfonylpiperidin-4-amine |
| 45. | 1-(4-{[(2-{3-[(4-Chlorophenyl)amino]prop-1-yn-1-yl}-1-ethyl-1H-indol-5-yl)methyl]amino}piperidin-1-yl)ethan-1-one |
| 46. | 6-tert-Butyl-N-[3-(1-ethyl-5-{[(1-methylpiperidin-4-yl)amino]methyl}-1H-indol-2-yl)prop-2-yn-1-yl]pyridine-3-carboxamide |
| 47. | N-(3-{1-Ethyl-5-[(methylamino)methyl]-1H-indol-2-yl}prop-2-yn-1-yl)-4-(trifluoromethyl)aniline |
| 48. | N-[(1-Ethyl-2-{3-[(4-methylphenyl)amino]prop-1-yn-1-yl}-1H-indol-5-yl)methyl]oxan-4-amine |
| 49. | N-(3-{1-ethyl-4-[(methylamino)methyl]-1H-indol-2-yl}prop-2-yn-1-yl)aniline |
| 50. | N-[3-(1-ethyl-4-{[4-(pyrrolidin-1-yl)piperidin-1-yl]methyl}-1H-indol-2-yl)prop-2-yn-1-yl]aniline |
| 51. | N-({1-ethyl-2-[3-(phenylamino)prop-1-yn-1-yl]-1H-indol-4-yl}methyl)-1-methylpiperidin-4-amine |
| 52. | 1-[(2-{3-[(4-chlorophenyl)arnino]prop-1-yn-1-yl}-1-ethyl-1H-indol-4-yl)methyl]piperidin-4-ol |
| 53. | 4-Chloro-N-[3-(1-ethyl-4-{[4-(pyrrolidin-1-yl)piperidin-1-yl]methyl}-1H-indol-2-yl)prop-2-yn-1-yl]aniline |
| 54. | 1-[(2-{3-[(4-chlorophenyl)amino]prop-1-yn-1-yl}-1-ethyl-1H-indol-4-yl)methyl]-N,N-dimethylpiperidin-4-amine |

TABLE 1-continued

Alkynyl indole compounds of the disclosure.

| Mol # | IUPAC name |
|---|---|
| 55. | 4-Chloro-N-(3-{1-ethyl-4-[(4-methylpiperazin-1-yl)methyl]-1H-indol-2-yl}prop-2-yn-1-yl)aniline |
| 56. | 1-{1-[(2-{3-[(4-Chlorophenyl)amino]prop-1-yn-1-yl}-1-ethyl-1H-indol-4-yl)methyl]piperidin-4-yl}piperidin-4-ol |
| 57. | 2-(5-{[3-(4-{[4-(4-Aminopiperidin-1-yl)piperidin-1-yl]methyl}-1-ethyl-1H-indol-2-yl)prop-2-yn-1-yl]amino}pyridin-2-yl)-2-methylpropanenitrile |
| 58. | 1-[(1-ethyl-2-{3-[(4-fluorophenyl)amino]prop-1-yn-1-yl}-1H-indol-5-yl)methyl]-N,N-dimethylpiperidin-4-amine |
| 59. | 4-N-({1-ethyl-2-[3-(phenylamino)prop-1-yn-1-yl]-1H-indol-5-yl}methyl)-1-N,1-N-dimethylcyclohexane-1,4-diamine |
| 60. | 4-chloro-N-(3-{1-ethyl-5-[(methylamino)methyl]-1H-indol-2-yl}prop-2-yn-1-yl)-3-fluoroaniline |
| 61. | 6-tert-butyl-N-(3-{1-ethyl-5-[(methylamino)methyl]-1H-indol-2-yl}prop-2-yn-1-yl)pyridine-3-carboxamide |
| 62. | N-(3-{1-ethyl-5-[(methylamino)methyl]-1H-indol-2-yl}prop-2-yn-1-yl)benzamide |
| 63. | 3-(3-{1-ethyl-5-[(methylamino)methyl]-1H-indol-2-yl}prop-2-yn-1-yl)-1-(4-methylphenyl)urea |
| 64. | 4-chloro-N-(3-{1-ethyl-5-[(methylamino)methyl]-1H-indol-2-yl}prop-2-yn-1-yl)aniline |
| 65. | 4-{[3-(1-ethyl-5-{[(oxan-4-yl)amino]methyl}-1H-indol-2-yl)prop-2-yn-1-yl]amino}benzonitrile |
| 66. | N-[(2-{3-[(4-chloro-3-fluorophenyl)amino]prop-1-yn-1-yl}-1-ethyl-1H-indol-5-yl)methyl]oxan-4-amine |
| 67. | 3-[3-(1-ethyl-5-{[(oxan-4-yl)amino]methyl}-1H-indol-2-yl)prop-2-yn-1-yl]-1-phenylurea |
| 68. | 6-tert-butyl-N-[3-(1-ethyl-5-{[(oxan-4-yl)amino]methyl}-1H-indol-2-yl)prop-2-yn-1-yl]pyridin-3-amine |
| 69. | 4-{[(2-{3-[(4-chlorophenyl)amino]prop-1-yn-1-yl}-1-ethyl-1H-indol-5-yl)methyl]amino}-1λ⁶-thiane-1,1-dione |
| 70. | N-[(2-{3-[(4-chlorophenyl)amino]prop-1-yn-1-yl}-1-ethyl-1H-indol-5-yl)methyl]-1-(2-methanesulfonylethyl)piperidin-4-amine |
| 71. | 1-(4-{[(2-{3-[(4-chlorophenyl)amino]prop-1-yn-1-yl}-1-ethyl-1H-indol-5-yl)methyl]amino}piperidin-1-yl)-2-(dimethylamino)ethan-1-one |
| 72. | 2-(4-{[(2-{3-[(4-chlorophenyl)amino]prop-1-yn-1-yl}-1-ethyl-1H-indol-5-yl)methyl]amino}piperidin-1-yl)-N,N-dimethylacetamide |
| 73. | 2-tert-butyl-N-[3-(1-ethyl-5-{[(1-methylpiperidin-4-yl)amino]methyl}-1H-indol-2-yl)prop-2-yn-1-yl]pyrimidin-5-amine |
| 74. | 2-methyl-2-(5-{[3-(5-{[(oxan-4-yl)amino]methyl}-1-(2,2,2-trifluoroethyl)-1H-indol-2-yl)prop-2-yn-1-yl]amino}pyridin-2-yl)propanenitrile |
| 75. | 2-[5-({3-[1-(2-fluoroethyl)-5-{[(oxan-4-yl)amino]methyl}-1H-indol-2-yl]prop-2-yn-1-yl}amino)pyridin-2-yl]-2-methylpropanenitrile |
| 76. | 3-(1-ethyl-5-{[(1-methylpiperidin-4-yl)amino]methyl}-1H-indol-2-yl)prop-2-yn-1-ol |
| 77. | 2-[5-({3-[1-(2-chloroethyl)-5-{[(oxan-4-yl)amino]methyl}-1H-indol-2-yl]prop-2-yn-1-yl}amino)pyridin-2-yl]-2-methylpropanenitrile |
| 78. | 2-[5-({3-[1-(2,2-difluoroethyl)-5-{[(oxan-4-yl)amino]methyl}-1H-indol-2-yl]prop-2-yn-1-yl}amino)pyridin-2-yl]-2-methylpropanenitrile |
| 79. | 6-chloro-N-[3-(1-ethyl-5-{[(1-methylpiperidin-4-yl)amino]methyl}-1H-indol-2-yl)prop-2-yn-1-yl]pyridin-3-amine |
| 80. | tert-butyl N-({3-ethyl-2-[3-(phenylamino)prop-1-yn-1-yl]-1H-indol-6-yl}methyl)-N-(oxan-4-yl)carbamate |
| 81. | 6-Chloro-N-[3-(1-ethyl-4-{[4-(pyrrolidin-1-yl)piperidin-1-yl]methyl}-1H-indol-2-yl)prop-2-yn-1-yl]pyridin-3-amine |
| 82. | 3-(1-ethyl-5-{[(1-methylpiperidin-4-yl)amino]methyl}-1H-indol-2-yl)prop-2-yn-1-yl benzoate |
| 83. | 2-[5-({3-[1-(2-chloroethyl)-5-{[(1-methylpiperidin-4-yl)amino]methyl}-1H-indol-2-yl]prop-2-yn-1-yl}amino)pyridin-2-yl]-2-methylpropanenitrile |
| 84. | N-(6-chloropyridin-3-yl)-3-(1-ethyl-5-{[(1-methylpiperidin-4-yl)amino]methyl}-1H-indol-2-yl)prop-2-ynamide |
| 85. | N-[6-(1-cyano-1-methylethyl)pyridin-3-yl]-3-(1-ethyl-5-{[(1-methylpiperidin-4-yl)amino]methyl}-1H-indol-2-yl)prop-2-ynamide |
| 86. | N-({3-ethyl-2-[3-(phenylamino)prop-1-yn-1-yl]-1H-indol-6-yl}methyl)oxan-4-amine |
| 87. | 2-[5-({3-[1-(2-chloroethyl)-4-{[4-(pyrrolidin-1-yl)piperidin-1-yl]methyl}-1H-indol-2-yl]prop-2-yn-1-yl}amino)pyridin-2-yl]-2-methylpropanenitrile |
| 88. | 2-(5-{[3-(5-{[(1-methanesulfonylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 89. | 2-[5-({3-[5-({[1-(2-methanesulfonylethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 90. | 2-(5-{[3-(5-{[(1-acetylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 91. | 2-{5-[(3-{5-[({1-[2-(dimethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 92. | 2-methyl-2-(5-{[3-(5-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 93. | 2-methyl-2-{5-[(3-{5-[(methylamino)methyl]-1-(2,2,2-trifluoroethyl)-1H-indol-2-yl}prop-2-yn-1-yl)amino]pyridin-2-yl}propanenitrile |
| 94. | 6-Chloro-N-[3-(5-{[(1-methylpiperidin-4-yl)amino]methyl}-1-(2,2,2-trifluoroethyl)-1H-indol-2-yl)prop-2-yn-1-yl]pyridin-3-amine |

TABLE 1-continued

Alkynyl indole compounds of the disclosure.

| Mol # | IUPAC name |
|---|---|
| 95. | 6-chloro-N-[3-(5-{[(oxan-4-yl)amino]methyl}-1-(2,2,2-trifluoroethyl)-1H-indol-2-yl)prop-2-yn-1-yl]pyridin-3-amine |
| 96. | 2-[5-({3-[1-(cyclopropylmethyl)-5-{[(oxan-4-yl)amino]methyl}-1H-indol-2-yl]prop-2-yn-1-yl}amino)pyridin-2-yl]-2-methylpropanenitrile |
| 97. | 2-(5-{[3-(4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 98. | 2-methyl-2-{5-[(3-{4-[(4-methylpiperazin-1-yl)methyl]-1-(2,2,2-trifluoroethyl)-1H-indol-2-yl}prop-2-yn-1-yl)amino]pyridin-2-yl}propanenitrile |
| 99. | 2-(5-{[3-(1-ethyl-7-fluoro-4-{[4-(pyrrolidin-1-yl)piperidin-1-yl]methyl}-1H-indol-2-yl)prop-2-yn-1-yl]amino}pyridin-2-yl)-2-methylpropanenitrile |
| 100. | 2-methyl-2-(5-{[3-(4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)propanenitrile |
| 101. | 2-(5-{[3-(4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 102. | N-(6-cyanopyridin-3-yl)-3-(1-ethyl-5-{[(1-methylpiperidin-4-yl)amino]methyl}-1H-indol-2-yl)prop-2-ynamide |
| 103. | N-[6-(1-cyano-1-methylethyl)pyridin-3-yl]-3-(5-{[(oxan-4-yl)amino]methyl}-1-(2,2,2-trifluoroethyl)-1H-indol-2-yl)prop-2-ynamide |
| 104. | N-[6-(1-cyano-1-methylethyl)pyridin-3-yl]-3-(5-{[(1-methylpiperidin-4-yl)amino]methyl}-1-(2,2,2-trifluoroethyl)-1H-indol-2-yl)prop-2-ynamide |
| 105. | 2-methyl-2-(5-{[3-(5-{[(oxan-4-yl)amino]methyl}-1-(oxiran-2-ylmethyl)-1H-indol-2-yl)prop-2-yn-1-yl]amino}pyridin-2-yl)propanenitrile |
| 106. | 2-(5-{[3-(5-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 107. | 2-methyl-2-[5-({3-[5-({[2-(morpholin-4-yl)ethyl]amino}methyl)-1-(2,2,2-trifluoroethyl)-1H-indol-2-yl]prop-2-yn-1-yl}amino)pyridin-2-yl]propanenitrile |
| 108. | 2-methyl-2-(5-{[3-(4-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 109. | 2-methyl-2-(5-{[3-(4-{[(oxan-4-yl)amino]methyl}-1-(2,2,2-trifluoroethyl)-1H-indol-2-yl)prop-2-yn-1-yl]amino}pyridin-2-yl)propanenitrile |
| 110. | 2-[5-({3-[5-({[2-(dimethylamino)ethyl]amino}methyl)-1-(2,2,2-trifluoroethyl)-1H-indol-2-yl]prop-2-yn-1-yl}amino)pyridin-2-yl]-2-methylpropanenitrile |
| 111. | 2-(5-{[3-(7-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 112. | 2-methyl-2-[5-({3-[1-(2,2,2-trifluoroethyl)-5-{[(2,2,2-trifluoroethyl)amino]methyl}-1H-indol-2-yl]prop-2-yn-1-yl}amino)pyridin-2-yl]propanenitrile |
| 113. | 2-[5-({3-[5-({[1-(2-hydroxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 114. | 2-[5-({3-[5-({[1-(2-methoxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 115. | 2-[5-({3-[5-({[4-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 116. | 2-methyl-2-{5-[(3-{5-[({1-[2-(morpholin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 117. | 2-(5-{[3-(4-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 118. | 2-methyl-2-{5-[(3-{4-[(methylamino)methyl]-1-(2,2,2-trifluoroethyl)-1H-indol-2-yl}prop-2-yn-1-yl)amino]pyridin-2-yl}propanenitrile |
| 119. | 2-{5-[(3-{4-[(4-acetylpiperazin-1-yl)methyl]-1-(2,2,2-trifluoroethyl)-1H-indol-2-yl}prop-2-yn-1-yl)amino]pyridin-2-yl}-2-methylpropanenitrile |
| 120. | 2-methyl-2-[5-({3-[4-(morpholin-4-ylmethyl)-1-(2,2,2-trifluoroethyl)-1H-indol-2-yl]prop-2-yn-1-yl}amino)pyridin-2-yl]propanenitrile |
| 121. | 2-(5-{[3-(4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 122. | 2-[5-({3-[4-(hydroxymethyl)-1-(2,2,2-trifluoroethyl)-1H-indol-2-yl]prop-2-yn-1-yl}amino)pyridin-2-yl]-2-methylpropanenitrile |
| 123. | 2-methyl-2-[5-({3-[4-({4-[2-(morpholin-4-yl)-2-oxoethyl]piperazin-1-yl}methyl)-1-(2,2,2-trifluoroethyl)-1H-indol-2-yl]prop-2-yn-1-yl}amino)pyridin-2-yl]propanenitrile |
| 124. | 2-(5-{[3-(3-ethyl-7-{[4-(pyrrolidin-1-yl)piperidin-1-yl]methyl}-1H-indol-2-yl)prop-2-yn-1-yl]amino}pyridin-2-yl)-2-methylpropanenitrile |
| 125. | methyl 5-{[3-(5-{[(oxan-4-yl)amino]methyl}-1-(2,2,2-trifluoroethyl)-1H-indol-2-yl)prop-2-yn-1-yl]amino}pyridine-2-carboxylate |
| 126. | N-methyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 127. | N-(2-hydroxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 128. | N-(2-methoxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 129. | 2-[(5-{[3-(5-{[(oxan-4-yl)amino]methyl}-1-(2,2,2-trifluoroethyl)-1H-indol-2-yl)prop-2-yn-1-yl]amino}pyridin-2-yl)formamido]acetic acid |
| 130. | 5-{[3-(5-{[(oxan-4-yl)amino]methyl}-1-(2,2,2-trifluoroethyl)-1H-indol-2-yl)prop-2-yn-1-yl]amino}pyridine-2-carboxylic acid |
| 131. | N-(2-methanesulfonylethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 132. | 2-[5-({3-[1-(cyanomethyl)-5-{[(oxan-4-yl)amino]methyl}-1H-indol-2-yl]prop-2-yn-1-yl}amino)pyridin-2-yl]-2-methylpropanenitrile |

TABLE 1-continued

Alkynyl indole compounds of the disclosure.

| Mol # | IUPAC name |
|---|---|
| 133. | 2-methyl-2-[5-({3-[1-(2-methylpropyl)-5-{[(oxan-4-yl)amino]methyl}-1H-indol-2-yl]prop-2-yn-1-yl}amino)pyridin-2-yl]propanenitrile |
| 134. | 2-methyl-2-{5-[(3-{4-[(oxan-4-yl)amino]-1-(2,2,2-trifluoroethyl)-1H-indol-2-yl}prop-2-yn-1-yl)amino]pyridin-2-yl}propanenitrile |
| 135. | 5-{[3-(5-{[(oxan-4-yl)amino]methyl}-1-(2,2,2-trifluoroethyl)-1H-indol-2-yl)prop-2-yn-1-yl]amino}pyridine-2-carbonitrile |
| 136. | N,N-dimethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 137. | N-(oxan-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 138. | 2-tert-butyl-N-[3-(5-{[(oxan-4-yl)amino]methyl}-1-(2,2,2-trifluoroethyl)-1H-indol-2-yl)prop-2-yn-1-yl]pyrimidin-5-amine |
| 139. | N-(1-methylpiperidin-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 140. | N-[6-(1-cyano-1-methylethyl)pyridin-3-yl]-3-[1-(2-fluoroethyl)-5-{[(oxan-4-yl)amino]methyl}-1H-indol-2-yl]prop-2-ynamide |
| 141. | 2-(5-{[3-(7-chloro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 142. | 2-(5-{[3-(6-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 143. | 2-(5-{[3-(1-ethyl-5-{[(oxan-4-yl)amino]methyl}-1H-pyrrolo[2,3-c]pyridin-2-yl)prop-2-yn-1-yl]amino}pyridin-2-yl)-2-methylpropanenitrile |
| 144. | 2-methyl-2-(5-{[3-(5-{[(oxan-4-yl)amino]methyl}-1-(2,2,2-trifluoroethyl)-1H-pyrrolo[2,3-c]pyridin-2-yl)prop-2-yn-1-yl]amino}pyridin-2-yl)propanenitrile |
| 145. | 2-(5-{[3-(5-{[4-(dimethylamino)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 146. | 2-(5-{[3-(7-chloro-4-{[4-(pyrrolidin-1-yl)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 147. | 2-(5-{[3-(4-{[4-(dimethylamino)-piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 148. | 2-(5-{[3-(4-{[4-(diethylamino)piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 149. | 2-(5-{[3-(6-fluoro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 150. | 2-(5-{[3-(6-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 151. | 2-(5-{[3-(5-{[(1-acetylpiperidin-4-yl)amino]methyl}-6-fluoro-1-(2,2,2-trifluoroethyl)-1H-indol-2-yl)prop-2-yn-1-yl]amino}pyridin-2-yl)-2-methylpropanenitrile |
| 152. | 2-(5-{[3-(6-chloro-4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 153. | 2-(5-{[3-(6-chloro-4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 154. | 2-(5-{[3-(6-chloro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 155. | 2-(5-{[3-(4-{[4-(2-methanesulfonyl-ethyl)piperazin-1-yl]methyl}-1-(2,2,2-trifluoroethyl)-1H-indol-2-yl)prop-2-yn-1-yl]amino}pyridin-2-yl)-2-methylpropanenitrile |
| 156. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)-N,N-dimethylacetamide |
| 157. | 2-methyl-2-{5-[(3-{4-[(3-oxopiperazin-1-yl)methyl]-1-(2,2,2-trifluoroethyl)-1H-indol-2-yl}prop-2-yn-1-yl)amino]pyridin-2-yl}propanenitrile |
| 158. | 2-methyl-2-[5-({3-[4-({4-[2-(morpholin-4-yl)-2-oxoethyl]piperidin-1-yl}methyl)-1-(2,2,2-trifluoroethyl)-1H-indol-2-yl]prop-2-yn-1-yl}amino)pyridin-2-yl]propanenitrile |
| 159. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)acetamide |
| 160. | N-[6-(1-cyano-1-methylethyl)pyridin-3-yl]-3-(4-{[4-(pyrrolidin-1-yl)piperidin-1-yl]methyl}-1-(2,2,2-trifluoroethyl)-1H-indol-2-yl)prop-2-ynamide |
| 161. | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)acetamide |
| 162. | 2-(5-{[3-(4-{[4-(2-aminoethyl)-piperazin-1-yl]methyl}-1-(2,2,2-trifluoroethyl)-1H-indol-2-yl)prop-2-yn-1-yl]amino}pyridin-2-yl)-2-methylpropanenitrile |
| 163. | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)-N,N-dimethylacetamide |
| 164. | 2-methyl-2-(5-{[3-(4-{[4-(morpholin-4-yl)piperidin-1-yl]methyl}-1-(2,2,2-trifluoroethyl)-1H-indol-2-yl)prop-2-yn-1-yl]amino}pyridin-2-yl)propanenitrile |
| 165. | 2-(5-{[3-(4-{[4-(4-aminopiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 166. | 2-methyl-2-[5-({3-[1-(oxiran-2-ylmethyl)-4-{[4-(pyrrolidin-1-yl)piperidin-1-yl]methyl}-1H-indol-2-yl]prop-2-yn-1-yl}amino)pyridin-2-yl]propanenitrile |
| 167. | 2-(5-{[3-(3-ethyl-6-{[(oxan-4-yl)amino]methyl}-1H-indol-2-yl)prop-2-yn-1-yl]amino}pyridin-2-yl)-2-methylpropanenitrile |
| 168. | 2-methyl-2-(5-{[3-(6-{[(oxan-4-yl)amino]methyl}-3-(2,2,2-trifluoroethyl)-1H-indol-2-yl)prop-2-yn-1-yl]amino}pyridin-2-yl)propanenitrile |
| 169. | 2-(5-{[3-(1-acetyl-3-ethyl-6-{[(oxan-4-yl)amino]methyl}-1H-indol-2-yl)prop-2-yn-1-yl]amino}pyridin-2-yl)-2-methylpropanenitrile |

TABLE 1-continued

Alkynyl indole compounds of the disclosure.

| Mol # | IUPAC name |
|---|---|
| 170. | 2-(5-{[3-(3-ethyl-6-{[(1-methylpiperidin-4-yl)amino]methyl}-1H-indol-2-yl)prop-2-yn-1-yl]amino}pyridin-2-yl)-2-methylpropanenitrile |
| 171. | 2-methyl-2-(5-{[3-(6-{[(1-methylpiperidin-4-yl)amino]methyl}-3-(2,2,2-trifluoroethyl)-1H-indol-2-yl)prop-2-yn-1-yl]amino}pyridin-2-yl)propanenitrile |
| 172. | 2-{5-[(3-{6-chloro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 173. | 2-(3-{[6-(1-cyano-1-methylethyl)pyridin-3-yl]amino}prop-1-yn-1-yl)-6-fluoro-N-(1-methylpiperidin-4-yl)-1-(2,2,2-trifluoroethyl)-1H-indole-4-carboxamide |
| 174. | 2-[5-({3-[6-fluoro-4-(4-methylpiperazine-1-carbonyl)-1-(2,2,2-trifluoroethyl)-1H-indol-2-yl]prop-2-yn-1-yl}amino)pyridin-2-yl]-2-methylpropanenitrile |
| 175. | 6-fluoro-2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |
| 176. | 2-{5-[(3-{6-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 177. | 5-[(3-{6-fluoro-4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 178. | 2-methyl-2-(5-{[3-(5-{[(oxan-4-yl)amino]methyl}-1-(2,2,2-trifluoroethyl)-1H-pyrrolo[2,3-b]pyridin-2-yl)prop-2-yn-1-yl]amino}pyridin-2-yl)propanenitrile |
| 179. | 2-methyl-2-{5-[(3-{4-[(1-methylpiperidin-4-yl)amino]-1-(2,2,2-trifluoroethyl)-1H-pyrrolo[2,3-b]pyridin-2-yl}prop-2-yn-1-yl)amino]pyridin-2-yl}propanenitrile |
| 180. | 2-(5-{[3-(7-chloro-1-ethyl-4-{[4-(pyrrolidin-1-yl)piperidin-1-yl]methyl}-1H-indol-2-yl)prop-2-yn-1-yl]amino}pyridin-2-yl)-2-methylpropanenitrile |
| 181. | 2-(5-{[3-(7-chloro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 182. | 2-(5-{[3-(7-chloro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 183. | 2-{5-[(3-{7-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 184. | 2-(5-{[3-(7-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 185. | 2-(5-{[3-(7-fluoro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 186. | 2-methyl-2-(5-{[3-(5-{[(oxan-4-yl)amino]methyl}-1-(2,2,2-trifluoroethyl)-1H-1,3-benzodiazol-2-yl)prop-2-yn-1-yl]amino}pyridin-2-yl)propanenitrile |
| 187. | N-{[2-(2-phenylethynyl)-1-(2,2,2-trifluoroethyl)-1H-1,3-benzodiazol-5-yl]methyl}oxan-4-amine |
| 188. | 2-methyl-2-(5-{[3-(5-{[(oxan-4-yl)amino]methyl}-1-(2,2,2-trifluoroethyl)-1H-pyrrolo[3,2-b]pyridin-2-yl)prop-2-yn-1-yl]amino}pyridin-2-yl)propanenitrile |
| 189. | 2-{3-[(4-methanesulfonylphenyl)amino]prop-1-yn-1-yl}-5-methyl-N-(1-methylpiperidin-4-yl)-1-(2,2,2-trifluoroethyl)-1H-indol-4-amine |
| 190. | 4-[(2-{3-[(4-methanesulfonylphenyl)amino]prop-1-yn-1-yl}-5-methyl-1-(2,2,2-trifluoroethyl)-1H-indol-4-yl)amino]-1$\lambda^6$-thiane-1,1-dione |
| 191. | 2-methyl-2-{5-[(3-{5-methyl-4-[(1-methylpiperidin-4-yl)amino]-1-(2,2,2-trifluoroethyl)-1H-indol-2-yl}prop-2-yn-1-yl)amino]pyridin-2-yl}propanenitrile |
| 192. | N-[1-(2-methanesulfonylethyl)piperidin-4-yl]-2-{3-[(4-methanesulfonylphenyl)amino]prop-1-yn-1-yl}-5-methyl-1-(2,2,2-trifluoroethyl)-1H-indol-4-amine |
| 193. | 4-[(3-{5-methyl-4-[(piperidin-4-yl)amino]-1-(2,2,2-trifluoroethyl)-1H-indol-2-yl}prop-2-yn-1-yl)amino]benzene-1-sulfonamide |
| 194. | 2-{3-[(4-methanesulfonylphenyl)amino]prop-1-yn-1-yl}-5-methyl-N-[1-(oxan-4-yl)piperidin-4-yl]-1-(2,2,2-trifluoroethyl)-1H-indol-4-amine |
| 195. | 2-{4-[(2-{3-[(4-methanesulfonylphenyl)amino]prop-1-yn-1-yl}-5-methyl-1-(2,2,2-trifluoroethyl)-1H-indol-4-yl)amino]piperidin-1-yl}ethan-1-ol |
| 196. | 2-[5-({3-[4-(methoxymethyl)-1-(2,2,2-trifluoroethyl)-1H-indol-2-yl]prop-2-yn-1-yl}amino)pyridin-2-yl]-2-methylpropanenitrile |
| 197. | 2-[5-({3-[4-(cyanomethyl)-1-(2,2,2-trifluoroethyl)-1H-indol-2-yl]prop-2-yn-1-yl}amino)pyridin-2-yl]-2-methylpropanenitrile |
| 198. | 2-methyl-2-[5-({3-[5-(morpholine-4-carbonyl)-1-(2,2,2-trifluoroethyl)-1H-indol-2-yl]prop-2-yn-1-yl}amino)pyridin-2-yl]propanenitrile |
| 199. | 2-methyl-2-[5-({3-[5-(4-methylpiperazine-1-carbonyl)-1-(2,2,2-trifluoroethyl)-1H-indol-2-yl]prop-2-yn-1-yl}amino)pyridin-2-yl]propanenitrile |
| 200. | 2-{5-[(3-{5-[4-(dimethylamino)piperidine-1-carbonyl]-1-(2,2,2-trifluoroethyl)-1H-indol-2-yl}prop-2-yn-1-yl)amino]pyridin-2-yl}-2-methylpropanenitrile |
| 201. | 2-(3-{[6-(1-cyano-1-methylethyl)pyridin-3-yl]amino}prop-1-yn-1-yl)-N-{1-[2-(dimethylamino)acetyl]piperidin-4-yl}-1-(2,2,2-trifluoroethyl)-1H-indole-5-carboxamide |
| 202. | 2-(3-{[6-(1-cyano-1-methylethyl)pyridin-3-yl]amino}prop-1-yn-1-yl)-N-(oxan-4-yl)-1-(2,2,2-trifluoroethyl)-1H-indole-5-carboxamide |
| 203. | 2-methyl-2-(5-{[3-(5-{1-[(oxan-4-yl)amino]ethyl}-1-(2,2,2-trifluoroethyl)-1H-indol-2-yl)prop-2-yn-1-yl]amino}pyridin-2-yl)propanenitrile |
| 204. | 2-methyl-2-{5-[(3-{4-[(1-methylpiperidin-4-yl)amino]-1-(2,2,2-trifluoroethyl)-1H-pyrrolo[3,2-c]pyridin-2-yl}prop-2-yn-1-yl)amino]pyridin-2-yl}propanenitrile |
| 205. | 2-methyl-2-[5-({3-[5-(morpholin-4-ylmethyl)-1-(2,2,2-trifluoroethyl)-1H-indol-2-yl]prop-2-yn-1-yl}amino)pyridin-2-yl]propanenitrile |
| 206. | 2-[5-({3-[5-({[1-(2-cyanoethyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |

TABLE 1-continued

Alkynyl indole compounds of the disclosure.

| Mol # | IUPAC name |
|---|---|
| 207. | 2-methyl-2-(5-{[3-(5-{[(1-methylazetidin-3-yl)amino]methyl}-1-(2,2,2-trifluoroethyl)-1H-indol-2-yl)prop-2-yn-1-yl]amino}pyridin-2-yl)propanenitrile |
| 208. | 2-methyl-2-(5-{[3-(5-{[(oxetan-3-yl)amino]methyl}-1-(2,2,2-trifluoroethyl)-1H-indol-2-yl)prop-2-yn-1-yl]amino}pyridin-2-yl)propanenitrile |
| 209. | 2-(5-{[3-(5-{[4-(dimethylamino)-piperidin-1-yl]methyl}-1-(2,2,2-trifluoroethyl)-1H-indol-2-yl)prop-2-yn-1-yl]amino}pyridin-2-yl)-2-methylpropanenitrile |
| 210. | 2-methyl-2-{5-[(3-{5-[({1-[2-(4-methylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 211. | 2-(5-{[3-(5-{[(1-methoxypropan-2-yl)amino]methyl}-1-(2,2,2-trifluoroethyl)-1H-indol-2-yl)prop-2-yn-1-yl]amino}pyridin-2-yl)-2-methylpropanenitrile |
| 212. | 2-methyl-2-(5-{[3-(5-{[(pyridin-4-ylmethyl)amino]methyl}-1-(2,2,2-trifluoroethyl)-1H-indol-2-yl)prop-2-yn-1-yl]amino}pyridin-2-yl)propanenitrile |
| 213. | 2-methyl-2-(5-{[3-(5-{[(pyridin-3-ylmethyl)amino]methyl}-1-(2,2,2-trifluoroethyl)-1H-indol-2-yl)prop-2-yn-1-yl]amino}pyridin-2-yl)propanenitrile |
| 214. | 2-[5-({3-[5-({[1-(dimethylamino)-propan-2-yl]amino}methyl)-1-(2,2,2-trifluoroethyl)-1H-indol-2-yl]prop-2-yn-1-yl}amino)pyridin-2-yl]-2-methylpropanenitrile |
| 215. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(oxan-4-yl)acetamide |
| 216. | 2-[5-({3-[5-({[1-(2-methoxyacetyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 217. | 2-methyl-2-{5-[(3-{5-[({1-[2-(oxan-4-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |
| 218. | 2-methyl-2-{5-[(3-{5-[({1-[2-(pyridin-3-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |
| 219. | 2-methyl-2-(5-{[3-(5-{[(1-{2-[(oxan-4-yl)amino]acetyl}piperidin-4-yl)amino]methyl}-1-(2,2,2-trifluoroethyl)-1H-indol-2-yl)prop-2-yn-1-yl]amino}pyridin-2-yl)-propanenitrile |
| 220. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-methyl-N-(propan-2-yl)acetamide |
| 221. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(2-methoxyethyl)-N-methylacetamide |
| 222. | 6-methanesulfonyl-N-[3-(5-{[(oxan-4-yl)amino]methyl}-1-(2,2,2-trifluoroethyl)-1H-indol-2-yl)prop-2-yn-1-yl]pyridin-3-amine |
| 223. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N,N-dimethylacetamide |
| 224. | 2-methyl-2-{5-[(3-{5-[({1-[2-oxo-2-(pyrrolidin-1-yl)ethyl]piperidin-4-yl}amino)methyl]-1-(2,2,2-trifluoroethyl)-1H-indol-2-yl}prop-2-yn-1-yl)amino]pyridin-2-yl}propanenitrile |
| 225. | 4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-N,N-dimethylpiperidine-1-carboxamide |
| 226. | 2-{5-[(3-{5-[({1-[2-(azetidin-1-yl)-2-oxoethyl]piperidin-4-yl}amino)-methyl]-1-(2,2,2-trifluoroethyl)-1H-indol-2-yl}prop-2-yn-1-yl)amino]-pyridin-2-yl}-2-methylpropanenitrile |
| 227. | 2-methyl-2-{5-[(3-{5-[({1-[2-(pyrrolidin-1-yl)acetyl]piperidin-4-yl}amino)methyl]-1-(2,2,2-trifluoroethyl)-1H-indol-2-yl}prop-2-yn-1-yl)amino]pyridin-2-yl}-propanenitrile |
| 228. | 2-(5-{[3-(5-{[(1-{2-[4-(dimethylamino)piperidin-1-yl]acetyl}piperidin-4-yl)amino]-methyl}-1-(2,2,2-trifluoroethyl)-1H-indol-2-yl)prop-2-yn-1-yl]amino}pyridin-2-yl)-2-methylpropanenitrile |
| 229. | 2-{5-[(3-{5-[({1-[2-(diethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 230. | 2-methyl-2-(5-{[3-(5-{[(1-{2-[methyl(propan-2-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile |
| 231. | 2-methyl-2-{5-[(3-{5-[({1-[2-(pyridin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 232. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-4-yl)acetamide |
| 233. | 2-methyl-2-{5-[(3-{5-[({1-[2-(morpholin-4-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 234. | 2-methyl-2-{5-[(3-{5-[({1-[2-(4-methylpiperazin-1-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 235. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-3-yl)acetamide |
| 236. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(1-methylpiperidin-4-yl)acetamide |
| 237. | 2-methyl-2-[5-({3-[5-({[4-(morpholin-4-yl)cyclohexyl]amino}methyl)-1-(2,2,2-trifluoroethyl)-1H-indol-2-yl]prop-2-yn-1-yl}amino)pyridin-2-yl]propanenitrile |
| 238. | 2-{5-[(3-{5-[({1-[2-(4-hydroxypiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 239. | 2-{5-[(3-{5-[({1-[2-(4-acetylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |

TABLE 1-continued

Alkynyl indole compounds of the disclosure.

| Mol # | IUPAC name |
|---|---|
| 240. | 2-(5-{[3-(5-{[(1,1-dioxo-1λ$^6$-thian-4-yl)amino]methyl}-1-(2,2,2-trifluoroethyl)-1H-indol-2-yl)prop-2-yn-1-yl]amino}pyridin-2-yl)-2-methylpropanenitrile |
| 241. | 2-{5-[(3-{5-[({1-[2-(1,1-dioxo-1λ$^6$,4-thiomorpholin-4-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 242. | 2-[5-({3-[5-({[1-(4-acetylpiperazine-1-carbonyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 243. | 2-(5-{[3-(5-{[(1-{2-[bis(2-hydroxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 244. | 2-methyl-2-{5-[(3-{5-[({1-[2-(3-oxopiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 245. | 2-methyl-2-[5-({3-[5-({[1-(morpholine-4-carbonyl)piperidin-4-yl]amino}-methyl)-1-(2,2,2-trifluoroethyl)-1H-indol-2-yl]prop-2-yn-1-yl}amino)pyridin-2-yl]propanenitrile |
| 246. | 2-methyl-2-(5-{[3-(5-{[(1-methylpiperidin-3-yl)amino]methyl}-1-(2,2,2-trifluoroethyl)-1H-indol-2-yl)prop-2-yn-1-yl]amino}pyridin-2-yl)propanenitrile |
| 247. | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]acetamide |
| 248. | 2-{5-[(3-{5-[({1-[2-(1H-imidazol-1-yl)acetyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 249. | 2-(5-{[3-(5-{[(1-{2-[(2-methoxyethyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 250. | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]methanesulfonamide |
| 251. | 2-methyl-2-(5-{[3-(5-{[(1-methyl-6-oxopiperidin-3-yl)amino]methyl}-1-(2,2,2-trifluoroethyl)-1H-indol-2-yl)prop-2-yn-1-yl]amino}pyridin-2-yl)propanenitrile |
| 252. | 2-[5-({3-[5-({[3-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 253. | 2-methyl-2-[5-({3-[5-({[1-(4-methylpiperazine-1-carbonyl)piperidin-4-yl]amino}methyl)-1-(2,2,2-trifluoroethyl)-1H-indol-2-yl]prop-2-yn-1-yl}amino)pyridin-2-yl]propanenitrile |
| 254. | 2-{5-[(3-{5-[({1-[4-(dimethylamino)piperidine-1-carbonyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 255. | 2-{5-[(3-{5-[({1-[2-(3-hydroxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 256. | 2-{5-[(3-{5-[({1-[2-(3-methoxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 257. | 2-methyl-2-[5-({3-[5-({[1-(2-{2-oxa-8-azaspiro[4.5]decan-8-yl}acetyl)-piperidin-4-yl]amino}methyl)-1-(2,2,2-trifluoroethyl)-1H-indol-2-yl]prop-2-yn-1-yl}amino)pyridin-2-yl]propanenitrile |
| 258. | 2-{5-[(3-{5-[({1-[2-(4-hydroxy-4-methylpiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 259. | 2-(5-{[3-(5-{[(1-{2-[bis(2-methoxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 260. | 2-(5-{[3-(5-{[(1-{2-[methoxy(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 261. | 2-(5-{[3-(5-{[(1-{2-[(2,3-dihydroxypropyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 262. | 2-methyl-2-(5-{[3-(5-{[(1-methyl-2-oxopiperidin-4-yl)amino]methyl}-1-(2,2,2-trifluoroethyl)-1H-indol-2-yl)prop-2-yn-1-yl]amino}pyridin-2-yl)propanenitrile |
| 263. | 2-methyl-2-(5-{[3-(5-{[(1-{2-[methyl(1-methylpiperidin-4-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile |
| 264. | 2-methyl-2-[5-({3-[5-({[1-(2-{9-methyl-3,9-diazaspiro[5.5]undecan-3-yl}acetyl)piperidin-4-yl]amino}methyl)-1-(2,2,2-trifluoroethyl)-1H-indol-2-yl]prop-2-yn-1-yl}amino)pyridin-2-yl]propanenitrile |
| 265. | 2-(5-{[3-(5-{[(1-{2-[3-(dimethyl-amino)pyrrolidin-1-yl]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 266. | N-[3-(5-{[(oxan-4-yl)amino]methyl}-1-(2,2,2-trifluoroethyl)-1H-indol-2-yl)prop-2-yn-1-yl]-6-(pyrrolidine-1-carbonyl)pyridin-3-amine |
| 267. | 6-(morpholine-4-carbonyl)-N-[3-(5-{[(oxan-4-yl)amino]methyl}-1-(2,2,2-trifluoroethyl)-1H-indol-2-yl)prop-2-yn-1-yl]pyridin-3-amine |
| 268. | 2-chloro-N-[3-(5-{[(oxan-4-yl)amino]-methyl}-1-(2,2,2-trifluoroethyl)-1H-indol-2-yl)prop-2-yn-1-yl]pyrimidin-5-amine |
| 269. | 5-{[3-(5-{[(oxan-4-yl)amino]methyl}-1-(2,2,2-trifluoroethyl)-1H-indol-2-yl)prop-2-yn-1-yl]amino}-N-phenylpyridine-2-carboxamide |
| 270. | N-methyl-5-{[3-(5-([(oxan-4-yl)amino]methyl}-1-(2,2,2-trifluoroethyl)-1H-indol-2-yl)prop-2-yn-1-yl]amino]-N-(propan-2-yl)pyridine-2-carboxamide |

TABLE 1-continued

Alkynyl indole compounds of the disclosure.

| Mol # | IUPAC name |
|---|---|
| 271. | 5-{[3-(5-{[(oxan-4-yl)amino]methyl}-1-(2,2,2-trifluoroethyl)-1H-indol-2-yl)prop-2-yn-1-yl]amino}-N-(pyridin-4-yl)pyridine-2-carboxamide |
| 272. | 5-{[3-(5-{[(oxan-4-yl)amino]methyl}-1-(2,2,2-trifluoroethyl)-1H-indol-2-yl)prop-2-yn-1-yl]amino}-N-(pyridin-3-yl)pyridine-2-carboxamide |
| 273. | N-(1-methylazetidin-3-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 274. | N,N-diethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 275. | 5-{[3-(5-{[(oxan-4-yl)amino]methyl}-1-(2,2,2-trifluoroethyl)-1H-indol-2-yl)prop-2-yn-1-yl]amino}-N-(oxetan-3-yl)pyridine-2-carboxamide |
| 276. | 1-(4-{[(2-{3-[(2-tert-butylpyrimidin-5-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 277. | 1-(4-{[(2-{3-[(6-chloropyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 278. | 5-[(3-{5-[({1-[2-(dimethylamino)-acetyl]piperidin-4-yl}amino)methyl]-1-(2,2,2-trifluoroethyl)-1H-indol-2-yl}prop-2-yn-1-yl)amino]-N-(1-methylpiperidin-4-yl)pyridine-2-carboxamide |
| 279. | 1-(4-{[(2-{3-[(4-chloro-3-fluorophenyl)amino]prop-1-yn-1-yl}-1-(2,2,2-trifluoroethyl)-1H-indol-5-yl)methyl]amino}piperidin-1-yl)-2-(dimethylamino)ethan-1-one |
| 280. | 2-(dimethylamino)-1-(4-{[(2-{3-[(6-methylpyridin-3-yl)amino]prop-1-yn-1-yl}-1-(2,2,2-trifluoroethyl)-1H-indol-5-yl)methyl]amino}piperidin-1-yl)ethan-1-one |
| 281. | 1-(4-{[(2-{3-[(6-tert-butylpyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 282. | N-[6-(1-cyano-1-methylethyl)pyridin-3-yl]-3-[1-(2-fluoroethyl)-5-{[(1-methylpiperidin-4-yl)amino]methyl}-1H-indol-2-yl]prop-2-ynamide |
| 283. | 2-{5-[(3-{5-[({1-[2-(dimethylamino)acetyl]piperidin-4-yl}amino)methyl]-1-ethyl-1H-indol-2-yl}prop-2-yn-1-yl)amino]pyridin-2-yl}-2-methylpropanenitrile |
| 284. | 2-[5-({3-[1-(2,2-difluoroethyl)-5-[({1-[2-(dimethylamino)acetyl]piperidin-4-yl}amino)methyl]-1H-indol-2-yl]prop-2-yn-1-yl}amino)pyridin-2-yl]-2-methylpropanenitrile |
| 285. | 2-{5-[(3-{5-[({1-[2-(dimethylamino)acetyl]piperidin-4-yl}amino)methyl]-1-(2-fluoroethyl)-1H-indol-2-yl}prop-2-yn-1-yl)amino]pyridin-2-yl}-2-methylpropanenitrile |
| 286. | N-(6-chloropyridin-3-yl)-3-(5-{[(1-methylpiperidin-4-yl)amino]methyl}-1-(2,2,2-trifluoroethyl)-1H-indol-2-yl)prop-2-ynamide |
| 287. | 2-(5-{[3-(5-{[(1-acetylpiperidin-4-yl)amino]methyl}-1-(oxiran-2-ylmethyl)-1H-indol-2-yl)prop-2-yn-1-yl]amino}pyridin-2-yl)-2-methylpropanenitrile |
| 288. | 2-methyl-2-{5-[(3-{5-[(oxan-4-yl)amino]-1-(2,2,2-trifluoroethyl)-1H-indol-2-yl}prop-2-yn-1-yl)amino]pyridin-2-yl}propanenitrile |
| 289. | 2-{5-[(3-{4-[(1-acetylpiperidin-4-yl)amino]-1-(2,2,2-trifluoroethyl)-1H-indol-2-yl}prop-2-yn-1-yl)amino]pyridin-2-yl}-2-methylpropanenitrile |
| 290. | 2-methyl-2-{5-[(3-{4-[(propan-2-yl)amino]-1-(2,2,2-trifluoroethyl)-1H-indol-2-yl}prop-2-yn-1-yl)amino]pyridin-2-yl}propanenitrile |
| 291. | 2-methyl-2-{5-[(3-{4-[(piperidin-4-yl)amino]-1-(2,2,2-trifluoroethyl)-1H-indol-2-yl}prop-2-yn-1-yl)amino]pyridin-2-yl}propanenitrile |
| 292. | 2-(5-{[3-(4-{[1-(2-methoxyethyl)-piperidin-4-yl]amino}-1-(2,2,2-trifluoroethyl)-1H-indol-2-yl)prop-2-yn-1-yl]amino}pyridin-2-yl)-2-methylpropanenitrile |
| 293. | 2-{5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridin-2-yl}-2-methylpropanenitrile |
| 294. | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(oxan-4-yl)urea |
| 295. | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(1-methylpiperidin-4-yl)urea |
| 296. | 2-(4-{[2-(3-{[6-(1-cyano-1-methylethyl)-pyridin-3-yl]amino}prop-1-yn-1-yl)-1-(2,2,2-trifluoroethyl)-1H-indol-4-yl]amino}piperidin-1-yl)-N,N-dimethylacetamide |
| 297. | 2-methyl-2-(5-{[3-(4-{[1-(propan-2-yl)piperidin-4-yl]amino}-1-(2,2,2-trifluoroethyl)-1H-indol-2-yl)prop-2-yn-1-yl]amino}pyridin-2-yl)propanenitrile |
| 298. | 2-methyl-2-(5-{[3-(4-{[1-(1-methylpiperidin-4-yl)piperidin-4-yl]amino}-1-(2,2,2-trifluoroethyl)-1H-indol-2-yl)prop-2-yn-1-yl]amino}pyridin-2-yl)propanenitrile |
| 299. | 4-{[2-(3-{[6-(1-cyano-1-methylethyl)-pyridin-3-yl]amino}prop-1-yn-1-yl)-1-(2,2,2-trifluoroethyl)-1H-indol-4-yl]amino}-N,N-dimethylpiperidine-1-carboxamide |
| 300. | N-[2-(3-{[6-(1-cyano-1-methylethyl)-pyridin-3-yl]amino}prop-1-yn-1-yl)-1-(2,2,2-trifluoroethyl)-1H-indol-4-yl]-4-methylpiperazine-1-carboxamide |
| 301. | 1-[2-(3-{[6-(1-cyano-1-methylethyl)pyridin-3-yl]amino}prop-1-yn-1-yl)-1-(2,2,2-trifluoroethyl)-1H-indol-4-yl]-3,3-dimethylurea |
| 302. | N-[2-(3-{[6-(1-cyano-1-methylethyl)-pyridin-3-yl]amino}prop-1-yn-1-yl)-1-(2,2,2-trifluoroethyl)-1H-indol-4-yl]morpholine-4-carboxamide |
| 303. | 2-{5-[(3-{4-[(4-hydroxycyclohexyl)-amino]-1-(2,2,2-trifluoroethyl)-1H-indol-2-yl}prop-2-yn-1-yl)amino]pyridin-2-yl}-2-methylpropanenitrile |
| 304. | 2-methyl-2-[5-({3-[4-({1-[2-(4-methylpiperazin-1-yl)-2-oxoethyl]-piperidin-4-yl}amino)-1-(2,2,2-trifluoroethyl)-1H-indol-2-yl]prop-2-yn-1-yl}amino)pyridin-2-yl]propanenitrile |
| 305. | 2-methyl-2-{5-[(3-{4-[(oxan-4-ylmethyl)amino]-1-(2,2,2-trifluoroethyl)-1H-indol-2-yl}prop-2-yn-1-yl)amino]pyridin-2-yl}propanenitrile |
| 306. | 2-{5-[(3-{4-[(1-ethylpiperidin-4-yl)amino]-1-(2,2,2-trifluoroethyl)-1H-indol-2-yl}prop-2-yn-1-yl)amino]pyridin-2-yl}-2-methylpropanenitrile |
| 307. | 2-(5-{[3-(4-{[1-(2-hydroxyethyl)piperidin-4-yl]amino}-1-(2,2,2-trifluoroethyl)-1H-indol-2-yl)prop-2-yn-1-yl]amino}pyridin-2-yl)-2-methylpropanenitrile |

TABLE 1-continued

Alkynyl indole compounds of the disclosure.

| Mol # | IUPAC name |
|---|---|
| 308. | 2-{5-[(3-{4-[(1-methanesulfonylpiperidin-4-yl)amino]-1-(2,2,2-trifluoroethyl)-1H-indol-2-yl}prop-2-yn-1-yl)amino]pyridin-2-yl}-2-methylpropanenitrile |
| 309. | 2-(5-{[3-(4-{[1-(2-methanesulfonyl-ethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 310. | 2-methyl-2-(5-{[3-(4-{[(1R,4R)-4-hydroxycyclohexyl]amino]-1-(2,2,2-trifluoroethyl)-1H-indol-2-yl)prop-2-yn-1-yl]amino}pyridin-2-yl)propanenitrile |
| 311. | 2-methyl-2-(5-{[3-(4-{[(1S,4S)-4-hydroxycyclohexyl]amino]-1-(2,2,2-trifluoroethyl)-1H-indol-2-yl)prop-2-yn-1-yl]amino}pyridin-2-yl)propanenitrile |
| 312. | 2-methyl-2-[5-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)pyridin-2-yl]propanenitrile |
| 313. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N,N-bis(2-methoxyethyl)acetamide |
| 314. | 2-methyl-2-{5-[(3-{4-[(pyrrolidin-3-yl)amino]-1-(2,2,2-trifluoroethyl)-1H-indol-2-yl}prop-2-yn-1-yl)amino]pyridin-2-yl}propanenitrile |
| 315. | 2-methyl-2-{5-[(3-{4-[(1-methylpyrrolidin-3-yl)amino]-1-(2,2,2-trifluoroethyl)-1H-indol-2-yl}prop-2-yn-1-yl)amino]pyridin-2-yl}propanenitrile |
| 316. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetamide |
| 317. | methyl 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetate |
| 318. | 2-[5-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 319. | 2-methyl-2-{5-[(3-{4-[(2-methylpiperidin-4-yl)amino]-1-(2,2,2-trifluoroethyl)-1H-indol-2-yl}prop-2-yn-1-yl)amino]pyridin-2-yl}propanenitrile |
| 320. | 2-{5-[(3-{4-[(1,1-dioxo-1$\lambda^6$-thiolan-3-yl)amino]-1-(2,2,2-trifluoroethyl)-1H-indol-2-yl}prop-2-yn-1-yl)amino]pyridin-2-yl}-2-methylpropanenitrile |
| 321. | 2-methyl-2-[5-({3-[4-({1-[2-oxo-2-(pyrrolidin-1-yl)ethyl]piperidin-4-yl}amino)-1-(2,2,2-trifluoroethyl)-1H-indol-2-yl]prop-2-yn-1-yl}amino)pyridin-2-yl]propanenitrile |
| 322. | 2-{5-[(3-{4-[(1-{2-[4-(dimethylamino)piperidin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 323. | 2-[5-({3-[4-({1-[2-(dimethylamino)acetyl]piperidin-4-yl}amino)-1-(2,2,2-trifluoroethyl)-1H-indol-2-yl]prop-2-yn-1-yl}amino)pyridin-2-yl]-2-methylpropanenitrile |
| 324. | 2-(5-{[3-(4-{[1-(1,1-dioxo-1$\lambda^6$-thian-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 325. | 2-(5-{[3-(4-{[1-(cyanomethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 326. | 2-methyl-2-[5-({3-[1-(2,2,2-trifluoroethyl)-4-{[1-(2,2,2-trifluoroethyl)piperidin-4-yl]amino}-1H-indol-2-yl]prop-2-yn-1-yl}amino)pyridin-2-yl]propanenitrile |
| 327. | 2-{5-[(3-{4-[(1-{2-[4-(2-methanesulfonylethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 328. | 2-[5-({3-[4-({1-[2-(1,1-dioxo-1$\lambda^6$,4-thiomorpholin-4-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 329. | 2-(5-{[3-(4-{[1-(1-methanesulfonylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 330. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)-N-methylacetamide |
| 331. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)acetamide |
| 332. | 2-[5-({3-[4-({1-[2-(4-methanesulfonylpiperazin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 333. | 2-{5-[(3-{4-[(1-{2-[4-(2-hydroxyethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 334. | 2-methyl-2-(5-{[3-(4-{[1-(oxan-4-yl)piperidin-4-yl]amino}-1-(2,2,2-trifluoroethyl)-1H-indol-2-yl)prop-2-yn-1-yl]amino}pyridin-2-yl)propanenitrile |
| 335. | 2-[5-({3-[4-({1-[1-(2-methanesulfonylethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 336. | 2-[5-({3-[4-({1-[1-(2-methoxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 337. | 2-[5-({3-[4-({1-[1-(2-hydroxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 338. | 2-[5-({3-[4-({1-[2-(dimethylamino)ethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 339. | 2-(5-{[3-(4-{[1-(1-acetylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 340. | 2-methyl-2-[5-({3-[4-({1-[(1R,4R)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |
| 341. | 2-methyl-2-[5-({3-[4-({1-[(1S,4S)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |

TABLE 1-continued

Alkynyl indole compounds of the disclosure.

| Mol # | IUPAC name |
|---|---|
| 342. | N-(1-methylpiperidin-4-yl)-2-{3-[(6-methylpyridin-3-yl)amino]prop-1-yn-1-yl}-1-(2,2,2-trifluoroethyl)-1H-indol-4-amine |
| 343. | 2-methyl-2-{5-[(3-{4-[(1-methylpiperidin-4-yl)amino]-1-(2,2,2-trifluoroethyl)-1H-indol-2-yl}prop-2-yn-1-yl)amino]pyridin-2-yl}propanenitrile |
| 344. | 5-[(3-{4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 345. | 5-[(3-{4-[(1-methylpiperidin-4-yl)amino]-1-(2,2,2-trifluoroethyl)-1H-indol-2-yl}prop-2-yn-1-yl)amino]pyridine-2-carbonitrile |
| 346. | N-[6-(1-cyano-1-methylethyl)pyridin-3-yl]-3-{4-[(1-methylpiperidin-4-yl)amino]-1-(2,2,2-trifluoroethyl)-1H-indol-2-yl}prop-2-ynamide |
| 347. | 2-{3-[(2-fluorophenyl)amino]prop-1-yn-1-yl}-N-(1-methylpiperidin-4-yl)-1-(2,2,2-trifluoroethyl)-1H-indol-4-amine |
| 348. | 2-{3-[(3-fluorophenyl)amino]prop-1-yn-1-yl}-N-(1-methylpiperidin-4-yl)-1-(2,2,2-trifluoroethyl)-1H-indol-4-amine |
| 349. | 4-amino-N-(3-{4-[(1-methylpiperidin-4-yl)amino]-1-(2,2,2-trifluoroethyl)-1H-indol-2-yl}prop-2-yn-1-yl)benzene-1-sulfonamide |
| 350. | 2-{3-[(6-tert-butylpyridin-3-yl)amino]prop-1-yn-1-yl}-N-(1-methylpiperidin-4-yl)-1-(2,2,2-trifluoroethyl)-1H-indol-4-amine |
| 351. | 2-{3-[(4-fluorophenyl)amino]prop-1-yn-1-yl}-N-(1-methylpiperidin-4-yl)-1-(2,2,2-trifluoroethyl)-1H-indol-4-amine |
| 352. | N,N-dimethyl-5-[(3-{4-[(1-methylpiperidin-4-yl)amino]-1-(2,2,2-trifluoroethyl)-1H-indol-2-yl}prop-2-yn-1-yl)amino]pyridine-2-carboxamide |
| 353. | 5-[(3-{4-[(1-methylpiperidin-4-yl)amino]-1-(2,2,2-trifluoroethyl)-1H-indol-2-yl}prop-2-yn-1-yl)amino]-N-(propan-2-yl)pyridine-2-carboxamide |
| 354. | N-(pyridin-3-yl)-5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridine-2-carboxamide |
| 355. | N-(pyridin-3-yl)-5-{[3-(4-{[(1S,4S)-4-(dimethylamino)cyclohexyl]amino}-1-(2,2,2-trifluoroethyl)-1H-indol-2-yl)prop-2-yn-1-yl]amino}pyridine-2-carboxamide |
| 356. | 2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |
| 357. | 6-tert-butyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 358. | 2-{3-[(6-chloropyridin-3-yl)amino]prop-1-yn-1-yl}-N-(1-methylpiperidin-4-yl)-1-(2,2,2-trifluoroethyl)-1H-indol-4-amine |
| 359. | 2-{4-[(3-{4-[(1-methylpiperidin-4-yl)amino]-1-(2,2,2-trifluoroethyl)-1H-indol-2-yl}prop-2-yn-1-yl)amino]phenyl}propan-2-ol |
| 360. | 6-methyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 361. | N-(1-methylpiperidin-4-yl)-1-(2,2,2-trifluoroethyl)-2-(3-{[6-(trifluoromethyl)pyridin-3-yl]amino}prop-1-yn-1-yl)-1H-indol-4-amine |
| 362. | 3-(3-{4-[(1-methylpiperidin-4-yl)amino]-1-(2,2,2-trifluoroethyl)-1H-indol-2-yl}prop-2-yn-1-yl)-1-phenylurea |
| 363. | 2-{3-[(4-tert-butyl-2-fluorophenyl)-amino]prop-1-yn-1-yl}-N-(1-methylpiperidin-4-yl)-1-(2,2,2-trifluoroethyl)-1H-indol-4-amine |
| 364. | 2-{3-fluoro-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 365. | 4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 366. | 2-{3-[(2,6-difluoro-4-methane-sulfonylphenyl)amino]prop-1-yn-1-yl}-N-(1-methylpiperidin-4-yl)-1-(2,2,2-trifluoroethyl)-1H-indol-4-amine |
| 367. | N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 368. | 2-{3-[(4-methanesulfonyl-3-methoxyphenyl)amino]prop-1-yn-1-yl}-N-(1-methylpiperidin-4-yl)-1-(2,2,2-trifluoroethyl)-1H-indol-4-amine |
| 369. | 2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 370. | 2-{3-[(5-methanesulfonylpyridin-2-yl)amino]prop-1-yn-1-yl}-N-(1-methylpiperidin-4-yl)-1-(2,2,2-trifluoroethyl)-1H-indol-4-amine |
| 371. | 2-{3-[(4-methanesulfonyl-2-methylphenyl)amino]prop-1-yn-1-yl}-N-(1-methylpiperidin-4-yl)-1-(2,2,2-trifluoroethyl)-1H-indol-4-amine |
| 372. | methyl 3-methoxy-4-[(3-{4-[(1-methylpiperidin-4-yl)amino]-1-(2,2,2-trifluoroethyl)-1H-indol-2-yl}prop-2-yn-1-yl)amino]benzoate |
| 373. | N-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}methanesulfonamide |
| 374. | 3-methoxy-4-[(3-{4-[(1-methylpiperidin-4-yl)amino]-1-(2,2,2-trifluoroethyl)-1H-indol-2-yl}prop-2-yn-1-yl)amino]benzonitrile |
| 375. | 3-methoxy-4-[(3-{4-[(1-methylpiperidin-4-yl)amino]-1-(2,2,2-trifluoroethyl)-1H-indol-2-yl}prop-2-yn-1-yl)amino]benzoic acid |
| 376. | 2-{3-[(2,4-dimethoxyphenyl)amino]prop-1-yn-1-yl}-N-(1-methylpiperidin-4-yl)-1-(2,2,2-trifluoroethyl)-1H-indol-4-amine |
| 377. | 2-{3-[(2-methoxypyridin-3-yl)amino]prop-1-yn-1-yl}-N-(1-methylpiperidin-4-yl)-1-(2,2,2-trifluoroethyl)-1H-indol-4-amine |
| 378. | 2-{3-[(5-fluoro-2-methoxyphenyl)-amino]prop-1-yn-1-yl}-N-(1-methylpiperidin-4-yl)-1-(2,2,2-trifluoroethyl)-1H-indol-4-amine |
| 379. | 2-{3-[(2-ethoxy-4-methane-sulfonylphenyl)amino]prop-1-yn-1-yl}-N-(1-methylpiperidin-4-yl)-1-(2,2,2-trifluoroethyl)-1H-indol-4-amine |

TABLE 1-continued

Alkynyl indole compounds of the disclosure.

| Mol # | IUPAC name |
|---|---|
| 380. | 2-{3-[(3-fluoro-2-methoxyphenyl)-amino]prop-1-yn-1-yl}-N-(1-methylpiperidin-4-yl)-1-(2,2,2-trifluoroethyl)-1H-indol-4-amine |
| 381. | 3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 382. | 2-{3-[(4-fluoro-2-methoxyphenyl)-amino]prop-1-yn-1-yl}-N-(1-methylpiperidin-4-yl)-1-(2,2,2-trifluoroethyl)-1H-indol-4-amine |
| 383. | 3-methoxy-4-[(3-{4-[(1-methylpiperidin-4-yl)amino]-1-(2,2,2-trifluoroethyl)-1H-indol-2-yl}prop-2-yn-1-yl)amino]-benzamide |
| 384. | 2-{3-[(2-fluoro-6-methoxyphenyl)-amino]prop-1-yn-1-yl}-N-(1-methylpiperidin-4-yl)-1-(2,2,2-trifluoroethyl)-1H-indol-4-amine |
| 385. | 2-{3-[(4-tert-butyl-2-methoxyphenyl)-amino]prop-1-yn-1-yl}-N-(1-methylpiperidin-4-yl)-1-(2,2,2-trifluoroethyl)-1H-indol-4-amine |
| 386. | 4-methoxy-3-[(3-{4-[(1-methylpiperidin-4-yl)amino]-1-(2,2,2-trifluoroethyl)-1H-indol-2-yl}prop-2-yn-1-yl)amino]-benzonitrile |
| 387. | 2-{3-[(5-tert-butyl-2-methoxyphenyl)-amino]prop-1-yn-1-yl}-N-(1-methylpiperidin-4-yl)-1-(2,2,2-trifluoroethyl)-1H-indol-4-amine |
| 388. | N-(1-methylpiperidin-4-yl)-2-[3-(phenylamino)prop-1-yn-1-yl]-1-(2,2,2-trifluoroethyl)-1H-indol-4-amine |
| 389. | 5-methanesulfonyl-2-[(3-{4-[(1-methylpiperidin-4-yl)amino]-1-(2,2,2-trifluoroethyl)-1H-indol-2-yl}prop-2-yn-1-yl)amino]benzonitrile |
| 390. | 2-(3-{[2-(2-fluoroethoxy)-4-methanesulfonylphenyl]amino}prop-1-yn-1-yl)-N-(1-methylpiperidin-4-yl)-1-(2,2,2-trifluoroethyl)-1H-indol-4-amine |
| 391. | 2-{3-[(3-methoxypyridin-4-yl)amino]prop-1-yn-1-yl}-N-(1-methylpiperidin-4-yl)-1-(2,2,2-trifluoroethyl)-1H-indol-4-amine |
| 392. | 2-{3-[(2-chloro-4-methanesulfonyl-phenyl)amino]prop-1-yn-1-yl}-N-(1-methylpiperidin-4-yl)-1-(2,2,2-trifluoroethyl)-1H-indol-4-amine |
| 393. | 2-{3-[(4-methoxyphenyl)amino]prop-1-yn-1-yl}-N-(1-methylpiperidin-4-yl)-1-(2,2,2-trifluoroethyl)-1H-indol-4-amine |
| 394. | 2-(3-{[4-methanesulfonyl-2-(2-methoxyethoxy)phenyl]amino}prop-1-yn-1-yl)-N-(1-methylpiperidin-4-yl)-1-(2,2,2-trifluoroethyl)-1H-indol-4-amine |
| 395. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridine-2-carbonitrile |
| 396. | 4-{[2-(3-{[6-(morpholine-4-carbonyl)pyridin-3-yl]amino}prop-1-yn-1-yl)-1-(2,2,2-trifluoroethyl)-1H-indol-4-yl]amino}-1$\lambda^6$-thiane-1,1-dione |
| 397. | 4-{[2-(3-{[6-(4-methylpiperazine-1-carbonyl)pyridin-3-yl]amino}prop-1-yn-1-yl)-1-(2,2,2-trifluoroethyl)-1H-indol-4-yl]amino}-1$\lambda^6$-thiane-1,1-dione |
| 398. | 4-[(2-{3-[(quinolin-3-yl)amino]prop-1-yn-1-yl}-1-(2,2,2-trifluoroethyl)-1H-indol-4-yl)amino]-1$\lambda^6$-thiane-1,1-dione |
| 399. | 4-[(2-{3-[(quinoxalin-6-yl)amino]prop-1-yn-1-yl}-1-(2,2,2-trifluoroethyl)-1H-indol-4-yl)amino]-1$\lambda^6$-thiane-1,1-dione |
| 400. | 4-[(2-{3-[(4-methanesulfonylphenyl)-amino]prop-1-yn-1-yl}-1-(2,2,2-trifluoroethyl)-1H-indol-4-yl)amino]-1$\lambda^6$-thiane-1,1-dione |
| 401. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridine-2-carboxamide |
| 402. | 4-[(2-{3-[(6-methoxypyridin-3-yl)amino]prop-1-yn-1-yl}-1-(2,2,2-trifluoroethyl)-1H-indol-4-yl)amino]-1$\lambda^6$-thiane-1,1-dione |
| 403. | 4-{[2-(3-{[6-(4-hydroxypiperidine-1-carbonyl)pyridin-3-yl]amino}prop-1-yn-1-yl)-1-(2,2,2-trifluoroethyl)-1H-indol-4-yl]amino}-1$\lambda^6$-thiane-1,1-dione |
| 404. | 4-[(2-{3-[(1-methyl-2-oxo-1,2-dihydropyridin-4-yl)amino]prop-1-yn-1-yl}-1-(2,2,2-trifluoroethyl)-1H-indol-4-yl)amino]-1$\lambda^6$-thiane-1,1-dione |
| 405. | 4-[(2-{3-[(2-methoxypyridin-4-yl)amino]prop-1-yn-1-yl}-1-(2,2,2-trifluoroethyl)-1H-indol-4-yl)amino]-1$\lambda^6$-thiane-1,1-dione |
| 406. | 2-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-fluorophenyl}-2-methylpropanenitrile |
| 407. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(1-methylpiperidin-4-yl)pyridine-2-carboxamide |
| 408. | 4-[(2-{3-[(2-fluoro-4-methanesulfonyl-phenyl)amino]prop-1-yn-1-yl}-1-(2,2,2-trifluoroethyl)-1H-indol-4-yl)amino]-1$\lambda^6$-thiane-1,1-dione |
| 409. | 4-{[2-(3-{[4-(ethanesulfonyl)-phenyl]amino}prop-1-yn-1-yl)-1-(2,2,2-trifluoroethyl)-1H-indol-4-yl]amino}-1$\lambda^6$-thiane-1,1-dione |
| 410. | 4-[(2-{3-[(2-tert-butylpyrimidin-5-yl)amino]prop-1-yn-1-yl}-1-(2,2,2-trifluoroethyl)-1H-indol-4-yl)amino]-1$\lambda^6$-thiane-1,1-dione |
| 411. | 3-{4-[(1,1-dioxo-1$\lambda^6$-thian-4-yl)amino]-1-(2,2,2-trifluoroethyl)-1H-indol-2-yl}-N-(4-methanesulfonyl-phenyl)-prop-2-ynamide |
| 412. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(oxan-4-yl)pyridine-2-carboxamide |
| 413. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(pyridin-3-yl)pyridine-2-carboxamide |
| 414. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-methylpyridine-2-carboxamide |
| 415. | 4-[(2-{3-[(3-chloro-4-methanesulfonylphenyl)amino]prop-1-yn-1-yl}-1-(2,2,2-trifluoroethyl)-1H-indol-4-yl)amino]-1$\lambda^6$-thiane-1,1-dione |
| 416. | N-(2,3-dihydroxypropyl)-5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridine-2-carboxamide |
| 417. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-hydroxypyridine-2-carboxamide |

TABLE 1-continued

Alkynyl indole compounds of the disclosure.

| Mol # | IUPAC name |
|---|---|
| 418. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(2-hydroxyethyl)pyridine-2-carboxamide |
| 419. | 5-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-hydroxy-N-methylpyridine-2-carboxamide |
| 420. | 4-amino-N-(3-{4-[(1,1-dioxo-1$\lambda^6$-thian-4-yl)amino]-1-(2,2,2-trifluoroethyl)-1H-indol-2-yl}prop-2-yn-1-yl)benzene-1-sulfonamide |
| 421. | 4-({2-[3-({pyrido[2,3-b]pyrazin-7-yl}amino)prop-1-yn-1-yl]-1-(2,2,2-trifluoroethyl)-1H-indol-4-yl}amino)-1$\lambda^6$-thiane-1,1-dione |
| 422. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-benzamide |
| 423. | 4-{[2-(3-{[2-(methylsulfanyl)pyrimidin-5-yl]amino}prop-1-yn-1-yl)-1-(2,2,2-trifluoroethyl)-1H-indol-4-yl]amino}-1$\lambda^6$-thiane-1,1-dione |
| 424. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]benzene-1-sulfonamide |
| 425. | 4-{[2-(3-{[4-(2-methylpropane-2-sulfonyl)phenyl]amino}prop-1-yn-1-yl)-1-(2,2,2-trifluoroethyl)-1H-indol-4-yl]amino}-1$\lambda^6$-thiane-1,1-dione |
| 426. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N,N-dimethylbenzene-1-sulfonamide |
| 427. | 4-{[1-(2,2,2-trifluoroethyl)-2-[2-(trimethylsilyl)ethynyl]-1H-indol-4-yl]amino}-1$\lambda^6$-thiane-1,1-dione |
| 428. | 4-[(2-{3-[(5-methanesulfonylpyridin-2-yl)amino]prop-1-yn-1-yl}-1-(2,2,2-trifluoroethyl)-1H-indol-4-yl)amino]-1$\lambda^6$-thiane-1,1-dione |
| 429. | 4-[(2-{3-[(4-methanesulfonyl-2-methoxyphenyl)amino]prop-1-yn-1-yl}-1-(2,2,2-trifluoroethyl)-1H-indol-4-yl)amino]-1$\lambda^6$-thiane-1,1-dione |
| 430. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-methylbenzene-1-sulfonamide |
| 431. | 4-{[2-ethynyl-1-(2,2,2-trifluoroethyl)-1H-indol-4-yl]amino}-1$\lambda^6$-thiane-1,1-dione |
| 432. | N-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}methanesulfonamide |
| 433. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzoic acid |
| 434. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzonitrile |
| 435. | 4-[(2-{3-[(5-fluoro-2-methoxyphenyl)amino]prop-1-yn-1-yl}-1-(2,2,2-trifluoroethyl)-1H-indol-4-yl)amino]-1$\lambda^6$-thiane-1,1-dione |
| 436. | 4-[(2-{3-[(2-methoxy-6-methylpyridin-3-yl)amino]prop-1-yn-1-yl}-1-(2,2,2-trifluoroethyl)-1H-indol-4-yl)amino]-1$\lambda^6$-thiane-1,1-dione |
| 437. | 4-[(2-{3-[(2-hydroxy-6-methylpyridin-3-yl)amino]prop-1-yn-1-yl}-1-(2,2,2-trifluoroethyl)-1H-indol-4-yl)amino]-1$\lambda^6$-thiane-1,1-dione |
| 438. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzamide |
| 439. | 4-[(2-{3-[(2-methoxypyridin-3-yl)amino]prop-1-yn-1-yl}-1-(2,2,2-trifluoroethyl)-1H-indol-4-yl)amino]-1$\lambda^6$-thiane-1,1-dione |
| 440. | 4-[(2-{3-[(4-fluoro-2-methoxyphenyl)amino]prop-1-yn-1-yl}-1-(2,2,2-trifluoroethyl)-1H-indol-4-yl)amino]-1$\lambda^6$-thiane-1,1-dione |
| 441. | 4-[(2-{3-[(5-tert-butyl-2-methoxyphenyl)amino]prop-1-yn-1-yl}-1-(2,2,2-trifluoroethyl)-1H-indol-4-yl)amino]-1$\lambda^6$-thiane-1,1-dione |
| 442. | 4-[(2-{3-[(2-ethoxy-4-methanesulfonylphenyl)amino]prop-1-yn-1-yl}-1-(2,2,2-trifluoroethyl)-1H-indol-4-yl)amino]-1$\lambda^6$-thiane-1,1-dione |
| 443. | 4-[(2-{3-[(3-fluoro-2-methoxyphenyl)-amino]prop-1-yn-1-yl}-1-(2,2,2-trifluoroethyl)-1H-indol-4-yl)amino]-1$\lambda^6$-thiane-1,1-dione |
| 444. | 4-({2-[3-(methylamino)prop-1-yn-1-yl]-1-(2,2,2-trifluoroethyl)-1H-indol-4-yl}amino)-1$\lambda^6$-thiane-1,1-dione |
| 445. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzene-1-sulfonamide |
| 446. | 4-[(2-{3-[(2-fluoro-6-methoxyphenyl)-amino]prop-1-yn-1-yl}-1-(2,2,2-trifluoroethyl)-1H-indol-4-yl)amino]-1$\lambda^6$-thiane-1,1-dione |
| 447. | 3-[(3-{4-[(1,1-dioxo-1$\lambda^6$-thian-4-yl)amino]-1-(2,2,2-trifluoroethyl)-1H-indol-2-yl}prop-2-yn-1-yl)amino]-4-methoxybenzonitrile |
| 448. | 4-[(2-{3-[(4-tert-butyl-2-methoxy-phenyl)amino]prop-1-yn-1-yl}-1-(2,2,2-trifluoroethyl)-1H-indol-4-yl)amino]-1$\lambda^6$-thiane-1,1-dione |
| 449. | 4-({2-[3-(phenylamino)prop-1-yn-1-yl]-1-(2,2,2-trifluoroethyl)-1H-indol-4-yl}amino)-1$\lambda^6$-thiane-1,1-dione |
| 450. | 4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}-1$\lambda^6$-thiane-1,1-dione |
| 451. | 2-[(3-{4-[(1,1-dioxo-1$\lambda^6$-thian-4-yl)amino]-1-(2,2,2-trifluoroethyl)-1H-indol-2-yl}prop-2-yn-1-yl)amino]-5-methanesulfonylbenzonitrile |
| 452. | 4-[(2-{3-[(2-chloro-4-methanesulfonyl-phenyl)amino]prop-1-yn-1-yl}-1-(2,2,2-trifluoroethyl)-1H-indol-4-yl)amino]-1$\lambda^6$-thiane-1,1-dione |
| 453. | 4-[(2-{3-[(4-methoxyphenyl)amino]prop-1-yn-1-yl}-1-(2,2,2-trifluoroethyl)-1H-indol-4-yl)amino]-1$\lambda^6$-thiane-1,1-dione |
| 454. | 4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}-1$\lambda^6$-thiane-1,1-dione |
| 455. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N,N-dimethylacetamide |

TABLE 1-continued

Alkynyl indole compounds of the disclosure.

| Mol # | IUPAC name |
|---|---|
| 456. | 2-methyl-2-(5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridin-2-yl)propanenitrile |
| 457. | 2-(5-((3-(4-(((1S,4S)-4-(dimethylamino)-cyclohexyl)amino)-1-(2,2,2-trifluoroethyl)-1H-indol-2-yl)prop-2-yn-1-yl)amino)pyridin-2-yl)-2-methylpropanenitrile |
| 458. | N-[1-(2-methanesulfonylethyl)piperidin-4-yl]-2-{3-[(4-methanesulfonylphenyl)-amino]prop-1-yn-1-yl}-1-(2,2,2-trifluoroethyl)-1H-indol-4-amine |
| 459. | 5-({3-[4-({1-[(dimethylcarbamoyl)methyl]piperidin-4-yl}amino)-1-(2,2,2-trifluoroethyl)-1H-indol-2-yl]prop-2-yn-1-yl}amino)pyridine-2-carboxamide |
| 460. | 5-{[3-(4-{[1-(2-methanesulfonylethyl)piperidin-4-yl]amino}-1-(2,2,2-trifluoroethyl)-1H-indol-2-yl)prop-2-yn-1-yl]amino}pyridine-2-carboxamide |
| 461. | 5-[(3-{4-[(piperidin-4-yl)amino]-1-(2,2,2-trifluoroethyl)-1H-indol-2-yl}prop-2-yn-1-yl)amino]pyridine-2-carboxamide |
| 462. | 5-{[3-(4-{[1-(carbamoylmethyl)piperidin-4-yl]amino}-1-(2,2,2-trifluoroethyl)-1H-indol-2-yl)prop-2-yn-1-yl]amino}pyridine-2-carboxamide |
| 463. | 5-{[3-(4-{[1-(2-hydroxyethyl)piperidin-4-yl]amino}-1-(2,2,2-trifluoroethyl)-1H-indol-2-yl)prop-2-yn-1-yl]amino}pyridine-2-carboxamide |
| 464. | 5-{[3-(4-{[1-(oxan-4-yl)piperidin-4-yl]amino}-1-(2,2,2-trifluoroethyl)-1H-indol-2-yl)prop-2-yn-1-yl]amino}pyridine-2-carboxamide |
| 465. | 5-{[3-(4-{[(1R,4R)-4-(dimethylamino)-cyclohexyl]amino}-1-(2,2,2-trifluoroethyl)-1H-indol-2-yl)prop-2-yn-1-yl]amino}pyridine-2-carboxamide |
| 466. | 4-{[3-(4-{[1-(2-methanesulfonyl-ethyl)piperidin-4-yl]amino}-1-(2,2,2-trifluoroethyl)-1H-indol-2-yl)prop-2-yn-1-yl]amino}benzene-1-sulfonamide |
| 467. | 4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |
| 468. | 5-{[3-(4-{[(1S,4S)-4-(dimethylamino)-cyclohexyl]amino}-1-(2,2,2-trifluoroethyl)-1H-indol-2-yl)prop-2-yn-1-yl]amino}pyridine-2-carboxamide |
| 469. | N,N-dimethyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 470. | 4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 471. | 2-{4-[(2-{3-[(4-sulfamoylphenyl)-amino]prop-1-yn-1-yl}-1-(2,2,2-trifluoroethyl)-1H-indol-4-yl)amino]-piperidin-1-yl}acetamide |
| 472. | 4-{[3-(4-{[1-(2-methoxyethyl)piperidin-4-yl]amino}-1-(2,2,2-trifluoroethyl)-1H-indol-2-yl)prop-2-yn-1-yl]amino}-N,N-dimethylbenzene-1-sulfonamide |
| 473. | 4-[(3-{4-[(oxan-4-yl)amino]-1-(2,2,2-trifluoroethyl)-1H-indol-2-yl}prop-2-yn-1-yl)amino]benzene-1-sulfonamide |
| 474. | 4-{[3-(4-{[1-(2-hydroxypropyl)piperidin-4-yl]amino}-1-(2,2,2-trifluoroethyl)-1H-indol-2-yl)prop-2-yn-1-yl]amino}benzene-1-sulfonamide |
| 475. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}benzene-1-sulfonamide |
| 476. | 4-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 477. | methyl 2-{4-[(2-{3-[(4-sulfamoylphenyl)-amino]prop-1-yn-1-yl}-1-(2,2,2-trifluoro-ethyl)-1H-indol-4-yl)amino]piperidin-1-yl}acetate |
| 478. | 4-{[3-(4-{[1-(2-hydroxyethyl)piperidin-4-yl]amino}-1-(2,2,2-trifluoroethyl)-1H-indol-2-yl)prop-2-yn-1-yl]amino}benzene-1-sulfonamide |
| 479. | 4-({3-[4-({1-[2-(2-hydroxyethoxy)ethyl]piperidin-4-yl}amino)-1-(2,2,2-trifluoroethyl)-1H-indol-2-yl]prop-2-yn-1-yl}amino)benzene-1-sulfonamide |
| 480. | N,N-dimethyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 481. | 4-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 482. | 2-{4-[(2-{3-[(4-sulfamoylphenyl)amino]prop-1-yn-1-yl}-1-(2,2,2-trifluoroethyl)-1H-indol-4-yl)amino]piperidin-1-yl}acetic acid |
| 483. | 4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 484. | N-methyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 485. | N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 486. | 4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 487. | N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 488. | 2-(dimethylamino)ethyl 2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetate |
| 489. | 2-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 490. | 2-chloro-4-[(3-{4-[(oxan-4-yl)amino]-1-(2,2,2-trifluoroethyl)-1H-indol-2-yl}prop-2-yn-1-yl)amino]benzene-1-sulfonamide |
| 491. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 492. | 4-{[3-(4-{[1-(2,3-dihydroxypropyl)-piperidin-4-yl]amino}-1-(2,2,2-trifluoro-ethyl)-1H-indol-2-yl)prop-2-yn-1-yl]amino}-3-methoxybenzene-1-sulfonamide |
| 493. | 3-methoxy-4-[(3-{4-[(piperidin-4-yl)amino]-1-(2,2,2-trifluoroethyl)-1H-indol-2-yl}prop-2-yn-1-yl)amino]benzene-1-sulfonamide |

TABLE 1-continued

Alkynyl indole compounds of the disclosure.

| Mol # | IUPAC name |
|---|---|
| 494. | 3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 495. | 3-methoxy-4-[(3-{4-[(oxan-4-yl)amino]-1-(2,2,2-trifluoroethyl)-1H-indol-2-yl}prop-2-yn-1-yl)amino]benzamide |
| 496. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzamide |
| 497. | 4-{[3-(4-{[1-(2,3-dihydroxypropyl)-piperidin-4-yl]amino}-1-(2,2,2-trifluoroethyl)-1H-indol-2-yl)prop-2-yn-1-yl]amino}-3-methoxybenzamide |
| 498. | 2-[5-({3-[1-(cyanomethyl)-4-[(1-methylpiperidin-4-yl)amino]-1H-indol-2-yl]prop-2-yn-1-yl}amino)pyridin-2-yl]-2-methylpropanenitrile |
| 499. | 2-[5-({3-[1-(3-methoxypropyl)-4-[(1-methylpiperidin-4-yl)amino]-1H-indol-2-yl]prop-2-yn-1-yl}amino)pyridin-2-yl]-2-methylpropanenitrile |
| 500. | 2-[5-({3-[1-(2-chloroethyl)-4-[(1-methylpiperidin-4-yl)amino]-1H-indol-2-yl]prop-2-yn-1-yl}amino)pyridin-2-yl]-2-methylpropanenitrile |
| 501. | 2-methyl-2-{5-[(3-{4-[(1-methylpiperidin-4-yl)amino]-1-(propan-2-yl)-1H-indol-2-yl}prop-2-yn-1-yl)amino]pyridin-2-yl}propanenitrile |
| 502. | 2-{5-[(3-{1-cyclopentyl-4-[(1-methylpiperidin-4-yl)amino]-1H-indol-2-yl}prop-2-yn-1-yl)amino]pyridin-2-yl}-2-methylpropanenitrile |
| 503. | 2-methyl-2-{5-[(3-{4-[(1-methylpiperidin-4-yl)amino]-1-(3,3,3-trifluoropropyl)-1H-indol-2-yl}prop-2-yn-1-yl)amino]pyridin-2-yl}propanenitrile |
| 504. | 1-(2-chloroethyl)-N-(1-methylpiperidin-4-yl)-2-{3-[(6-methylpyridin-3-yl)amino]-prop-1-yn-1-yl}-1H-indol-4-amine |
| 505. | 1-(2-chloroethyl)-N-(1-methylpiperidin-4-yl)-2-{3-[(6-methylpyridin-3-yl)amino]-prop-1-yn-1-yl}-1H-indol-4-amine |
| 506. | 1-(2-chloroethyl)-2-{3-[(4-chlorophenyl)-amino]prop-1-yn-1-yl}-N-(1-methylpiperidin-4-yl)-1H-indol-4-amine |
| 507. | 2-[5-({3-[1-(1-cyanoethyl)-4-[(1-methylpiperidin-4-yl)amino]-1H-indol-2-yl]prop-2-yn-1-yl}amino)pyridin-2-yl]-2-methylpropanenitrile |
| 508. | 2-[5-({3-[1-(cyanomethyl)-4-[(1,1-dioxo-1$\lambda^6$-thian-4-yl)amino]-1H-indol-2-yl]prop-2-yn-1-yl}amino)pyridin-2-yl]-2-methylpropanenitrile |
| 509. | 4-[(2-{3-[(4-methanesulfonylphenyl)amino]prop-1-yn-1-yl}-1-(oxiran-2-ylmethyl)-1H-indol-4-yl)amino]-1$\lambda^6$-thiane-1,1-dione |
| 510. | 2-{3-[(4-methanesulfonylphenyl)-amino]prop-1-yn-1-yl}-N-[1-(oxan-4-yl)piperidin-4-yl]-1-(oxiran-2-ylmethyl)-1H-indol-4-amine |
| 511. | 4-[(2-{3-[(4-methanesulfonyl-2-methoxyphenyl)amino]prop-1-yn-1-yl}-1-(oxiran-2-ylmethyl)-1H-indol-4-yl)amino]-1$\lambda^6$-thiane-1,1-dione |
| 512. | 2-{3-[(4-methanesulfonyl-2-methoxy-phenyl)amino]prop-1-yn-1-yl}-N-[1-(oxan-4-yl)piperidin-4-yl]-1-(oxiran-2-ylmethyl)-1H-indol-4-amine |
| 513. | 1-[6-(1-cyano-1-methylethyl)pyridin-3-yl]-3-(3-{4-[(1-methylpiperidin-4-yl)amino]-1-(2,2,2-trifluoroethyl)-1H-indol-2-yl}prop-2-yn-1-yl)urea |
| 514. | 1-(6-methanesulfonylpyridin-3-yl)-3-(3-{4-[(1-methylpiperidin-4-yl)amino]-1-(2,2,2-trifluoroethyl)-1H-indol-2-yl}prop-2-yn-1-yl)urea |
| 515. | 1-[6-(1-cyano-1-methylethyl)pyridin-3-yl]-3-(3-{4-[(1,1-dioxo-1$\lambda^6$-thian-4-yl)amino]-1-(2,2,2-trifluoroethyl)-1H-indol-2-yl}prop-2-yn-1-yl)urea |
| 516. | 3-(3-{4-[(1,1-dioxo-1$\lambda^6$-thian-4-yl)amino]-1-(2,2,2-trifluoroethyl)-1H-indol-2-yl}prop-2-yn-1-yl)-1-(6-methanesulfonylpyridin-3-yl)urea |
| 517. | 1-(6-cyanopyridin-3-yl)-3-(3-{4-[(1-methylpiperidin-4-yl)amino]-1-(2,2,2-trifluoroethyl)-1H-indol-2-yl}prop-2-yn-1-yl)urea |
| 518. | 1-(6-cyanopyridin-3-yl)-3-(3-{4-[(1,1-dioxo-1$\lambda^6$-thian-4-yl)amino]-1-(2,2,2-trifluoroethyl)-1H-indol-2-yl}prop-2-yn-1-yl)urea |
| 519. | 3-(3-{4-[(1,1-dioxo-1$\lambda^6$-thian-4-yl)amino]-1-(2,2,2-trifluoroethyl)-1H-indol-2-yl}prop-2-yn-1-yl)-1-(quinoxalin-6-yl)urea |
| 520. | N-(3-{4-[(1,1-dioxo-1$\lambda^6$-thian-4-yl)amino]-1-(2,2,2-trifluoroethyl)-1H-indol-2-yl}prop-2-yn-1-yl)-4-methylpiperazine-1-carboxamide |
| 521. | N-(3-{4-[(1,1-dioxo-1$\lambda^6$-thian-4-yl)amino]-1-(2,2,2-trifluoroethyl)-1H-indol-2-yl}prop-2-yn-1-yl)morpholine-4-carboxamide |
| 522. | 4-[(2-{3-[(6-methanesulfonylpyridin-3-yl)amino]prop-1-yn-1-yl}-1-(2,2,2-trifluoroethyl)-1H-indol-4-yl)amino]-1$\lambda^6$-thiane-1,1-dione |
| 523. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-N,N-dimethylacetamide |
| 524. | N-(1-ethylpiperidin-4-yl)-2-{3-[(6-methanesulfonylpyridin-3-yl)amino]prop-1-yn-1-yl}-1-(2,2,2-trifluoroethyl)-1H-indol-4-amine |
| 525. | N-[1-(2-methanesulfonylethyl)piperidin-4-yl]-2-{3-[(6-methanesulfonylpyridin-3-yl)amino]prop-1-yn-1-yl}-1-(2,2,2-trifluoroethyl)-1H-indol-4-amine |
| 526. | 2-{3-[(6-methanesulfonylpyridin-3-yl)amino]prop-1-yn-1-yl}-N-[1-(1-methylpiperidin-4-yl)piperidin-4-yl]-1-(2,2,2-trifluoroethyl)-1H-indol-4-amine |
| 527. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}ethan-1-ol |
| 528. | 4-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1$\lambda^6$-thiane-1,1-dione |
| 529. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 530. | 2-{3-[(4-methanesulfonylphenyl)amino]prop-1-yn-1-yl}-N-(oxan-4-yl)-1-(2,2,2-trifluoroethyl)-1H-indol-4-amine |

TABLE 1-continued

Alkynyl indole compounds of the disclosure.

| Mol # | IUPAC name |
|---|---|
| 531. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}ethan-1-ol |
| 532. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 533. | 2-{3-[(4-methanesulfonylphenyl)amino]prop-1-yn-1-yl}-N-[1-(1-methylpiperidin-4-yl)piperidin-4-yl]-1-(2,2,2-trifluoroethyl)-1H-indol-4-amine |
| 534. | N-(2,3-dihydroxypropyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}-N-methylacetamide |
| 535. | 4-N-(2-{3-[(4-methanesulfonylphenyl)-amino]prop-1-yn-1-yl}-1-(2,2,2-trifluoroethyl)-1H-indol-4-yl)-1-N,1-N-dimethylcyclohexane-1,4-diamine |
| 536. | (1S,4S)-4-N-(2-{3-[(4-methanesulfonyl-phenyl)amino]prop-1-yn-1-yl}-1-(2,2,2-trifluoroethyl)-1H-indol-4-yl)-1-N,1-N-dimethylcyclohexane-1,4-diamine |
| 537. | 2-{3-[(4-methanesulfonylphenyl)-amino]prop-1-yn-1-yl}-N-[1-(oxan-4-yl)piperidin-4-yl]-1-(2,2,2-trifluoroethyl)-1H-indol-4-amine |
| 538. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 539. | 1-(4-hydroxypiperidin-1-yl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}ethan-1-one |
| 540. | 2-{3-[(4-methanesulfonylphenyl)-amino]prop-1-yn-1-yl}-N-(piperidin-4-yl)-1-(2,2,2-trifluoroethyl)-1H-indol-4-amine |
| 541. | N-{1-[1-(2-methanesulfonylethyl)piperidin-4-yl]piperidin-4-yl}-2-{3-[(4-methanesulfonylphenyl)amino]prop-1-yn-1-yl}-1-(2,2,2-trifluoroethyl)-1H-indol-4-amine |
| 542. | 2-{3-[(4-methanesulfonylphenyl)-amino]prop-1-yn-1-yl}-N-[1-(2-methoxyethyl)piperidin-4-yl]-1-(2,2,2-trifluoroethyl)-1H-indol-4-amine |
| 543. | 3-{4-[(2-{3-[(4-methane-sulfonylphenyl)-amino]prop-1-yn-1-yl}-1-(2,2,2-trifluoroethyl)-1H-indol-4-yl)amino]piperidin-1-yl}propanenitrile |
| 544. | 2-{3-[(4-methanesulfonylphenyl)-amino]prop-1-yn-1-yl}-N-(1-methylpiperidin-4-yl)-1-(2,2,2-trifluoroethyl)-1H-indol-4-amine |
| 545. | 2-{4-[(2-{3-[(4-methane-sulfonylphenyl)-amino]prop-1-yn-1-yl}-1-(2,2,2-trifluoroethyl)-1H-indol-4-yl)amino]piperidin-1-yl}acetamide |
| 546. | 4-{4-[(2-{3-[(4-methane-sulfonylphenyl)-amino]prop-1-yn-1-yl}-1-(2,2,2-trifluoroethyl)-1H-indol-4-yl)amino]piperidin-1-yl}-1$\lambda^6$-thiane-1,1-dione |
| 547. | 2-{4-[(2-{3-[(4-methane-sulfonylphenyl)amino]prop-1-yn-1-yl}-1-(2,2,2-trifluoroethyl)-1H-indol-4-yl)amino]piperidin-1-yl}-N-methylacetamide |
| 548. | 2-(3-{[4-(ethanesulfonyl)phenyl]amino}prop-1-yn-1-yl)-N-(1-methylpiperidin-4-yl)-1-(2,2,2-trifluoroethyl)-1H-indol-4-amine |
| 549. | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}ethan-1-ol |
| 550. | 2-{3-[(2-fluoro-4-methane-sulfonylphenyl)-amino]prop-1-yn-1-yl}-N-[1-(2-methanesulfonylethyl)-piperidin-4-yl]-1-(2,2,2-trifluoroethyl)-1H-indol-4-amine |
| 551. | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}acetamide |
| 552. | 2-{3-[(2-fluoro-4-methane-sulfonylphenyl)-amino]prop-1-yn-1-yl}-N-(1-methylpiperidin-4-yl)-1-(2,2,2-trifluoroethyl)-1H-indol-4-amine |
| 553. | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}-2-methoxyethan-1-one |
| 554. | 2-{3-[(4-methanesulfonyl-phenyl)amino]prop-1-yn-1-yl}-N-(1-methylpyrrolidin-3-yl)-1-(2,2,2-trifluoroethyl)-1H-indol-4-amine |
| 555. | N-hydroxy-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 556. | 3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |
| 557. | 2-{3-[(2-fluoro-4-methanesulfonyl-phenyl)amino]prop-1-yn-1-yl}-N-[1-(1-methylpiperidin-4-yl)piperidin-4-yl]-1-(2,2,2-trifluoroethyl)-1H-indol-4-amine |
| 558. | 2-(3-{[4-(ethanesulfonyl)phenyl]amino}prop-1-yn-1-yl)-N-[1-(1-methylpiperidin-4-yl)piperidin-4-yl]-1-(2,2,2-trifluoroethyl)-1H-indol-4-amine |
| 559. | 2-{3-[(2-fluoro-4-methanesulfonyl-phenyl)amino]prop-1-yn-1-yl}-N-(oxan-4-yl)-1-(2,2,2-trifluoroethyl)-1H-indol-4-amine |
| 560. | 2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethan-1-ol |
| 561. | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propan-2-ol |
| 562. | 2-(3-{[4-(ethanesulfonyl)-phenyl]amino}prop-1-yn-1-yl)-N-[1-(2-methanesulfonylethyl)piperidin-4-yl]-1-(2,2,2-trifluoroethyl)-1H-indol-4-amine |
| 563. | 4-{[1-(2,2,2-trifluoroethyl)-2-{3-[(4-trifluoromethanesulfonylphenyl)amino]prop-1-yn-1-yl}-1H-indol-4-yl]amino}-1$\lambda^6$-thiane-1,1-dione |
| 564. | 2-(4-{[1-(2,2,2-trifluoroethyl)-2-{3-[(4-trifluoromethanesulfonylphenyl)amino]prop-1-yn-1-yl}-1H-indol-4-yl]amino}piperidin-1-yl)ethan-1-ol |
| 565. | N-(1-methylpiperidin-4-yl)-1-(2,2,2-trifluoroethyl)-2-{3-[(4-trifluoromethanesulfonylphenyl)amino]prop-1-yn-1-yl}-1H-indol-4-amine |
| 566. | 2-{3-[(4-methanesulfonyl-phenyl)amino]prop-1-yn-1-yl}-N-[1-(1-methylpyrrolidin-3-yl)piperidin-4-yl]-1-(2,2,2-trifluoroethyl)-1H-indol-4-amine |
| 567. | 2-{3-[(4-methanesulfonyl-phenyl)amino]prop-1-yn-1-yl}-N-[1-(3-methanesulfonylpropyl)piperidin-4-yl]-1-(2,2,2-trifluoroethyl)-1H-indol-4-amine |
| 568. | 2-(3-{[4-(ethanesulfonyl)-phenyl]amino}prop-1-yn-1-yl)-N-[1-(2-methoxyethyl)piperidin-4-yl]-1-(2,2,2-trifluoroethyl)-1H-indol-4-amine |

TABLE 1-continued

Alkynyl indole compounds of the disclosure.

| Mol # | IUPAC name |
|---|---|
| 569. | 4-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)-1λ⁶-thiane-1,1-dione |
| 570. | 2-(3-{[4-(ethanesulfonyl)-phenyl]amino}prop-1-yn-1-yl)-N-[1-(oxan-4-yl)piperidin-4-yl]-1-(2,2,2-trifluoroethyl)-1H-indol-4-amine |
| 571. | N-[1-(2-methanesulfonylethyl)-piperidin-4-yl]-1-(2,2,2-trifluoroethyl)-2-{3-[(4-trifluoromethane-sulfonylphenyl)amino]prop-1-yn-1-yl}-1H-indol-4-amine |
| 572. | N-[1-(oxan-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 573. | N-[1-(1-methylpiperidin-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 574. | 2-{3-[(2-fluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |
| 575. | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetonitrile |
| 576. | 2-{3-[(2-fluoro-4-methanesulfonylphenyl)amino]prop-1-yn-1-yl}-N-[1-(2-methoxyethyl)piperidin-4-yl]-1-(2,2,2-trifluoroethyl)-1H-indol-4-amine |
| 577. | 2-{3-[(3-chloro-4-methanesulfonylphenyl)amino]prop-1-yn-1-yl}-N-[1-(oxan-4-yl)piperidin-4-yl]-1-(2,2,2-trifluoroethyl)-1H-indol-4-amine |
| 578. | 2-{3-[(2,6-difluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |
| 579. | 2-{3-[(3-chloro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 580. | 2-{4-[(2-{3-[(3-chloro-4-methanesulfonylphenyl)amino]prop-1-yn-1-yl}-1-(2,2,2-trifluoroethyl)-1H-indol-4-yl)amino]piperidin-1-yl}ethan-1-ol |
| 581. | (2S)-3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |
| 582. | N-(5-aminopentyl)-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 583. | 2-{3-[(2,6-difluoro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 584. | 2-(3-{[4-(ethanesulfonyl)phenyl]-amino}prop-1-yn-1-yl)-N-(oxan-4-yl)-1-(2,2,2-trifluoroethyl)-1H-indol-4-amine |
| 585. | 2-(4-{[2-(3-{[4-(ethanesulfonyl)phenyl]amino}prop-1-yn-1-yl)-1-(2,2,2-trifluoroethyl)-1H-indol-4-yl]amino}piperidin-1-yl)acetonitrile |
| 586. | 2-(3-{[4-(2-methylpropane-2-sulfonyl)phenyl]amino}prop-1-yn-1-yl)-N-[1-(oxan-4-yl)piperidin-4-yl]-1-(2,2,2-trifluoroethyl)-1H-indol-4-amine |
| 587. | 2-(2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}ethoxy)ethan-1-ol |
| 588. | 1-{4-[(2-{3-[(2-fluoro-4-methane-sulfonylphenyl)amino]prop-1-yn-1-yl}-1-(2,2,2-trifluoroethyl)-1H-indol-4-yl)amino]piperidin-1-yl}propan-2-ol |
| 589. | 3-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}propane-1,2-diol |
| 590. | (1S,4S)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 591. | 3-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propane-1,2-diol |
| 592. | 2-(3-{[4-(ethanesulfonyl)-phenyl]amino}prop-1-yn-1-yl)-N-[1-(3-methanesulfonylpropyl)-piperidin-4-yl]-1-(2,2,2-trifluoroethyl)-1H-indol-4-amine |
| 593. | 1-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propan-2-ol |
| 594. | 2-[2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethoxy]ethan-1-ol |
| 595. | (1R,4R)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethyl-cyclohexane-1,4-diamine |
| 596. | 2-{3-[(2,6-difluoro-4-methanesulfonylphenyl)amino]prop-1-yn-1-yl}-N-[1-(2-methanesulfonylethyl)piperidin-4-yl]-1-(2,2,2-trifluoroethyl)-1H-indol-4-amine |
| 597. | 4-{4-[(2-{3-[(2,6-difluoro-4-methanesulfonylphenyl)amino]prop-1-yn-1-yl}-1-(2,2,2-trifluoroethyl)-1H-indol-4-yl)amino]piperidin-1-yl}-1λ⁶-thiane-1,1-dione |
| 598. | 2-{3-[(4-methanesulfonyl-3-methoxyphenyl)amino]prop-1-yn-1-yl}-N-[1-(oxan-4-yl)piperidin-4-yl]-1-(2,2,2-trifluoroethyl)-1H-indol-4-amine |
| 599. | 2-{3-[(4-methanesulfonyl-3-methoxyphenyl)amino]prop-1-yn-1-yl}-N-[1-(2-methoxyethyl)piperidin-4-yl]-1-(2,2,2-trifluoroethyl)-1H-indol-4-amine |
| 600. | 4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 601. | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetic acid |
| 602. | 2-hydroxyethyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |
| 603. | 2-{3-[(4-methanesulfonylphenyl)-amino]prop-1-yn-1-yl}-N-(2-methylpiperidin-4-yl)-1-(2,2,2-trifluoroethyl)-1H-indol-4-amine |
| 604. | 2-{4-[(2-{3-[(4-methanesulfonyl-3-methoxyphenyl)amino]prop-1-yn-1-yl}-1-(2,2,2-trifluoroethyl)-1H-indol-4-yl)amino]piperidin-1-yl}ethan-1-ol |
| 605. | (2S)-2-(2-{4-[(2-{3-[(4-methane-sulfonylphenyl)amino]prop-1-yn-1-yl}-1-(2,2,2-trifluoroethyl)-1H-indol-4-yl)amino]piperidin-1-yl}acetamido)pentanedioic acid |
| 606. | 1,5-dimethyl (2S)-2-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentanedioate |

TABLE 1-continued

Alkynyl indole compounds of the disclosure.

| Mol # | IUPAC name |
|---|---|
| 607. | N-(4-carbamimidamidobutyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetamide |
| 608. | 2-{3-[(4-methanesulfonyl-2-methoxyphenyl)amino]prop-1-yn-1-yl}-N-(oxan-4-yl)-1-(2,2,2-trifluoroethyl)-1H-indol-4-amine |
| 609. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-ol |
| 610. | 2-{3-[(5-methanesulfonylpyridin-2-yl)amino]prop-1-yn-1-yl}-N-(oxan-4-yl)-1-(2,2,2-trifluoroethyl)-1H-indol-4-amine |
| 611. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 612. | 4-[(2-{3-[(2,4-dimethoxyphenyl)-amino]prop-1-yn-1-yl}-1-(2,2,2-trifluoroethyl)-1H-indol-4-yl)amino]-1$\lambda^6$-thiane-1,1-dione |
| 613. | methyl 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzoate |
| 614. | 2-{3-[(4-methanesulfonyl-2-methoxyphenyl)amino]prop-1-yn-1-yl}-N-[1-(2-methanesulfonylethyl)-piperidin-4-yl]-1-(2,2,2-trifluoroethyl)-1H-indol-4-amine |
| 615. | 2-{3-[(4-methanesulfonyl-2-methoxyphenyl)amino]prop-1-yn-1-yl}-N-[1-(2-methoxyethyl)piperidin-4-yl]-1-(2,2,2-trifluoroethyl)-1H-indol-4-amine |
| 616. | (1S,4S)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |
| 617. | (1R,4R)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |
| 618. | 2-{3-[(4-methanesulfonyl-2-methoxyphenyl)amino]prop-1-yn-1-yl}-N-[1-(oxan-4-yl)piperidin-4-yl]-1-(2,2,2-trifluoroethyl)-1H-indol-4-amine |
| 619. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-o |
| 620. | 2-{3-[(4-methanesulfonyl-2-methoxyphenyl)amino]prop-1-yn-1-yl}-N-[1-(1-methylpyrrolidin-3-yl)piperidin-4-yl]-1-(2,2,2-trifluoroethyl)-1H-indol-4-amine |
| 621. | 2-{3-[(4-methanesulfonyl-2-methoxyphenyl)amino]prop-1-yn-1-yl}-N-(2-methylpiperidin-4-yl)-1-(2,2,2-trifluoroethyl)-1H-indol-4-amine |
| 622. | 2-{3-[(4-methanesulfonyl-2-methoxyphenyl)amino]prop-1-yn-1-yl}-N-(piperidin-4-yl)-1-(2,2,2-trifluoroethyl)-1H-indol-4-amine |
| 623. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 624. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetamide |
| 625. | 2-{3-[(4-methanesulfonyl-2-methoxyphenyl)amino]prop-1-yn-1-yl}-N-[1-(1-methylpiperidin-4-yl)piperidin-4-yl]-1-(2,2,2-trifluoroethyl)-1H-indol-4-amine |
| 626. | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}piperidin-4-ol |
| 627. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 628. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-N,N-dimethylacetamide |
| 629. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetonitrile |
| 630. | methyl 2-{4-[(2-{3-[(4-methane-sulfonyl-2-methoxyphenyl)amino]prop-1-yn-1-yl}-1-(2,2,2-trifluoroethyl)-1H-indol-4-yl)amino]piperidin-1-yl}acetate |
| 631. | 1-(4-hydroxypiperidin-1-yl)-2-{4-[(2-{3-[(4-methanesulfonyl-2-methoxy-phenyl)amino]prop-1-yn-1-yl}-1-(2,2,2-trifluoroethyl)-1H-indol-4-yl)amino]piperidin-1-yl}ethan-1-one |
| 632. | 2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethan-1-ol |
| 633. | -[(1R,4R)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 634. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetic acid |
| 635. | (1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 636. | (1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 637. | 2-{3-[(4-methanesulfonyl-2-methoxyphenyl)amino]prop-1-yn-1-yl}-1-(2,2,2-trifluoroethyl)-1H-indol-4-amine |
| 638. | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}-3-methylpyrrolidin-3-ol |
| 639. | (3R,4R)-1-{4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl}-pyrrolidine-3,4-diol |
| 640. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboximidamide |
| 641. | 1-[(1S,4S)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 642. | 4-[(2-{3-[(3-methoxypyridin-4-yl)amino]prop-1-yn-1-yl}-1-(2,2,2-trifluoroethyl)-1H-indol-4-yl)amino]-1$\lambda^6$-thiane-1,1-dione |
| 643. | 2-{3-[(4-methanesulfonyl-2-methoxyphenyl)amino]prop-1-yn-1-yl}-N-[(1S,4S)-4-(morpholin-4-yl)cyclohexyl]-1-(2,2,2-trifluoroethyl)-1H-indol-4-amine |

TABLE 1-continued

Alkynyl indole compounds of the disclosure.

| Mol # | IUPAC name |
|---|---|
| 644. | 2-{3-[(4-methanesulfonyl-2-methoxyphenyl)amino]prop-1-yn-1-yl}-N-[(1R,4R)-4-(morpholin-4-yl)cyclohexyl]-1-(2,2,2-trifluoroethyl)-1H-indol-4-amine |
| 645. | 2-(3-{[2-(2-fluoroethoxy)-4-methanesulfonylphenyl]amino}prop-1-yn-1-yl)-N-[1-(oxan-4-yl)piperidin-4-yl]-1-(2,2,2-trifluoroethyl)-1H-indol-4-amine |
| 646. | 4-{[2-(3-{[4-methanesulfonyl-2-(trifluoromethyl)phenyl]amino}prop-1-yn-1-yl)-1-(2,2,2-trifluoroethyl)-1H-indol-4-yl]amino}-1$\lambda^6$-thiane-1,1-dione |
| 647. | 2-(3-{[4-methanesulfonyl-2-(trifluoromethyl)phenyl]amino}prop-1-yn-1-yl)-N-(1-methylpiperidin-4-yl)-1-(2,2,2-trifluoroethyl)-1H-indol-4-amine |
| 648. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 649. | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzene-1-sulfonamide |
| 650. | 3-methoxy-4-[(3-{4-[(piperidin-4-yl)amino]-1-(2,2,2-trifluoroethyl)-1H-indol-2-yl}prop-2-yn-1-yl)amino]-benzamide |
| 651. | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzamide |
| 652. | 3-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)propane-1,2-diol |
| 653. | 3-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)propane-1,2-diol |
| 654. | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)acetamide |
| 655. | 2-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-1-(4-methylpiperazin-1-yl)ethan-1-one |
| 656. | 2-(3-{[2-(2-fluoroethoxy)-4-methanesulfonylphenyl]amino}prop-1-yn-1-yl)-N-(oxan-4-yl)-1-(2,2,2-trifluoroethyl)-1H-indol-4-amine |
| 657. | 2-(3-{[2-(2-fluoroethoxy)-4-methanesulfonylphenyl]amino}prop-1-yn-1-yl)-N-[1-(1-methylpiperidin-4-yl)piperidin-4-yl]-1-(2,2,2-trifluoroethyl)-1H-indol-4-amine |
| 658. | 4-[(2-{3-[(4-methoxypyridin-3-yl)amino]prop-1-yn-1-yl}-1-(2,2,2-trifluoroethyl)-1H-indol-4-yl)amino]-1$\lambda^6$-thiane-1,1-dione |
| 659. | S-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}-2-hydroxyethane-1-sulfonamido |
| 660. | 2-hydroxy-S-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}ethane-1-sulfonamido |
| 661. | 2-methyl-2-[5-({3-[4-(morpholin-4-yl)-1-(2,2,2-trifluoroethyl)-1H-indol-2-yl]prop-2-yn-1-yl}amino)pyridin-2-yl]propanenitrile |
| 662. | -{4-[(2-{3-[(4-methanesulfonylphenyl)amino]prop-1-yn-1-yl}-1-(2,2,2-trifluoroethyl)-1H-indol-4-yl)amino]piperidin-1-yl}-N-[5-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentyl]acetamide |
| 663. | 6-[(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetyl)oxy]hexyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |
| 664. | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 665. | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetamide |
| 666. | 2-(3-{[4-methanesulfonyl-2-(2-methoxyethoxy)phenyl]amino}prop-1-yn-1-yl)-N-[1-(oxan-4-yl)piperidin-4-yl]-1-(2,2,2-trifluoroethyl)-1H-indol-4-amine |
| 667. | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)ethan-1-ol |
| 668. | 3-methoxy-4-[(3-{4-[(oxan-4-yl)amino]-1-(2,2,2-trifluoroethyl)-1H-indol-2-yl}prop-2-yn-1-yl)amino]benzoic acid |
| 669. | 2-{2-[(3-{4-[(1,1-dioxo-1$\lambda^6$-thian-4-yl)amino]-1-(2,2,2-trifluoroethyl)-1H-indol-2-yl}prop-2-yn-1-yl)amino]-5-methanesulfonylphenoxy}acetamide |
| 670. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboxamide |
| 671. | 2-{3-[(4-methoxypyridin-3-yl)amino]prop-1-yn-1-yl}-N-(1-methylpiperidin-4-yl)-1-(2,2,2-trifluoroethyl)-1H-indol-4-amine |
| 672. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carbothioamide |
| 673. | 4-[(2-{3-[(6-methanesulfonyl-4-methoxypyridin-3-yl)amino]prop-1-yn-1-yl}-1-(2,2,2-trifluoroethyl)-1H-indol-4-yl)amino]-1$\lambda^6$-thiane-1,1-dione |
| 674. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |
| 675. | 4-{[2-(3-{[4-(ethanesulfonyl)-2-methoxyphenyl]amino}prop-1-yn-1-yl)-1-(2,2,2-trifluoroethyl)-1H-indol-4-yl]amino}-1$\lambda^6$-thiane-1,1-dione |
| 676. | 2-(3-{[4-(ethanesulfonyl)-2-methoxyphenyl]amino}prop-1-yn-1-yl)-N-[1-(oxan-4-yl)piperidin-4-yl]-1-(2,2,2-trifluoroethyl)-1H-indol-4-amine |
| 677. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoic acid |
| 678. | methyl 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoate |

TABLE 1-continued

Alkynyl indole compounds of the disclosure.

| Mol # | IUPAC name |
|---|---|
| 679. | methyl 3-methoxy-4-[(3-{4-[(oxan-4-yl)amino]-1-(2,2,2-trifluoroethyl)-1H-indol-2-yl}prop-2-yn-1-yl)amino]benzoate |
| 680. | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzamide |
| 681. | 4-[(2-{3-[(4-methanesulfonyl-2-methoxyphenyl)amino]prop-1-yn-1-yl}-1-(2,2,2-trifluoroethyl)-1H-indol-4-yl)amino]-N-methylpiperidine-1-carboximidamide |
| 682. | 2-{3-[(6-methanesulfonyl-4-methoxypyridin-3-yl)amino]prop-1-yn-1-yl}-N-(1-methylpiperidin-4-yl)-1-(2,2,2-trifluoroethyl)-1H-indol-4-amine |
| 683. | 2-{3-[(4-methanesulfonyl-2-methoxyphenyl)amino]prop-1-yn-1-yl}-N-[1-(pyridin-4-yl)piperidin-4-yl]-1-(2,2,2-trifluoroethyl)-1H-indol-4-amine |
| 684. | 3-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)propane-1,2-diol |
| 685. | 2-(3-{[4-(ethanesulfonyl)-2-methoxyphenyl]amino}prop-1-yn-1-yl)-N-(1-methylpiperidin-4-yl)-1-(2,2,2-trifluoroethyl)-1H-indol-4-amine |
| 686. | 2-hydroxy-S-{3-methoxy-4-[(3-{4-[(oxan-4-yl)amino]-1-(2,2,2-trifluoroethyl)-1H-indol-2-yl}prop-2-yn-1-yl)amino]phenyl}ethane-1-sulfonamido |
| 687. | 2-(3-{[4-methanesulfonyl-2-(2,2,2-trifluoroethoxy)phenyl]amino}prop-1-yn-1-yl)-N-(1-methylpiperidin-4-yl)-1-(2,2,2-trifluoroethyl)-1H-indol-4-amine |
| 688. | 4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}-1$\lambda^6$-thiane-1,1-dione |
| 689. | 2-hydroxy-S-(3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}phenyl)ethane-1-sulfonamido |
| 690. | S-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxyphenyl)-2-hydroxyethane-1-sulfonamido |
| 691. | 2-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 692. | 3-methoxy-4-{[3-(4-{[(1S,4S)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 693. | 3-methoxy-4-{[3-(4-{[(1R,4R)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 694. | 3-methoxy-4-{[3-(4-{[(1S,4S)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 695. | 3-methoxy-4-{[3-(4-{[(1R,4R)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 696. | 2-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}-2-methylpropanenitrile |
| 697. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 698. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 699. | (3S,4S)-1-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]pyrrolidine-3,4-diol |
| 700. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 701. | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 702. | 2-{3-[(4-methanesulfonyl-2-methoxyphenyl)amino]prop-1-yn-1-yl}-N,N-dimethyl-1-(2,2,2-trifluoroethyl)-1H-indol-4-amine |
| 703. | 3-methoxy-4-[(3-{4-[(2-methoxyethyl)amino]-1-(2,2,2-trifluoroethyl)-1H-indol-2-yl}prop-2-yn-1-yl)amino]benzene-1-sulfonamide |
| 704. | 2-[(2-{3-[(2-methoxy-4-sulfamoylphenyl)amino]prop-1-yn-1-yl}-1-(2,2,2-trifluoroethyl)-1H-indol-4-yl)amino]acetamide |
| 705. | 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide |
| 706. | N-(2-{3-[(4-methanesulfonyl-2-methoxyphenyl)amino]prop-1-yn-1-yl}-1-(2,2,2-trifluoroethyl)-1H-indol-4-yl)acetamide |
| 707. | 3-(2-{3-[(4-methanesulfonyl-2-methoxyphenyl)amino]prop-1-yn-1-yl}-1-(2,2,2-trifluoroethyl)-1H-indol-4-yl)-1-(1-methylpiperidin-4-yl)urea |
| 708. | 3-methoxy-4-{[3-(4-{[(1-methylpiperidin-4-yl)carbamoyl]amino}-1-(2,2,2-trifluoroethyl)-1H-indol-2-yl)prop-2-yn-1-yl]amino}benzamide |
| 709. | N-(2-{3-[(4-methanesulfonyl-2-methoxyphenyl)amino]prop-1-yn-1-yl}-1-(2,2,2-trifluoroethyl)-1H-indol-4-yl)-4-methylpiperazine-1-carboxamide |
| 710. | N-(2-{3-[(4-carbamoyl-2-methoxyphenyl)amino]prop-1-yn-1-yl}-1-(2,2,2-trifluoroethyl)-1H-indol-4-yl)-4-methylpiperazine-1-carboxamide |
| 711. | 3-(2-{3-[(4-methanesulfonyl-2-methoxyphenyl)amino]prop-1-yn-1-yl}-1-(2,2,2-trifluoroethyl)-1H-indol-4-yl)-1-[(1S,4S)-4-(dimethylamino)cyclohexyl]urea |
| 712. | 1-(2-(3-((2-methoxy-4-(methylsulfonyl)phenyl)amino)prop-1-yn-1-yl)-1-(2,2,2-trifluoroethyl)-1H-indol-4-yl)-3-(pyridin-4-yl)urea |
| 713. | 3-(2-{3-[(4-methanesulfonyl-2-methoxyphenyl)amino]prop-1-yn-1-yl}-1-(2,2,2-trifluoroethyl)-1H-indol-4-yl)-1-[(1R,4R)-4-(dimethylamino)cyclohexyl]urea |
| 714. | 3-(2-{3-[(4-methanesulfonyl-2-methoxyphenyl)amino]prop-1-yn-1-yl}-1-(2,2,2-trifluoroethyl)-1H-indol-4-yl)-1-[1-(2-methoxyethyl)piperidin-4-yl]urea |
| 715. | 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea |

TABLE 1-continued

Alkynyl indole compounds of the disclosure.

| Mol # | IUPAC name |
|---|---|
| 716. | 1-[1-(2,3-dihydroxypropyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea |
| 717. | 2-(4-{[(2-{3-[(4-methanesulfonyl-2-methoxyphenyl)amino]prop-1-yn-1-yl}-1-(2,2,2-trifluoroethyl)-1H-indol-4-yl)carbamoyl]amino}piperidin-1-yl)acetamide |
| 718. | 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide |
| 719. | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol |
| 720. | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine |
| 721. | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide |
| 722. | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine |
| 723. | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide |
| 724. | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide |
| 725. | 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide |
| 726. | rel-(1R,3R)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 727. | rac-(1R,3S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 728. | (1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamineQ |
| 729. | rac-(1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 730. | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 731. | 3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide |
| 732. | 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide |
| 733. | 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide |
| 734. | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide |
| 735. | 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide |
| 736. | 3-[(2-{3-[(4-methanesulfonyl-2-methoxyphenyl)amino]prop-1-yn-1-yl}-1-(2,2,2-trifluoroethyl)-1H-indol-4-yl)amino]cyclohexane-1-carboxylic acid |
| 737. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 738. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 739. | 2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 740. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$-methylcyclohexane-1,4-diamine |
| 741. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 742. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 743. | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 744. | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 745. | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 746. | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 747. | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 748. | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 749. | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 750. | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 751. | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 752. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |

TABLE 1-continued

Alkynyl indole compounds of the disclosure.

| Mol # | IUPAC name |
|---|---|
| 753. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 754. | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 755. | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 756. | (1S,4S)-N$^4$-(2-{3-[(4-methanesulfonyl-2-methoxyphenyl)amino]prop-1-yn-1-yl}-1-(2,2,2-trifluoroethyl)-1H-indol-4-yl)-N$^1$-(2-methoxyethyl)-N$^1$-methylcyclohexane-1,4-diamine |
| 757. | (1R,4R)-N$^4$-(2-{3-[(4-methanesulfonyl-2-methoxyphenyl)amino]prop-1-yn-1-yl}-1-(2,2,2-trifluoroethyl)-1H-indol-4-yl)-N$^1$-(2-methoxyethyl)-N$^1$-methylcyclohexane-1,4-diamine |
| 758. | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 759. | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 760. | 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 761. | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 762. | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 763. | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide |
| 764. | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine |
| 765. | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide |
| 766. | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one |
| 767. | (1R,4R)-N$^4$-[2-(3-{[2-methoxy-4-(morpholine-4-sulfonyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 768. | (1S,4S)-N$^4$-[2-(3-{[2-methoxy-4-(morpholine-4-sulfonyl)phenyl]amino}prop-1-yn-1-yl)-1-(2,2,2-trifluoroethyl)-1H-indol-4-yl]-N$^1$,N$^1$-dimethylcyclohexane-1,4-diamine |
| 769. | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 770. | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 771. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 772. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 773. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 774. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 775. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 776. | (1R,4R)-N$^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-N$^1$,N$^1$-dimethylcyclohexane-1,4-diamine |
| 777. | (1R,4R)-N$^4$-(2-{3-[(4-methanesulfonyl-2-methoxyphenyl)amino]prop-1-yn-1-yl}-1-[(oxiran-2-yl)methyl]-1H-indol-4-yl)-N$^1$,N$^1$-dimethylcyclohexane-1,4-diamine |
| 778. | 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile |
| 779. | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol |
| 780. | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol |
| 781. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile |
| 782. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile |
| 783. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide |
| 784. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide |
| 785. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide |
| 786. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide |

TABLE 1-continued

Alkynyl indole compounds of the disclosure.

| Mol # | IUPAC name |
|---|---|
| 787. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol |
| 788. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol |
| 789. | (1R,4R)-$N^4$-[2-(3-{[4-methanesulfonyl-2-(2-methoxyethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 790. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 791. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 792. | (1R,4R)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 793. | (1S,4S)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 794. | (1S,4S)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 795. | (1R,4R)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |
| 796. | (1S,4S)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |
| 797. | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 798. | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 799. | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 800. | (1R,4R)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 801. | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 802. | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 803. | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 804. | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 805. | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 806. | 3-(fluoromethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 807. | 3-(fluoromethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 808. | (1S,4S)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 809. | (1R,4R)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 810. | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide |
| 811. | (1S,4S)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 812. | (1R,4R)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 813. | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 814. | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 815. | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide |
| 816. | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide |
| 817. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 818. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 819. | (1R,4R)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 820. | (1S,4S)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 821. | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile |
| 822. | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile |
| 823. | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 824. | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide |
| 825. | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 826. | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 827. | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 828. | (1R,4R)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 829. | (1S,4S)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 830. | (1R,4R)-$N^4$-(2-{3-[(4-chloro-2-methoxyphenyl)amino]prop-1-yn-1-yl}-1-(2,2,2-trifluoroethyl)-1H-indol-4-yl)-$N^1$,$N^1$-dimethylcyclohexane-1,4-diamine |
| 831. | (1S,4S)-$N^1$-(2-(3-((4-chloro-2-methoxyphenyl)amino)prop-1-yn-1-yl)-1-(2,2,2-trifluoroethyl)-1H-indol-4-yl)-$N^4$,$N^4$-dimethylcyclohexane-1,4-diamine |
| 832. | 4-((3-(4-(((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 833. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 834. | (1R,4R)-$N^4$-[2-(3-{[2-methoxy-4-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 835. | (1S,4S)-$N^1$-(2-(3-((2-methoxy-4-(trifluoromethyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 836. | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 837. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide |
| 838. | (1S,4S)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 839. | (1R,4R)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 840. | (1R,4R)-$N^4$-(2-{3-[(4-methanesulfonyl-2-methylphenyl)amino]prop-1-yn-1-yl}-1-(2,2,2-trifluoroethyl)-1H-indol-4-yl)-$N^1$,$N^1$-dimethylcyclohexane-1,4-diamine |
| 841. | (1S,4S)-$N^1$,$N^1$-dimethyl-$N^4$-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine |
| 842. | (1R,4R)-$N^4$-[2-(3-{[4-methanesulfonyl-2-(trifluoromethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 843. | (1S,4S)-$N^1$,$N^1$-dimethyl-$N^4$-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine |
| 844. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide |
| 845. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxy-N-methylbenzamide |
| 846. | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 847. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide |
| 848. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 849. | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 850. | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 851. | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 852. | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 853. | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 854. | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide |
| 855. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 856. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |

TABLE 1-continued

Alkynyl indole compounds of the disclosure.

| Mol # | IUPAC name |
|---|---|
| 857. | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 858. | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 859. | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide |
| 860. | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 861. | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide |
| 862. | (1R,4R)-$N^1$,$N^1$-diethyl-$N^4$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 863. | (1S,4S)-$N^1$,$N^1$-diethyl-$N^4$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 864. | 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 865. | 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 866. | 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 867. | 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 868. | 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 869. | 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 870. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 871. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 872. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 873. | 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 874. | 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile |
| 875. | 4-(({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 876. | 1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 877. | 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 878. | 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine |
| 879. | 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine |
| 880. | 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 881. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 882. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 883. | N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 884. | N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide |
| 885. | 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile |
| 886. | 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile |
| 887. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 888. | 2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine |
| 889. | 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine |
| 890. | 3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 891. | 3-methoxy-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzenesulfonamide |
| 892. | 3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide |
| 893. | 3-methoxy-N-methyl-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzamide |
| 894. | 2-{3-[(4-methanesulfonyl-2-methoxyphenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine |
| 895. | N-((1S,4S)-4-(2-azaspiro[3.3]heptan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 896. | 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide |
| 897. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide |
| 898. | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide |
| 899. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide |
| 900. | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine |
| 901. | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide |
| 902. | 2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 903. | 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 904. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 905. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 906. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 907. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 908. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 909. | N-(3-methoxy-4-{[3-(4-{[(1S,4S)-4-}2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 910. | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 911. | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 912. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 913. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 914. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 915. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 916. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 917. | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 918. | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide |
| 919. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 920. | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |

TABLE 1-continued

Alkynyl indole compounds of the disclosure.

| Mol # | IUPAC name |
|---|---|
| 921. | 2-(3-{[4-methanesulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 922. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 923. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 924. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 925. | 2-(5-methanesulfonyl-2-([3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 926. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 927. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide |
| 928. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 929. | 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 930. | 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 931. | 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 932. | 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 933. | 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine |
| 934. | 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 935. | 2-{3-[(2-ethoxy-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 936. | 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 937. | 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 938. | N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 939. | N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 940. | 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 941. | 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 942. | 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 943. | 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 944. | 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 945. | 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 946. | 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine |
| 947. | N-((1R,4R)-4-(2-oxa-6-azaspiro[3.3]heptan-6-yl)cyclohexyl)-2-(3-(2-amino-4-(methylsulfonyl)phenoxy)prop-1-yn-1-yl)-1-(2,2,2-trifluoroethyl)-1H-indol-4-amine |

TABLE 1-continued

Alkynyl indole compounds of the disclosure.

| Mol # | IUPAC name |
|---|---|
| 948. | 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 949. | 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile |
| 950. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile |
| 951. | 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile |
| 952. | 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 953. | 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 954. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide |
| 955. | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 956. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide |
| 957. | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 958. | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 959. | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 960. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide |
| 961. | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 962. | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 963. | 4-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 964. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 965. | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 966. | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 967. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 968. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 969. | N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 970. | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 971. | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 972. | N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 973. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 974. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide |
| 975. | 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |

TABLE 1-continued

Alkynyl indole compounds of the disclosure.

| Mol # | IUPAC name |
|---|---|
| 976. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide |
| 977. | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 978. | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine |
| 979. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 980. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 981. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid |
| 982. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid |
| 983. | 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 984. | N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine |
| 985. | 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 986. | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine |
| 987. | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 988. | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine |
| 989. | 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 990. | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine |
| 991. | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 992. | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 993. | 2-{3-[(4-methanesulfonyl-2-methoxyphenyl)amino]prop-1-yn-1-yl}-N-[(1S,4S)-4-{7-oxa-2-azaspiro[3.5]nonan-2-yl}cyclohexyl]-1-(2,2,2-trifluoroethyl)-1H-indol-4-amine |
| 994. | 2-{3-[(4-methanesulfonyl-2-methoxyphenyl)amino]prop-1-yn-1-yl}-N-[(1R,4R)-4-{7-oxa-2-azaspiro[3.5]nonan-2-yl}cyclohexyl]-1-(2,2,2-trifluoroethyl)-1H-indol-4-amine |
| 995. | 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 996. | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 997. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 998. | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 999. | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1000. | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1001. | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile |
| 1002. | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1003. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1004. | 2-(5-methanesulfonyl-2-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1005. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |

TABLE 1-continued

Alkynyl indole compounds of the disclosure.

Mol # IUPAC name

1006. N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide
1007. N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide
1008. N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide
1009. methyl 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate
1010. methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate
1011. 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid
1012. 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid
1013. 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine
1014. 2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine
1015. 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine
1016. 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide
1017. 3-(fluoromethoxy)-4-{[3-(4-{[(1S,4S)-4-{7-oxa-2-azaspiro[3,5]nonan-2-yl}cyclohexyl]amino}-1-(2,2,2-trifluoroethyl)-1H-indol-2-yl)prop-2-yn-1-yl]amino}benzene-1-sulfonamide
1018. 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide
1019. 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide
1020. 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide
1021. 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzenesulfonamide
1022. 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine
1023. N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine
1024. N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine
1025. N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine
1026. 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one
1027. 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide
1028. 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide
1029. N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine
1030. N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine
1031. 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide
1032. 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide
1033. 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide
1034. 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide
1035. 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide
1036. 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine TABLE 1-continued Alkynyl indole compounds of the disclosure.

| Mol # | IUPAC name |
|---|---|
| 1037. | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine |
| 1038. | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1039. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1040. | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine |
| 1041. | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine |
| 1042. | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1043. | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1044. | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1045. | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1046. | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine |
| 1047. | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine |
| 1048. | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine |
| 1049. | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine |
| 1050. | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine |
| 1051. | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine |
| 1052. | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide |
| 1053. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide |
| 1054. | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1055. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide |
| 1056. | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide |
| 1057. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide |
| 1058. | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1059. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide |
| 1060. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1061. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1062. | 4-[(1R,4R)-4-[2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^6$-thiomorpholine-1,1-dione |
| 1063. | 4-(((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide |
| 1064. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1065. | 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1066. | 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1067. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1068. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1-oxide |
| 1069. | 3-methoxy-N-methyl-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzamide |
| 1070. | 3-methoxy-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1071. | 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide |
| 1072. | 3-methoxy-4-{[3-(4-{[(1R,4R)-4-(1,1-dioxo-1$\lambda^6$-thiomorpholin-4-yl)cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1073. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide |
| 1074. | 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine |
| 1075. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1076. | 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1077. | 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1078. | 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1079. | 3-(cyanomethoxy)-4-]{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1080. | 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1081. | 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1082. | 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1083. | 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine |
| 1084. | N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1085. | 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1086. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide |
| 1087. | 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1088. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1089. | 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1090. | 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1091. | 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine |
| 1092. | 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine |
| 1093. | N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1094. | N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1095. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1096. | N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1097. | N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1098. | 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1099. | 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1100. | 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1101. | 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1102. | 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1103. | 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1104. | 2-{3-[(2-ethoxy-4-methanesulfonylphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1105. | 2-{3-[(2-ethoxy-4-methanesulfonylphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1106. | N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1107. | 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile |
| 1108. | 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile |
| 1109. | 3-methoxy-N-methyl-4-{[3-(4-{[(1R,4R)-4-[2-oxa-8-azaspiro[4.5]decan-8-yl]cyclohexyl]amino}-1-(2,2,2-trifluoroethyl)-1H-indol-2-yl)prop-2-yn-1-yl]amino}benzamide |
| 1110. | 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine |
| 1111. | 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide |
| 1112. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1113. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1114. | 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine |
| 1115. | N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1116. | 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide |
| 1117. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide |
| 1118. | 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide |
| 1119. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzenesulfonamide |
| 1120. | 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide |
| 1121. | 3-methoxy-N-methyl-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzamide |
| 1122. | 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide |
| 1123. | 3-methoxy-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzenesulfonamide |
| 1124. | 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine |
| 1125. | 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine |
| 1126. | -{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine |
| 1127. | 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide |
| 1128. | 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide |
| 1129. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)-N-methylbenzamide |
| 1130. | 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide |
| 1131. | 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzenesulfonamide |
| 1132. | 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine |

TABLE 1-continued

Alkynyl indole compounds of the disclosure.

| Mol # | IUPAC name |
|---|---|
| 1133. | 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine |
| 1134. | 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide |
| 1135. | 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide |
| 1136. | 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine |
| 1137. | 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine |
| 1138. | 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide |
| 1139. | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide |
| 1140. | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide |
| 1141. | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide |
| 1142. | 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine |
| 1143. | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine |
| 1144. | 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide |
| 1145. | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide |
| 1146. | 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide |
| 1147. | 3-methoxy-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzenesulfonamide |
| 1148. | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one |
| 1149. | 2-(3-((2-methoxy-4-(methylsulfonyl)phenyl)amino)prop-1-yn-1-yl)-N-((1R,4R)-4-morpholinocyclohexyl)-1-(oxiran-2-ylmethyl)-1H-indol-4-amine |
| 1150. | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile |
| 1151. | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1152. | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1153. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1154. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1155. | 1-[1-(2-hydroxyethyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea |
| 1156. | 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide |
| 1157. | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol |
| 1158. | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine |
| 1159. | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide |
| 1160. | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine |
| 1161. | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide |
| 1162. | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide |
| 1163. | 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide |

TABLE 1-continued

Alkynyl indole compounds of the disclosure.

| Mol # | IUPAC name |
|---|---|
| 1164. | rel-(1R,3R)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 1165. | rac-(1R,3S)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 1166. | (1R,2S)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 1167. | rac-(1R,2S)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 1168. | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 1169. | 3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide |
| 1170. | 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide |
| 1171. | 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide |
| 1172. | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide |
| 1173. | 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide |
| 1174. | 3-[(2-{3-[(4-methanesulfonyl-2-methoxyphenyl)amino]prop-1-yn-1-yl}-1-(2,2,2-trifluoroethyl)-1H-indol-4-yl)amino]cyclohexane-1-carboxylic acid |
| 1175. | 2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1176. | (1R,2R,4S)-2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1177. | 2-fluoro-N$^1$-(2-{3-[(4-methanesulfonyl-2-methoxyphenyl)amino]prop-1-yn-1-yl}-1-(2,2,2-trifluoroethyl)-1H-indol-4-yl)-N$^4$-methylcyclohexane-1,4-diamine |
| 1178. | (1R,2R,4S)-2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)-N$^4$-methylcyclohexane-1,4-diamine |
| 1179. | 2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1180. | (1R,2R,4S)-2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1181. | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 1182. | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 1183. | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 1184. | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 1185. | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 1186. | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1187. | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1188. | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1189. | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1190. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1191. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1192. | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1193. | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1194. | (1S,4S)-N$^4$-(2-{3-[(4-methanesulfonyl-2-methoxyphenyl)amino]prop-1-yn-1-yl}-1-(2,2,2-trifluoroethyl)-1H-indol-4-yl)-N$^1$-(2-methoxyethyl)-N$^1$-methylcyclohexane-1,4-diamine |
| 1195. | (1R,4R)-N$^4$-(2-{3-[(4-methanesulfonyl-2-methoxyphenyl)amino]prop-1-yn-1-yl}-1-(2,2,2-trifluoroethyl)-1H-indol-4-yl)-N$^1$-(2-methoxyethyl)-N$^1$-methylcyclohexane-1,4-diamine |
| 1196. | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 1197. | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |

TABLE 1-continued

Alkynyl indole compounds of the disclosure.

| Mol # | IUPAC name |
|---|---|
| 1198. | 4-((3-(4-((((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 1199. | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1200. | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1201. | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide |
| 1202. | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine |
| 1203. | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide |
| 1204. | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one |
| 1205. | (1R,4R)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1206. | (1S,4S)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1207. | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1208. | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1209. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1210. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1211. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1212. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1213. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1214. | (1R,4R)-$N^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-$N^1$,$N^1$-dimethylcyclohexane-1,4-diamine |
| 1215. | (1R,4R)-$N^4$-{2-{3-[(4-methanesulfonyl-2-methoxyphenyl)amino]prop-1-yn-1-yl}-1-[(oxiran-2-yl)methyl]-1H-indol-4-yl}-$N^1$,$N^1$-dimethylcyclohexane-1,4-diamine |
| 1216. | 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile |
| 1217. | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol |
| 1218. | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol |
| 1219. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile |
| 1220. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile |
| 1221. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide |
| 1222. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide |
| 1223. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide |
| 1224. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide |
| 1225. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol |
| 1226. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol |
| 1227. | (1R,4R)-$N^4$-[2-(3-{[4-methanesulfonyl-2-(2-methoxyethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1228. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1229. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1230. | (1R,4R)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1231. | (1S,4S)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1232. | (1S,4S)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 1233. | (1R,4R)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |

TABLE 1-continued

Alkynyl indole compounds of the disclosure.

| Mol # | IUPAC name |
|---|---|
| 1234. | (1S,4S)-N$^4$-(2-{3-[(2-ethoxy-4-methanesulfonylphenyl)amino]prop-1-yn-1-yl}-1-(2,2,2-trifluoroethyl)-1H-indol-4-yl)-N$^1$,N$^1$-dimethylcyclohexane-1,4-diamine |
| 1235. | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1236. | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1237. | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1238. | (1R,4R)-N$^4$-{2-[3-(2-amino-4-methanesulfonylphenoxy)prop-1-yn-1-yl]-1-(2,2,2-trifluoroethyl)-1H-indol-4-yl}-N$^1$,N$^1$-dimethylcyclohexane-1,4-diamine |
| 1239. | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1240. | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1241. | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1242. | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1243. | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1244. | 3-(fluoromethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1245. | 3-(fluoromethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1246. | (1S,4S)-N$^4$-(2-{3-[4-methanesulfonyl-2-(methylamino)phenoxy]prop-1-yn-1-yl}-1-(2,2,2-trifluoroethyl)-1H-indol-4-yl)-N$^1$,N$^1$-dimethylcyclohexane-1,4-diamine |
| 1247. | (1R,4R)-N$^4$-(2-{3-[4-methanesulfonyl-2-(methylamino)phenoxy]prop-1-yn-1-yl}-1-(2,2,2-trifluoroethyl)-1H-indol-4-yl)-N$^1$,N$^1$-dimethylcyclohexane-1,4-diamine |
| 1248. | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide |
| 1249. | (1S,4S)-N$^4$-(2-{3-[2-(dimethylamino)-4-methanesulfonylphenoxy]prop-1-yn-1-yl}-1-(2,2,2-trifluoroethyl)-1H-indol-4-yl)-N$^1$,N$^1$-dimethylcyclohexane-1,4-diamine |
| 1250. | (1R,4R)-N$^4$-(2-{3-[2-(dimethylamino)-4-methanesulfonylphenoxy]prop-1-yn-1-yl}-1-(2,2,2-trifluoroethyl)-1H-indol-4-yl)-N$^1$,N$^1$-dimethylcyclohexane-1,4-diamine |
| 1251. | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1252. | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1253. | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide |
| 1254. | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide |
| 1255. | (1R,4R)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1256. | (1S,4S)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine |
| 1257. | (1R,4R)-N$^4$-[2-(3-{[4-(ethanesulfonyl)-2-methoxyphenyl]amino}prop-1-yn-1-yl)-1-(2,2,2-trifluoroethyl)-1H-indol-4-yl]-N$^1$,N$^1$-dimethylcyclohexane-1,4-diamine |
| 1258. | (1S,4S)-N$^4$-[2-(3-{[4-(ethanesulfonyl)-2-methoxyphenyl]amino}prop-1-yn-1-yl)-1-(2,2,2-trifluoroethyl)-1H-indol-4-yl]-N$^1$,N$^1$-dimethylcyclohexane-1,4-diamine |
| 1259. | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile |
| 1260. | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile |
| 1261. | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1262. | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide |
| 1263. | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1264. | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1265. | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1266. | (1R,4R)-N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine |
| 1267. | (1S,4S)-N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine |
| 1268. | (1R,4R)-N$^4$-(2-{3-[(4-chloro-2-methoxyphenyl)amino]prop-1-yn-1-yl}-1-(2,2,2-trifluoroethyl)-1H-indol-4-yl)-N$^1$,N$^1$-dimethylcyclohexane-1,4-diamine |
| 1269. | (1S,4S)-N$^1$-(2-(3-((4-chloro-2-methoxyphenyl)amino)prop-1-yn-1-yl)-1-(2,2,2-trifluoroethyl)-1H-indol-4-yl)-N$^4$,N$^4$-dimethylcyclohexane-1,4-diamine |
| 1270. | 4-((3-(4-(((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide |

TABLE 1-continued

Alkynyl indole compounds of the disclosure.

| Mol # | IUPAC name |
|---|---|
| 1271. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 1272. | (1R,4R)-$N^4$-[2-(3-{[2-methoxy-4-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1273. | (1S,4S)-$N^1$-(2-(3-((2-methoxy-4-(trifluoromethyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1274. | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1275. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide |
| 1276. | (1S,4S)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1277. | (1R,4R)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1278. | (1R,4R)-$N^4$-(2-{3-[(4-methanesulfonyl-2-methylphenyl)amino]prop-1-yn-1-yl}-1-(2,2,2-trifluoroethyl)-1H-indol-4-yl)-$N^1$,$N^1$-dimethylcyclohexane-1,4-diamine |
| 1279. | (1S,4S)-$N^1$,$N^1$-dimethyl-$N^4$-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine |
| 1280. | (1R,4R)-$N^4$-[2-(3-{[4-methanesulfonyl-2-(trifluoromethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1281. | (1S,4S)-$N^1$,$N^1$-dimethyl-$N^4$-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine |
| 1282. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide |
| 1283. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxy-N-methylbenzamide |
| 1284. | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 1285. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide |
| 1286. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 1287. | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 1288. | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 1289. | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1290. | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1291. | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1292. | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide |
| 1293. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 1294. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 1295. | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1296. | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1297. | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide |
| 1298. | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1299. | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide |
| 1300. | (1R,4R)-$N^1$,$N^1$-diethyl-$N^4$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 1301. | (1S,4S)-$N^1$,$N^1$-diethyl-$N^4$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |

TABLE 1-continued

Alkynyl indole compounds of the disclosure.

| Mol # | IUPAC name |
|---|---|
| 1302. | 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1303. | 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1304. | 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1305. | 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1306. | 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1307. | 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1308. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 1309. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 1310. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 1311. | 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 1312. | 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile |
| 1313. | 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 1314. | 1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 1315. | 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 1316. | 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine |
| 1317. | 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine |
| 1318. | 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 1319. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1320. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1321. | N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 1322. | N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide |
| 1323. | 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile |
| 1324. | 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile |
| 1325. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1326. | 2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine |
| 1327. | 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine |
| 1328. | 3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide |
| 1329. | 3-methoxy-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzenesulfonamide |
| 1330. | 3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide |
| 1331. | 3-methoxy-N-methyl-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzamide |
| 1332. | 2-{3-[(4-methanesulfonyl-2-methoxyphenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine |
| 1333. | N-((1S,4S)-4-(2-azaspiro[3.3]heptan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1334. | 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide |
| 1335. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide |

TABLE 1-continued

Alkynyl indole compounds of the disclosure.

| Mol # | IUPAC name |
|---|---|
| 1336. | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide |
| 1337. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide |
| 1338. | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine |
| 1339. | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide |
| 1340. | 2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1341. | 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1342. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1343. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1344. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 1345. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 1346. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 1347. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 1348. | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 1349. | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 1350. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1351. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1352. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 1353. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 1354. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1355. | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1356. | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide |
| 1357. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1358. | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1359. | 2-(3-{[4-methanesulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 1360. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 1361. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 1362. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 1363. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 1364. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |

TABLE 1-continued

Alkynyl indole compounds of the disclosure.

Mol #   IUPAC name

1365. N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide 1366. 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate 1367. 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1368. 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1369. 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine 1370. 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine 1371. 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine 1372. 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine 1373. 2-{3-[(2-ethoxy-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine 1374. 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1375. 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1376. N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1377. N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1378. 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1379. 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1380. 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1381. 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1382. 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine 1383. 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine 1384. 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine 1385. N-((1R,4R)-4-(2-oxa-6-azaspiro[3.3]heptan-6-yl)cyclohexyl)-2-(3-(2-amino-4-(methylsulfonyl)phenoxy)prop-1-yn-1-yl)-1-(2,2,2-trifluoroethyl)-1H-indol-4-amine 1386. 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1387. 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile 1388. 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile 1389. 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile 1390. 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile 1391. 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide 1392. 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide TABLE 1-continued Alkynyl indole compounds of the disclosure.

| Mol # | IUPAC name |
|---|---|
| 1393. | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1394. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide |
| 1395. | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1396. | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1397. | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1398. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide |
| 1399. | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1400. | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1401. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 1402. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 1403. | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 1404. | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 1405. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 1406. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 1407. | N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1408. | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1409. | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 1410. | N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 1411. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1412. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide |
| 1413. | 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1414. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide |
| 1415. | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1416. | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine |
| 1417. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 1418. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 1419. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid |
| 1420. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid |
| 1421. | 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |

TABLE 1-continued

Alkynyl indole compounds of the disclosure.

| Mol # | IUPAC name |
|---|---|
| 1422. | N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine |
| 1423. | 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1424. | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine |
| 1425. | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1426. | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine |
| 1427. | 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1428. | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine |
| 1429. | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1430. | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1431. | 2-{3-[(4-methanesulfonyl-2-methoxyphenyl)amino]prop-1-yn-1-yl}-N-[(1S,4S)-4-{7-oxa-2-azaspiro[3.5]nonan-2-yl}cyclohexyl]-1-(2,2,2-trifluoroethyl)-1H-indol-4-amine |
| 1432. | 2-{3-[(4-methanesulfonyl-2-methoxyphenyl)amino]prop-1-yn-1-yl}-N-[(1R,4R)-4-{7-oxa-2-azaspiro[3.5]nonan-2-yl}cyclohexyl]-1-(2,2,2-trifluoroethyl)-1H-indol-4-amine |
| 1433. | 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1434. | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1435. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1436. | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1437. | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1438. | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1439. | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile |
| 1440. | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1441. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1442. | 2-(5-methanesulfonyl-2-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1443. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1444. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1445. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1446. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1447. | methyl 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate |
| 1448. | methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate |
| 1449. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid |

TABLE 1-continued

Alkynyl indole compounds of the disclosure.

| Mol # | IUPAC name |
|---|---|
| 1450. | 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid |
| 1451. | 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine |
| 1452. | 2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine |
| 1453. | 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine |
| 1454. | 3-(fluoromethoxy)-4-{[3-(4-{[(1R,4R)-4-{7-oxa-2-azaspiro[3.5]nonan-2-yl]cyclohexyl]amino}-1-(2,2,2-trifluoroethyl)-1H-indol-2-yl)prop-2-yn-1-yl]amino}benzene-1-sulfonamide |
| 1455. | 3-(fluoromethoxy)-4-{[3-(4-{[(1S,4S)-4-{7-oxa-2-azaspiro[3.5]nonan-2-yl]cyclohexyl]amino}-1-(2,2,2-trifluoroethyl)-1H-indol-2-yl)prop-2-yn-1-yl]amino}benzene-1-sulfonamide |
| 1456. | 3-methoxy-N-methyl-4-{[3-(4-{[(1R,4R)-4-{6-oxa-2-azaspiro[3.5]nonan-2-yl]cyclohexyl]amino}-1-(2,2,2-trifluoroethyl)-1H-indol-2-yl)prop-2-yn-1-yl]amino}benzamide |
| 1457. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide |
| 1458. | 3-methoxy-4-{[3-(4-{[(1R,4R)-4-{6-oxa-2-azaspiro[3.5]nonan-2-yl]cyclohexyl]amino}-1-(2,2,2-trifluoroethyl)-1H-indol-2-yl)prop-2-yn-1-yl]amino}benzene-1-sulfonamide |
| 1459. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzenesulfonamide |
| 1460. | 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine |
| 1461. | N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1462. | N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1463. | N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1464. | 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one |
| 1465. | 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1466. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1467. | N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1468. | N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1469. | 3-methoxy-4-{[3-(4-{[(1R,4R)-4-{7-oxa-2-azaspiro[3.5]nonan-2-yl]cyclohexyl]amino}-1-(2,2,2-trifluoroethyl)-1H-indol-2-yl)prop-2-yn-1-yl]amino}benzamide |
| 1470. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1471. | 3-methoxy-4-{[3-(4-{[(1R,4R)-4-{6-oxa-2-azaspiro[3.5]nonan-2-yl]cyclohexyl]amino}-1-(2,2,2-trifluoroethyl)-1H-indol-2-yl)prop-2-yn-1-yl]amino}benzamide |
| 1472. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1473. | 2-fluoro-5-methoxy-N-methyl-4-{[3-(4-{[(1R,4R)-4-{7-oxa-2-azaspiro[3.5]nonan-2-yl]cyclohexyl]amino}-1-(2,2,2-trifluoroethyl)-1H-indol-2-yl)prop-2-yn-1-yl]amino}benzamide |
| 1474. | 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine |
| 1475. | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine |
| 1476. | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1477. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1478. | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine |
| 1479. | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine |
| 1480. | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1481. | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1482. | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1483. | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1484. | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine |
| 1485. | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine |
| 1486. | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine |
| 1487. | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine |
| 1488. | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine |
| 1489. | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine |
| 1490. | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide |
| 1491. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide |
| 1492. | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1493. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide |
| 1494. | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide |
| 1495. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide |
| 1496. | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1497. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide |
| 1498. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1499. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1500. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^6$-thiomorpholine-1,1-dione |
| 1501. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide |
| 1502. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1503. | 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1504. | 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1505. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1506. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1-oxide |
| 1507. | 3-methoxy-N-methyl-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzamide |
| 1508. | 3-methoxy-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1509. | 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide |
| 1510. | 3-methoxy-4-{[3-(4-{[(1R,4R)-4-(1,1-dioxo-1$\lambda^6$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1511. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide |
| 1512. | 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine |
| 1513. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1514. | 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1515. | 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1516. | 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1517. | 3-(cyanomethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |

TABLE 1-continued

Alkynyl indole compounds of the disclosure.

| Mol # | IUPAC name |
|---|---|
| 1518. | 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1519. | 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1520. | 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1521. | 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine |
| 1522. | N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1523. | 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1524. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide |
| 1525. | 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1526. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1527. | 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1528. | 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1529. | 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine |
| 1530. | 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine |
| 1531. | N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1532. | N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1533. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1534. | N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1535. | N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1536. | 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1537. | 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1538. | 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1539. | 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1540. | 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1541. | 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1542. | 2-{3-[(2-ethoxy-4-methanesulfonylphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1543. | 2-{3-[(2-ethoxy-4-methanesulfonylphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1544. | N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1545. | 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile |
| 1546. | 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile |

TABLE 1-continued

Alkynyl indole compounds of the disclosure.

Mol # IUPAC name 1547. 3-methoxy-N-methyl-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzamide
1548. 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine
1549. 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide
1550. 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide
1551. 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide
1552. 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine
1553. N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine
1554. 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide
1555. 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide
1556. 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide
1557. 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzenesulfonamide
1558. 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide
1559. 3-methoxy-N-methyl-4-((3-(4-(((1S,4S)-4-(pyrrolidin-1-yl)cyclohexyl]amino}-1-(2,2,2-trifluoroethyl)-1H-indol-2-yl)prop-2-yn-1-yl)amino)benzamide
1560. 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide
1561. 3-methoxy-4-((3-(4-(((1S,4S)-4-(pyrrolidin-1-yl)cyclohexyl]amino}-1-(2,2,2-trifluoroethyl)-1H-indol-2-yl)prop-2-yn-1-yl)amino)benzenesulfonamide
1562. 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine
1563. 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine
1564. 2-{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine
1565. 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide
1566. 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide
1567. 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)-N-methylbenzamide
1568. 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide
1569. 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzenesulfonamide
1570. 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine
1571. 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine
1572. 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide
1573. 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide
1574. 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine
1575. 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine
1576. 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide TABLE 1-continued Alkynyl indole compounds of the disclosure.

| Mol # | IUPAC name |
|---|---|
| 1577. | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide |
| 1578. | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide |
| 1579. | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide |
| 1580. | 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine |
| 1581. | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine |
| 1582. | 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide |
| 1583. | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide |
| 1584. | 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide |
| 1585. | 3-methoxy-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzenesulfonamide |
| 1586. | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one |
| 1587. | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile |
| 1588. | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1589. | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1590. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1591. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1592. | 1-{3-[(2-{3-[(4-methanesulfonyl-2-methoxyphenyl)amino]prop-1-yn-1-yl}-1-(2,2,2-trifluoroethyl)-1H-indol-4-yl)amino]pyrrolidin-1-yl}-3-methoxypropan-2-ol |
| 1593. | N-[3-(4-{[1-(2-hydroxy-3-methoxypropyl)pyrrolidin-3-yl]amino}-1-(2,2,2-trifluoroethyl)-1H-indol-2-yl)prop-2-yn-1-yl]benzamide |
| 1594. | 1-{3-[(2-{3-[(4-methanesulfonylphenyl)amino]prop-1-yn-1-yl}-1-(2,2,2-trifluoroethyl)-1H-indol-4-yl)amino]pyrrolidin-1-yl}-3-methoxypropan-2-ol |
| 1595. | 2-{3-[(4-methanesulfonyl-2-methoxyphenyl)amino]prop-1-yn-1-yl}-N-[1-(oxan-4-yl)pyrrolidin-3-yl]-1-(2,2,2-trifluoroethyl)-1H-indol-4-amine |
| 1596. | 2-(3-{[2-methoxy-4-(morpholine-4-sulfonyl)phenyl]amino}prop-1-yn-1-yl)-N-(piperidin-4-yl)-1-(2,2,2-trifluoroethyl)-1H-indol-4-amine |
| 1597. | 3-methoxy-N,N-dimethyl-4-[(3-{4-[(piperidin-4-yl)amino]-1-(2,2,2-trifluoroethyl)-1H-indol-2-yl}prop-2-yn-1-yl)amino]benzene-1-sulfonamide |
| 1598. | 2-{5-methanesulfonyl-2-[(3-{4-[(piperidin-4-yl)amino]-1-(2,2,2-trifluoroethyl)-1H-indol-2-yl}prop-2-yn-1-yl)amino]phenoxy}acetonitrile |
| 1599. | 3-methoxy-4-((3-(4-(piperidin-4-ylamino)-1-(2,2,2-trifluoroethyl)-1H-indol-2-yl)prop-2-yn-1-yl)amino)benzamide |
| 1600. | 2-{3-[(4-methanesulfonyl-2-methoxyphenyl)amino]prop-1-yn-1-yl}-N-[(3R)-piperidin-3-yl]-1-(2,2,2-trifluoroethyl)-1H-indol-4-amine |
| 1601. | 3-methoxy-4-{[3-(4-{[(2S,4S)-2-methylpiperidin-4-yl]amino}-1-(2,2,2-trifluoroethyl)-1H-indol-2-yl)prop-2-yn-1-yl]amino}benzene-1-sulfonamide |
| 1602. | 3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide |
| 1603. | 2-(3-{[4-methanesulfonyl-2-(trifluoromethoxy)phenyl]amino}prop-1-yn-1-yl)-N-(1-methylpiperidin-4-yl)-1-(2,2,2-trifluoroethyl)-1H-indol-4-amine |
| 1604. | N-(1-methylpiperidin-4-yl)-2-(3-((4-(methylsulfonyl)-2-(2,2,2-trifluoroethoxy)phenyl)amino)prop-1-yn-1-yl)-1-(2,2,2-trifluoroethyl)-1H-indol-4-amine |
| 1605. | 2-{4-methoxy-5-[(3-{4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 1606. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(1,2-oxazol-3-yl)benzene-1-sulfonamide |
| 1607. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzene-1-sulfonamide |
| 1608. | 3-methoxy-N-(5-methyl-1,2-oxazol-3-yl)-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1609. | N-(2-hydroxyethyl)-3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1610. | 3-methoxy-N,N-dimethyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |

TABLE 1-continued

Alkynyl indole compounds of the disclosure.

Mol # IUPAC name 1611. 4-[(3-{6-fluoro-4-[(1-methylpiperidin-4-yl)amino]-1-(2,2,2-trifluoroethyl)-1H-indol-2-yl}prop-2-yn-1-yl)amino]-3-methoxybenzene-1-sulfonamide
1612. 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine
1613. 2-(3-((4-methoxy-6-(methylsulfonyl)pyridin-3-yl)amino)prop-1-yn-1-yl)-N-(1-methylpiperidin-4-yl)-1-(2,2,2-trifluoroethyl)-1H-indol-4-amine
1614. 3-methoxy-N-(2-methoxyethyl)-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide
1615. 2-{3-[(4-methanesulfonyl-2-methoxyphenyl)(methyl)amino]prop-1-yn-1-yl}-N-(1-methylpiperidin-4-yl)-1-(2,2,2-trifluoroethyl)-1H-indol-4-amine
1616. 1-(4-{3-methoxy-4-[(3-{4-[(1-methylpiperidin-4-yl)amino]-1-(2,2,2-trifluoroethyl)-1H-indol-2-yl}prop-2-yn-1-yl)amino]benzenesulfonyl}piperazin-1-yl)ethan-1-one
1617. 2-(3-{[2-methoxy-4-(morpholine-4-sulfonyl)phenyl]amino}prop-1-yn-1-yl)-N-(1-methylpiperidin-4-yl)-1-(2,2,2-trifluoroethyl)-1H-indol-4-amine
1618. 3-methoxy-4-((3-(4-((1-methylpiperidin-4-yl)amino)-1-(2,2,2-trifluoroethyl)-1H-indol-2-yl)prop-2-yn-1-yl)amino)benzoic acid
1619. 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide
1620. N,N-bis(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide
1621. 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide
1622. 2-[3-({2-methoxy-4-[(4-methylpiperazin-1-yl)sulfonyl]phenyl}amino)prop-1-yn-1-yl]-N-(1-methylpiperidin-4-yl)-1-(2,2,2-trifluoroethyl)-1H-indol-4-amine
1623. 5-methanesulfonyl-2-[(3-{4-[(1-methylpiperidin-4-yl)amino]-1-(2,2,2-trifluoroethyl)-1H-indol-2-yl}prop-2-yn-1-yl)amino]phenol
1624. 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine
1625. 2-{3-[2-(dimethylamino)-4-methanesulfonylphenoxy]prop-1-yn-1-yl}-N-(1-methylpiperidin-4-yl)-1-(2,2,2-trifluoroethyl)-1H-indol-4-amine
1626. 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetonitrile
1627. 2-(3-{[2-(fluoromethoxy)-4-methanesulfonylphenyl]amino}prop-1-yn-1-yl)-N-(1-methylpiperidin-4-yl)-1-(2,2,2-trifluoroethyl)-1H-indol-4-amine
1628. 2-(3-{[2-methoxy-4-(morpholine-4-carbonyl)phenyl]amino}prop-1-yn-1-yl)-N-(1-methylpiperidin-4-yl)-1-(2,2,2-trifluoroethyl)-1H-indol-4-amine
1629. 1-{3-methoxy-4-[(3-{4-[(1-methylpiperidin-4-yl)amino]-1-(2,2,2-trifluoroethyl)-1H-indol-2-yl}prop-2-yn-1-yl)amino]benzoyl}piperidin-4-ol
1630. 3-(3-(4-((1-methylpiperidin-4-yl)amino)-1-(2,2,2-trifluoroethyl)-1H-indol-2-yl)prop-2-yn-1-yl)-6-(methylsulfonyl)benzo[d]oxazol-2(3H)-one
1631. 2-(3-{[2-methoxy-4-(5-methoxypyridin-3-yl)phenyl]amino}prop-1-yn-1-yl)-N-(1-methylpiperidin-4-yl)-1-(2,2,2-trifluoroethyl)-1H-indol-4-amine
1632. 2-{3-[(5-methanesulfonyl-2-methoxyphenyl)amino]prop-1-yn-1-yl}-N-(1-methylpiperidin-4-yl)-1-(2,2,2-trifluoroethyl)-1H-indol-4-amine
1633. N-(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzamide
1634. 3-methoxy-N-(2-methoxyethyl)-4-[(3-{4-[(1-methylpiperidin-4-yl)amino]-1-(2,2,2-trifluoroethyl)-1H-indol-2-yl}prop-2-yn-1-yl)amino]benzamide
1635. 3-methoxy-N-(1-methylpiperidin-4-yl)-4-[(3-{4-[(1-methylpiperidin-4-yl)amino]-1-(2,2,2-trifluoroethyl)-1H-indol-2-yl}prop-2-yn-1-yl)amino]benzamide
1636. 2-[3-({4-[4-(dimethylamino)piperidine-1-carbonyl]-2-methoxyphenyl}amino)prop-1-yn-1-yl]-N-(1-methylpiperidin-4-yl)-1-(2,2,2-trifluoroethyl)-1H-indol-4-amine
1637. 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzamide
1638. 2-(3-{[2-methoxy-4-(4-methylpiperazine-1-carbonyl)phenyl]amino}prop-1-yn-1-yl)-N-(1-methylpiperidin-4-yl)-1-(2,2,2-trifluoroethyl)-1H-indol-4-amine
1639. 2-{3-[(2-methoxy-4-{2-oxa-6-azaspiro[3.3]heptane-6-carbonyl}phenyl)amino]prop-1-yn-1-yl}-N-(1-methylpiperidin-4-yl)-1-(2,2,2-trifluoroethyl)-1H-indol-4-amine
1640. 2-(3-{[2-methoxy-4-(pyridin-3-yl)phenyl]amino}prop-1-yn-1-yl)-N-(1-methylpiperidin-4-yl)-1-(2,2,2-trifluoroethyl)-1H-indol-4-amine
1641. 2-(3-{[2-methoxy-4-(pyridin-4-yl)phenyl]amino}prop-1-yn-1-yl)-N-(1-methylpiperidin-4-yl)-1-(2,2,2-trifluoroethyl)-1H-indol-4-amine
1642. N-(3-{4-[(1-methylpiperidin-4-yl)amino]-1-(2,2,2-trifluoroethyl)-1H-indol-2-yl}prop-2-yn-1-yl)pyridine-3-carboxamide
1643. 2-(3-{[2-methoxy-4-(1,3-oxazol-2-yl)phenyl]amino}prop-1-yn-1-yl)-N-(1-methylpiperidin-4-yl)-1-(2,2,2-trifluoroethyl)-1H-indol-4-amine
1644. 2-{3-[(3-methanesulfonylphenyl)amino]prop-1-yn-1-yl}-N-(1-methylpiperidin-4-yl)-1-(2,2,2-trifluoroethyl)-1H-indol-4-amine
1645. N-(1-methylpiperidin-4-yl)-2-[3-({4-[(morpholin-4-yl)methyl]phenyl}amino)prop-1-yn-1-yl]-1-(2,2,2-trifluoroethyl)-1H-indol-4-amine
1646. 2-(3-{[2-methoxy-4-(1,3-thiazol-2-yl)phenyl]amino}prop-1-yn-1-yl)-N-(1-methylpiperidin-4-yl)-1-(2,2,2-trifluoroethyl)-1H-indol-4-amine
1647. 2-[3-({2-methoxy-4-[1-(2-methoxyethyl)-1H-pyrazol-4-yl]phenyl}amino)prop-1-yn-1-yl]-N-(1-methylpiperidin-4-yl)-1-(2,2,2-trifluoroethyl)-1H-indol-4-amine
1648. 2-{3-[(2-methoxy-4-{7-oxa-2-azaspiro[3.5]nonane-2-carbonyl}phenyl)amino]prop-1-yn-1-yl}-N-(1-methylpiperidin-4-yl)-1-(2,2,2-trifluoroethyl)-1H-indol-4-amine TABLE 1-continued Alkynyl indole compounds of the disclosure.

| Mol # | IUPAC name |
|---|---|
| 1649. | 2-{3-[(4-chloro-2-methoxyphenyl)amino]prop-1-yn-1-yl}-N-(1-methylpiperidin-4-yl)-1-(2,2,2-trifluoroethyl)-1H-indol-4-amine |
| 1650. | 2-(3-(((3S,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine |
| 1651. | 2-fluoro-5-methoxy-4-[(3-{4-[(1-methylpiperidin-4-yl)amino]-1-(2,2,2-trifluoroethyl)-1H-indol-2-yl}prop-2-yn-1-yl)amino]benzamide |
| 1652. | 2-(3-{[2-methoxy-4-(trifluoromethyl)phenyl]amino}prop-1-yn-1-yl)-N-(1-methylpiperidin-4-yl)-1-(2,2,2-trifluoroethyl)-1H-indol-4-amine |
| 1653. | 2-fluoro-5-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide |
| 1654. | 2-{3-[(4-methanesulfonyl-2-methoxyphenyl)amino]prop-1-yn-1-yl}-N-(1-methylpiperidin-4-yl)-1-[(oxiran-2-yl)methyl]-1H-indol-4-amine |
| 1655. | 2-(3-((2-ethoxy-4-(methylsulfonyl)phenyl)amino)prop-1-yn-1-yl)-N-(1-methylpiperidin-4-yl)-1-(2,2,2-trifluoroethyl)-1H-indol-4-amine |
| 1656. | 2-{3-[(2-fluoro-4-methanesulfonyl-6-methoxyphenyl)amino]prop-1-yn-1-yl}-N-(1-methylpiperidin-4-yl)-1-(2,2,2-trifluoroethyl)-1H-indol-4-amine |
| 1657. | 2-{3-[(4-methanesulfonyl-2-methoxyphenyl)amino]prop-1-yn-1-yl}-3-methyl-N-(1-methylpiperidin-4-yl)-1-(2,2,2-trifluoroethyl)-1H-indol-4-amine |
| 1658. | 2-(3-(((3R,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine |
| 1659. | 2-{3-[(5-fluoro-4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1660. | 2-{3-[(5-methanesulfonylthiophen-2-yl)amino]prop-1-yn-1-yl}-N-(1-methylpiperidin-4-yl)-1-(2,2,2-trifluoroethyl)-1H-indol-4-amine |
| 1661. | N-methyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide |
| 1662. | N,N-dimethyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide |
| 1663. | 5-[(3-{4-[(1-methylpiperidin-4-yl)amino]-1-(2,2,2-trifluoroethyl)-1H-indol-2-yl}prop-2-yn-1-yl)amino]thiophene-2-carboxylic acid |
| 1664. | 2-(3-((4-methoxypyridin-3-yl)amino)prop-1-yn-1-yl)-N-(1-methylpiperidin-4-yl)-1-(2,2,2-trifluoroethyl)-1H-indol-4-amine |
| 1665. | 2-(2-((3-(4-((1-methylpiperidin-4-yl)amino)-1-(2,2,2-trifluoroethyl)-1H-indol-2-yl)prop-2-yn-1-yl)amino)-5-(methylsulfonyl)phenoxy)acetamide |
| 1666. | N-(2-hydroxyethyl)-3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide |
| 1667. | 4-((2-(3-((2-methoxy-4-(methylsulfonyl)phenyl)amino)prop-1-yn-1-yl)-1-(2,2,2-trifluoroethyl)-1H-indol-4-yl)amino)-1-methylpiperidin-2-one |
| 1668. | 2-{3-[(4-methanesulfonyl-2-methoxyphenyl)amino]prop-1-yn-1-yl}-N-[(3R,4S)-3-methoxy-1-methylpiperidin-4-yl]-1-(2,2,2-trifluoroethyl)-1H-indol-4-amine |
| 1669. | 2-{3-[(4-methanesulfonyl-2-methoxyphenyl)amino]prop-1-yn-1-yl}-N-[(3S,4R)-3-methoxy-1-methylpiperidin-4-yl]-1-(2,2,2-trifluoroethyl)-1H-indol-4-amine |
| 1670. | 2-{3-[(4-methanesulfonyl-2-methoxyphenyl)amino]prop-1-yn-1-yl}-N-[(3S,4R)-3-methoxy-1-methylpiperidin-4-yl]-N-methyl-1-(2,2,2-trifluoroethyl)-1H-indol-4-amine |
| 1671. | N-(1-ethylpiperidin-4-yl)-2-(3-{[2-(fluoromethoxy)-4-methanesulfonylphenyl]amino}prop-1-yn-1-yl)-1-(2,2,2-trifluoroethyl)-1H-indol-4-amine |
| 1672. | 4-[(3-{4-[(1-ethylpiperidin-4-yl)amino]-1-(2,2,2-trifluoroethyl)-1H-indol-2-yl}prop-2-yn-1-yl)amino]-3-methoxy-N-methylbenzamide |
| 1673. | 2-{2-[(3-{4-[(1-ethylpiperidin-4-yl)amino]-1-(2,2,2-trifluoroethyl)-1H-indol-2-yl}prop-2-yn-1-yl)amino]-5-methanesulfonylphenoxy}acetonitrile |
| 1674. | N-(1-ethylpiperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1675. | 4-[(3-{4-[(1-ethylpiperidin-4-yl)amino]-1-(2,2,2-trifluoroethyl)-1H-indol-2-yl}prop-2-yn-1-yl)amino]-3-methoxybenzene-1-sulfonamide |
| 1676. | 3-methoxy-N-methyl-4-{[3-(4-{[1-(propan-2-yl)piperidin-4-yl]amino}-1-(2,2,2-trifluoroethyl)-1H-indol-2-yl)prop-2-yn-1-yl]amino}benzamide |
| 1677. | 2-(5-methanesulfonyl-2-{[3-(4-{[1-(propan-2-yl)piperidin-4-yl]amino}-1-(2,2,2-trifluoroethyl)-1H-indol-2-yl)prop-2-yn-1-yl]amino}phenoxy)acetonitrile |
| 1678. | 2-(3-{[2-(fluoromethoxy)-4-methanesulfonylphenyl]amino}prop-1-yn-1-yl)-N-[1-(propan-2-yl)piperidin-4-yl]-1-(2,2,2-trifluoroethyl)-1H-indol-4-amine |
| 1679. | 2-{3-[(4-methanesulfonyl-2-methoxyphenyl)amino]prop-1-yn-1-yl}-N-[1-(propan-2-yl)piperidin-4-yl]-1-(2,2,2-trifluoroethyl)-1H-indol-4-amine |
| 1680. | 3-methoxy-4-{[3-(4-{[1-(propan-2-yl)piperidin-4-yl]amino}-1-(2,2,2-trifluoroethyl)-1H-indol-2-yl)prop-2-yn-1-yl]amino}benzene-1-sulfonamide |
| 1681. | 2-[2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethoxy]ethan-1-ol |
| 1682. | 4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1683. | 3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzene-1-sulfonamide |
| 1684. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(1,2-oxazol-3-yl)benzene-1-sulfonamide |
| 1685. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzenesulfonamide |
| 1686. | 4-({3-[4-({1-[(2S)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide |

TABLE 1-continued

Alkynyl indole compounds of the disclosure.

| Mol # | IUPAC name |
|---|---|
| 1687. | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1688. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(5-methyl-1,2-oxazol-3-yl)benzene-1-sulfonamide |
| 1689. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(oxan-4-yl)benzene-1-sulfonamide |
| 1690. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-N-(2-hydroxyethyl)-3-methoxy-N-methylbenzene-1-sulfonamide |
| 1691. | 2-(5-{[3-(4-{[1-(2,3-dihydroxypropyl)piperidin-4-yl]amino}-1-(2,2,2-trifluoroethyl)-1H-indol-2-yl)prop-2-yn-1-yl]amino}-4-methoxypyridin-2-yl)-2-methylpropanenitrile |
| 1692. | N-(2-hydroxyethyl)-3-methoxy-N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 1693. | 3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diol |
| 1694. | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 1695. | (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 1696. | 3-[4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)piperidin-1-yl]propane-1,2-diol |
| 1697. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoic acid |
| 1698. | methyl 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoate |
| 1699. | 3-methoxy-4-[(3-{4-[(1-{[(4R)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide |
| 1700. | (4R)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1701. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1702. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}EtOAc |
| 1703. | N-(1-{[(4R)-2,2-dimethyl-1,3-dioxolan-4-yl]methyl}piperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1704. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate |
| 1705. | 4-[(3-{4-[(1-{[(4R)-2,2-dimethyl-1,3-dioxolan-4-yl]methyl}piperidin-4-yl)amino]-1-(2,2,2-trifluoroethyl)-1H-indol-2-yl}prop-2-yn-1-yl)amino]-3-methoxybenzene-1-sulfonamide |
| 1706. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1707. | 1-(4-((2-(3-((4-(ethylsulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol |
| 1708. | 1-ethoxy-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol |
| 1709. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(2-methoxyethyl)-N-methylbenzene-1-sulfonamide |
| 1710. | 1-(acetyloxy)-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1711. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1712. | 3-methoxy-4-{[3-(4-{[1-(2-methoxyacetyl)piperidin-4-yl]amino}-1-(2,2,2-trifluoroethyl)-1H-indol-2-yl)prop-2-yn-1-yl]amino}benzene-1-sulfonamide |
| 1713. | 1-(4-(N-(2-(3-((2-methoxy-4-(methylsulfonyl)phenyl)amino)prop-1-yn-1-yl)-1-(2,2,2-trifluoroethyl)-1H-indol-4-yl)acetamido)piperidin-1-yl)propan-2-yl acetate |
| 1714. | 1-[4-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzenesulfonyl)piperazin-1-yl]ethan-1-one |
| 1715. | (4S)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1716. | 1-(acetyloxy)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate |
| 1717. | N-[1-(2,3-dimethoxypropyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1718. | 4-{[3-(4-{[1-(2,3-dimethoxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1719. | 3-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)propane-1,2-diol |
| 1720. | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzamide |
| 1721. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl 2-methylpropanoate |

TABLE 1-continued

Alkynyl indole compounds of the disclosure.

| Mol # | IUPAC name |
|---|---|
| 1722. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl propanoate |
| 1723. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(propanoyloxy)propan-2-yl propanoate |
| 1724. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-(propanoyloxy)propan-2-yl propanoate |
| 1725. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate |
| 1726. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate |
| 1727. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate |
| 1728. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate |
| 1729. | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl 2-methylpropanoate |
| 1730. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl acetate |
| 1731. | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl propanoate |
| 1732. | N,N-bis(2-hydroxyethyl)-4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1733. | 4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxy-N-methylbenzamide |
| 1734. | (S)-4-((3-(4-((1-(2-hydroxy-3-methoxypropyl)piperidin-4-yl)amino)-1-(2,2,2-trifluoroethyl)-1H-indol-2-yl)prop-2-yn-1-yl)amino)-3-methoxy-N-methylbenzamide |
| 1735. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate |
| 1736. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1737. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl 2-methylpropanoate |
| 1738. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzamide |
| 1739. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate |
| 1740. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |
| 1741. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate |
| 1742. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate |
| 1743. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)acetamide |
| 1744. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)propanamide |
| 1745. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl propanoate |
| 1746. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzene-1-sulfonamide |
| 1747. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate |
| 1748. | (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1749. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1750. | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1751. | 3-methoxy-4-((3-(4-((1-(2-methoxyethyl)piperidin-4-yl)amino)-1-(2,2,2-trifluoroethyl)-1H-indol-2-yl)prop-2-yn-1-yl)amino)benzenesulfonamide |
| 1752. | 2-(3-((2-methoxy-4-(methylsulfonyl)phenyl)amino)prop-1-yn-1-yl)-N-(1-(2-methoxyethyl)piperidin-4-yl)-1-(2,2,2-trifluoroethyl)-1H-indol-4-amine |
| 1753. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzamide |
| 1754. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 1755. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}EtOAc |

TABLE 1-continued

Alkynyl indole compounds of the disclosure.

Mol # | IUPAC name 1756. 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate
1757. 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide
1758. 2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenol
1759. 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide
1760. 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide
1761. N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)-N-methylpropanamide
1762. 1-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol
1763. 1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)tetradecan-1-one
1764. 1-methoxy-3-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)propan-2-yl propanoate
1765. 1-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate
1766. (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol
1767. (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol
1768. 1-{4-[(2-{3-[(2-ethoxy-4-methanesulfonylphenyl)amino]prop-1-yn-1-yl}-1-(2,2,2-trifluoroethyl)-1H-indol-4-yl)amino]piperidin-1-yl}-3-methoxypropan-2-ol
1769. 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide
1770. 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-(propan-2-yl)benzamide
1771. 3-hydroxy-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}benzene-1-sulfonamide
1772. (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate
1773. N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(N-propionylsulfamoyl)phenyl)propionamide
1774. 1-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)-3-methoxypropan-2-ol
1775. (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate
1776. N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)acetamide
1777. N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)propionamide
1778. N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)isobutyramide
1779. 2-(2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenoxy)acetonitrile
1780. 1-{4-[(2-{3-[(4-methanesulfonyl-2-methoxyphenyl)amino]prop-1-yn-1-yl}-5-methoxy-1-(2,2,2-trifluoroethyl)-1H-indol-4-yl)amino]piperidin-1-yl}-3-methoxypropan-2-ol
1781. 1-(4-{[2-(3-{[2-(2-hydroxyethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol
1782. 1-(4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}piperidin-1-yl)-3-methoxypropan-2-ol
1783. 1-[4-({2-[3-(2-amino-4-methanesulfonylphenoxy)prop-1-yn-1-yl]-1-(2,2,2-trifluoroethyl)-1H-indol-4-yl}amino)piperidin-1-yl]-3-methoxypropan-2-ol
1784. 4-({3-[4-({1-[(2R)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide
1785. 4-({3-[4-({1-[(2S)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide
1786. 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide
1787. 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide
1788. 1-{4-[(2-{3-[4-methanesulfonyl-2-(methylamino)phenoxy]prop-1-yn-1-yl}-1-(2,2,2-trifluoroethyl)-1H-indol-4-yl)amino]piperidin-1-yl}-3-methoxypropan-2-ol
1789. 3-(2-fluoroethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide
1790. 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-(2-methoxyethoxy)-N-methylbenzamide TABLE 1-continued Alkynyl indole compounds of the disclosure.

| Mol # | IUPAC name |
|---|---|
| 1791. | 3-(cyanomethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1792. | N-ethyl-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide |
| 1793. | 1-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate |
| 1794. | 1-methoxy-3-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)propan-2-yl propanoate |
| 1795. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-methylbenzamide |
| 1796. | 3-(2-cyanoethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1797. | 1-ethoxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-ol |
| 1798. | 2-(2-{[3-(4-{[1-(2-hydroxypropyl)piperidin-4-yl]amino}-1-(2,2,2-trifluoroethyl)-1H-indol-2-yl)prop-2-yn-1-yl]amino}-5-methanesulfonylphenoxy)acetonitrile |
| 1799. | 1-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1800. | 3-(fluoromethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1801. | 1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1802. | 2-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxyphenyl)-2-methylpropanenitrile |
| 1803. | (2S)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1804. | (2R)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1805. | 1-(4-{[2-(3-{[2-(difluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1806. | 3-(2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propoxy)propane-1,2-diol |
| 1807. | 1-{4-[(2-{3-[(5-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1808. | 3-(3-(4-((1-(2-hydroxy-3-methoxypropyl)piperidin-4-yl)amino)-1-(2,2,2-trifluoroethyl)-1H-indol-2-yl)prop-2-yn-1-yl)-6-(methylsulfonyl)benzo[d]oxazol-2(3H)-one |
| 1809. | 1-{4-[(2-{3-[(4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1810. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(2,2,2-trifluoroethoxy)propan-2-ol |
| 1811. | 4-hydroxy-9-[(2-{3-[(4-methanesulfonyl-2-methoxyphenyl)amino]prop-1-yn-1-yl}-1-(2,2,2-trifluoroethyl)-1H-indol-4-yl)amino]-2-oxa-6$\lambda^5$-azaspiro[5.5]undecan-6-ylium |
| 1812. | 2-{3-[(4-methanesulfonyl-2-methoxyphenyl)amino]prop-1-yn-1-yl}-N-[1-(3-methoxypropyl)piperidin-4-yl]-1-(2,2,2-trifluoroethyl)-1H-indol-4-amine |
| 1813. | 1-{4-[(2-{3-[(4-methanesulfonyl-2-methoxyphenyl)amino]prop-1-yn-1-yl}-3-methyl-1-(2,2,2-trifluoroethyl)-1H-indol-4-yl)amino]piperidin-1-yl}-3-methoxypropan-2-ol |
| 1814. | 1-{4-[(2-{3-[(5-fluoro-4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1815. | 2-{3-[(4-methanesulfonyl-2-methoxyphenyl)amino]prop-1-yn-1-yl}-N-[1-(oxetan-3-yl)piperidin-4-yl]-1-(2,2,2-trifluoroethyl)-1H-indol-4-amine |
| 1816. | 2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1817. | (R)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1818. | (S)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1819. | 2-(3-((2-methoxy-4-(methylsulfonyl)phenyl)amino)prop-1-yn-1-yl)-N-(1-((tetrahydrofuran-2-yl)methyl)piperidin-4-yl)-1-(2,2,2-trifluoroethyl)-1H-indol-4-amine |
| 1820. | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxybenzamide |
| 1821. | 1-methoxy-3-(4-((2-(3-(((3S,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol |
| 1822. | 1-(4-{[2-(3-{[4-(cyclopropanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1823. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propanenitrile |
| 1824. | 4-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)butanenitrile |
| 1825. | 2-{3-[(4-methanesulfonyl-2-methoxyphenyl)amino]prop-1-yn-1-yl}-N-{1-[(oxolan-2-yl)methyl]piperidin-4-yl}-1-(2,2,2-trifluoroethyl)-1H-indol-4-amine |
| 1826. | 1-methoxy-3-(4-{[2-(3-{[2-methoxy-4-(trifluoromethyl)phenyl]amino}prop-1-yn-1-yl)-1-(2,2,2-trifluoroethyl)-1H-indol-4-yl]amino}piperidin-1-yl)propan-2-ol |
| 1827. | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxy-N-methylbenzamide |

TABLE 1-continued

Alkynyl indole compounds of the disclosure.

| Mol # | IUPAC name |
|---|---|
| 1828. | 1-(4-{[2-(3-{[4-(benzenesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1829. | 2-{3-[(4-methanesulfonyl-2-methoxyphenyl)amino]prop-1-yn-1-yl}-N-[1-(2-methoxy-2-methylpropyl)piperidin-4-yl]-1-(2,2,2-trifluoroethyl)-1H-indol-4-amine |
| 1830. | 2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-ol |
| 1831. | 1-methoxy-3-(4-{[2-(3-{[2-methoxy-4-(propane-2-sulfonyl)phenyl]amino}prop-1-yn-1-yl)-1-(2,2,2-trifluoroethyl)-1H-indol-4-yl]amino}piperidin-1-yl)propan-2-ol |
| 1832. | 1-{3-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1833. | 1-methoxy-3-(4-((2-(3-(((3R,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol |
| 1834. | 1-{4-[(2-{3-[(4-methanesulfonyl-2-methoxyphenyl)amino]prop-1-yn-1-yl}-1-propyl-1H-indol-4-yl)amino]piperidin-1-yl}-3-methoxypropan-2-ol |
| 1835. | 1-(4-{[1-(2-fluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1836. | 2-(4-{[1-(2-hydroxy-3-methoxypropyl)piperidin-4-yl]amino}-2-{3-[(4-methanesulfonyl-2-methoxyphenyl)amino]prop-1-yn-1-yl}-1H-indol-1-yl)acetonitrile |
| 1837. | 1-(4-{[1-(2-chloroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1838. | rac-1-[(3R,4S)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol |
| 1839. | rac-1-[(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol |
| 1840. | 1-{4-[(2-{3-[(4-methanesulfonyl-2-methylphenyl)amino]prop-1-yn-1-yl}-1-(2,2,2-trifluoroethyl)-1H-indol-4-yl)amino]piperidin-1-yl}-3-methoxypropan-2-ol |
| 1841. | 1-[4-({1-[(2,2-difluorocyclopropyl)methyl]-2-{3-[(4-methanesulfonyl-2-methoxyphenyl)amino]prop-1-yn-1-yl}-1H-indol-4-yl}amino)piperidin-1-yl]-3-methoxypropan-2-ol |
| 1842. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzoic acid |
| 1843. | 2-{3-[(4-methanesulfonyl-2-methoxyphenyl)amino]prop-1-yn-1-yl}-N-[1-(3-methanesulfonylpropyl)piperidin-4-yl]-1-(2,2,2-trifluoroethyl)-1H-indol-4-amine |
| 1844. | 4-{[3-(4-{[1-(3-methanesulfonylpropyl)piperidin-4-yl]amino}-1-(2,2,2-trifluoroethyl)-1H-indol-2-yl)prop-2-yn-1-yl]amino}-3-methoxybenzoic acid |
| 1845. | 1-(4-{[2-(3-{[4-methanesulfonyl-2-(trifluoromethyl)phenyl]amino}prop-1-yn-1-yl)-1-(2,2,2-trifluoroethyl)-1H-indol-4-yl]amino}piperidin-1-yl)-3-methoxypropan-2-ol |
| 1846. | 1-(4-{[1-(2,2-difluoroethyl)-2-{3-[(4-methanesulfonyl-2-methoxyphenyl)ino]prop-1-yn-1-yl}-1H-indol-4-yl]amino}piperidin-1-yl)-3-methoxypropan-2-ol |
| 1847. | 1-(4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}piperidin-1-yl)-3-methoxypropan-2-ol |
| 1848. | 1-{4-[(2-{3-[(4-methanesulfonyl-2-methoxyphenyl)amino]prop-1-yn-1-yl}-1-(3,3,3-trifluoropropyl)-1H-indol-4-yl)amino]piperidin-1-yl}-3-methoxypropan-2-ol |
| 1849. | 1-(4-{[1-(2,2-difluoropropyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1850. | 1-{4-[(2-{3-[(2-chloro-4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1851. | 1-{4-[(2-{3-[(2-fluoro-4-methanesulfonyl-6-methoxyphenyl)amino]prop-1-yn-1-yl}-1-(2,2,2-trifluoroethyl)-1H-indol-4-yl)amino]piperidin-1-yl}-3-methoxypropan-2-ol |
| 1852. | 1-(4-((2-(3-((4-((6-oxa-3-azabicyclo[3.1.1]heptan-3-yl)sulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol |
| 1853. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate |
| 1854. | 1-{4-[(2-{3-[(4-chloro-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1855. | 2-(2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethoxy)ethan-1-ol |
| 1856. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-N-(2-hydroxyethyl)-3-methoxybenzenesulfonamide |
| 1857. | 2-{3-[(4-methanesulfonyl-2-methoxyphenyl)amino]prop-1-yn-1-yl}-N-[1-(4-methyl-1,3-thiazol-2-yl)piperidin-4-yl]-1-(2,2,2-trifluoroethyl)-1H-indol-4-amine |
| 1858. | N-(1-cyclopropylpiperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1859. | 4-[(3-{4-[(1-cyclopropylpiperidin-4-yl)amino]-1-(2,2,2-trifluoroethyl)-1H-indol-2-yl}prop-2-yn-1-yl)amino]-3-methoxybenzoic acid |
| 1860. | 2-{3-[(4-methanesulfonyl-2-methoxyphenyl)amino]prop-1-yn-1-yl}-N-{1-[(3R)-oxolan-3-yl]piperidin-4-yl}-1-(2,2,2-trifluoroethyl)-1H-indol-4-amine |
| 1861. | 2-{3-[(4-methanesulfonyl-2-methoxyphenyl)amino]prop-1-yn-1-yl}-N-{1-[(3S)-oxolan-3-yl]piperidin-4-yl}-1-(2,2,2-trifluoroethyl)-1H-indol-4-amine |
| 1862. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzoic acid |
| 1863. | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzamide |

TABLE 1-continued

Alkynyl indole compounds of the disclosure.

| Mol # | IUPAC name |
|---|---|
| 1864. | N-(2-hydroxyethyl)-3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide |
| 1865. | 3-methoxy-4-((3-(4-(((1'-methyl-[1,4'-bipiperidin]-4-yl)amino)-1-(2,2,2-trifluoroethyl)-1H-indol-2-yl)prop-2-yn-1-yl)amino)benzamide |
| 1866. | 3-methoxy-4-((3-(4-(((1-(2-(4-methylpiperazin-1-yl)-2-oxoethyl)piperidin-4-yl)amino)-1-(2,2,2-trifluoroethyl)-1H-indol-2-yl)prop-2-yn-1-yl)amino)benzamide |
| 1867. | 2-{2-[(3-{4-[(1-acetylpiperidin-4-yl)amino]-1-(2,2,2-trifluoroethyl)-1H-indol-2-yl}prop-2-yn-1-yl)amino]-5-methanesulfonylphenoxy}acetonitrile |
| 1868. | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1869. | 2-hydroxy-1-{4-[(2-{3-[(2-hydroxy-4-methanesulfonylphenyl)amino]prop-1-yn-1-yl}-1-(2,2,2-trifluoroethyl)-1H-indol-4-yl)amino]piperidin-1-yl}ethan-1-one |
| 1870. | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 1871. | N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1872. | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1873. | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1874. | N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1875. | N-((3S,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1876. | 1-(4-((2-(3-((2-methoxy-4-(methylsulfonyl)phenyl)amino)prop-1-yn-1-yl)-1-(2,2,2-trifluoroethyl)-1H-indol-4-yl)amino)-2-rnethylpiperidin-1-yl)ethan-1-one |
| 1877. | 1-{4-[(2-{3-[(4-methanesulfonyl-2-methoxyphenyl)amino]prop-1-yn-1-yl}-1-(2,2,2-trifluoroethyl)-1H-indol-4-yl)amino]-2-methylpiperidin-1-yl}ethan-1-one |
| 1878. | 4-{[3-(4-{[(2S,4S)-1-acetyl-2-methylpiperidin-4-yl]amino}-1-(2,2,2-trifluoroethyl)-1H-indol-2-yl)prop-2-yn-1-yl]amino}-3-methoxybenzene-1-sulfonamide |
| 1879. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxyethan-1-one |
| 1880. | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one |
| 1881. | 2-methoxy-1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-one |
| 1882. | 3-methoxy-4-((3-(4-((1-(2-methoxyacetyl)piperidin-4-yl)amino)-1-(2,2,2-trifluoroethyl)-1H-indol-2-yl)prop-2-yn-1-yl)amino)benzenesulfonamide |
| 1883. | 4-{[3-(4-{[1-(2-hydroxypropanoyl)piperidin-4-yl]amino}-1-(2,2,2-trifluoroethyl)-1H-indol-2-yl)prop-2-yn-1-yl]amino}-3-methoxybenzene-1-sulfonamide |
| 1884. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-oxopropanenitrile |
| 1885. | 4-{[3-(4-{[1-(2-cyanoacetyl)piperidin-4-yl]amino}-1-(2,2,2-trifluoroethyl)-1H-indol-2-yl)prop-2-yn-1-yl]amino}-3-methoxybenzene-1-sulfonamide |
| 1886. | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxybenzene-1-sulfonamide |
| 1887. | 4-[(3-{4-[(1-acetylpiperidin-4-yl)amino]-1-(2,2,2-trifluoroethyl)-1H-indol-2-yl}prop-2-yn-1-yl)amino]-3-methoxybenzene-1-sulfonamide |
| 1888. | 2-(dimethylamino)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 1889. | 4-((3-(4-((1-(dimethylglycyl)piperidin-4-yl)amino)-1-(2,2,2-trifluoroethyl)-1H-indol-2-yl)prop-2-yn-1-yl)amino)-3-methoxybenzenesulfonamide |
| 1890. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methylpropan-1-one |
| 1891. | 3-methoxy-4-{[3-(4-{[1-(2-methylpropanoyl)piperidin-4-yl]amino}-1-(2,2,2-trifluoroethyl)-1H-indol-2-yl)prop-2-yn-1-yl]amino}benzene-1-sulfonamide |
| 1892. | 4-((2-(3-((2-methoxy-4-(methylsulfonyl)phenyl)amino)prop-1-yn-1-yl)-1-(2,2,2-trifluoroethyl)-1H-indol-4-yl)amino)-N,N-dimethylpiperidine-1-carboxamide |
| 1893. | 4-[(3-{4-[(1-acetylpiperidin-4-yl)amino]-1-(2,2,2-trifluoroethyl)-1H-indol-2-yl}prop-2-yn-1-yl)amino]-3-methoxy-N,N-dimethylbenzene-1-sulfonamide |
| 1894. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one |
| 1895. | 3-methoxy-4-[(3-{4-[(1-propanoylpiperidin-4-yl)amino]-1-(2,2,2-trifluoroethyl)-1H-indol-2-yl}prop-2-yn-1-yl)amino]benzene-1-sulfonamide |
| 1896. | 1-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)ethan-1-one |
| 1897. | 3-methoxy-4-[(3-{4-[(1-{[(4S)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide |
| 1898. | N-((3-methoxy-4-((3-(4-((1-((2-oxo-1,3-dioxolan-4-yl)methyl)piperidin-4-yl)amino)-1-(2,2,2-trifluoroethyl)-1H-indol-2-yl)prop-2-yn-1-yl)amino)phenyl)sulfonyl)propionamide |
| 1899. | N-[3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzenesulfonyl]acetamide |
| 1900. | 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide |

TABLE 1-continued

Alkynyl indole compounds of the disclosure.

| Mol # | IUPAC name |
|---|---|
| 1901. | 2-(3-((2-methoxy-4-(methylsulfonyl)phenyl)amino)prop-1-yn-1-yl)-N-(octahydroindolizin-7-yl)-1-(2,2,2-trifluoroethyl)-1H-indol-4-amine |
| 1902. | N-[(7R,8aS)-octahydroindolizin-7-yl]-2-{3-[(4-methanesulfonyl-2-methoxyphfenyl)amino]prop-1-yn-1-yl}-1-(2,2,2-trifluoroethyl)-1H-indol-4-amine |
| 1903. | N-[(7R,8aR)-octahydroindolizin-7-yl]-2-{3-[(4-methanesulfonyl-2-methoxyphenyl)amino]prop-1-yn-1-yl}-1-(2,2,2-trifluoroethyl)-1H-indol-4-amine |
| 1904. | rac-(3R,4S)-3-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-4-ol |
| 1905. | rac-(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-3-ol |
| 1906. | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide |
| 1907. | rac-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1908. | N-((3S,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1909. | N-[(3S,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1910. | N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1911. | N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1912. | N-[(3R,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1913. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1914. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1915. | rac-methyl 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1916. | rac-methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1917. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1918. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1919. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1920. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1921. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1922. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide |
| 1923. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1924. | 2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide |
| 1925. | 2-fluoro-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide |
| 1926. | 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1927. | 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1928. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1929. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1930. | methyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1931. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1932. | methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1933. | rac-N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1934. | rac-4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1935. | rac-ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1936. | rac-ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1937. | (2R)-1-(acetyloxy)-3-[(3RS,4SR)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |

TABLE 1-continued

Alkynyl indole compounds of the disclosure.

| Mol # | IUPAC name |
|---|---|
| 1938. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1939. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1940. | N-[(3S,4R)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1941. | N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1942. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1943. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1944. | rac-2-hydroxypropyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1945. | 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-N-isopropyl-3-methoxybenzamide |
| 1946. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide |
| 1947. | 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1948. | 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1949. | rac-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide |
| 1950. | N-[(3S,4R)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1951. | N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1952. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide |
| 1953. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide |
| 1954. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide |
| 1955. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide |
| 1956. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide |
| 1957. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide |
| 1958. | rac-N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1959. | ethyl 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1960. | ethyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate |
| 1961. | ethyl 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoate |
| 1962. | ethyl 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoate |
| 1963. | ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1964. | 2-fluoro-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide |
| 1965. | 2-fluoro-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide |
| 1966. | 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 1967. | 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 1968. | rac-N-(2-{bis[(pyridin-2-yl)methyl]amino}ethyl)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1969. | rac-N-[(3R,4S)-3-fluoro-1-methylpiperidin-4-yl]-2-{3-[(4-methanesulfonyl-2-methoxyphenyl)amino]prop-1-yn-1-yl}-N-methyl-1-(2,2,2-trifluoroethyl)-1H-indol-4-amine |
| 1970. | rac-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid |
| 1971. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1972. | 2-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methanesulfonylphenol |
| 1973. | 2-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methanesulfonylphenol |

TABLE 1-continued

Alkynyl indole compounds of the disclosure.

| Mol # | IUPAC name |
|---|---|
| 1974. | rac-6-fluoro-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1975. | N-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide |
| 1976. | N-(4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide |
| 1977. | ethyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1978. | ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1979. | N-[(3R,4S)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine |
| 1980. | N-[(3S,4R)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine |
| 1981. | 2-{3-[(2-ethoxy-4-methanesulfonylphenyl)amino]prop-1-yn-1-yl}-N-[(3S,4R)-3-fluoro-1-methylpiperidin-4-yl]-1-(2,2,2-trifluoroethyl)-1H-indol-4-amine |
| 1982. | 2-{3-[(2-ethoxy-4-methanesulfonylphenyl)amino]prop-1-yn-1-yl}-N-[(3R,4S)-3-fluoro-1-methylpiperidin-4-yl]-1-(2,2,2-trifluoroethyl)-1H-indol-4-amine |
| 1983. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 1984. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 1985. | N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1986. | N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1987. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide |
| 1988. | 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzamide |
| 1989. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxy-N-methylbenzamide |
| 1990. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzoic acid |
| 1991. | 2-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol |
| 1992. | 2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol |
| 1993. | 2-(dimethylamino)-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 1994. | 2-(dimethylamino)-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 1995. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxy-N-methylbenzamide |
| 1996. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzoic acid |
| 1997. | N-[(3S,4R)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1998. | N-[(3R,4S)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1999. | 4-{[3-(4-{[(3S,4R)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2000. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2001. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2002. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one |
| 2003. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one |
| 2004. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one |
| 2005. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one |
| 2006. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzamide |
| 2007. | 4-{[3-(4-{[(3R,4S)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2008. | N-[(7S,8R)-7-fluoro-1,4-dioxaspiro[4.5]decan-8-yl]-2-{3-[(4-methanesulfonyl-2-methoxyphenyl)amino]prop-1-yn-1-yl}-1-(2,2,2-trifluoroethyl)-1H-indol-4-amine |
| 2009. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol |

TABLE 1-continued

Alkynyl indole compounds of the disclosure.

| Mol # | IUPAC name |
|---|---|
| 2010. | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2011. | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2012. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2013. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2014. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2015. | 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2016. | methyl 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate |
| 2017. | methyl 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate |
| 2018. | (R)-1-((3R,4S)-3-fluoro-4-((2-(3-((2-fluoro-6-methoxy-4-(methylsulfonyl)phenyl)amino)prop-1-yn-1-yl)-1-propyl-1H-indol-4-yl)amino)piperidin-1-yl)-3-methoxypropan-2-ol |
| 2019. | (R)-1-((3R,4S)-4-((1-allyl-2-(3-((2-fluoro-6-methoxy-4-(methylsulfonyl)phenyl)amino)prop-1-yn-1-yl)-1H-indol-4-yl)amino)-3-fluoropiperidin-1-yl)-3-methoxypropan-2-ol |
| 2020. | 4-{[3-(4-{[(3S,4R)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 2021. | 4-{[3-(4-{[(3R,4S)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 2022. | (2R)-1-[(3RS,4SR)-3-fluoro-4-[(2-{3-[(4-methanesulfonyl-2-methoxyphenyl)amino]prop-1-yn-1-yl}-1-propyl-1H-indol-4-yl)amino]piperidin-1-yl]-3-methoxypropan-2-ol |
| 2023. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2024. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2025. | 4-((3-(4-(((3R,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2026. | (2R)-1-(acetyloxy)-3-[(3R,4S)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 2027. | N-[(2R)-2,3-dihydroxypropyl]-4-{[3-(4-{[(3RS,4SR)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2028. | (2R)-1-(acetyloxy)-3-[(3S,4R)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 2029. | rac-N-(2-{bis[(pyridin-2-yl)methyl]amino}ethyl)-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide |
| 2030. | 2-amino-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2031. | 2-amino-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2032. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol |
| 2033. | 3-(4-(((3S,4R)-3-fluoro-1-methylpiperidin-4-yl)amino)-1-(2,2,2-trifluoroethyl)-1H-indol-2-yl)prop-2-yn-1-ol |
| 2034. | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine |
| 2035. | methyl 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate |
| 2036. | 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid |
| 2037. | methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate |
| 2038. | methyl 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate |
| 2039. | methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate |
| 2040. | methyl 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate |
| 2041. | methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate |
| 2042. | 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid |

TABLE 1-continued

Alkynyl indole compounds of the disclosure.

Mol #    IUPAC name 2043. methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate
2044. N-[(3S,4R)-3-fluoro-1-methylpiperidin-4-yl]-2-{3-[(2-methoxy-4-{2-oxa-6-azaspiro[3.3]heptane-6-carbonyl}phenyl)amino]prop-1-yn-1-yl}-1-(2,2,2-trifluoroethyl)-1H-indol-4-amine
2045. N-[(3S,4R)-3-fluoro-1-methylpiperidin-4-yl]-2-{3-[(2-methoxy-4-{7-oxa-2-azaspiro[3.5]nonane-2-carbonyl}phenyl)amino]prop-1-yn-1-yl}-1-(2,2,2-trifluoroethyl)-1H-indol-4-amine
2046. 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid
2047. N-[(3S,4R)-3-fluoro-1-methylpiperidin-4-yl]-2-(3-{[2-methoxy-4-(morpholine-4-carbonyl)phenyl]amino}prop-1-yn-1-yl)-1-(2,2,2-trifluoroethyl)-1H-indol-4-amine
2048. N-[(3S,4R)-3-fluoro-1-methylpiperidin-4-yl]-2-(3-{[2-methoxy-4-(4-methylpiperazine-1-carbonyl)phenyl]amino}prop-1-yn-1-yl)-1-(2,2,2-trifluoroethyl)-1H-indol-4-amine
2049. 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid
2050. 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid
2051. methyl 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate
2052. methyl 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate
2053. methyl 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate
2054. 2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)acetamide
2055. 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1,3-thiazol-2-yl)benzamide
2056. 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1-methylpiperidin-4-yl)benzamide
2057. 1-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoyl)piperidin-4-ol
2058. 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid
2059. 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid
2060. tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate
2061. 2-(3-((4-(ethylsulfonyl)-2-methoxyphenyl)amino)prop-1-yn-1-yl)-N-((3S,4R)-3-fluoropiperidin-4-yl)-1-(2,2,2-trifluoroethyl)-1H-indol-4-amine
2062. 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[2-(morpholin-4-yl)ethyl]benzamide
2063. 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid
2064. 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid
2065. 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid
2066. tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate
2067. (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioic acid
2068. (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoic acid
2069. 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid
2070. 1,5-dimethyl (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioate
2071. 2-[3-({4-[4-(dimethylamino)piperidine-1-carbonyl]-2-methoxyphenyl}amino)prop-1-yn-1-yl]-N-[(3S,4R)-3-fluoro-1-methylpiperidin-4-yl]-1-(2,2,2-trifluoroethyl)-1H-indol-4-amine
2072. 4-{[3-(4-{[(3S,4R)-1-(carboxymethyl)-3-fluoropiperidin-4-yl]amino}-1-(2,2,2-trifluoroethyl)-1H-indol-2-yl)prop-2-yn-1-yl]amino}-3-methoxybenzoic acid
2073. 2-(3-{[4-(ethanesulfonyl)-2-methoxyphenyl]amino}prop-1-yn-1-yl)-N-[(3S,4R)-3-fluoropiperidin-4-yl]-1-(2,2,2-trifluoroethyl)-1H-indol-4-amine
2074. (1R,2R,4S)-2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine
2075. (1R,2R,4S)-2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine
2076. (1S,3R,4R)-3-fluoro-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$,$N^1$-dimethylcyclohexane-1,4-diamine TABLE 1-continued Alkynyl indole compounds of the disclosure.

| Mol # | IUPAC name |
|---|---|
| 2077. | 2-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)ethan-1-ol |
| 2078. | N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2079. | 2-{3-[(2-ethoxy-4-methanesulfonylphenyl)amino]prop-1-yn-1-yl}-N-[(3S,4R)-3-fluoropiperidin-4-yl]-1-(2,2,2-trifluoroethyl)-1H-indol-4-amine |
| 2080. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide |
| 2081. | N-ethyl-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide |
| 2082. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methyl-N-(propan-2-yl)benzamide |
| 2083. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide |
| 2084. | N-[2-(diethylamino)ethyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2085. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxyethyl)-3-methoxybenzamide |
| 2086. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2R,3R,4R,5S,6R)-2,4,5-trihydroxy-6-(hydroxymethyl)oxan-3-yl]benzamide |
| 2087. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(1-hydroxypropan-2-yl)-3-methoxybenzamide |
| 2088. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2R)-1-hydroxypropan-2-yl]-3-methoxybenzamide |
| 2089. | N-[3-(4-{[(3S,4R)-3-fluoro-1-methylpiperidin-4-yl]amino}-1-(2,2,2-trifluoroethyl)-1H-indol-2-yl)prop-2-yn-1-yl]cyclopropanecarboxamide |
| 2090. | (1R,2R)-N-[3-(4-{[(3S,4R)-3-fluoro-1-methylpiperidin-4-yl]amino}-1-(2,2,2-trifluoroethyl)-1H-indol-2-yl)prop-2-yn-1-yl]-2-phenylcyclopropane-1-carboxamide |
| 2091. | N-[3-(4-{[(3S,4R)-3-fluoro-1-methylpiperidin-4-yl]amino}-1-(2,2,2-trifluoroethyl)-1H-indol-2-yl)prop-2-yn-1-yl]-1-methyl-1H-pyrrole-3-carboxamide |
| 2092. | 1-ethyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide |
| 2093. | 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide |
| 2094. | methyl (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoate |
| 2095. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-((R)-2-hydroxypropyl)-3-methoxybenzamide |
| 2096. | rac-4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 2097. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-((S)-2-hydroxypropyl)-3-methoxybenzamide |
| 2098. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide |
| 2099. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2S)-2-hydroxypropyl]-3-methoxybenzamide |
| 2100. | N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2101. | N-[(2R)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2102. | N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2103. | N-(1,5-dihydroxypentan-3-yl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2104. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(3-hydroxy-2-methoxypropyl)-3-methoxybenzamide |
| 2105. | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-[(2-methylpropanoyl)oxy]propan-2-yl 2-methylpropanoate |
| 2106. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2-oxo-1,3-dioxolan-4-yl)methyl]benzamide |
| 2107. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-methanesulfonylethyl)-3-methoxybenzamide |
| 2108. | 1-(acetyloxy)-3-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propan-2-yl acetate |
| 2109. | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-(propanoyloxy)propan-2-yl propanoate |

TABLE 1-continued

Alkynyl indole compounds of the disclosure.

| Mol # | IUPAC name |
|---|---|
| 2110. | 2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propyl 2-methylpropanoate |
| 2111. | (S)-5-ethoxy-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-oxopentanoic acid |
| 2112. | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamine |
| 2113. | (S)-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-methoxy-5-oxopentanoic acid |
| 2114. | (S)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2115. | (S)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2116. | (S)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2117. | (S)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2118. | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2119. | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2120. | (R)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2121. | (R)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2122. | (R)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2123. | (R)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2124. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide |
| 2125. | 1-(3,3-difluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2126. | 2-{3-[(4-methanesulfonyl-2-methoxyphenyl)amino]prop-1-yn-1-yl}-N-(1-methylazepan-4-yl)-1-(2,2,2-trifluoroethyl)-1H-indol-4-amine |
| 2127. | 1-{4-[(2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol |
| 2128. | 2-{3-[(4-methanesulfonyl-2-methoxyphenyl)amino]prop-1-yn-1-yl}-N-{8-methyl-8-azabicyclo[3.2.1]octan-3-yl}-1-(2,2,2-trifluoroethyl)-1H-indol-4-amine |
| 2129. | 2-(3-{[4-methanesulfonyl-2-(trifluoromethoxy)phenyl]amino}prop-1-yn-1-yl)-N-(oxan-4-yl)-1-(2,2,2-trifluoroethyl)-1H-indol-4-amine |
| 2130. | 3-methoxy-4-[(3-{4-[(oxan-4-yl)amino]-1-(2,2,2-trifluoroethyl)-1H-indol-2-yl}prop-2-yn-1-yl)amino]-N-(1,2-oxazol-3-yl)benzene-1-sulfonamide |
| 2131. | 3-methoxy-N-(oxan-4-yl)-4-[(3-{4-[(oxan-4-yl)amino]-1-(2,2,2-trifluoroethyl)-1H-indol-2-yl}prop-2-yn-1-yl)amino]benzene-1-sulfonamide |
| 2132. | 3-methoxy-N-(5-methyl-1,2-oxazol-3-yl)-4-[(3-{4-[(oxan-4-yl)amino]-1-(2,2,2-trifluoroethyl)-1H-indol-2-yl}prop-2-yn-1-yl)amino]benzene-1-sulfonamide |
| 2133. | 2-{4-methoxy-5-[(3-{4-[(oxan-4-yl)amino]-1-(2,2,2-trifluoroethyl)-1H-indol-2-yl}prop-2-yn-1-yl)amino]pyridin-2-yl}-2-methylpropanenitrile |
| 2134. | N-(2-hydroxyethyl)-3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2135. | 6-fluoro-2-{3-[(4-methanesulfonyl-2-methoxyphenyl)amino]prop-1-yn-1-yl}-N-(oxan-4-yl)-1-(2,2,2-trifluoroethyl)-1H-indol-4-amine |
| 2136. | 4-[(3-{6-fluoro-4-[(oxan-4-yl)amino]-1-(2,2,2-trifluoroethyl)-1H-indol-2-yl}prop-2-yn-1-yl)amino]-3-methoxybenzene-1-sulfonamide |
| 2137. | 3-methoxy-N,N-dimethyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2138. | 3-methoxy-N-(2-methoxyethyl)-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2139. | 1-(4-{3-methoxy-4-[(3-{4-[(oxan-4-yl)amino]-1-(2,2,2-trifluoroethyl)-1H-indol-2-yl}prop-2-yn-1-yl)amino]benzenesulfonyl}piperazin-1-yl)ethan-1-one |
| 2140. | 2-(3-{[2-methoxy-4-(morpholine-4-sulfonyl)phenyl]amino}prop-1-yn-1-yl)-N-(oxan-4-yl)-1-(2,2,2-trifluoroethyl)-1H-indol-4-amine |
| 2141. | 3-methoxy-N-methyl-4-[(3-{4-[(oxan-4-yl)amino]-1-(2,2,2-trifluoroethyl)-1H-indol-2-yl}prop-2-yn-1-yl)amino]benzamide |

TABLE 1-continued

Alkynyl indole compounds of the disclosure.

| Mol # | IUPAC name |
|---|---|
| 2142. | 3-methoxy-4-((3-(4-((tetrahydro-2H-pyran-4-yl)amino)-1-(2,2,2-trifluoroethyl)-1H-indol-2-yl)prop-2-yn-1-yl)amino)benzoic acid |
| 2143. | methyl 3-methoxy-4-((3-(4-((tetrahydro-2H-pyran-4-yl)amino)-1-(2,2,2-trifluoroethyl)-1H-indol-2-yl)prop-2-yn-1-yl)amino)benzoate |
| 2144. | 3-methoxy-4-((3-(4-((tetrahydro-2H-pyran-4-yl)amino)-1-(2,2,2-trifluoroethyl)-1H-indol-2-yl)prop-2-yn-1-yl)amino)benzamide |
| 2145. | 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide |
| 2146. | N,N-bis(2-hydroxyethyl)-3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 2147. | 3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2148. | 5-methanesulfonyl-2-[(3-{4-[(oxan-4-yl)amino]-1-(2,2,2-trifluoroethyl)-1H-indol-2-yl}prop-2-yn-1-yl)amino]phenol |
| 2149. | 3-methoxy-4-[(3-{5-methoxy-4-[(oxan-4-yl)amino]-1-(2,2,2-trifluoroethyl)-1H-indol-2-yl}prop-2-yn-1-yl)amino]benzene-1-sulfonamide |
| 2150. | 2-[3-({2-methoxy-4-[(4-methylpiperazin-1-yl)sulfonyl]phenyl}amino)prop-1-yn-1-yl]-N-(oxan-4-yl)-1-(2,2,2-trifluoroethyl)-1H-indol-4-amine |
| 2151. | 2-{3-[(4-methanesulfonyl-2-methoxyphenyl)amino]prop-1-yn-1-yl}-5-methoxy-N-(oxan-4-yl)-1-(2,2,2-trifluoroethyl)-1H-indol-4-amine |
| 2152. | 3-methoxy-4-[(3-{6-methoxy-4-[(oxan-4-yl)amino]-1-(2,2,2-trifluoroethyl)-1H-indol-2-yl}prop-2-yn-1-yl)amino]benzene-1-sulfonamide |
| 2153. | 5-methanesulfonyl-2-[(3-{4-[(oxan-4-yl)amino]-1-(2,2,2-trifluoroethyl)-1H-indol-2-yl}prop-2-yn-1-yl)amino]phenyl propanoate |
| 2154. | N-(2-hydroxyethyl)-3-methoxy-4-((3-(4-((tetrahydro-2H-pyran-4-yl)amino)-1-(2,2,2-trifluoroethyl)-1H-indol-2-yl)prop-2-yn-1-yl)amino)benzenesulfonamide |
| 2155. | 2-{3-[(4-methanesulfonyl-2-methoxyphenyl)amino]prop-1-yn-1-yl}-N-[(2S,4R)-2-methyloxan-4-yl]-1-(2,2,2-trifluoroethyl)-1H-indol-4-amine |
| 2156. | 2-{3-[(4-methanesulfonyl-2-methoxyphenyl)amino]prop-1-yn-1-yl}-N-[(2S,4S)-2-methyloxan-4-yl]-1-(2,2,2-trifluoroethyl)-1H-indol-4-amine |
| 2157. | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzene-1-sulfonamide |
| 2158. | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzene-1-sulfonamide |
| 2159. | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzamide |
| 2160. | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzamide |
| 2161. | rac-N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2162. | 2-(3-((2-methoxy-4-(methylsulfonyl)phenyl)amino)prop-1-yn-1-yl)-N-((3R,4S)-3-methoxytetrahydro-2H-pyran-4-yl)-1-(2,2,2-trifluoroethyl)-1H-indol-4-amine |
| 2163. | 2-(3-((2-methoxy-4-(methylsulfonyl)phenyl)amino)prop-1-yn-1-yl)-N-((3S,4S)-3-methoxytetrahydro-2H-pyran-4-yl)-1-(2,2,2-trifluoroethyl)-1H-indol-4-amine |
| 2164. | N-[(3S,4S)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2165. | N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2166. | 2-{3-[(4-methanesulfonyl-2-methoxyphenyl)amino]prop-1-yn-1-yl}-N-[(2R,4R,6S)-2,6-dimethyloxan-4-yl]-1-(2,2,2-trifluoroethyl)-1H-indol-4-amine |
| 2167. | 2-{3-[(4-methanesulfonyl-2-methoxyphenyl)amino]prop-1-yn-1-yl}-N-[(2R,4S,6S)-2,6-dimethyloxan-4-yl]-1-(2,2,2-trifluoroethyl)-1H-indol-4-amine |
| 2168. | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzamide |
| 2169. | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzamide |
| 2170. | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzene-1-sulfonamide |
| 2171. | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzene-1-sulfonamide |
| 2172. | 4-((2-(3-((4-methoxypyridin-3-yl)amino)prop-1-yn-1-yl)-1-(2,2,2-trifluoroethyl)-1H-indol-4-yl)amino)tetrahydro-2H-thiopyran 1,1-dioxide |
| 2173. | 2-{5-[(3-{4-[(1,1-dioxo-1$\lambda^6$-thian-4-yl)amino]-1-(2,2,2-trifluoroethyl)-1H-indol-2-yl}prop-2-yn-1-yl)amino]-4-methoxypyridin-2-yl}-2-methylpropanenitrile |
| 2174. | 4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}-1$\lambda^6$-thiane-1,1-dione |
| 2175. | 4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}-1$\lambda^6$-thiane-1,1-dione |
| 2176. | 4-({2-[3-({2-[2-(dimethylamino)ethoxy]-4-methanesulfonylphenyl}amino)prop-1-yn-1-yl]-1-(2,2,2-trifluoroethyl)-1H-indol-4-yl}amino)-1$\lambda^6$-thiane-1,1-dione |
| 2177. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-(2-hydroxyethyl)-3-methoxy-N-methylbenzene-1-sulfonamide |
| 2178. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-(1,2-oxazol-3-yl)benzene-1-sulfonamide |
| 2179. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxy-N-(5-methyl-1,2-oxazol-3-yl)benzene-1-sulfonamide |

TABLE 1-continued

Alkynyl indole compounds of the disclosure.

| Mol # | IUPAC name |
|---|---|
| 2180. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(oxan-4-yl)benzene-1-sulfonamide |
| 2181. | N-(2,3-dihydroxypropyl)-4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxybenzene-1-sulfonamide |
| 2182. | N-[2-(dimethylamino)ethyl]-4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-methylbenzene-1-sulfonamide |
| 2183. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N,N-dimethylbenzene-1-sulfonamide |
| 2184. | 4-({2-[3-({4-[(4-acetylpiperazin-1-yl)sulfonyl]-2-methoxyphenyl}amino)prop-1-yn-1-yl]-1-(2,2,2-trifluoroethyl)-1H-indol-4-yl}amino)-1λ$^6$-thiane-1,1-dione |
| 2185. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(2-methoxyethyl)-N-methylbenzene-1-sulfonamide |
| 2186. | 4-[(2-{3-[(2-methoxy-4-{2-oxa-6-azaspiro[3.3]heptane-6-sulfonyl}phenyl)amino]prop-1-yn-1-yl}-1-(2,2,2-trifluoroethyl)-1H-indol-4-yl)amino]-1λ$^6$-thiane-1,1-dione |
| 2187. | 4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)-1λ$^6$-thiane-1,1-dione |
| 2188. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-methylbenzamide |
| 2189. | 4-((2-(3-((4-methoxy-6-(methylsulfonyl)pyridin-3-yl)amino)prop-1-yn-1-yl)-1-(2,2,2-trifluoroethyl)-1H-indol-4-yl)amino)tetrahydro-2H-thiopyran 1,1-dioxide |
| 2190. | 4-((2-(3-((4-(methylsulfonyl)-2-(2,2,2-trifluoroethoxy)phenyl)amino)prop-1-yn-1-yl)-1-(2,2,2-trifluoroethyl)-1H-indol-4-yl)amino)tetrahydro-2H-thiopyran 1,1-dioxide |
| 2191. | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide |
| 2192. | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide |
| 2193. | N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide |
| 2194. | 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide |

TABLE 2

Aryl-linked indole compounds of the disclosure.

| Mol # | Structure IUPAC name |
|---|---|
| 2195. | 4-{4-[(1,1-dioxo-1λ$^6$-thian-4-yl)amino]-1-(2,2,2-trifluoroethyl)-1H-indol-2-yl}benzamide |
| 2196. | 4-({2-[4-(aminomethyl)phenyl]-1-(2,2,2-trifluoroethyl)-1H-indol-4-yl}amino)-1λ$^6$-thiane-1,1-dione |
| 2197. | 4-[(2-{4-[(methylamino)methyl]phenyl}-1-(2,2,2-trifluoroethyl)-1H-indol-4-yl)amino]-1λ$^6$-thiane-1,1-dione |
| 2198. | tert-butyl N-[(4-{4-[(1,1-dioxo-1λ$^6$-thian-4-yl)amino]-1-(2,2,2-trifluoroethyl)-1H-indol-2-yl}phenyl)methyl]-N-methylcarbamate |
| 2199. | 4-{4-[(1,1-dioxo-1λ$^6$-thian-4-yl)amino]-1-(2,2,2-trifluoroethyl)-1H-indol-2-yl}-N-methylbenzamide |
| 2200. | tert-butyl N-[(4-{4-[(1,1-dioxo-1λ$^6$-thian-4-yl)amino]-1-(2,2,2-trifluoroethyl)-1H-indol-2-yl}phenyl)methyl]carbamate |
| 2201. | 2-(5-{[(4-{4-[(1,1-dioxo-1λ$^6$-thian-4-yl)amino]-1-(2,2,2-trifluoroethyl)-1H-indol-2-yl}phenyl)methyl]amino}pyridin-2-yl)-2-methylpropanenitrile |
| 2202. | 4-{[2-(4-{[(4-methanesulfonylphenyl)amino]methyl}phenyl)-1-(2,2,2-trifluoroethyl)-1H-indol-4-yl]amino}-1λ$^6$-thiane-1,1-dione |
| 2203. | 4-[(2-{4-[(phenylamino)methyl]phenyl}-1-(2,2,2-trifluoroethyl)-1H-indol-4-yl)amino]-1λ$^6$-thiane-1,1-dione |
| 2204. | 3-{4-[(1,1-dioxo-1λ$^6$-thian-4-yl)amino]-1-(2,2,2-trifluoroethyl)-1H-indol-2-yl}benzonitrile |
| 2205. | 4-{[2-(2-fluoro-4-methylphenyl)-1-(2,2,2-trifluoroethyl)-1H-indol-4-yl]amino}-1λ$^6$-thiane-1,1-dione |
| 2206. | 4-{[2-(3-chlorophenyl)-1-(2,2,2-trifluoroethyl)-1H-indol-4-yl]amino}-1λ$^6$-thiane-1,1-dione |
| 2207. | -{[2-(3-methoxyphenyl)-1-(2,2,2-trifluoroethyl)-1H-indol-4-yl]amino}-1λ$^6$-thiane-1,1-dione |
| 2208. | 4-{[2-(4-chlorophenyl)-1-(2,2,2-trifluoroethyl)-1H-indol-4-yl]amino}-1λ$^6$-thiane-1,1-dione |
| 2209. | 4-tert-butyl-N-[(4-{4-[(1,1-dioxo-1λ$^6$-thian-4-yl)amino]-1-(2,2,2-trifluoroethyl)-1H-indol-2-yl}phenyl)methyl]benzamide |
| 2210. | 4-cyano-N-[(4-{4-[(1,1-dioxo-1λ$^6$-thian-4-yl)amino]-1-(2,2,2-trifluoroethyl)-1H-indol-2-yl}phenyl)methyl]benzamide |

TABLE 2-continued

Aryl-linked indole compounds of the disclosure.

| Mol # | Structure IUPAC name |
|---|---|
| 2211. | 4-chloro-N-[(4-{4-[(1,1-dioxo-1$\lambda^6$-thian-4-yl)amino]-1-(2,2,2-trifluoroethyl)-1H-indol-2-yl}phenyl)methyl]benzamide |
| 2212. | 3-[6-(1-cyano-1-methylethyl)pyridin-3-yl]-1-[(4-{4-[(1,1-dioxo-1$\lambda$6-thian-4-yl)amino]-1-(2,2,2-trifluoroethyl)-1H-indol-2-yl}phenyl)methyl]urea |
| 2213. | 3-[(4-{4-[(1,1-dioxo-1$\lambda^6$-thian-4-yl)amino]-1-(2,2,2-trifluoroethyl)-1H-indol-2-yl}phenyl)methyl]-1-phenylurea |
| 2214. | 3-{4-[(1,1-dioxo-1$\lambda^6$-thian-4-yl)amino]-1-(2,2,2-trifluoroethyl)-1H-indol-2-yl}benzoic acid |
| 2215. | 4-({2-[3-(dimethylamino)phenyl]-1-(2,2,2-trifluoroethyl)-1H-indol-4-yl}amino)-1$\lambda^6$-thiane-1,1-dione |
| 2216. | 3-{4-[(1,1-dioxo-1$\lambda^6$-thian-4-yl)amino]-1-(2,2,2-trifluoroethyl)-1H-indol-2-yl}-N-methylbenzamide |
| 2217. | 4-{4-[(11-dioxo-1$\lambda^6$-thian-4-yl)amino]-1-(2,2,2-trifluoroethyl)-1H-indol-2-yl}benzoic acid |
| 2218. | 4-[(2-{4-[(morpholin-4-yl)methyl]phenyl}-1-(2,2,2-trifluoroethyl)-1H-indol-4-yl)amino]-1$\lambda^6$-thiane-1,1-dione |
| 2219. | methyl N-(3-{4-[(1,1-dioxo-1$\lambda^6$-thian-4-yl)amino]-1-(2,2,2-trifluoroethyl)-1H-indol-2-yl}phenyl)carbamate |
| 2220. | 1-(4-{4-[(1,1-dioxo-1$\lambda^6$-thian-4-yl)amino]-1-(2,2,2-trifluoroethyl)-1H-indol-2-yl}phenyl)cyclopropane-1-carbonitrile |
| 2221. | 4-({2-[4-(hydroxymethyl)phenyl]-1-(2,2,2-trifluoroethyl)-1H-indol-4-yl}amino)-1$\lambda^6$-thiane-1,1-dione |
| 2222. | 1-[(4-{4-[(1,1-dioxo-1$\lambda^6$-thian-4-yl)amino]-1-(2,2,2-trifluoroethyl)-1H-indol-2-yl}phenyl)methyl]-3-(4-methanesulfonylphenyl)urea |
| 2223. | 4-{[2-(4-{[(6-methanesulfonylpyridin-3-yl)amino]methyl(phenyl)-1-(2,2,2-trifluoroethyl)-1H-indol-4-yl]amino}-1$\lambda^6$-thiane-1,1-dione |
| 2224. | 2-(4-{[(4-methanesulfonylphenyl)amino]methyl}phenyl)-N-[1-(oxan-4-yl)piperidin-4-yl]-1-(2,2,2-trifluoroethyl)-1H-indol-4-amine |
| 2225. | 2-(4-{[(6-methylpyridin-3-yl)amino]methyl}phenyl)-N-[1-(oxan-4-yl)piperidin-4-yl]-1-(2,2,2-trifluoroethyl)-1H-indol-4-amine |
| 2226. | 2-(4-{[(4-chlorophenyl)amino]methyl}phenyl)-N-[1-(oxan-4-yl)piperidin-4-yl]-1-(2,2,2-trifluoroethyl)-1H-indol-4-amine |
| 2227. | 2-(4-{[(4-methoxyphenyl)amino]methyl(phenyl)-N-[1-(oxan-4-yl)piperidin-4-yl]-1-(2,2,2-trifluoroethyl)-1H-indol-4-amine |
| 2228. | 2-(4-{[(3-chlorophenyl)amino]methyl}phenyl)-N-[1-(oxan-4-yl)piperidin-4-yl]-1-(2,2,2-trifluoroethyl)-1H-indol-4-amine |
| 2229. | 6-methyl-N-{[4-(5-{[(1-methylpiperidin-4-yl)amino]methyl}-1-(2,2,2-trifluoroethyl)-1H-indol-2-yl)phenyl]methyl}pyridin-3-amine |
| 2230. | N-{[2-(4-{[(4-methanesulfonylphenyl)amino]methyl}phenyl)-1-(2,2,2-trifluoroethyl)-1H-indol-5-yl]methyl}-1-methylpiperidin-4-amine |
| 2231. | 2-(5-amino-[1,1'-biphenyl]-3-yl)-N-(1-methylpiperidin-4-yl)-1-(2,2,2-trifluoroethyl)-1H-indol-4-amine |
| 2232. | 2-{4-[amino(phenyl)methyl]phenyl}-N-(1-methylpiperidin-4-yl)-1-(2,2,2-trifluoroethyl)-1H-indol-4-amine |
| 2233. | 2-(4-(amino(cyclohexyl)methyl)phenyl)-N-(1-methylpiperidin-4-yl)-1-(2,2,2-trifluoroethyl)-1H-indol-4-amine |
| 2234. | 2-{4-[(cyclopentylamino)methyl]phenyl}-N-(1-methylpiperidin-4-yl)-1-(2,2,2-trifluoroethyl)-1H-indol-4-amine |
| 2235. | 2-(4-{1-[(4-methanesulfonylphenyl)amino]ethyl}phenyl)-N-(1-methylpiperidin-4-yl)-1-(2,2,2-trifluoroethyl)-1H-indol-4-amine |
| 2236. | (+/−)-2-{4-[(cyclopropylamino)methyl]phenyl}-N-[(3R,4S)-3-fluoro-1-methylpiperidin-4-yl]-1-(2,2,2-trifluoroethyl)-1H-indol-4-amine |
| 2237. | (+/−)-N-[(3R,4S)-3-fluoro-1-methylpiperidin-4-yl]-2-(4-{[(4-methanesulfonyl-2-methoxyphenyl)amino]methyl}phenyl)-1-(2,2,2-trifluoroethyl)-1H-indol-4-amine |
| 2238. | N-[(3R,4S)-3-fluoro-1-methylpiperidin-4-yl]-2-(4-{[(4-methanesulfonylphenyl)amino]methyl(phenyl)-1-(2,2,2-trifluoroethyl)-1H-indol-4-amine |
| 2239. | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}benzamide |
| 2240. | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}cyclopropanecarboxamide |
| 2241. | 1-methoxy-3-(4-{[2-(3-methyl-2H-indazol-6-yl)-1-(2,2,2-trifluoroethyl)-1H-indol-4-yl]amino}piperidin-1-yl)propan-2-ol |
| 2242. | 1-(4-{[2-(2H-indazol-6-yl)-1-(2,2,2-trifluoroethyl)-1H-indol-4-yl]amino}piperidin-1-yl)-3-methoxypropan-2-ol |
| 2243. | 4-{[1-(2-hydroxy-3-methoxypropyl)piperidin-4-yl]amino}-1-(2,2,2-trifluoroethyl)-2',3'-dihydro-1H,1'H-[2,6'-biindol]-2'-one |
| 2244. | 4-(4-((1-(2-hydroxy-3-methoxypropyl)piperidin-4-yl)amino)-1-(2,2,2-trifluoroethyl)-1H-indol-2-yl)isoindolin-1-one |
| 2245. | N-[3-(4-{[1-(2-hydroxy-3-methoxypropyl)piperidin-4-yl]amino}-1-(2,2,2-trifluoroethyl)-1H-indol-2-yl)phenyl]acetamide |

TABLE 3

Heteroaryl-linked indole compounds of the disclosure.

| Mol # | IUPAC name |
|---|---|
| 2246. | 4-((2-(6-methoxypyridin-3-yl)-1-(2,2,2-trifluoroethyl)-1H-indol-4-yl)amino)tetrahydro-2H-thiopyran 1,1-dioxide-indol-4-amine |
| 2247. | 4-((2-(6-methylpyridin-3-yl)-1-(2,2,2-trifluoroethyl)-1H-indol-4-yl)amino)tetrahydro-2H-thiopyran 1,1-dioxide |
| 2248. | 4-((2-(6-(dimethylamino)pyridin-3-yl)-1-(2,2,2-trifluoroethyl)-1H-indol-4-yl)amino)tetrahydro-2H-thiopyran 1,1-dioxide |
| 2249. | 4-((2-(quinolin-4-yl)-1-(2,2,2-trifluoroethyl)-1H-indol-4-yl)amino)tetrahydro-2H-thiopyran 1,1-dioxide |
| 2250. | 4-((2-(2-fluoropyridin-3-yl)-1-(2,2,2-trifluoroethyl)-1H-indol-4-yl)amino)tetrahydro-2H-thiopyran 1,1-dioxide |
| 2251. | 1-(4-((2-(5-aminopyridin-3-yl)-1-(2,2,2-trifluoroethyl)-1H-indol-4-yl)amino)piperidin-1-yl)-3-methoxypropan-2-ol |
| 2252. | 2-(2-amino-6-phenylpyridin-4-yl)-N-(1-methylpiperidin-4-yl)-1-(2,2,2-trifluoroethyl)-1H-indol-4-amine |
| 2253. | 5-(4-((1,1-dioxidotetrahydro-2H-thiopyran-4-yl)amino)-1-(2,2,2-trifluoroethyl)-1H-indol-2-yl)-N-methylpicolinamide |
| 2254. | 2-(2-amino-6-phenylpyrimidin-4-yl)-N-(1-methylpiperidin-4-yl)-1-(2,2,2-trifluoroethyl)-1H-indol-4-amine |
| 2255. | 2-(2-amino-6-(cyclohex-1-en-1-yl)pyrimidin-4-yl)-N-(1-methylpiperidin-4-yl)-1-(2,2,2-trifluoroethyl)-1H-indol-4-amine |
| 2256. | 2-(2-amino-6-cyclohexylpyrimidin-4-yl)-N-(1-methylpiperidin-4-yl)-1-(2,2,2-trifluoroethyl)-1H-indol-4-amine |
| 2257. | 2-(2-(methylamino)pyrimidin-4-yl)-N-(1-methylpiperidin-4-yl)-1-(2,2,2-trifluoroethyl)-1H-indol-4-amine |
| 2258. | 2-(2-aminopyrimidin-4-yl)-N-(1-methylpiperidin-4-yl)-1-(2,2,2-trifluoroethyl)-1H-indol-4-amine |
| 2259. | 4-{[2-(1-methyl-1H-pyrazol-3-yl)-1-(2,2,2-trifluoroethyl)-1H-indol-4-yl]amino}-1$\lambda^6$-thiane-1,1-dione |
| 2260. | 4-({2-[1-(2-hydroxyethyl)-1H-pyrazol-4-yl]-1-(2,2,2-trifluoroethyl)-1H-indol-4-yl}amino)-1$\lambda^6$-thiane-1,1-dione |
| 2261. | 4-[(2-{1-[(pyridin-3-yl)methyl]-1H-pyrazol-4-yl}-1-(2,2,2-trifluoroethyl)-1H-indol-4-yl)amino]-1$\lambda^6$-thiane-1,1-dione |
| 2262. | 4-((2-(1-(2-methoxyethyl)-1H-pyrazol-4-yl)-1-(2,2,2-trifluoroethyl)-1H-indol-4-yl)amino)tetrahydro-2H-thiopyran 1,1-dioxide |
| 2263. | 4-[(2-{1-[(pyridin-4-yl)methyl]-1H-pyrazol-4-yl}-1-(2,2,2-trifluoroethyl)-1H-indol-4-yl)amino]-1$\lambda^6$-thiane-1,1-dione |
| 2264. | 2-(5-amino-1-phenyl-1H-pyrazol-3-yl)-N-(1-methylpiperidin-4-yl)-1-(2,2,2-trifluoroethyl)-1H-indol-4-amine |
| 2265. | 2-{5-[amino(phenyl)methyl]-1H-pyrazol-3-yl}-N-(1-methylpiperidin-4-yl)-1-(2,2,2-trifluoroethyl)-1H-indol-4-amine |
| 2266. | 2-(5-amino-1H-pyrazol-3-yl)-N-(1-methylpiperidin-4-yl)-1-(2,2,2-trifluoroethyl)-1H-indol-4-amine |
| 2267. | 2-(5-{[(4-methanesulfonylphenyl)amino]methyl}-1H-pyrazol-3-yl)-N-(1-methylpiperidin-4-yl)-1-(2,2,2-trifluoroethyl)-1H-indol-4-amine |
| 2268. | 2-[5-(methylamino)-1H-pyrazol-3-yl]-N-(1-methylpiperidin-4-yl)-1-(2,2,2-trifluoroethyl)-1H-indol-4-amine |
| 2269. | 2-(5-{[(4-methanesulfonylphenyl)amino]methyl}-1,3,4-thiadiazol-2-yl)-N-(1-methylpiperidin-4-yl)-1-(2,2,2-trifluoroethyl)-1H-indol-4-amine |
| 2270. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2271. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}benzamide |
| 2272. | (+/−)-N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2273. | (+/−)-N-[(3R,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2274. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopentanecarboxamide |
| 2275. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}thiophene-2-carboxamide |
| 2276. | 1-fluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2277. | (+/−)-2,2-difluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2278. | (+/−)-(1R,2S)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2279. | (+/−)-(1R,2R)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2280. | N-[(5-{4-[(1-methylpiperidin-4-yl)amino]-1-(2,2,2-trifluoroethyl)-1H-indol-2-yl}-1,3,4-thiadiazol-2-yl)methyl]cyclopropanecarboxamide |
| 2281. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}oxetane-3-carboxamide |

TABLE 3-continued

Heteroaryl-linked indole compounds of the disclosure.

| Mol # | IUPAC name |
|---|---|
| 2282. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclobutanecarboxamide |
| 2283. | (+/−)-methyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate |
| 2284. | methyl 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoate |
| 2285. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}-1-methylpiperidine-4-carboxamide |
| 2286. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-2-carboxamide |
| 2287. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-3-carboxamide |
| 2288. | (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine |
| 2289. | (+/−)-benzyl N-{[5-(4-{[(3R,4S)-3-fluoro-1-methylpipendin-4-yl]amino}-1-(2,2,2-trifluoroethyl)-1H-indol-2-yl)-1,3,4-thiadiazol-2-yl]methyl}carbamate |
| 2290. | N-[(5-{4-[(1-methylpiperidin-4-yl)amino]-1-(2,2,2-trifluoroethyl)-1H-indol-2-yl}-1,3,4-thiadiazol-2-yl)methyl]-4-[(morpholin-4-yl)methyl]benzamide |
| 2291. | N-[(5-{4-[(1-methylpiperidin-4-yl)amino]-1-(2,2,2-trifluoroethyl)-1H-indol-2-yl}-1,3,4-thiadiazol-2-yl)methyl]-3-[(morpholin-4-yl)methyl]benzamide |
| 2292. | N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2293. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2294. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-4-carboxamide |
| 2295. | 2-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2296. | 3-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2297. | 4-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2298. | (+/−)-(1S,2S)-N-[(5-{4-[(1-methylpiperidin-4-yl)amino]-1-(2,2,2-trifluoroethyl)-1H-indol-2-yl}-1,3,4-thiadiazol-2-yl)methyl]-2-phenylcyclopropane-1-carboxamide |
| 2299. | 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoic acid |
| 2300. | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide |
| 2301. | 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea |
| 2302. | 2-methyl-N-[(5-{4-[(1-methylpiperidin-4-yl)amino]-1-(2,2,2-trifluoroethyl)-1H-indol-2-yl}-1,3,4-thiadiazol-2-yl)methyl]propanamide |
| 2303. | N-[(5-{4-[(1-methylpiperidin-4-yl)amino]-1-(2,2,2-trifluoroethyl)-1H-indol-2-yl}-1,3,4-thiadiazol-2-yl)methyl]acetamide |
| 2304. | N-[(5-{4-[(1-methylpiperidin-4-yl)amino]-1-(2,2,2-trifluoroethyl)-1H-indol-2-yl}-1,3,4-thiadiazol-2-yl)methyl]-2-phenylacetamide |
| 2305. | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]acetamide |
| 2306. | N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2307. | N-[(3S,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2308. | 4-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2309. | 3-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2310. | N-[(5-{4-[(1-methylpiperidin-4-yl)amino]-1-(2,2,2-trifluoroethyl)-1H-indol-2-yl}-1,3,4-thiadiazol-2-yl)methyl]butanamide |
| 2311. | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2312. | 2-[5-(aminomethyl)-1,3,4-thiadiazol-2-yl]-N-(1-methylpiperidin-4-yl)-1-(2,2,2-trifluoroethyl)-1H-indol-4-amine |
| 2313. | 3,3-dimethyl-1-[(5-{4-[(1-methylpiperidin-4-yl)amino]-1-(2,2,2-trifluoroethyl)-1H-indol-2-yl}-1,3,4-thiadiazol-2-yl)methyl]urea |
| 2314. | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide |
| 2315. | benzyl N-{[5-(4-{[(3S,4R)-3-fluoropiperidin-4-yl]amino}-1-(2,2,2-trifluoroethyl)-1H-indol-2-yl)-1,3,4-thiadiazol-2-yl]methyl}carbamate |
| 2316. | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2317. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-4-carboxamide |

TABLE 3-continued

Heteroaryl-linked indole compounds of the disclosure.

| Mol # | IUPAC name |
|---|---|
| 2318. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-5-carboxamide |
| 2319. | 1-ethyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2320. | (+/−)-methyl (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate |
| 2321. | (+/−)-(1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid |
| 2322. | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide |
| 2323. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide |
| 2324. | N-[(5-{4-[(1-methylpiperidin-4-yl)amino]-1-(2,2,2-trifluoroethyl)-1H-indol-2-yl}-1,3,4-thiadiazol-2-yl)methyl]-2-(thiophen-2-yl)cyclopropane-1-carboxamide |
| 2325. | N-(1-methylpiperidin-4-yl)-2-(5-{[(pyrrolidin-3-yl)amino]methyl}-1,3,4-thiadiazol-2-yl)-1-(2,2,2-trifluoroethyl)-1H-indol-4-amine |
| 2326. | (+/−)-(1R,2S)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid |
| 2327. | N-(1-methylpiperidin-4-yl)-2-(5-{[(1H-pyrazol-4-yl)amino]methyl}-1,3,4-thiadiazol-2-yl)-1-(2,2,2-trifluoroethyl)-1H-indol-4-amine |
| 2328. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide |
| 2329. | N-((3S,4R)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine |
| 2330. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide |
| 2331. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide |
| 2332. | 2-(5-((dimethylamino)methyl)-1,3,4-thiadiazol-2-yl)-N-((3S,4R)-3-fluoro-1-methylpiperidin-4-yl)-1-(2,2,2-trifluoroethyl)-1H-indol-4-amine |
| 2333. | N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine |
| 2334. | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide |
| 2335. | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}benzamide |
| 2336. | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide |
| 2337. | N-[(2-{4-[(1-methylpiperidin-4-yl)amino]-1-(2,2,2-trifluoroethyl)-1H-indol-2-yl}-1,3-thiazol-5-yl)methyl]benzamide |
| 2338. | (+/−)-N-[(3R,4S)-3-fluoro-1-methylpiperidin-4-yl]-2-(1,3-thiazol-2-yl)-1-(2,2,2-trifluoroethyl)-1H-indol-4-amine |
| 2339. | N-[(2-{4-[(1-methylpiperidin-4-yl)amino]-1-(2,2,2-trifluoroethyl)-1H-indol-2-yl}-1,3-thiazol-5-yl)methyl]cyclopropanecarboxamide |
| 2340. | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide |
| 2341. | (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine |
| 2342. | 2-(4-(aminomethyl)thiazol-2-yl)-N-((3S,4R)-3-fluoro-1-methylpiperidin-4-yl)-1-(2,2,2-trifluoroethyl)-1H-indol-4-amine |
| 2343. | (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine |
| 2344. | N-[(3S,4R)-3-fluoro-1-methylpiperidin-4-yl]-2-(5-{[(4-methanesulfonyl-2-methoxyphenyl)amino]methyl}-1,3-thiazol-2-yl)-1-(2,2,2-trifluoroethyl)-1H-indol-4-amine |
| 2345. | 2-(5-{[(4-methanesulfonylphenyl)amino]methyl}thiophen-2-yl)-N-(1-methylpiperidin-4-yl)-1-(2,2,2-trifluoroethyl)-1H-indol-4-amine |
| 2346. | (+/−)-N-[(3R,4S)-3-fluoro-1-methylpiperidin-4-yl]-2-(5-{[(4-methanesulfonyl-2-methoxyphenyl)amino]methyl}thiophen-2-yl)-1-(2,2,2-trifluoroethyl)-1H-indol-4-amine |
| 2347. | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}benzamide |
| 2348. | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide |
| 2349. | N-(1-methylpiperidin-4-yl)-2-(5-(((4-(methylsulfonyl)phenyl)amino)methyl)thiophen-2-yl)-1-(2,2,2-trifluoroethyl)-1H-indol-4-amine |
| 2350. | N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide |
| 2351. | N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine |
| 2352. | 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine |

TABLE 3-continued

Heteroaryl-linked indole compounds of the disclosure.

| Mol # | IUPAC name |
|---|---|
| 2353. | N-(1-methylpiperidin-4-yl)-2-{5-[(phenylamino)methyl]-1,3,4-oxadiazol-2-yl]-1-(2,2,2-trifluoroethyl)-1H-indol-4-amine |
| 2354. | 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine |
| 2355. | N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarboxamide |
| 2356. | 2-(5-{[(4-methanesulfonylphenyl)amino]methyl}-1,3,4-oxadiazol-2-yl)-N-(1-methylpiperidin-4-yl)-1-(2,2,2-trifluoroethyl)-1H-indol-4-amine |
| 2357. | N-(1-methylpiperidin-4-yl)-2-(5-{[(1H-pyrazol-4-yl)amino]methyl}-1,3,4-oxadiazol-2-yl)-1-(2,2,2-trifluoroethyl)-1H-indol-4-amine |
| 2358. | 2-(5-(aminomethyl)-1,3,4-oxadiazol-2-yl)-N-(1-methylpiperidin-4-yl)-1-(2,2,2-trifluoroethyl)-1H-indol-4-amine |
| 2359. | (+/−)-N-[(3R,4S)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine |
| 2360. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-2-methoxybenzamide |
| 2361. | (+/−)-2-[5-(aminomethyl)-1,3,4-oxadiazol-2-yl]-N-[(3R,4S)-3-fluoro-1-methylpiperidin-4-yl]-1-(2,2,2-trifluoroethyl)-1H-indol-4-amine |
| 2362. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-4-methoxybenzamide |
| 2363. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}benzamide |
| 2364. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-3-methoxybenzamide |
| 2365. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}thiophene-2-carboxamide |
| 2366. | (+/−)-2-(5-{[(cyclopropylmethyl)amino]methyl}-1,3,4-oxadiazol-2-yl)-N-[(3R,4S)-3-fluoro-1-methylpiperidin-4-yl]-1-(2,2,2-trifluoroethyl)-1H-indol-4-amine |
| 2367. | (+/−)-N-[(3R,4S)-3-fluoro-1-methylpiperidin-4-yl]-2-(5-{[(3-methanesulfonylphenyl)amino]methyl}-1,3,4-oxadiazol-2-yl)-1-(2,2,2-trifluoroethyl)-1H-indol-4-amine |
| 2368. | (+/−)-N-[(3R,4R)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine |
| 2369. | (+/−)-2-(5-((bis(cyclopropylmethyl)amino)methyl)-1,3,4-oxadiazol-2-yl)-N-((3R,4S)-3-fluoro-1-methylpiperidin-4-yl)-1-(2,2,2-trifluoroethyl)-1H-indol-4-amine |
| 2370. | (+/−)-N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine |
| 2371. | (+/−)-N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2372. | (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine |
| 2373. | (+/−)-N-((3S,4S)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2374. | N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)benzamide |
| 2375. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)thiophene-2-carboxamide |
| 2376. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-2-methoxybenzamide |
| 2377. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-3-methoxybenzamide |
| 2378. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-4-methoxybenzamide |
| 2379. | (+/−)-2-(5-(((cyclopropylmethyl)amino)methyl)-1,3,4-oxadiazol-2-yl)-N-((3S,4R)-3-fluoro-1-methylpiperidin-4-yl)-1-(2,2,2-trifluoroethyl)-1H-indol-4-amine |
| 2380. | (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2381. | 2-(3-{[(4-methanesulfonylphenyl)amino]methyl}-1,2,4-oxadiazol-5-yl)-N-(1-methylpiperidin-4-yl)-1-(2,2,2-trifluoroethyl)-1H-indol-4-amine |
| 2382. | N-[(5-{4-[(1-methylpiperidin-4-yl)amino]-1-(2,2,2-trifluoroethyl)-1H-indol-2-yl}-1,2,4-oxadiazol-3-yl)methyl]cyclopropanecarboxamide |
| 2383. | N-[(5-{4-[(1-methylpiperidin-4-yl)amino]-1-(2,2,2-trifluoroethyl)-1H-indol-2-yl}-1,2,4-oxadiazol-3-yl)methyl]benzamide |
| 2384. | N-[(5-{4-[(1-methylpiperidin-4-yl)amino]-1-(2,2,2-trifluoroethyl)-1H-indol-2-yl}-1,2,4-oxadiazol-3-yl)methyl]thiophene-2-carboxamide |
| 2385. | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-4-carboxamide |
| 2386. | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-3-carboxamide |

TABLE 3-continued

Heteroaryl-linked indole compounds of the disclosure.

| Mol # | IUPAC name |
|---|---|
| 2387. | N-(1-methylpiperidin-4-yl)-2-{5-[(phenylamino)methyl]-1,2,4-oxadiazol-3-yl}-1-(2,2,2-trifluoroethyl)-1H-indol-4-amine |
| 2388. | N-[(3-{4-[(1-methylpiperidin-4-yl)amino]-1-(2,2,2-trifluoroethyl)-1H-indol-2-yl}-1,2,4-oxadiazol-5-yl)methyl]thiophene-2-carboxamide |
| 2389. | N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2390. | (+/−)-(1S,2R)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2391. | N-[(3-{4-[(1-methylpiperidin-4-yl)amino]-1-(2,2,2-trifluoroethyl)-1H-indol-2-yl}-1,2,4-oxadiazol-5-yl)methyl]cyclopropanecarboxamide |
| 2392. | (+/−)-(1S,2S)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2393. | 4-chloro-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2394. | N-[(3-{4-[(1-methylpiperidin-4-yl)amino]-1-(2,2,2-trifluoroethyl)-1H-indol-2-yl}-1,2,4-oxadiazol-5-yl)methyl]-1,3-thiazole-2-carboxamide |
| 2395. | 4-fluoro-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2396. | 4-cyano-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2397. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrrole-3-carboxamide |
| 2398. | 3-[(3-{4-[(1-methylpiperidin-4-yl)amino]-1-(2,2,2-trifluoroethyl)-1H-indol-2-yl}-1,2,4-oxadiazol-5-yl)methyl]-1-phenylurea |
| 2399. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-4-carboxamide |
| 2400. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-3-carboxamide |
| 2401. | (+/−)-(1R,2R)-N-[(3-{4-[(1-methylpiperidin-4-yl)amino]-1-(2,2,2-trifluoroethyl)-1H-indol-2-yl}-1,2,4-oxadiazol-5-yl)methyl]-2-phenylcyclopropane-1-carboxamide |
| 2402. | (+/−)-(1R,2R)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2403. | (+/−)-(1R,2S)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2404. | N-[(3-{4-[(oxan-4-yl)amino]-1-(2,2,2-trifluoroethyl)-1H-indol-2-yl}-1,2,4-oxadiazol-5-yl)methyl]cyclopropanecarboxamide |
| 2405. | N-({3-[4-(benzylamino)-1-(2,2,2-trifluoroethyl)-1H-indol-2-yl]-1,2,4-oxadiazol-5-yl}methyl)cyclopropanecarboxamide |
| 2406. | N-[(3-{4-[(1-acetylpiperidin-4-yl)amino]-1-(2,2,2-trifluoroethyl)-1H-indol-2-yl}-1,2,4-oxadiazol-5-yl)methyl]cyclopropanecarboxamide |
| 2407. | N-[(3-{4-[(1,1-dioxo-1λ$^6$-thian-4-yl)amino]-1-(2,2,2-trifluoroethyl)-1H-indol-2-yl}-1,2,4-oxadiazol-5-yl)methyl]cyclopropanecarboxamide |
| 2408. | N-[(3-{4-[(1-benzylpiperidin-4-yl)amino]-1-(2,2,2-trifluoroethyl)-1H-indol-2-yl}-1,2,4-oxadiazol-5-yl)methyl]cyclopropanecarboxamide |
| 2409. | N-[(3-{4-[(1-cyclopropylpiperidin-4-yl)amino]-1-(2,2,2-trifluoroethyl)-1H-indol-2-yl}-1,2,4-oxadiazol-5-yl)methyl]cyclopropanecarboxamide |
| 2410. | N-[(3-{4-[(cyclopropylmethyl)amino]-1-(2,2,2-trifluoroethyl)-1H-indol-2-yl}-1,2,4-oxadiazol-5-yl)methyl]cyclopropanecarboxamide |
| 2411. | N-[(3-{4-[(cyclobutylmethyl)amino]-1-(2,2,2-trifluoroethyl)-1H-indol-2-yl}-1,2,4-oxadiazol-5-yl)methyl]cyclopropanecarboxamide |
| 2412. | (+/−)-N-[(3-{4-[(pyrrolidin-3-yl)amino]-1-(2,2,2-trifluoroethyl)-1H-indol-2-yl}-1,2,4-oxadiazol-5-yl)methyl]cyclopropanecarboxamide |
| 2413. | N-[(3-{4-[(1-ethylpiperidin-4-yl)amino]-1-(2,2,2-trifluoroethyl)-1H-indol-2-yl}-1,2,4-oxadiazol-5-yl)methyl]cyclopropanecarboxamide |
| 2414. | (+/−)-N-[(3-{4-[(1-methylpyrrolidin-3-yl)amino]-1-(2,2,2-trifluoroethyl)-1H-indol-2-yl}-1,2,4-oxadiazol-5-yl)methyl]cyclopropanecarboxamide |
| 2415. | N-{[3-(4-{[(2l6zetidine-3-yl)methyl]amino}-1-(2,2,2-trifluoroethyl)-1H-indol-2-yl)-1,2,4-oxadiazol-5-yl]methyl}cyclopropanecarboxamide |
| 2416. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2417. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2418. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2419. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2420. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide |
| 2421. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |

TABLE 3-continued

Heteroaryl-linked indole compounds of the disclosure.

| Mol # | IUPAC name |
|---|---|
| 2422. | (+/−)-N-[(3R,4S)-3-fluoro-1-methylpiperidin-4-yl]-2-(5-{[(4-methanesulfonylphenyl)amino]methyl}-1,2,4-oxadiazol-3-yl)-1-(2,2,2-trifluoroethyl)-1H-indol-4-amine |
| 2423. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide |
| 2424. | (+/−)-1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2425. | (+/−)-(1R,2R)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2426. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide |
| 2427. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide |
| 2428. | (+/−)-N-[(3R,4S)-3-fluoro-1-methylpiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine |
| 2429. | (+/−)-1-tert-butyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2430. | (+/−)-(1R,2R)-N-{[3-(4-{[(3RS,4SR)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2431. | 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2432. | 1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2433. | (+/−)-N-[(3R,4S)-3-fluoropiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine |
| 2434. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2435. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2436. | (+/−)-N-[(3R,4S)-3-fluoropiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine |
| 2437. | (+/−)-N-[(3R,4S)-3-fluoro-1-methylpiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine |
| 2438. | (1RS,2RS)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2439. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2440. | (1RS,2SR)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2441. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}indolizine-2-carboxamide |
| 2442. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-imidazole-4-carboxamide |
| 2443. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2444. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrrole-3-carboxamide |
| 2445. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-4-carboxamide |
| 2446. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-2-carboxamide |
| 2447. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide |
| 2448. | N-[(3S,4R)-3-fluoropiperidin-4-yl]-2-(5-{[(1H-pyrazol-4-yl)amino]methyl}-1,2,4-oxadiazol-3-yl)-1-(2,2,2-trifluoroethyl)-1H-indol-4-amine |
| 2449. | benzyl N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamate |
| 2450. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide |

TABLE 3-continued

Heteroaryl-linked indole compounds of the disclosure.

| Mol # | IUPAC name |
|---|---|
| 2451. | (1S,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2452. | (1R,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2453. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-methylthiophene-3-carboxamide |
| 2454. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-methylthiophene-3-carboxamide |
| 2455. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-fluorophenyl)cyclopropane-1-carboxamide |
| 2456. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-methylthiophene-3-carboxamide |
| 2457. | (1s,3r)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide |
| 2458. | 5-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2459. | N-[(3S,4R)-3-fluoropiperidin-4-yl]-2-(5-{[(1H-pyrazol-5-yl)amino]methyl}-1,2,4-oxadiazol-3-yl)-1-(2,2,2-trifluoroethyl)-1H-indol-4-amine |
| 2460. | 2-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2461. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyrazolo[1,5-a]pyridine-2-carboxamide |
| 2462. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}imidazo[1,2-a]pyridine-2-carboxamide |
| 2463. | 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2464. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,5-dimethyl-1H-pyrrole-3-carboxamide |
| 2465. | 4-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2466. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzenesulfonamide |
| 2467. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclobutanecarboxamide |
| 2468. | (1r,3s)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide |
| 2469. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-fluorophenyl)cyclopropane-1-carboxamide |
| 2470. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-methyl-1H-pyrazol-4-yl)cyclopropane-1-carboxamide |
| 2471. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyridin-2-yl)cyclopropane-1-carboxamide |
| 2472. | N-[(3S,4R)-3-fluoro-1-methylpiperidin-4-yl]-2-(5-{[(1H-pyrazol-4-yl)amino]methyl}-1,2,4-oxadiazol-3-yl)-1-(2,2,2-trifluoroethyl)-1H-indol-4-amine |
| 2473. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}acetamide |
| 2474. | 1-[2-(dimethylamino)ethyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2475. | N-[(3S,4R)-3-fluoro-1-methylpiperidin-4-yl]-2-(5-{[(1H-pyrazol-5-yl)amino]methyl}-1,2,4-oxadiazol-3-yl)-1-(2,2,2-trifluoroethyl)-1H-indol-4-amine |
| 2476. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide |
| 2477. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-4-carboxamide |
| 2478. | (1S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide |
| 2479. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(4-methylpiperazin-1-yl)methyl]cyclopropane-1-carboxamide |
| 2480. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(3-fluorophenyl)cyclopropane-1-carboxamide |

TABLE 3-continued

Heteroaryl-linked indole compounds of the disclosure.

| Mol # | IUPAC name |
|---|---|
| 2481. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-1,2,3-triazole-4-carboxamide |
| 2482. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-hydroxypropan-2-yl)-1H-pyrrole-3-carboxamide |
| 2483. | 2-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]acetic acid |
| 2484. | (1R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide |
| 2485. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylpropyl)-1H-pyrrole-3-carboxamide |
| 2486. | 1-(cyclopropylmethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2487. | 3-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2488. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(pyrrolidin-1-yl)benzamide |
| 2489. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxypropyl)-1H-pyrrole-3-carboxamide |
| 2490. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(morpholin-4-yl)methyl]cyclopropane-1-carboxamide |
| 2491. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide |
| 2492. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(propylamino)methyl]cyclopropane-1-carboxamide |
| 2493. | 3-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]propanoic acid |
| 2494. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxyethyl)-1H-pyrrole-3-carboxamide |
| 2495. | 1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2496. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxy-2-methylpropyl)-1H-pyrrole-3-carboxamide |
| 2497. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxy-2-methylpropyl)-1H-pyrrole-3-carboxamide |
| 2498. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxypropyl)-1H-pyrrole-3-carboxamide |
| 2499. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-6-carboxamide |
| 2500. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrazole-4-carboxamide |
| 2501. | 4-(4,4-difluoropiperidin-1-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2502. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-5-carboxamide |
| 2503. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-5-carboxamide |
| 2504. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-5-carboxamide |
| 2505. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(morpholin-4-yl)benzamide |
| 2506. | 2-[5-(aminomethyl)-1,2,4-oxadiazol-3-yl]-N-[(3S,4R)-3-fluoro-1-methylpiperidin-4-yl]-1-(2,2,2-trifluoroethyl)-1H-indol-4-amine |
| 2507. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(morpholin-4-yl)benzamide |
| 2508. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(pyrrolidin-1-yl)benzamide |

TABLE 3-continued

Heteroaryl-linked indole compounds of the disclosure.

| Mol # | IUPAC name |
|---|---|
| 2509. | (1R,2R)-2-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2510. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(pyrrolidin-1-yl)methyl]cyclopropane-1-carboxamide |
| 2511. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-5-carboxamide |
| 2512. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-6-carboxamide |
| 2513. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-imidazole-5-carboxamide |
| 2514. | (1R,2R)-2-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2515. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-5-carboxamide |
| 2516. | (1S,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide |
| 2517. | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2518. | N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2519. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-6-carboxamide |
| 2520. | (+/−)-N-{[5-(4-{[(3R,4S)-3-fluoro-1-methylpiperidin-4-yl]amino(-1-(2,2,2-trifluoroethyl)-1H-indol-2-yl)-1,2,4-oxadiazol-3-yl]methyl}cyclopropanecarboxamide |
| 2521. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}benzamide |
| 2522. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-2-carboxamide |
| 2523. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-3-carboxamide |
| 2524. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}-1,3-thiazole-5-carboxamide |
| 2525. | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-fluoropropan-2-yl)-1H-pyrrole-3-carboxamide |
| 2526. | N-((3-(4-(((3S,4R)-1-ethyl-3-fluoropiperidin-4-yl)amino)-1-(2,2,2-trifluoroethyl)-1H-indol-2-yl)-1,2,4-oxadiazol-5-yl)methyl)-1-(2-fluoroethyl)-1H-pyrrole-3-carboxamide |
| 2527. | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-methoxypropan-2-yl)-1H-pyrrole-3-carboxamide |

Example 2: Retrospective Confirmatory Testing for a p53 Y220C Mutation

NGS is used to perform retrospective confirmatory testing for a p53 Y220C mutation in blood or solid tissue. If a patient does not have a p53 Y220C mutation detected at the pre-screening step, the patient may be enrolled prospectively.

DNA is obtained from a cancer sample of a patient. The DNA is sequenced using NGS to determine the entire p53 coding region, including TP53 exons, introns, and splice sites. Dysfunctional p53 is inferred from the identification of substitutions, indels, frameshift mutations, splice site mutation, insertions or deletions, copy number variants, large deletions, or polymorphisms. Minimum tumor content is 20%. Average read depth is about 750 reads/amplicon. The lower limit of detection is 5% mutant allele at an average read depth of ≥450 reads per amplicon. When the average read depth is <450 reads per amplicon, the limit of detection is 15% mutant allele.

Detection of TP53 gene copy number is based on the number of TP53 amplicon reads from a tumor compared with the average number reads across 14 normal DNA samples. Limits of the assay: the loss of one or more alleles is determined if tumor content is >60% (99% sensitivity); the loss of two alleles is determined if tumor sample content is >30% (99% sensitivity). More than 10% of tumors with wild-type TP53 have a copy number less than 0.5 (<0.5).

A patient with a confirmed Y220C mutation is given a regimen comprising a therapeutically-effective amount of a compound of the disclosure or a pharmaceutically-acceptable salt thereof.

EMBODIMENTS

The following non-limiting embodiments provide illustrative examples of the invention, but do not limit the scope of the invention.

Embodiment 1. A method of treating a condition in a subject in need thereof, the method comprising administering to the subject a therapeutically-effective amount of a small molecule compound, wherein the subject has been previously determined to have a mutation in a TP53 gene that encodes a p53 mutant in the subject based on an assay performed on a biological sample of the subject, wherein the small molecule compound does not contain arsenic, antimony, or bismuth.

Embodiment 2. A method of treating a condition in a subject in need thereof, the method comprising: a) based on a result of an assay performed on a biological sample of the subject, determining that the subject harbors a mutation in a TP53 gene that encodes a p53 mutant protein; b) based on the result of the assay, administering to the subject a therapeutically-effective amount of a small molecule compound, wherein the small molecule compound does not contain arsenic, antimony, or bismuth.

Embodiment 3. The method of embodiment 1 or 2, further comprising obtaining the biological sample of the subject.

Embodiment 4. The method of any one of embodiments 1-3, further comprising performing the assay on the biological sample of the subject to detect the mutation in the TP53 gene that encodes the p53 mutant in the subject.

Embodiment 5. The method of any one of embodiments 1-4, wherein the administering of the therapeutically-effective amount of the small molecule compound to the subject reduces a likelihood of denaturation of the p53 mutant in the subject.

Embodiment 6. The method of any one of embodiments 1-5, wherein the administering of the therapeutically-effective amount of the small molecule compound to the subject reactivates a p53 pathway in the subject.

Embodiment 7. The method of any one of embodiments 1-6, wherein the administering of the therapeutically-effective amount of the small molecule compound to the subject increases anti-cancer activity of the p53 mutant in the subject.

Embodiment 8. The method of any one of embodiments 1-7, wherein the small molecule compound increases an ability of the p53 mutant to bind DNA.

Embodiment 9. The method of any one of embodiments 1-8, wherein the small molecule compound induces a conformational change in the p53 mutant.

Embodiment 10. The method of any one of embodiments 1-9, wherein the small molecule compound selectively binds the p53 mutant as compared to a wild type p53.

Embodiment 11. The method of any one of embodiments 1-10, wherein the therapeutically effective amount is from about 50 mg to about 2000 mg.

Embodiment 12. The method of any one of embodiments 1-11, wherein the small molecule compound increases stability of a biologically-active conformation of the p53 mutant relative to the stability of the biologically-active conformation of the p53 mutant in absence of the small molecule compound.

Embodiment 13. The method of any one of embodiments 1-12, wherein the mutation in the TP53 gene deactivates a p53 pathway in the subject.

Embodiment 14. The method of any one of embodiments 1-13, wherein the subject has a cancer, wherein the cancer expresses the p53 mutant.

Embodiment 15. The method of any one of embodiments 1-14, wherein the mutation is at amino acid 220.

Embodiment 16. The method of any one of embodiments 1-15, wherein the p53 mutant is a p53 Y220C.

Embodiment 17. The method of any one of embodiments 1-16, wherein the p53 mutant has a reduced ability to bind to DNA in the subject as compared to wild-type p53.

Embodiment 18. The method of any one of embodiments 1-17, wherein the TP53 gene contains a frameshift mutation.

Embodiment 19. The method of any one of embodiments 1-18, wherein the TP53 gene contains a splice site mutation.

Embodiment 20. The method of any one of embodiments 1-19, wherein the TP53 gene contains an insertion mutation.

Embodiment 21. The method of any one of embodiments 1-20, wherein the TP53 gene contains a deletion mutation.

Embodiment 22. The method of any one of embodiments 1-21, wherein the TP53 gene contains a substitution mutation.

Embodiment 23. The method of any one of embodiments 1-22, wherein the TP53 gene contains a copy number variation.

Embodiment 24. The method of any one of embodiments 1-23, wherein the TP53 gene contains a copy number loss.

Embodiment 25. The method of any one of embodiments 1-24, wherein the TP53 gene contains a single nucleotide polymorphism.

Embodiment 26. The method of any one of embodiments 1-25, wherein the assay is DNA sequencing.

Embodiment 27. The method of any one of embodiments 1-26, wherein the assay is next-generation DNA sequencing.

Embodiment 28. The method of any one of embodiments 1-27, wherein the assay is RNA sequencing.

Embodiment 29. The method of any one of embodiments 1-28, wherein the biological sample is a liquid biopsy.

Embodiment 30. The method of any one of embodiments 1-28, wherein the biological sample is a blood sample.

Embodiment 31. The method of any one of embodiments 1-28, wherein the biological sample is circulating tumor DNA.

Embodiment 32. The method of any one of embodiments 1-28, wherein the biological sample is cell free DNA.

Embodiment 33. The method of any one of embodiments 1-28, wherein the biological sample is a solid tumor sample.

Embodiment 34. The method of any one of embodiments 1-33, wherein the condition is a cancer.

Embodiment 35. The method of any one of embodiments 1-34, wherein the condition is ovarian cancer.

Embodiment 36. The method of any one of embodiments 1-34, wherein the condition is breast cancer.

Embodiment 37. The method of any one of embodiments 1-34, wherein the condition is lung cancer.

Embodiment 38. The method of any one of embodiments 1-37, wherein the administration is oral.

Embodiment 39. The method of any one of embodiments 1-37, wherein the administration is intravenous.

Embodiment 40. The method of any one of embodiments 1-37, wherein the administration is subcutaneous.

Embodiment 41. The method of any one of embodiments 1-37, wherein the administration is topical.

Embodiment 42. The method of any one of embodiments 1-41, wherein the subject is human.

Embodiment 43. The method of any one of embodiments 1-42, wherein the compound is of the formula:

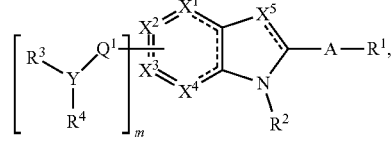

wherein:

each ------- is independently a single bond or a double bond;

$X^1$ is $CR^5$, $CR^5R^6$, N, $NR^5$, O, S, C=O, C=S, or a carbon atom connected to $Q^1$;

$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N, $NR^9$, O, S, C=O, C=S, or a carbon atom connected to $Q^1$;

$X^4$ is $CR^{11}$, $CR^{11}R^{12}$, N, $NR^{11}$, O, S, C=O, C=S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

A is a linking group;

$Q^1$ is C=O, C=S, C=$CR^{14}R^{15}$, C=$NR^{14}$, alkylene, alkenylene, or alkynylene, each of which is independently substituted or unsubstituted, or a bond;

m is 1, 2, 3, or 4;

Y is N, O, or absent;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 44. The method of embodiment 43, wherein A is alkylene, alkenylene, or alkynylene, each of which is substituted or unsubstituted.

Embodiment 45. The method of embodiment 43, wherein A is aryl, heteroaryl, or heterocyclyl, each of which is substituted or unsubstituted.

Embodiment 46. The method of embodiment 43 or 44, wherein the compound is of the formula:

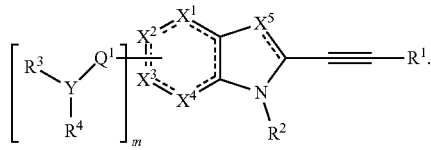

Embodiment 47. The method of any one of embodiments 43-46, wherein $Q^1$ is $C_1$-alkylene.

Embodiment 48. The method of any one of embodiments 43-46, wherein $Q^1$ is a bond.

Embodiment 49. The method of any one of embodiments 43-48, wherein m is 1.

Embodiment 50. The method of any one of embodiments 43-48, wherein m is 2.

Embodiment 51. The method of any one of embodiments 43-50, wherein Y is N.

Embodiment 52. The method of any one of embodiments 43-50, wherein Y is O.

Embodiment 53. The method of any one of embodiments 43-52, wherein each $R^3$ and $R^4$ is independently alkyl, alkylene, alkenyl, alkenylene, alkynyl, aryl, heteroaryl, or heterocyclyl, each of which is independently substituted or unsubstituted; or hydrogen.

Embodiment 54. The method of any one of embodiments 43-53, wherein $R^3$ is alkyl, alkylene, alkenyl, alkenylene, alkynyl, each of which is independently substituted or unsubstituted; and $R^4$ is aryl, heteroaryl, or heterocyclyl, each of which is independently substituted or unsubstituted.

Embodiment 55. The method of any one of embodiments 43-53, wherein $R^3$ is H; and $R^4$ is aryl, heteroaryl, or heterocyclyl, each of which is independently substituted or unsubstituted.

Embodiment 56. The method of any one of embodiments 43-55, wherein $R^{13}$ is hydrogen.

Embodiment 57. The method of any one of embodiments 43, 44, 46, 48, 49, 51, or 53-56, wherein the compound is of the formula:

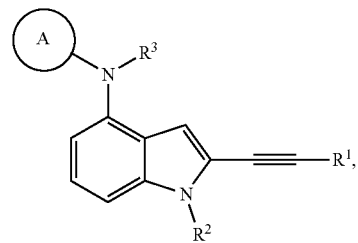

wherein ring A is a cyclic group that is substituted or unsubstituted.

Embodiment 58. The method of any one of embodiments 43-57, wherein $R^2$ is substituted or unsubstituted alkyl.

Embodiment 59. The method of any one of embodiments 43-58, wherein $R^2$ is methyl, ethyl, propyl, iso-propyl, butyl, or tert-butyl, each of which is substituted or unsubstituted.

Embodiment 60. The method of any one of embodiments 43-59, wherein $R^2$ is substituted ethyl.

Embodiment 61. The method of any one of embodiments 43-60, wherein $R^2$ is trifluoroethyl.

Embodiment 62. The method of any one of embodiments 43, 44, 46, 48, 51, or 53-61, wherein the compound is of the formula:

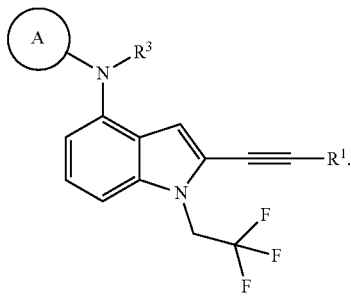

Embodiment 63. The method of any one of embodiments 43, 44, 46, 48, 51, or 53-62, wherein ring A is aryl, heteroaryl, or heterocyclyl, each of which is substituted or unsubstituted.

Embodiment 64. The method of any one of embodiments 43, 44, 46, 48, 51, or 53-63, wherein ring A is substituted aryl.

Embodiment 65. The method of any one of embodiments 43, 44, 46, 48, 51, or 53-63, wherein ring A is substituted heteroaryl.

Embodiment 66. The method of any one of embodiments 43, 44, 46, 48, 51, or 53-63, wherein ring A is substituted heterocyclyl.

Embodiment 67. The method of any one of embodiments 43-66, wherein $R^1$ is alkyl, alkenyl, —C(O)$R^{16}$, —C(O)O$R^{16}$, or —C(O)N$R^{16}R^{17}$, each of which is unsubstituted or substituted.

Embodiment 68. The method of any one of embodiments 43-67, wherein $R^1$ is substituted alkyl.

Embodiment 69. The method of any one of embodiments 43-68, wherein $R^1$ is alkyl substituted with N$R^{16}R^{17}$.

Embodiment 70. The method of any one of embodiments 43, 44, 46, 48, 51, or 53-69, wherein the compound is of the formula:

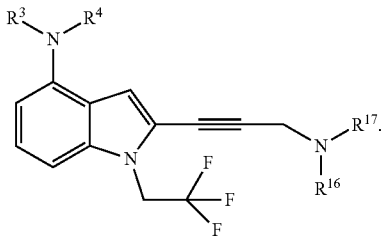

Embodiment 71. The method of any one of embodiments 43-70, wherein each $R^{16}$ and $R^{17}$ is independently alkyl, alkenyl, aryl, heteroaryl, heterocyclyl, each of which is independently substituted or unsubstituted; or hydrogen.

Embodiment 72. The method of any one of embodiments 43-71, wherein $R^{16}$ is hydrogen or alkyl.

Embodiment 73. The method of any one of embodiments 43-72, wherein $R^{17}$ is aryl, heteroaryl, or heterocyclyl, each of which is independently substituted or unsubstituted.

Embodiment 74. The method of any one of embodiments 43-73, wherein $R^{17}$ is substituted aryl.

Embodiment 75. The method of any one of embodiments 43-74, wherein $R^{17}$ is substituted phenyl.

Embodiment 76. The method of any one of embodiments 43-74, wherein $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 77. The method of any one of embodiments 43-76, wherein $R^{17}$ is phenyl substituted with methoxy.

Embodiment 78. The method of any one of embodiments 43-76, wherein $R^{17}$ is phenyl substituted with a substituted sulfoxide group.

Embodiment 79. The method of any one of embodiments 43-76, wherein $R^{17}$ is phenyl substituted with a carboxyl group.

Embodiment 80. The method of any one of embodiments 43-76, wherein $R^{17}$ is phenyl substituted with an amide group.

Embodiment 81. The method of embodiment 43, wherein the compound is 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide.

Embodiment 82. The method of embodiment 43, wherein the compound is 2-(3-((2-methoxy-4-(methylsulfonyl)phenyl)amino)prop-1-yn-1-yl)-N-((1r,4r)-4-morpholinocyclohexyl)-1-(oxiran-2-ylmethyl)-1H-indol-4-amine.

Embodiment 83. The method of embodiment 43, wherein the compound is 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide.

Embodiment 84. The method of embodiment 43, wherein the compound is 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-m ethoxy-N-methylbenzamide.

Embodiment 85. The method of embodiment 43, wherein the compound is N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide.

Embodiment 86. The method of embodiment 43, wherein the compound is 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide.

Embodiment 87. The method of embodiment 43, wherein the compound is N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide.

Embodiment 88. The method of embodiment 43, wherein the compound is 3-methoxy-4-((3-(4-(3-(l-methylpiperidin-4-yl)ureido)-1-(2,2,2-trifluoroethyl)-1H-indol-2-yl)prop-2-yn-1-yl)amino)benzamide.

Embodiment 89. The method of embodiment 43, wherein the compound is N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine.

What is claimed is:

1. A method of treating a subject suffering from a cancer having a 53-deactivating mutation in a TP53 gene that encodes a 53 mutant protein, the method comprising administering to the subject a therapeutically effective amount of compound,
   wherein the subject has been previously determined to have the p53-deactivating mutation in the TP53 gene that encodes the p53 mutant protein in the subject based on an assay performed on a biological sample of the subject,
   wherein the compound is:
   4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide;
   N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine; or
   N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide,
   or a pharmaceutically-acceptable salt thereof.

2. The method of claim 1, further comprising obtaining the biological sample of the subject.

3. The method of claim 1, further comprising performing the assay on the biological sample of the subject to detect the p53-deactivating mutation in the TP53 gene that encodes the p53 mutant in the subject.

4. The method of claim 1, wherein the therapeutically effective amount is from about 50 mg to about 3000 mg.

5. The method of claim 1, wherein the p53 mutant is a p53 Y220C.

6. The method of claim 1, wherein the assay is next-generation DNA sequencing.

7. The method of claim 1, wherein the biological sample is a liquid biopsy.

8. The method of claim 1, wherein the biological sample is a solid tumor sample.

9. The method of claim 1, wherein the cancer is lung cancer.

10. The method of claim 1, wherein the administration is oral.

11. The method of claim 1, wherein the subject is human.

12. The method of claim 1, wherein the mutation is a substitution mutation.

13. The method of claim 1, wherein the mutation is a single nucleotide polymorphism.

14. The method of claim 1, wherein the compound is:
N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide.

15. The method of claim 1, wherein the compound is:
4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide.

16. The method of claim 1, wherein the compound is:
N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine.

* * * * *

UNITED STATES PATENT AND TRADEMARK OFFICE
CERTIFICATE OF CORRECTION

| | | |
|---|---|---|
| PATENT NO. | : 12,419,880 B2 | Page 1 of 1 |
| APPLICATION NO. | : 17/351880 | |
| DATED | : September 23, 2025 | |
| INVENTOR(S) | : Melissa Dumble | |

It is certified that error appears in the above-identified patent and that said Letters Patent is hereby corrected as shown below:

In the Claims

Claim 1; Column 367; Lines 51-52:
Delete: "53-deactivating mutation in a TP53 gene that encodes a 53 mutant protein"
And replace with: --p53-deactivating mutation in a TP53 gene that encodes a p53 mutant protein--

Claim 1; Column 367; Line 54:
Delete: "compound"
And replace with: --a compound--

Signed and Sealed this
Thirtieth Day of December, 2025

John A. Squires
*Director of the United States Patent and Trademark Office*